United States Patent
Smolinski et al.

(12)

(10) Patent No.: US 10,973,828 B2
(45) Date of Patent: *Apr. 13, 2021

(54) BIARYL COMPOSITIONS AND METHODS FOR MODULATING A KINASE CASCADE

(71) Applicant: Athenex, Inc., Buffalo, NY (US)

(72) Inventors: Michael P. Smolinski, Amherst, NY (US); Nader N. Nasief Abdel-Sayed, Fort Erie (CA); David G. Hangauer, Jr., Lancaster, NY (US)

(73) Assignee: Athenex, Inc., Buffalo, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/232,229

(22) Filed: Dec. 26, 2018

(65) Prior Publication Data
US 2019/0125754 A1 May 2, 2019

Related U.S. Application Data

(62) Division of application No. 15/676,203, filed on Aug. 14, 2017, now Pat. No. 10,213,435.

(60) Provisional application No. 62/374,201, filed on Aug. 12, 2016.

(51) Int. Cl.
| | |
|---|---|
| *A61K 31/5377* | (2006.01) |
| *C07D 413/10* | (2006.01) |
| *C07D 413/14* | (2006.01) |
| *A61K 9/00* | (2006.01) |
| *A61K 31/496* | (2006.01) |
| *C07C 233/13* | (2006.01) |
| *C07C 233/22* | (2006.01) |
| *C07D 213/56* | (2006.01) |
| *C07D 213/64* | (2006.01) |
| *C07D 213/74* | (2006.01) |
| *C07D 239/34* | (2006.01) |
| *C07D 401/12* | (2006.01) |
| *C07D 403/04* | (2006.01) |

(52) U.S. Cl.
CPC ........ *A61K 31/5377* (2013.01); *A61K 9/0053* (2013.01); *A61K 31/496* (2013.01); *C07C 233/13* (2013.01); *C07C 233/22* (2013.01); *C07D 213/56* (2013.01); *C07D 213/64* (2013.01); *C07D 213/74* (2013.01); *C07D 239/34* (2013.01); *C07D 401/12* (2013.01); *C07D 403/04* (2013.01); *C07D 413/10* (2013.01); *C07D 413/14* (2013.01); *A61K 9/0019* (2013.01); *A61K 9/0085* (2013.01)

(58) Field of Classification Search
CPC . A61K 31/5377; C07D 413/10; C07D 413/14
See application file for complete search history.

(56) References Cited

U.S. PATENT DOCUMENTS

| | | |
|---|---|---|
| 4,642,903 A | 2/1987 | Davies |
| 4,855,326 A | 8/1989 | Fuisz |
| 5,380,473 A | 1/1995 | Bogue |
| 5,518,730 A | 5/1996 | Fuisz |
| 5,578,322 A | 11/1996 | Shiozawa |
| 5,587,172 A | 12/1996 | Cherukuri et al. |
| 5,607,697 A | 3/1997 | Alkire et al. |
| 5,616,344 A | 4/1997 | Battist et al. |
| 5,622,719 A | 4/1997 | Myers et al. |
| 5,631,023 A | 5/1997 | Kearney et al. |
| 6,277,406 B1 | 8/2001 | Fuisz et al. |
| 6,471,992 B1 | 10/2002 | Yoo et al. |
| 7,034,049 B1 | 4/2006 | Pevarello et al. |
| 7,300,931 B2 | 11/2007 | Hangauer |
| 7,851,470 B2 | 12/2010 | Hangauer et al. |
| 7,935,697 B2 | 5/2011 | Hangauer et al. |
| 7,939,529 B2 | 5/2011 | Hangauer et al. |
| 7,968,574 B2 | 6/2011 | Hangauer et al. |
| 8,003,641 B2 | 8/2011 | Hangauer |
| 8,236,799 B2 | 8/2012 | Hangauer |
| 8,293,739 B2 | 10/2012 | Hangauer et al. |
| 8,309,549 B2 | 11/2012 | Hangauer et al. |
| 8,598,169 B2 | 12/2013 | Hangauer |
| 8,748,423 B2 | 6/2014 | Hangauer et al. |
| 8,901,297 B2 | 12/2014 | Hangauer et al. |
| 8,980,890 B2 | 3/2015 | Hangauer |
| 9,556,120 B2 | 1/2017 | Hangauer et al. |
| 9,580,387 B2 | 2/2017 | Hangauer |
| 9,655,903 B2 | 5/2017 | Hangauer |
| 10,213,435 B2 | 2/2019 | Smolinski et al. |
| 2002/0032191 A1 | 3/2002 | Lowe |
| 2009/0149510 A1 | 6/2009 | Hangauer |
| 2010/0249130 A1 | 9/2010 | Hangauer |
| 2017/0101378 A1 | 4/2017 | Hangauer et al. |
| 2017/0196874 A1 | 7/2017 | Hangauer |

FOREIGN PATENT DOCUMENTS

KR      10-1328273 B1    11/2013

OTHER PUBLICATIONS

Chou and Talalay, "Quantitative analysis of dose-effect relationships: the combined effects of multiple drugs or enzyme inhibitors", *Advances in Enzyme Regulation*, vol. 22, pp. 27-55 (1984).

*Primary Examiner* — Alicia L Otton
(74) *Attorney, Agent, or Firm* — Cooley LLP; Heidi A. Erlacher; Chen Chen

(57) ABSTRACT

The application relates to biaryl compounds, pharmaceutical compositions comprising the compounds, and methods of use the compounds for treating cell proliferation disorders.

18 Claims, 55 Drawing Sheets

| Parameter | Compound Y | Compound 121 |
|---|---|---|
| Potency<br>GI$_{50}$, U87 glioblastoma cell line<br>GI$_{50}$, CCD-1106 KERTr keratinocyte cell line<br>% late-apoptotic @ 100 nM, CCD-1106 KERTr keratinocyte cells | 80 nM<br>20 nM<br>6.3% | 7 nM<br>2 nM<br>6.9% |
| Oral bioavailability<br>(mouse, single experiment) | 39% | 35% |
| Brain penetration<br>(Brain:plasma average) | 1.0 | 1.6 |
| Half-life (mouse) | 0.4 h | 0.96 h |
| Solubility<br>• pH 4.4<br>• pH 7.4 | 2 uM<br>1 uM | 46 uM<br>17 uM |

FIG. 52

BIARYL COMPOSITIONS AND METHODS FOR MODULATING A KINASE CASCADE

RELATED APPLICATION

This application is a division of U.S. application Ser. No. 15/676,203, filed on Aug. 14, 2017 (now allowed), which claims priority to, and the benefit of, U.S. Provisional Application No. 62/374,201, filed on Aug. 12, 2016, the contents of each of which are incorporated herein by reference in their entireties.

BACKGROUND

Signal transduction is any process by which a cell converts one kind of signal or stimulus into another. One class of molecules involved in signal transduction is the kinase family of enzymes.

Protein kinases are a large class of enzymes which catalyze the transfer of the □-phosphate from ATP to the hydroxyl group on the side chain of Ser/Thr or Tyr in proteins and peptides and are intimately involved in the control of various important cell functions, perhaps most notably: signal transduction, differentiation, and proliferation.

Phosphorylation of proteins by kinases is an important mechanism in signal transduction for regulation of enzyme activity. The tyrosine kinases are divided into two groups; those that are cytoplasmic proteins and the transmembrane receptor-linked kinases.

Because kinases are involved in the regulation of a wide variety of normal cellular signal transduction pathways (e.g., cell growth, differentiation, survival, adhesion, migration, etc.), kinases are thought to play a role in a variety of diseases and disorders. Thus, modulation of kinase signaling cascades may be an important way to treat or prevent such diseases and disorders. One promising potential therapeutic use for protein kinase or protein phosphatase inhibitors is as anti-cancer agents.

Small molecule interference with tubulin dynamics has broad and profound effect on a cell. When small molecules bind to tubulin they can interfere with the dynamics of microtubules formed from tubulin, either by stabilizing the formed microtubules so they cannot break down or by preventing new formation of microtubules by polymerization.

The effect of small molecules interfering with tubulin dynamics can manifest in the suppression of the cell's ability to proliferate. Interference by small molecules on tubulin dynamics can force the cell to arrest at the G2/M point in the cell cycle, ceasing mitosis, and triggering apoptosis. This action makes these small molecules efficacious in treating human diseases associated with uncontrolled cell proliferation. Efficacy in treating hyper-proliferative disorders has been proven by compounds such as Paclitaxel (a microtubule stabilizer) and Vinblastin (a tubulin polymerization inhibitor) in human subjects.

Tubulin-targeting small molecules can also affect vascularization of tissue. Several tubulin polymerization inhibitors have been demonstrated to affect the abnormal vascularization of tumors. These effects manifest in, e.g., normalization of the vascular network and cutting off blood flow to cancerous tumors, resulting in necrosis. These vascular effects may also be useful for other disease states resulting from abnormal vascularization, such as ocular myopathy.

There is a need for small molecule compounds that modulate the kinase signaling cascade as well as tubulin dynamics. The present application addresses such need.

SUMMARY

Compounds of the application are useful in modulating a component of the kinase signaling cascade or in targeting tubulin. Some compounds may be useful in modulation of more than one component of a kinase signaling cascade. The compounds of the present application are useful as pharmaceutical agents. The compounds of the application may be useful for modulating regulation of a kinase which may be involved in a normal cellular signal transduction pathway (e.g., cell growth, differentiation, survival, adhesion, migration, etc.), or a kinase involved in a disease or disorder. The compounds of the application are useful as tubulin polymerization inhibitors.

The compounds of the application are useful in treating diseases and disorders that are modulated by tyrosine kinase inhibition. For example, the compounds of the application are useful in treating diseases and disorders that are modulated by Src kinase. The compounds of the application may also be useful in treating diseases and disorders that are modulated by focal adhesion kinase (FAK). The compounds of the application may also be useful in treating diseases and disorders that are related to tubulin or tubulin polymerization.

For example, the compounds of the application may be useful as anti-proliferative agents, for treating mammals, such as for treating humans and animals. The compounds of the application may be used without limitation, for example, as anti-cancer agents. The compounds of the application may be soluble in aqueous solution and in general organic solvents.

The present application relates to a compound of formula (A):

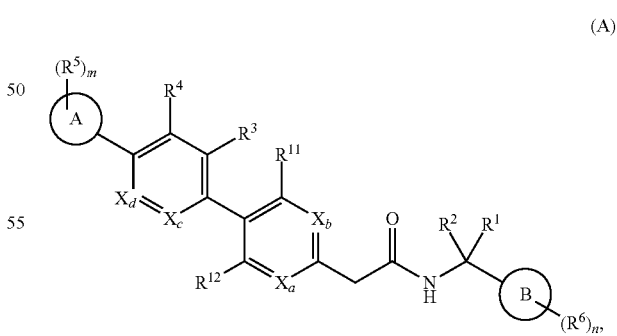

(A)

or a pharmaceutically acceptable salt, solvate, or prodrug thereof, wherein each of the variables in formula (A) is defined and exemplified herein.

In one aspect, a compound of formula (A) is a compound of any one of formula (I), (II), (III), (IVa)-(IVd), (Va)-(Vd), (VIa)-(VId), or (VIIa)-(VIIe):

(I)
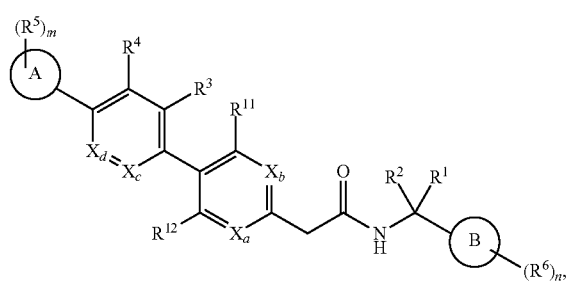
(II)
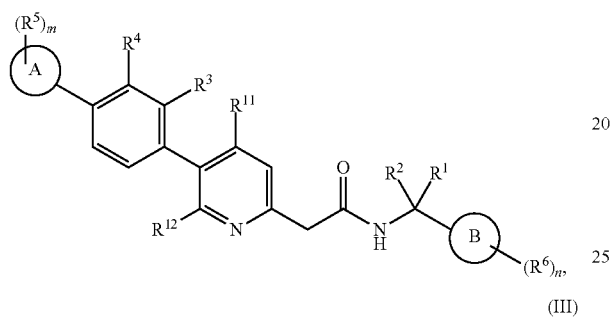
(III)
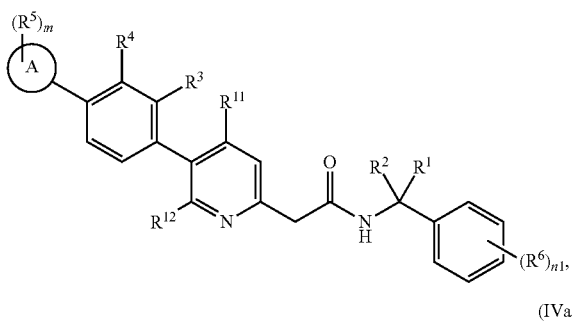
(IVa)
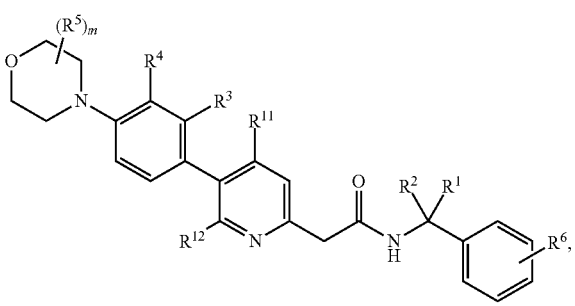
(IVb)
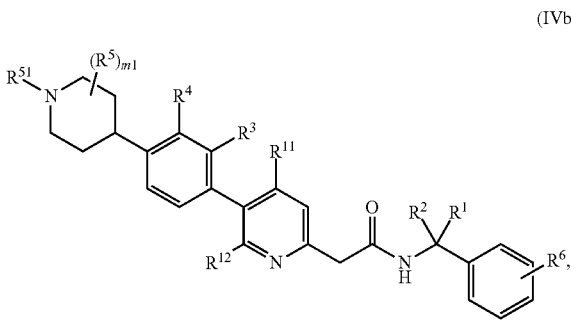
(IVc)
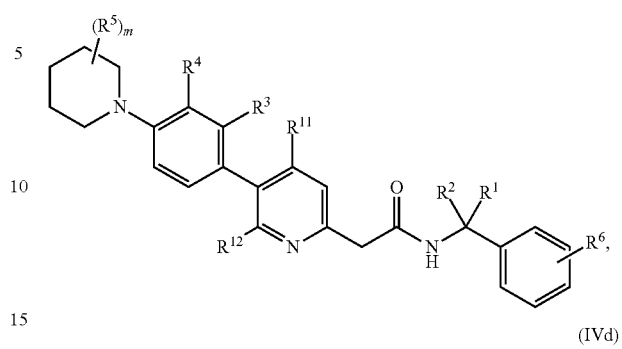
(IVd)
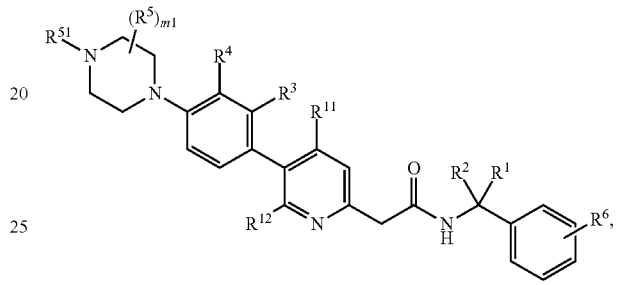
(Va)
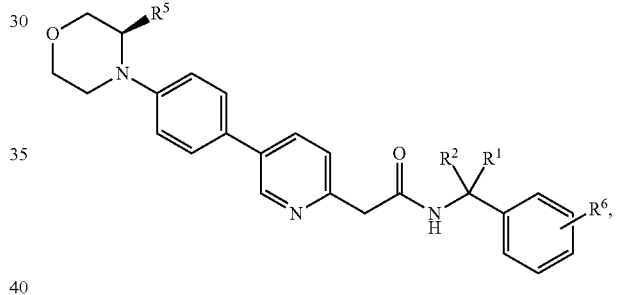
(Vb)
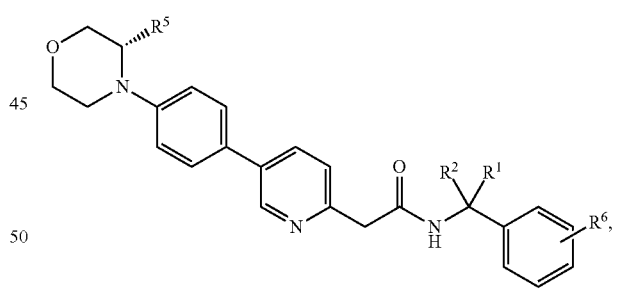
(Vc)
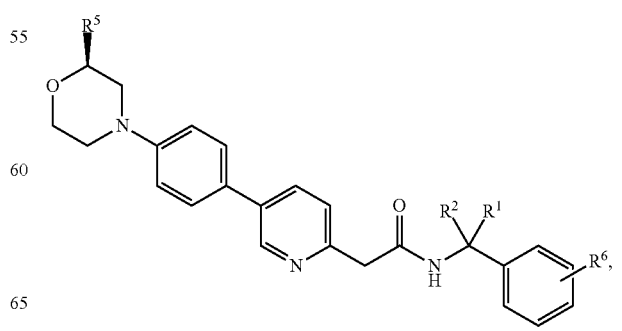

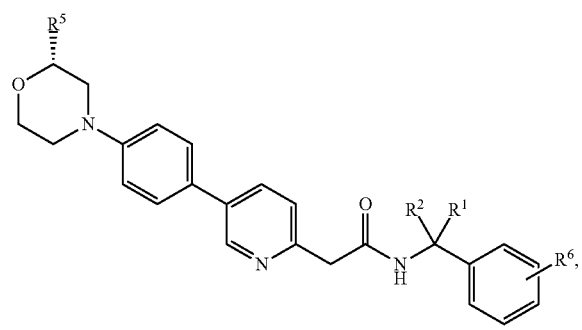
(Vd)
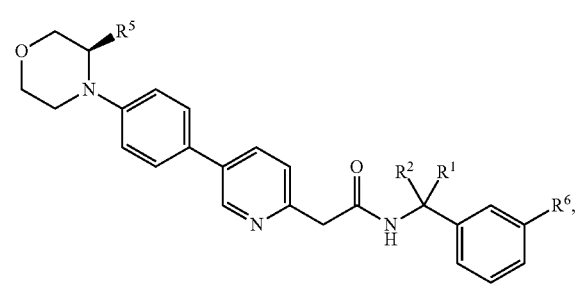
(VIa)
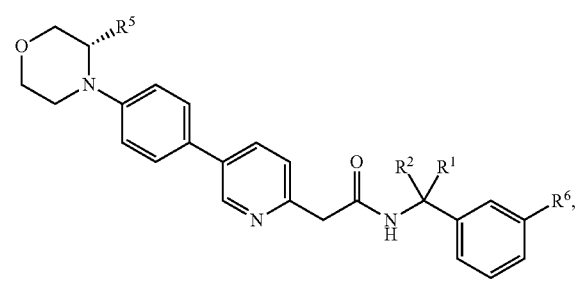
(VIb)
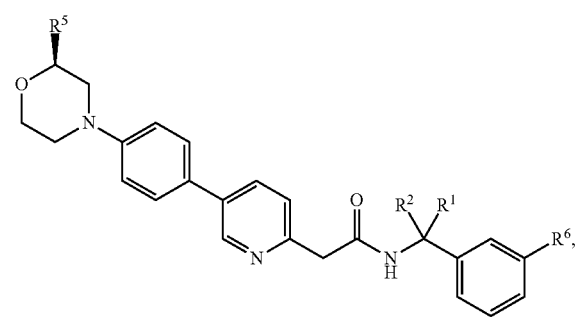
(VIc)
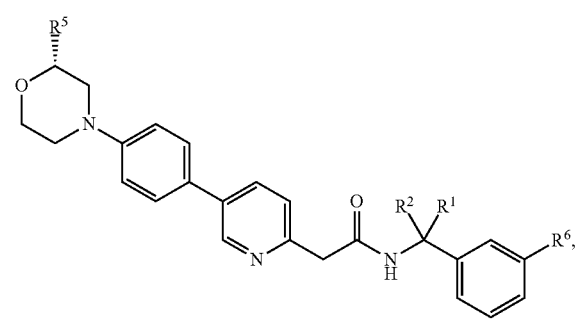
(VId)
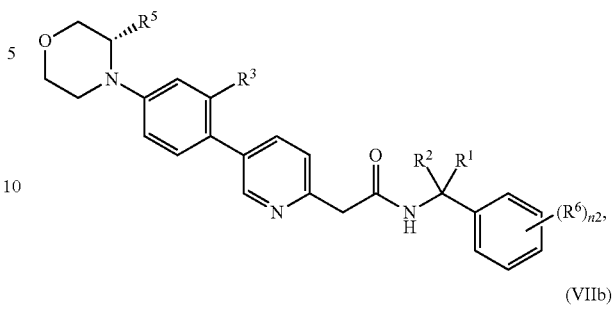
(VIIa)
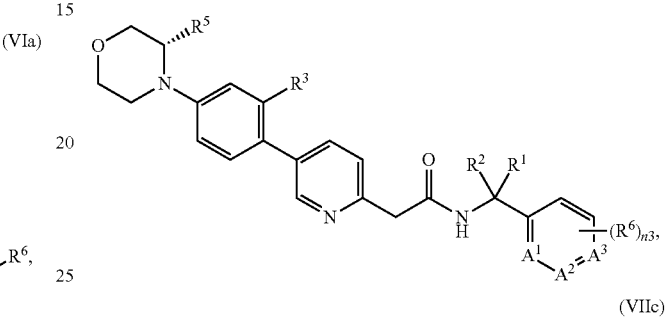
(VIIb)
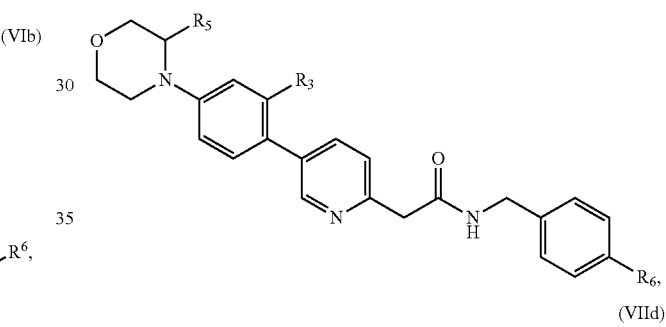
(VIIc)
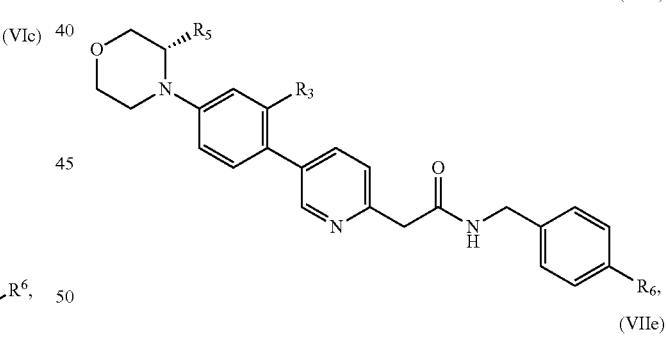
(VIId)
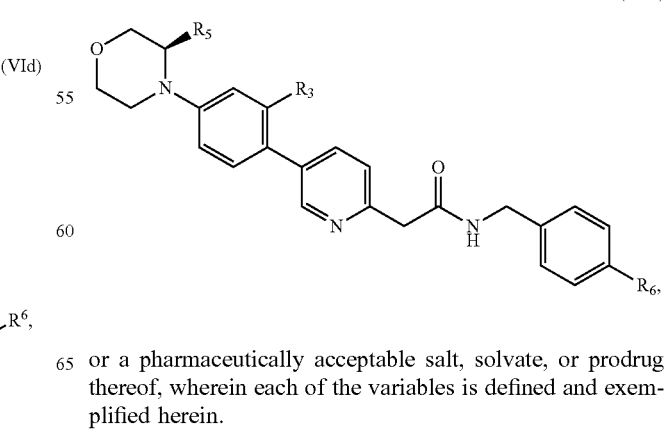
(VIIe)
or a pharmaceutically acceptable salt, solvate, or prodrug thereof, wherein each of the variables is defined and exemplified herein.

In one aspect, the application relates to a pharmaceutical composition comprising a compound of the application, or a pharmaceutically acceptable salt, solvate, or prodrug thereof and a pharmaceutically acceptable carrier.

In one aspect, the application relates to a method of preventing or treating a disease or disorder comprising administering to a subject in need thereof an effective amount of a compound of the application, or a pharmaceutically acceptable salt, solvate, or prodrug thereof, or a pharmaceutical composition of the application.

In one aspect, the application relates to the use of a compound of the application, or a pharmaceutically acceptable salt, solvate, or prodrug thereof, or a pharmaceutical composition of the application for preventing or treating a disease or disorder in a subject in need thereof.

In one aspect, the application relates to the use of a compound of the application, or a pharmaceutically acceptable salt, solvate, or prodrug thereof, or a pharmaceutical composition of the application in the manufacture of a medicament for preventing or treating a disease or disorder in a subject in need thereof.

In one aspect, the application relates to a compound of the application, or a pharmaceutically acceptable salt, solvate, or prodrug thereof, or a pharmaceutical composition of the application for use in preventing or treating a disease or disorder in a subject in need thereof.

The above description sets forth rather broadly the more important features of the present application in order that the detailed description thereof that follows may be understood, and in order that the present contributions to the art may be better appreciated. Other objects and features of the present application will become apparent from the following detailed description considered in conjunction with the examples.

24B is a graph indicating the determination of the $GI_{50}$ for Compound 121 and cisplatin in HUH-7 cells.

Figure 1A:
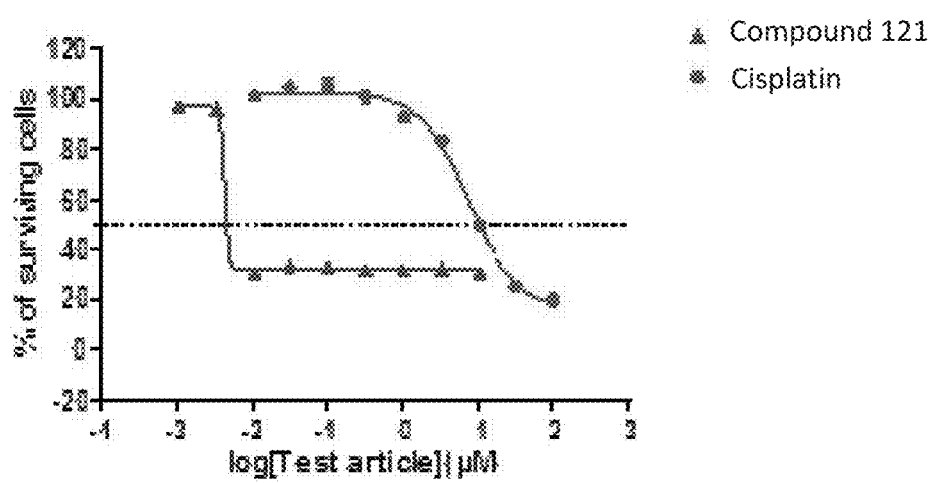
FIG. 1A is a graph indicating the determination of the $IC_{50}$ for Compound 121 and cisplatin in TJ905 cells.
Figure 1B:
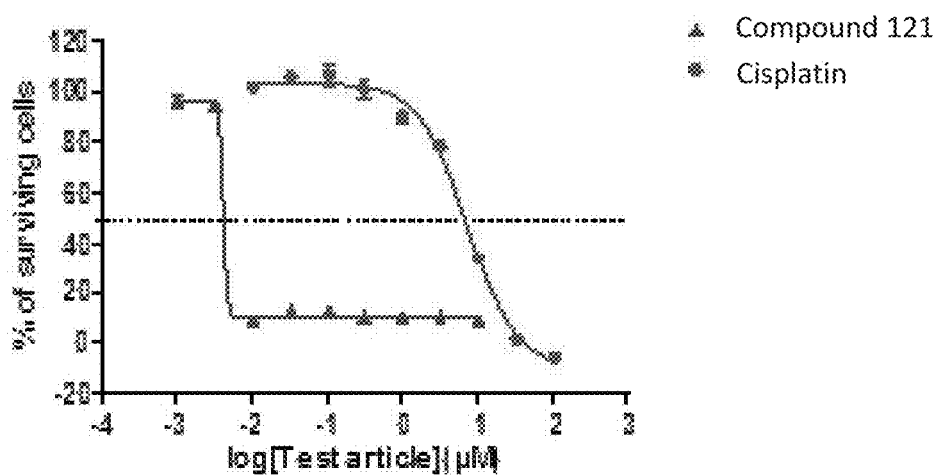
FIG. 1B is a graph indicating the determination of the $GI_{50}$ for Compound 121 and cisplatin in TJ905 cells.
Figure 2A:
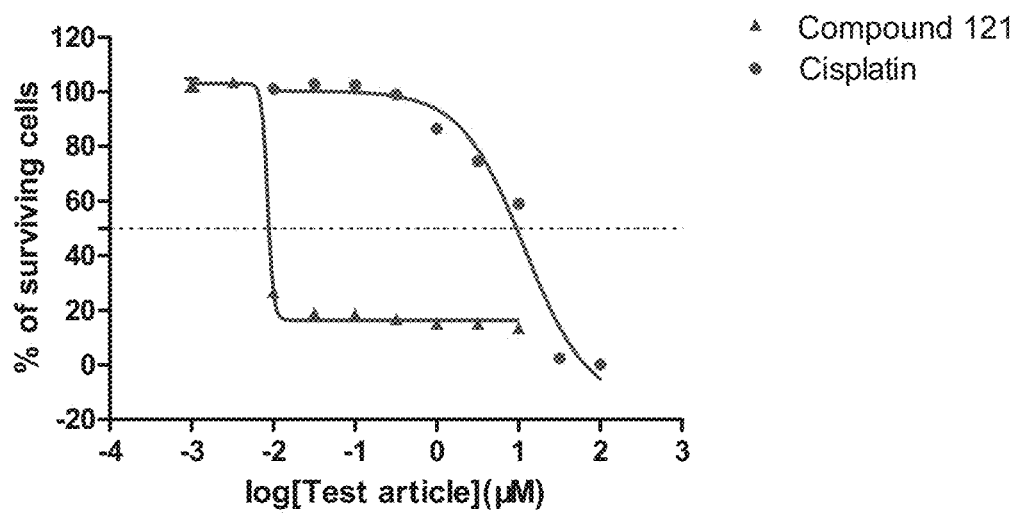
FIG. 2A is a graph indicating the determination of the $IC_{50}$ for Compound 121 and cisplatin in JEG-3 cells.
Figure 2B:
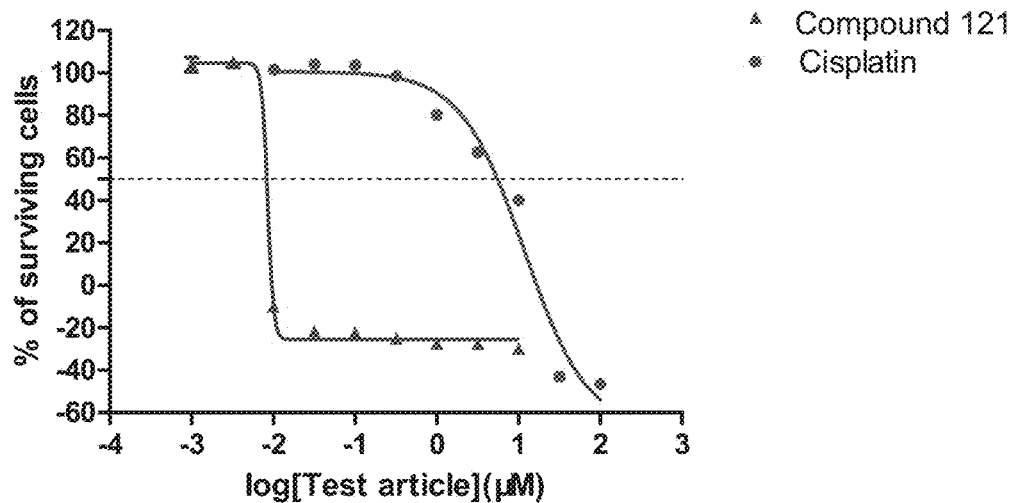
FIG. 2B is a graph indicating the determination of the $GI_{50}$ for Compound 121 and cisplatin in JEG-3 cells.
Figure 3A:
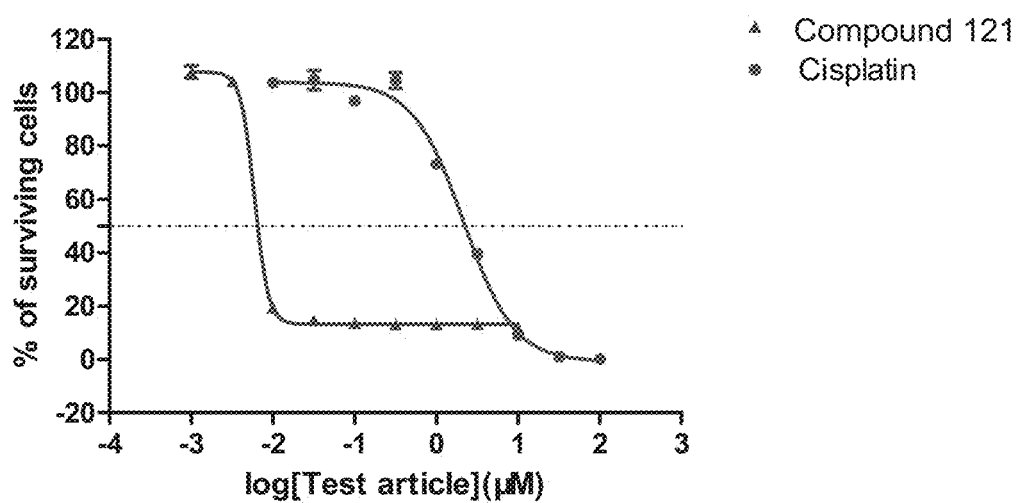
FIG. 3A is a graph indicating the determination of the $IC_{50}$ for Compound 121 and cisplatin in SW579 cells.
Figure 3B:
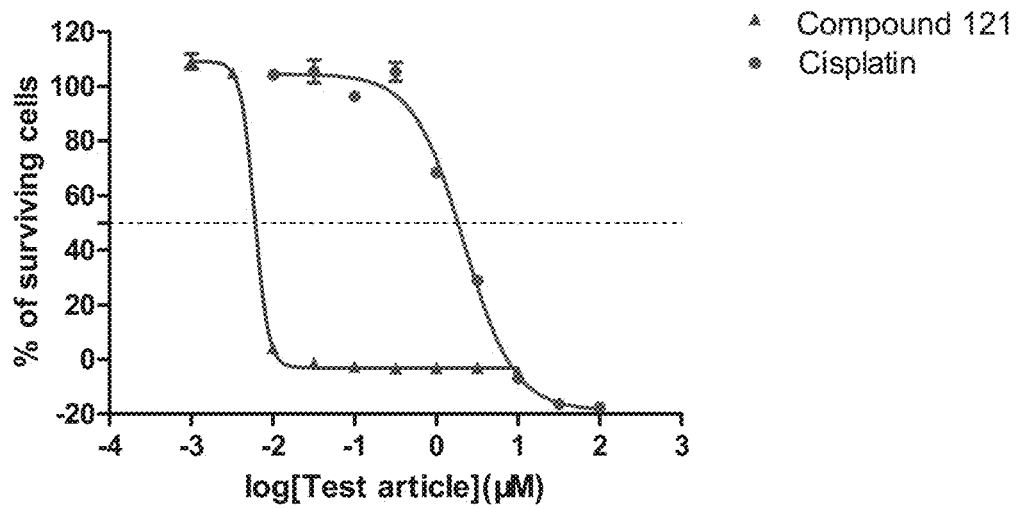
FIG. 3B is a graph indicating the determination of the $GI_{50}$ for Compound 121 and cisplatin in SW579 cells.
Figure 4A:
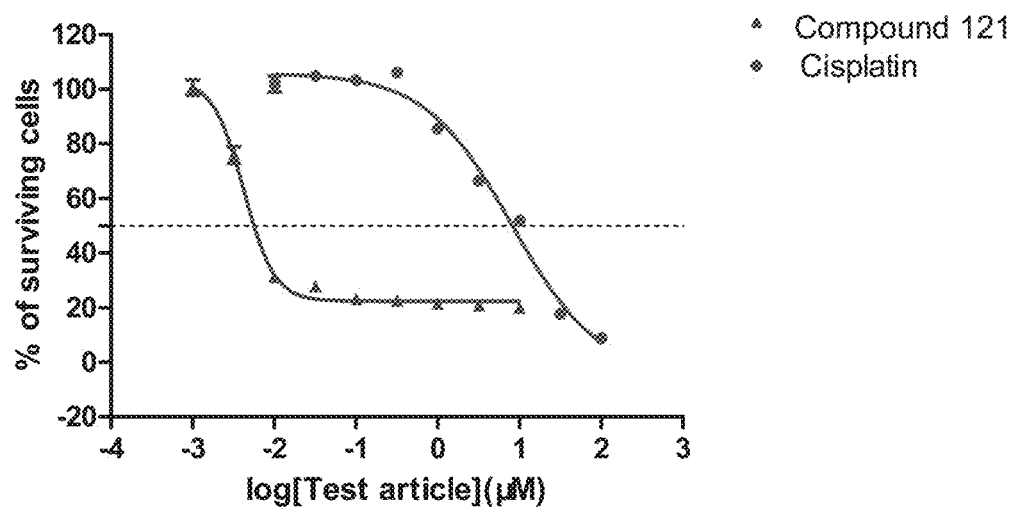
FIG. 4A is a graph indicating the determination of the $IC_{50}$ for Compound 121 and cisplatin in KYSE-150 cells.
Figure 4B:
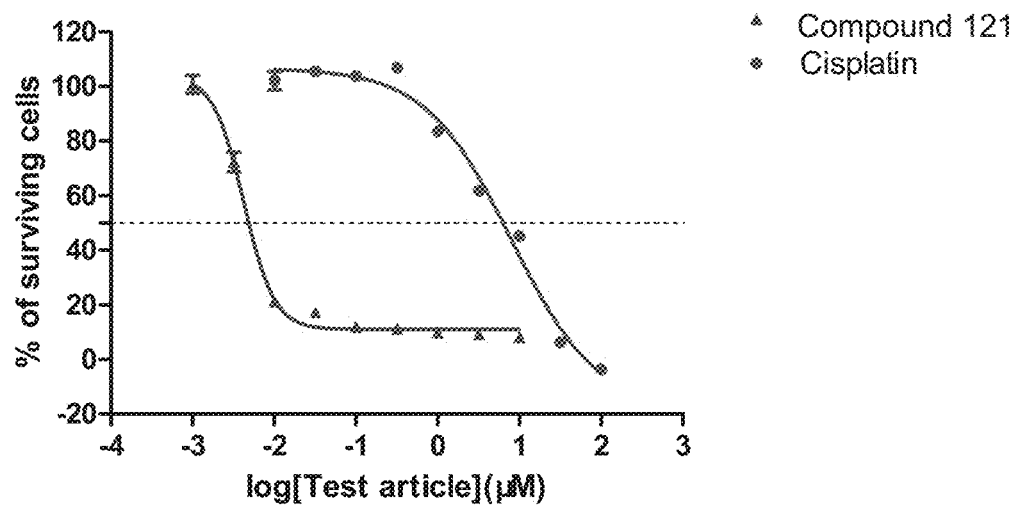
FIG. 4B is a graph indicating the determination of the $GI_{50}$ for Compound 121 and cisplatin in KYSE-150 cells.
Figure 5A:
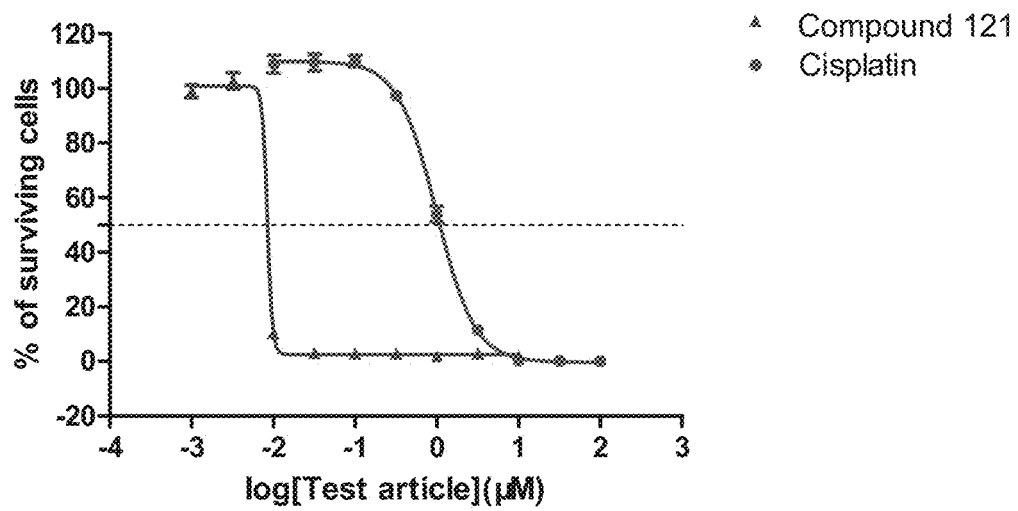
FIG. 5A is a graph indicating the determination of the $IC_{50}$ for Compound 121 and cisplatin in 143B cells.
Figure 5B:
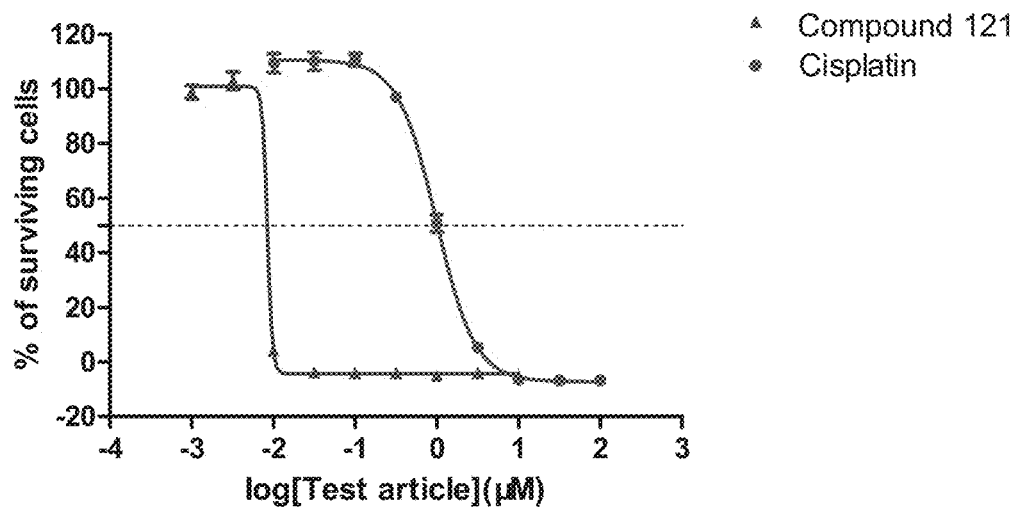
FIG. 5B is a graph indicating the determination of the $GI_{50}$ for Compound 121 and cisplatin in 143B cells.
Figure 6A:
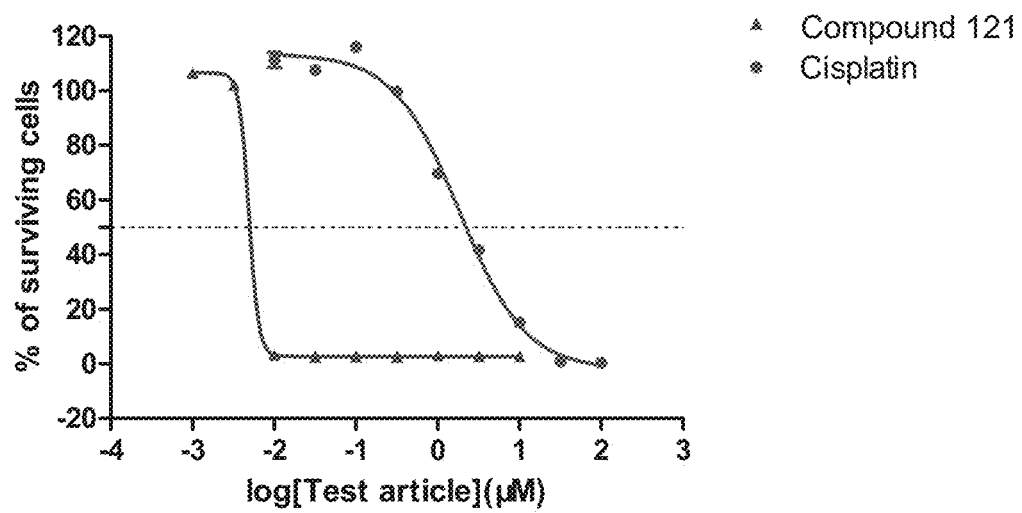
FIG. 6A is a graph indicating the determination of the $IC_{50}$ for Compound 121 and cisplatin in HT-1080 cells.
Figure 6B:
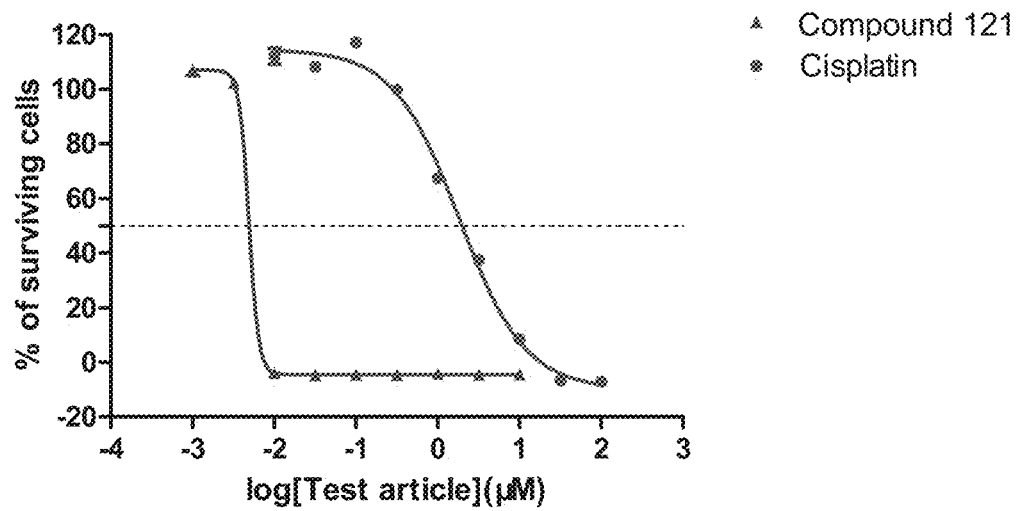
FIG. 6B is a graph indicating the determination of the $GI_{50}$ for Compound 121 and cisplatin in HT-1080 cells.
Figure 7A:
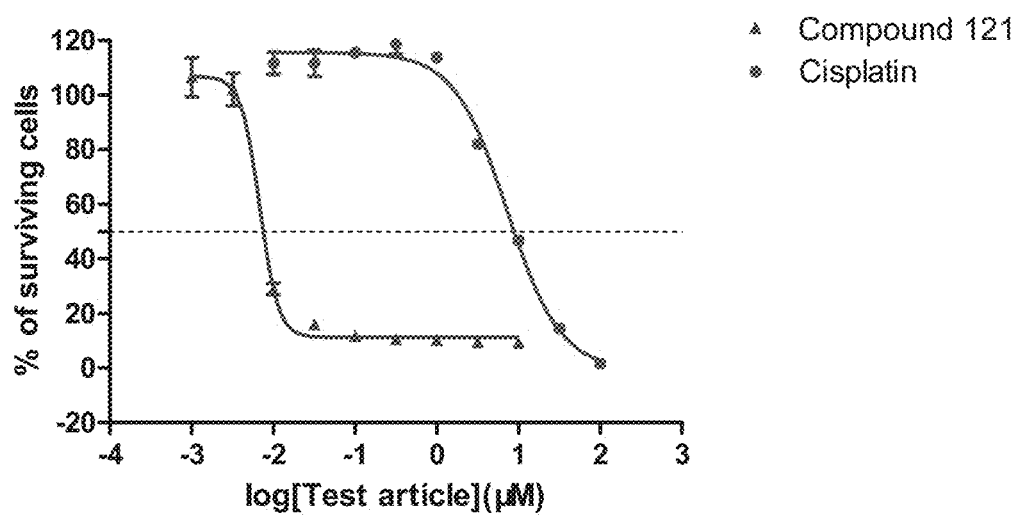
FIG. 7A is a graph indicating the determination of the $IC_{50}$ for Compound 121 and cisplatin in KP4 cells.
Figure 7B:
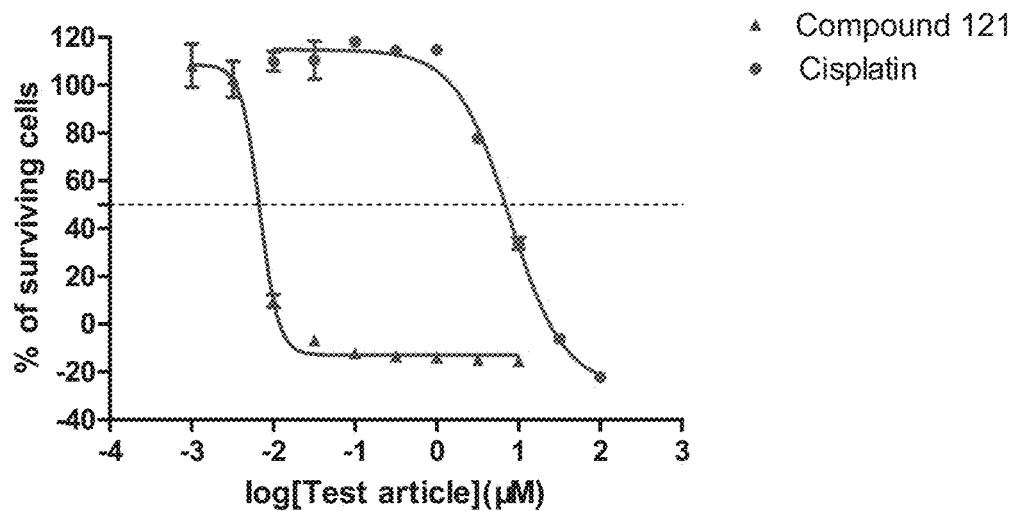
FIG. 7B is a graph indicating the determination of the $GI_{50}$ for Compound 121 and cisplatin in KP4 cells.
Figure 8A:
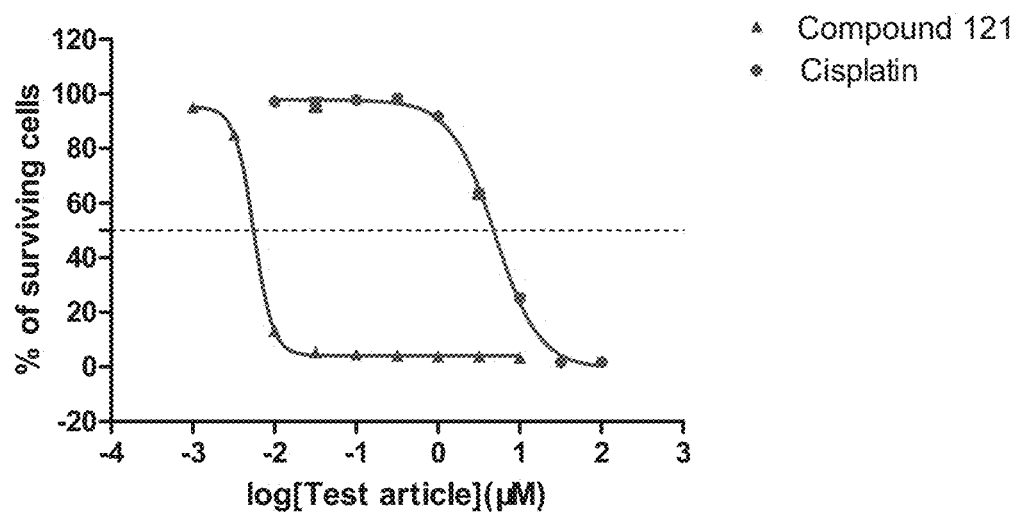
FIG. 8A is a graph indicating the determination of the $IC_{50}$ for Compound 121 and cisplatin in HCT-15 cells.
Figure 8B:
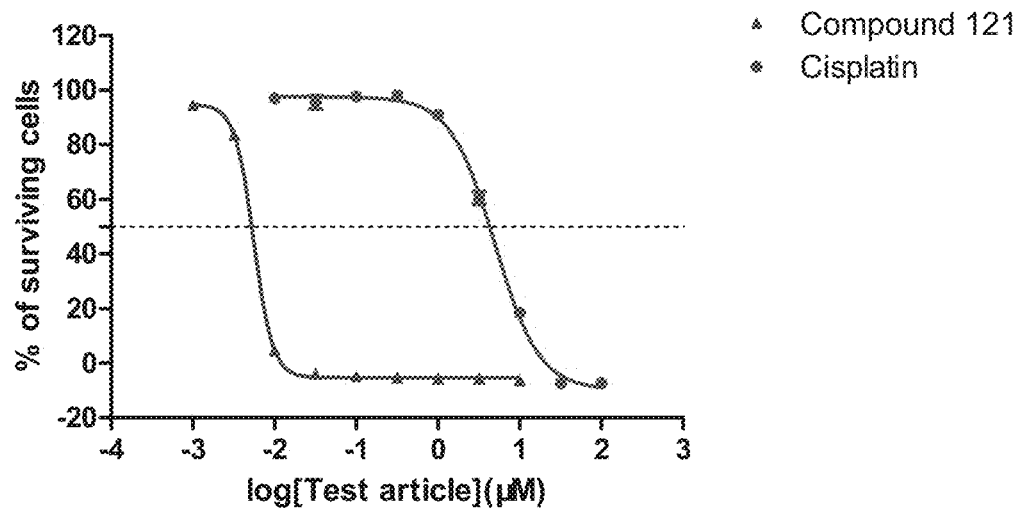
FIG. 8B is a graph indicating the determination of the $GI_{50}$ for Compound 121 and cisplatin in HCT-15 cells.
Figure 9A:
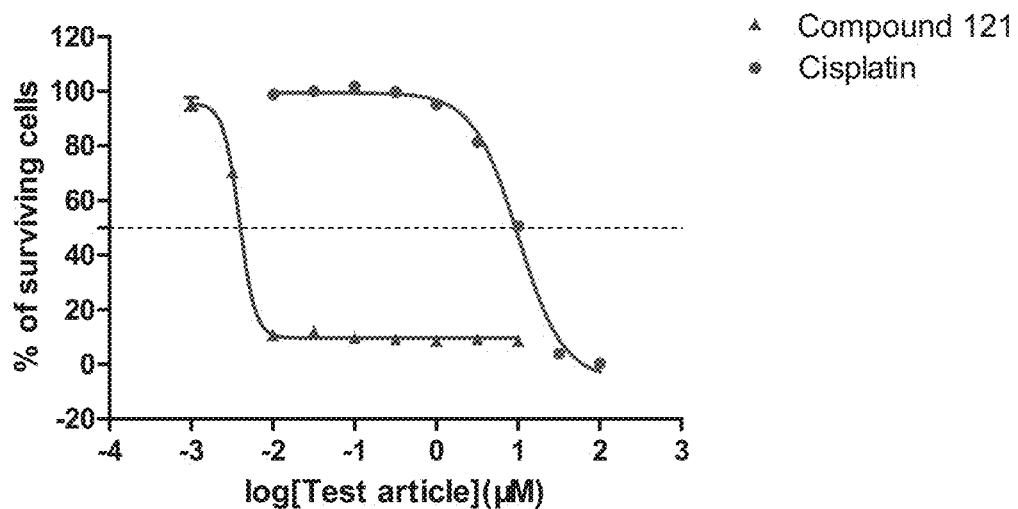
FIG. 9A is a graph indicating the determination of the $IC_{50}$ for Compound 121 and cisplatin in SK-N-FI cells.
Figure 9B:
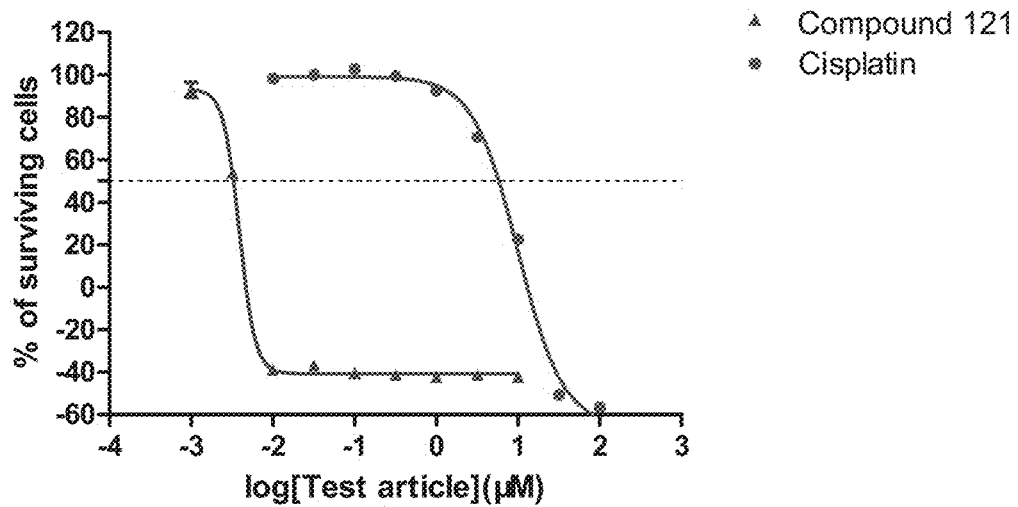
FIG. 9B is a graph indicating the determination of the $GI_{50}$ for Compound 121 and cisplatin in SK-N-FI cells.
Figure 10A:
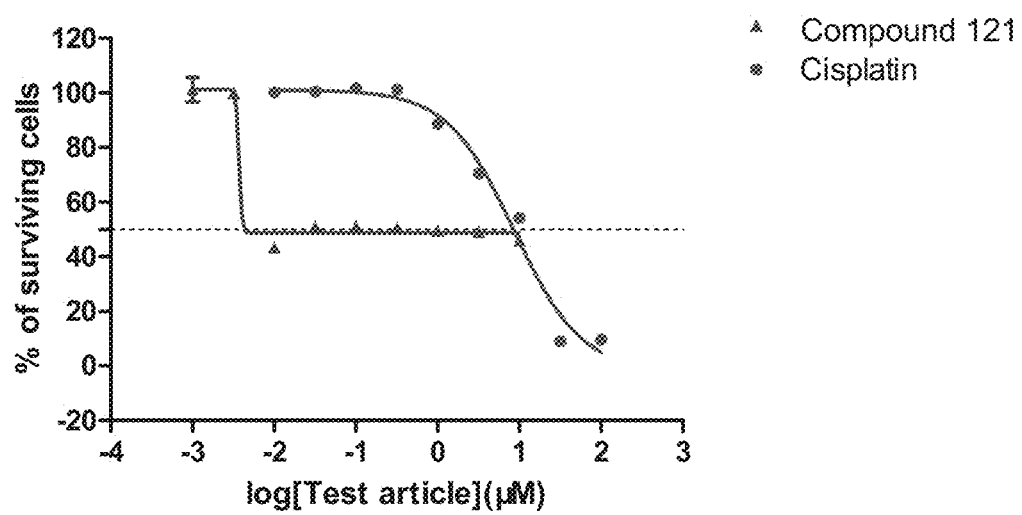
FIG. 10A is a graph indicating the determination of the $IC_{50}$ for Compound 121 and cisplatin in HuCCT1 cells.
Figure 10B:
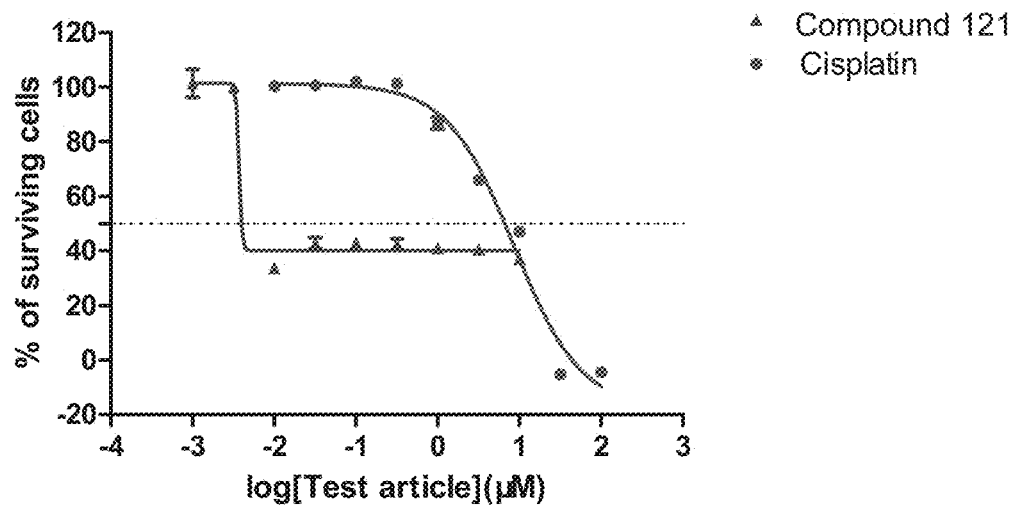
FIG. 10B is a graph indicating the determination of the $GI_{50}$ for Compound 121 and cisplatin in HuCCT1 cells.
Figure 11A:
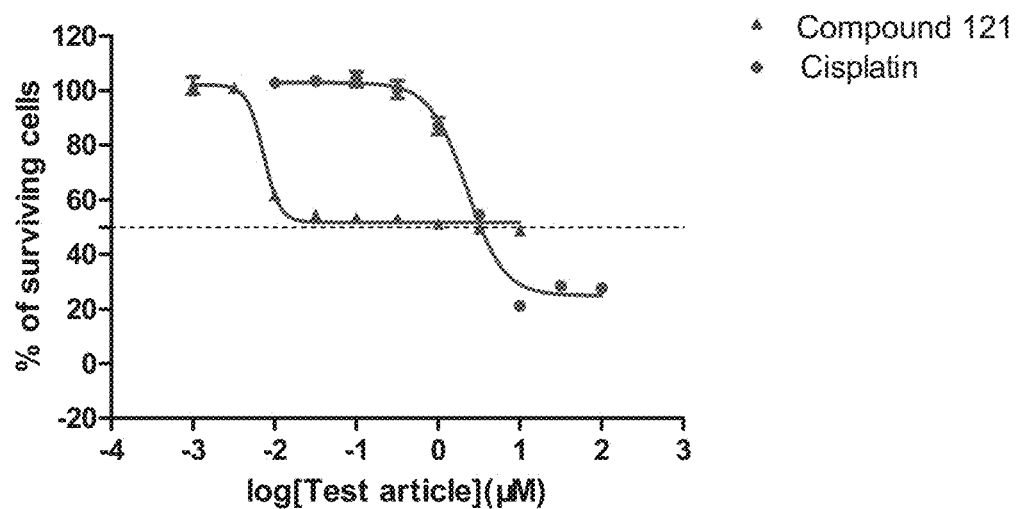
FIG. 11A is a graph indicating the determination of the $IC_{50}$ for Compound 121 and cisplatin in AsPC-1 cells.
Figure 11B:
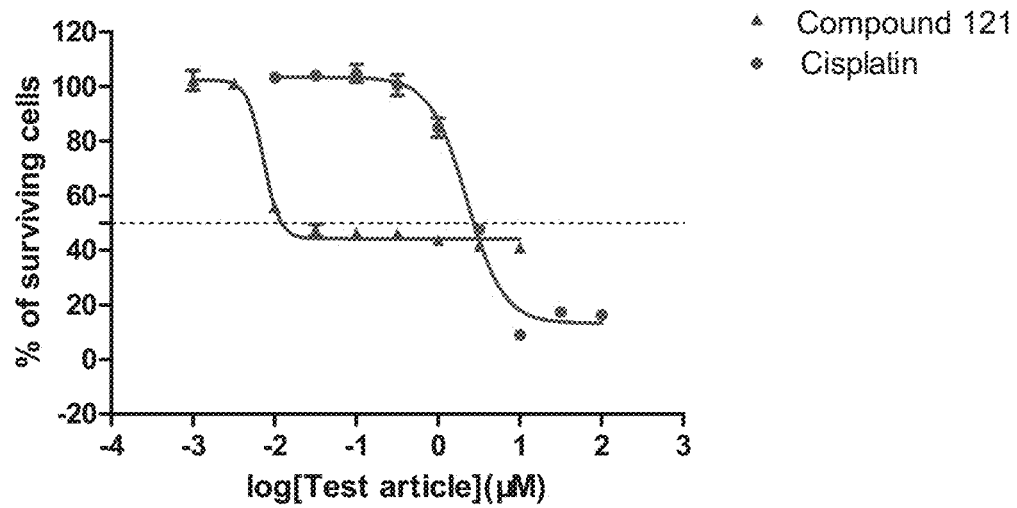
FIG. 11B is a graph indicating the determination of the $GI_{50}$ for Compound 121 and cisplatin in AsPC-1 cells.
Figure 12A:
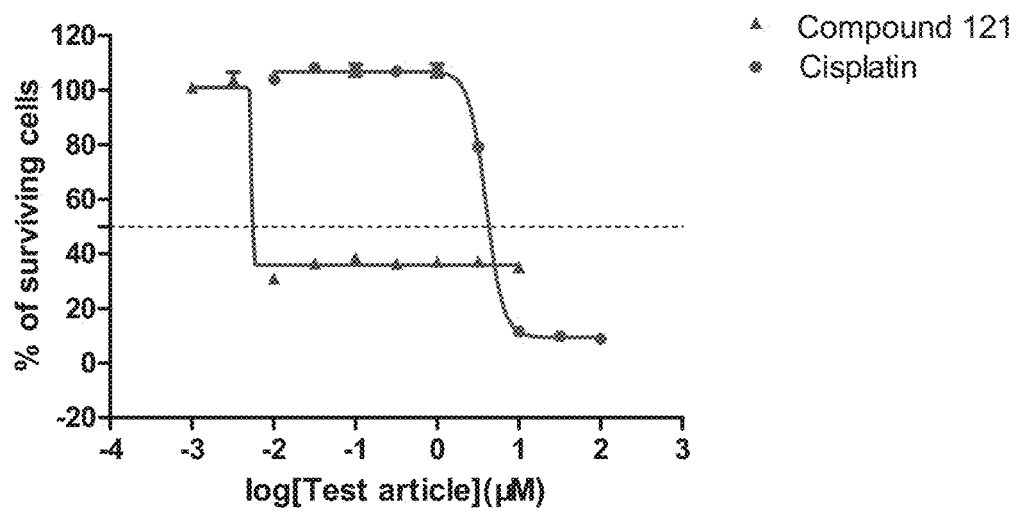
FIG. 12A is a graph indicating the determination of the $IC_{50}$ for Compound 121 and cisplatin in OVCAR-3 cells.
Figure 12B:
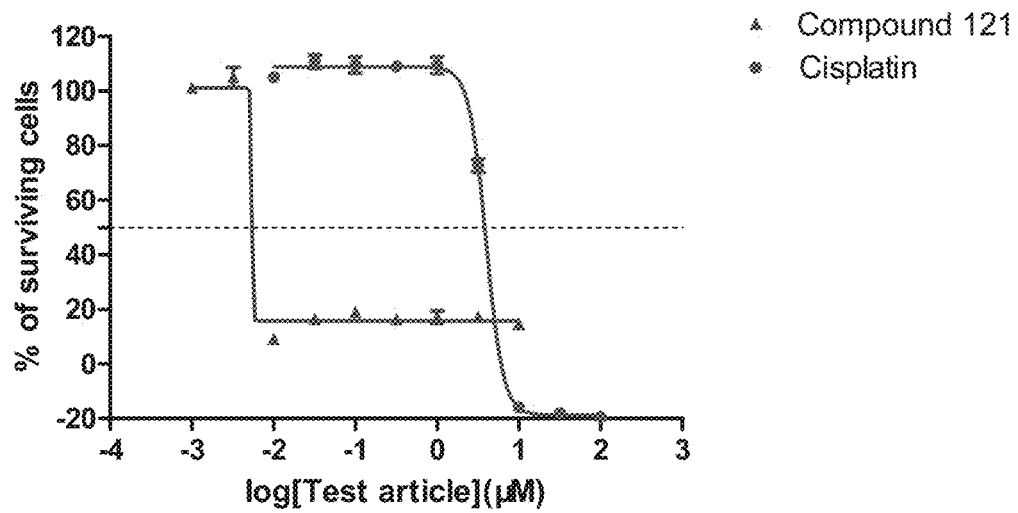
FIG. 12B is a graph indicating the determination of the $GI_{50}$ for Compound 121 and cisplatin in OVCAR-3 cells.
Figure 13A:
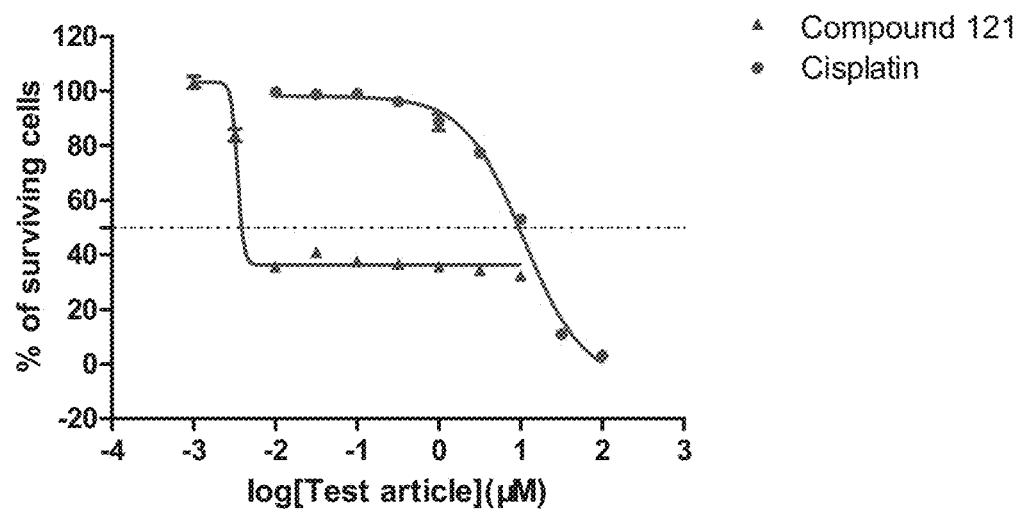
FIG. 13A is a graph indicating the determination of the $IC_{50}$ for Compound 121 and cisplatin in MDA-MB-453 cells.
Figure 13B:
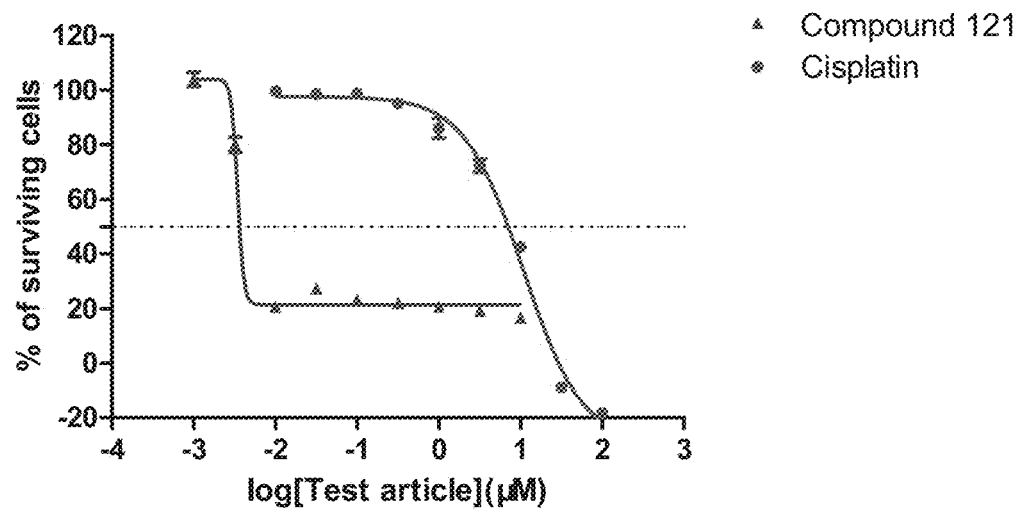
FIG. 13B is a graph indicating the determination of the $GI_{50}$ for Compound 121 and cisplatin in MDA-MB-453 cells.
Figure 14A:
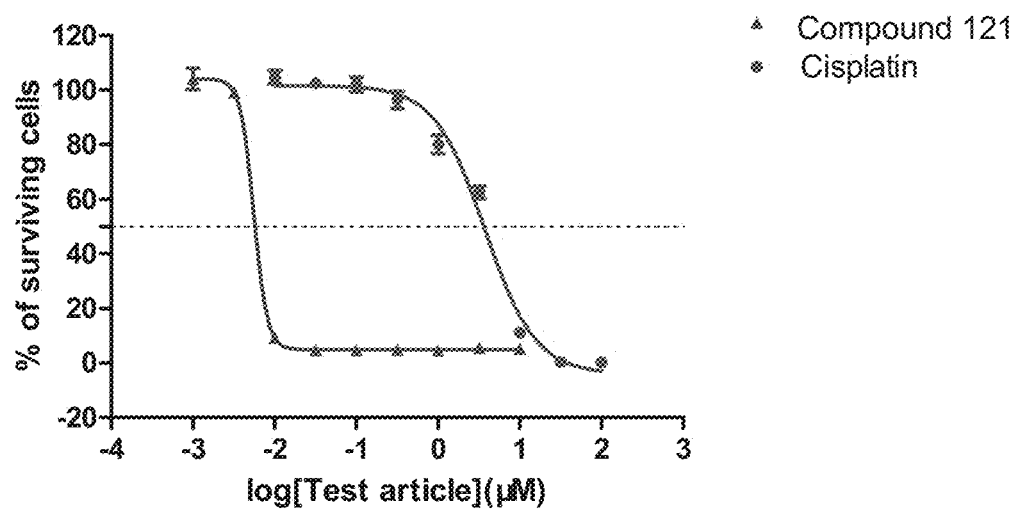
FIG. 14A is a graph indicating the determination of the $IC_{50}$ for Compound 121 and cisplatin in RPMI 8226 cells.
Figure 14B:
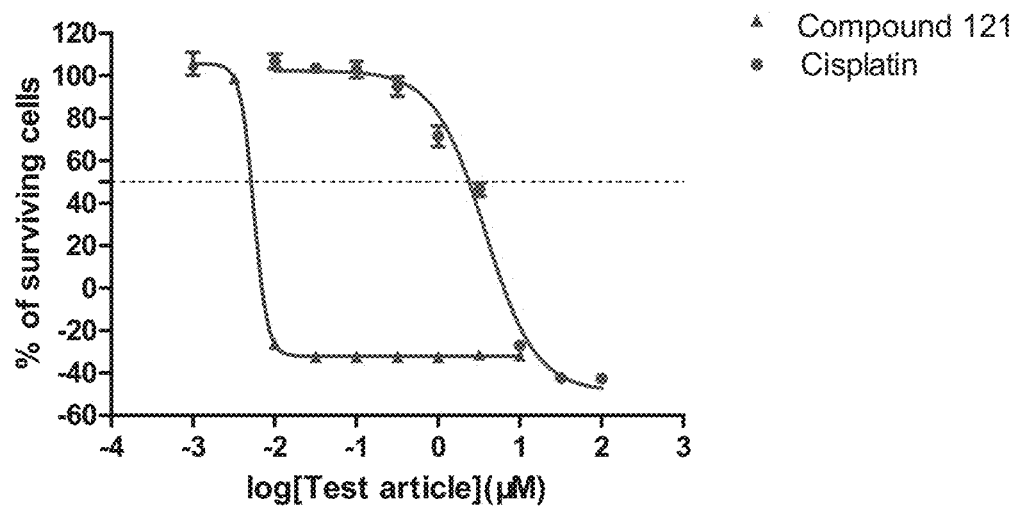
FIG. 14B is a graph indicating the determination of the $GI_{50}$ for Compound 121 and cisplatin in RPMI 8226 cells.
Figure 15A:
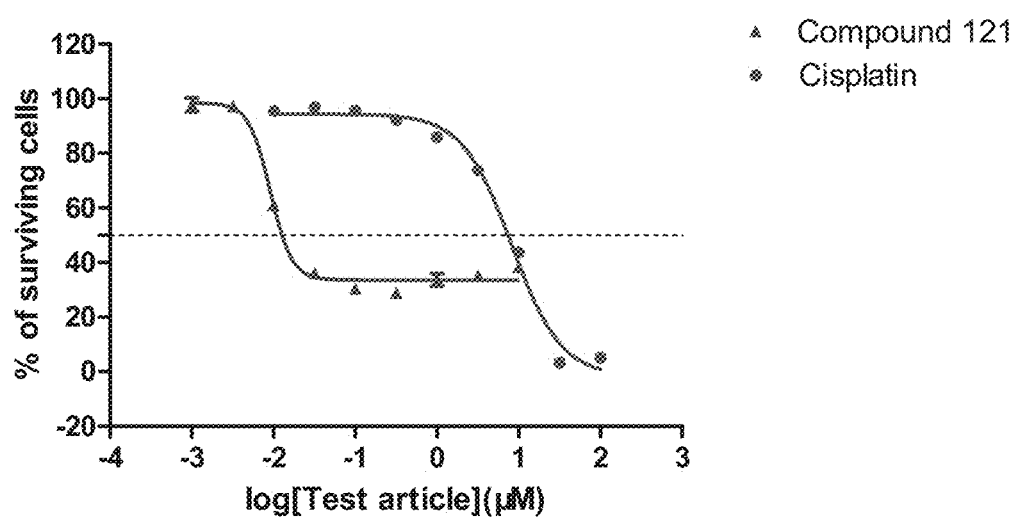
FIG. 15A is a graph indicating the determination of the $IC_{50}$ for Compound 121 and cisplatin in NCI-H226 cells.
Figure 15B:
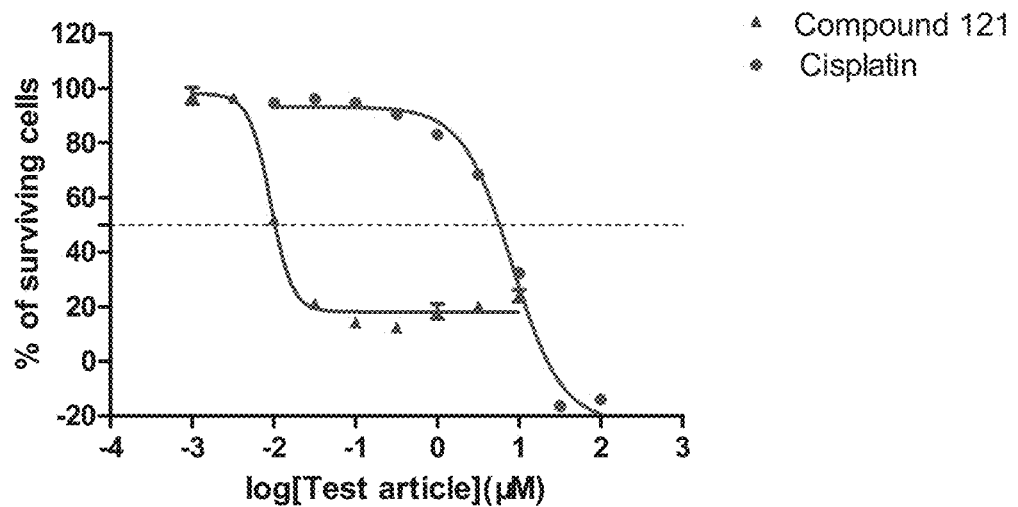
FIG. 15B is a graph indicating the determination of the $GI_{50}$ for Compound 121 and cisplatin in NCI-H226 cells.
Figure 16A:
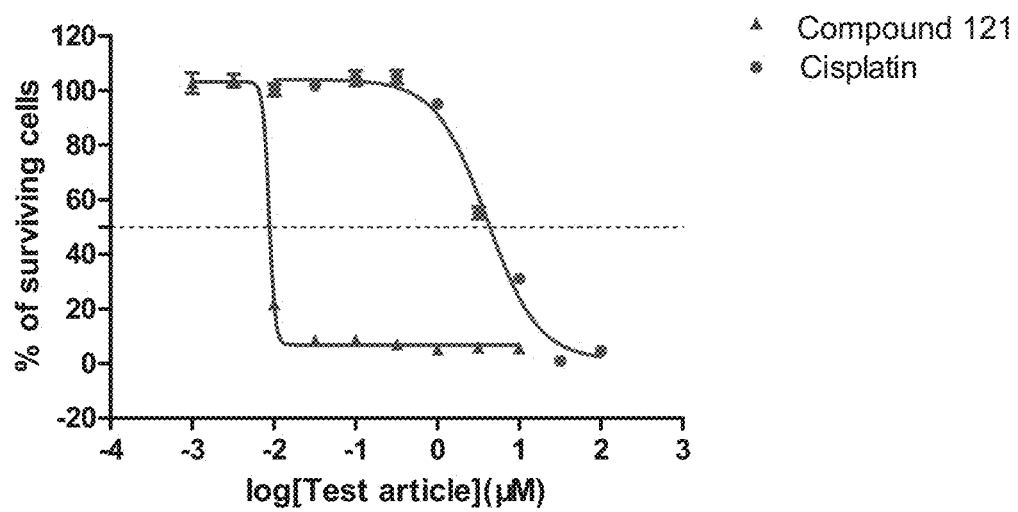
FIG. 16A is a graph indicating the determination of the $IC_{50}$ for Compound 121 and cisplatin in HCT-116 cells.
Figure 16B:
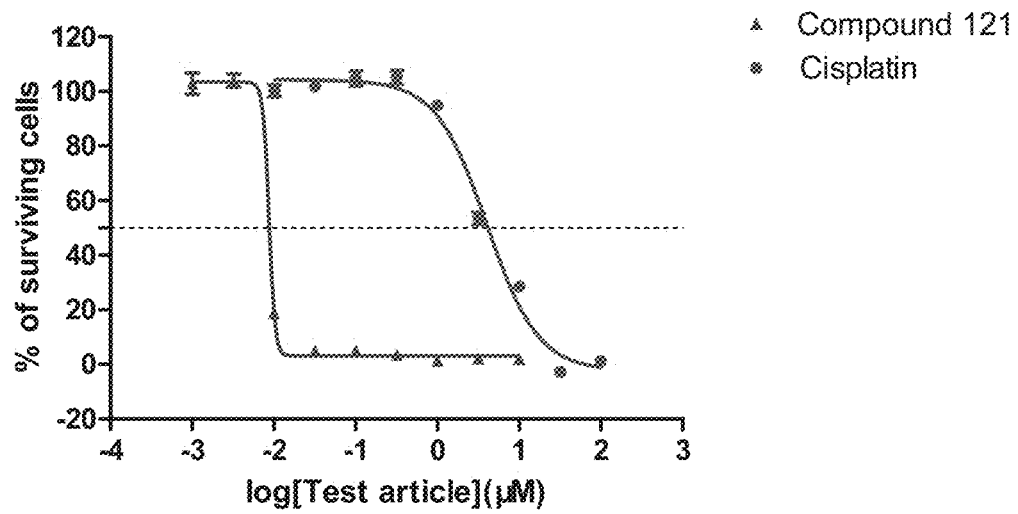
FIG. 16B is a graph indicating the determination of the $GI_{50}$ for Compound 121 and cisplatin in HCT-116 cells.
Figure 17A:
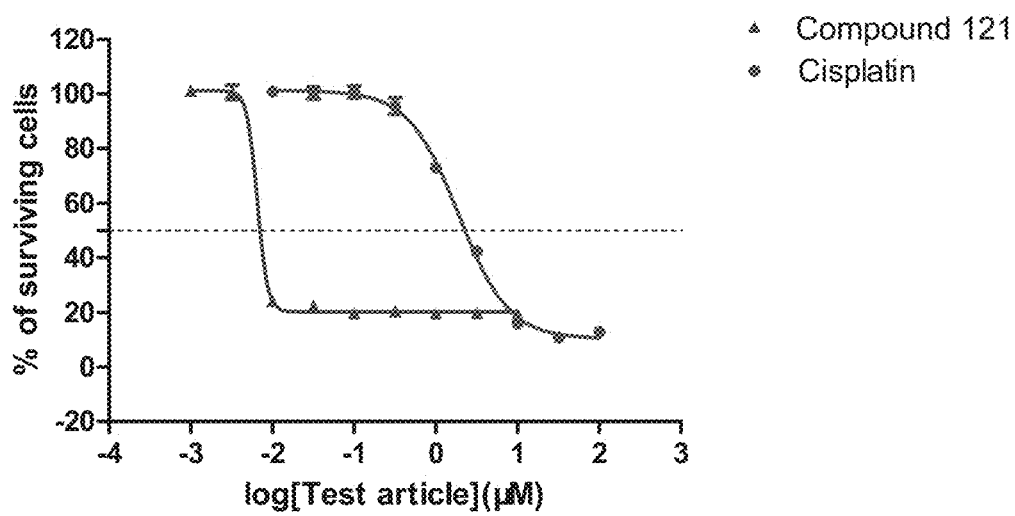
FIG. 17A is a graph indicating the determination of the $IC_{50}$ for Compound 121 and cisplatin in JHH-5 cells.
Figure 17B:
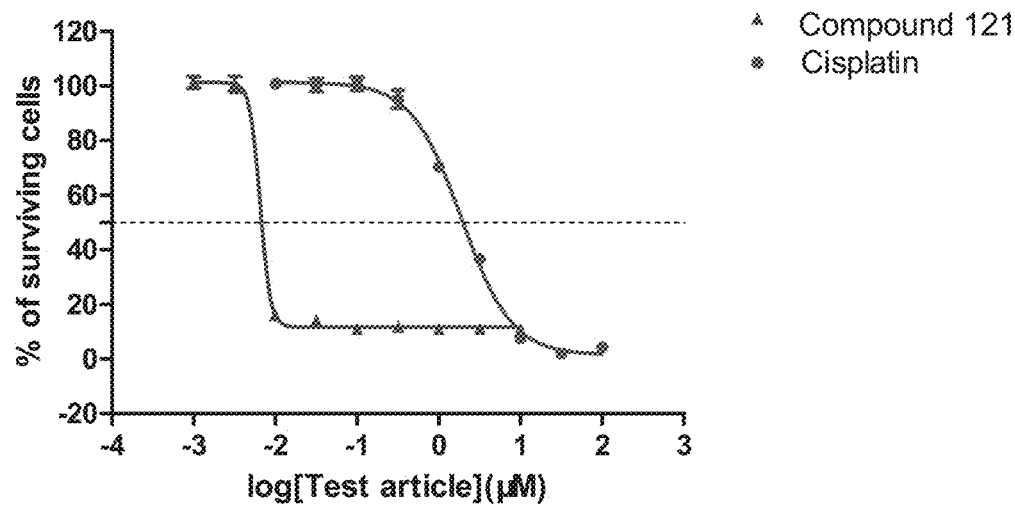
FIG. 17B is a graph indicating the determination of the $GI_{50}$ for Compound 121 and cisplatin in JHH-5 cells.
Figure 18A:
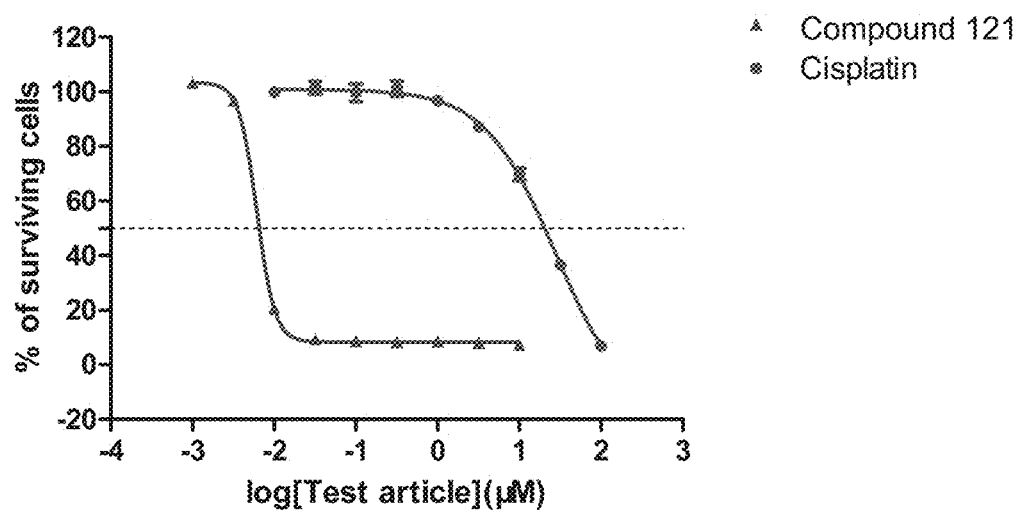
FIG. 18A is a graph indicating the determination of the $IC_{50}$ for Compound 121 and cisplatin in A-172 cells.
Figure 18B:
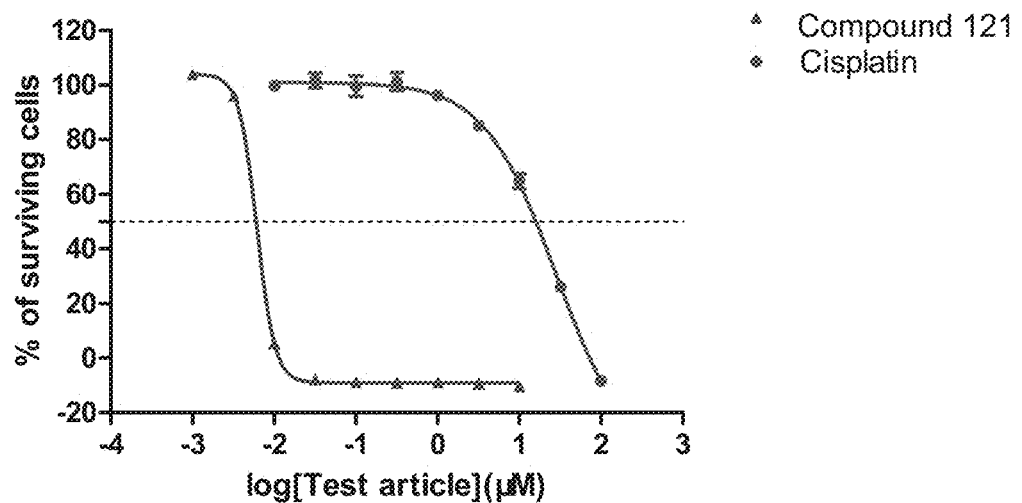
FIG. 18B is a graph indicating the determination of the $GI_{50}$ for Compound 121 and cisplatin in A-172 cells.
Figure 19A:
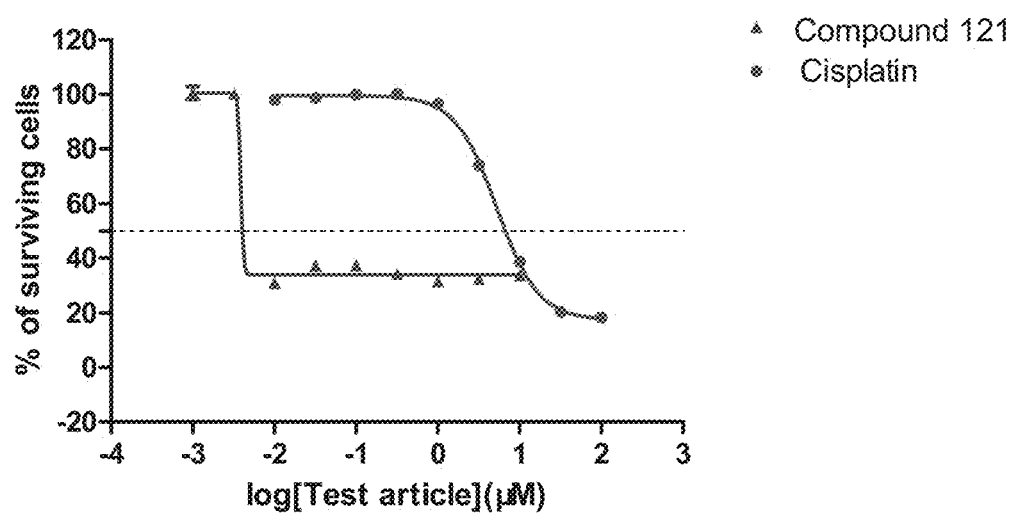
FIG. 19A is a graph indicating the determination of the $IC_{50}$ for Compound 121 and cisplatin in SK-OV-3 cells.
Figure 19B:
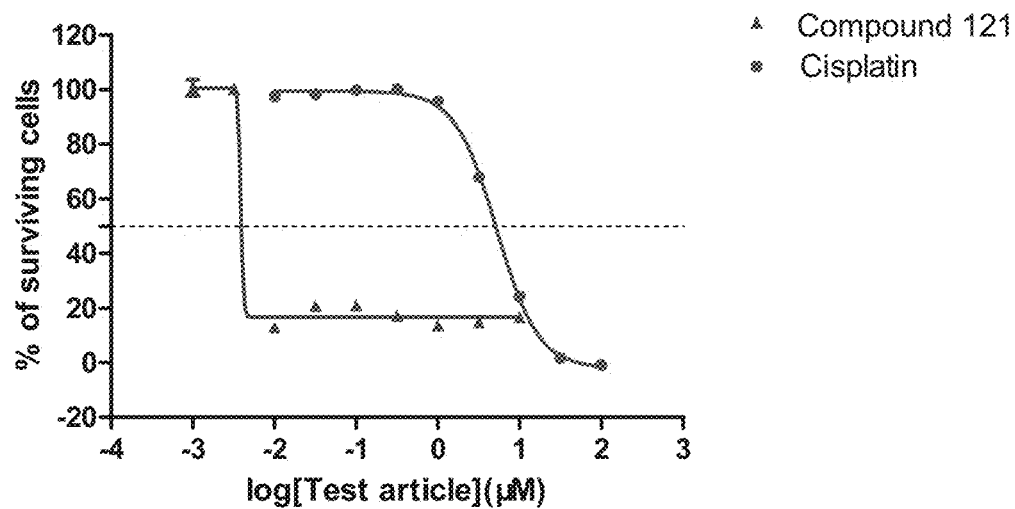
FIG. 19B is a graph indicating the determination of the $GI_{50}$ for Compound 121 and cisplatin in SK-OV-3 cells.
Figure 20A:
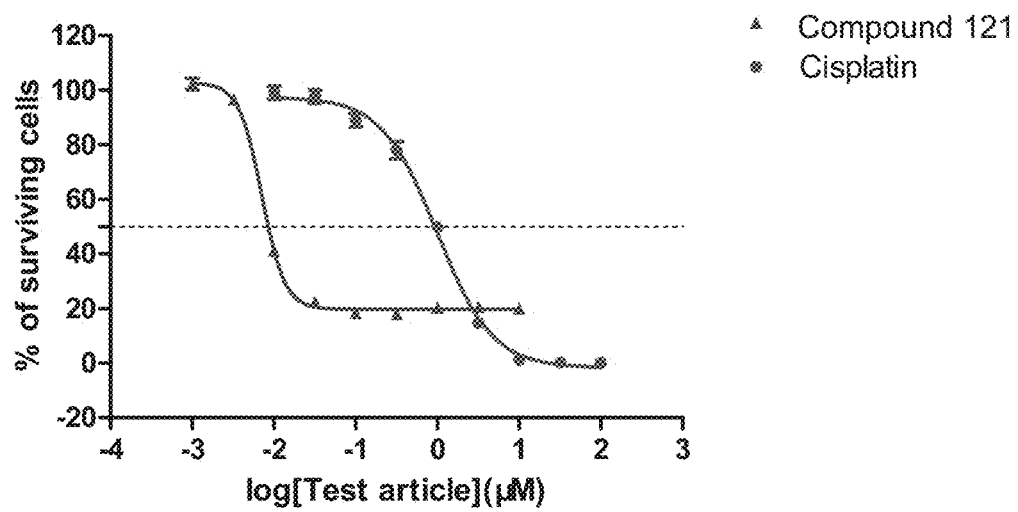
FIG. 20A is a graph indicating the determination of the $IC_{50}$ for Compound 121 and cisplatin in MDA-MB-468 cells.
Figure 20B:
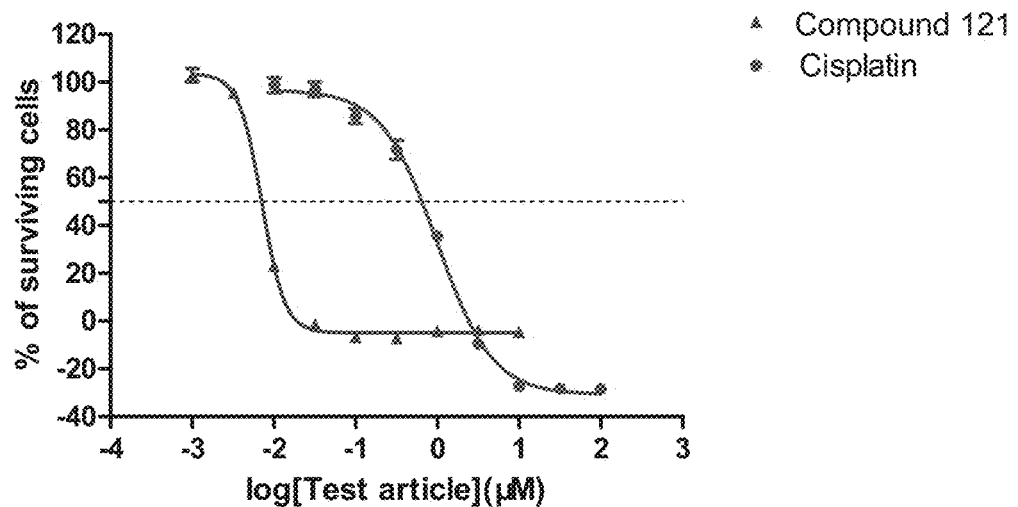
FIG. 20B is a graph indicating the determination of the $GI_{50}$ for Compound 121 and cisplatin in MDA-MB-468 cells.
Figure 21A:
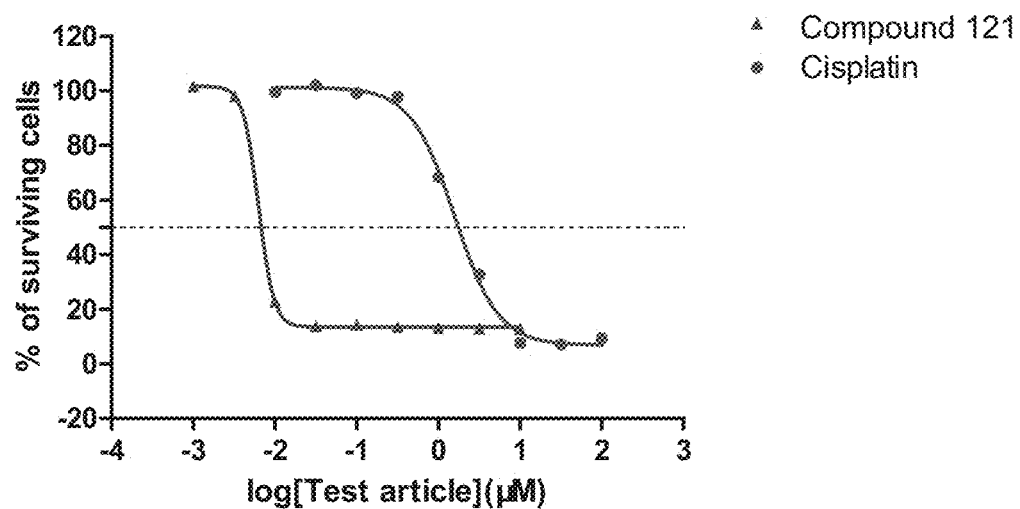
FIG. 21A is a graph indicating the determination of the $IC_{50}$ for Compound 121 and cisplatin in NCI-H1155 cells.
Figure 21B:
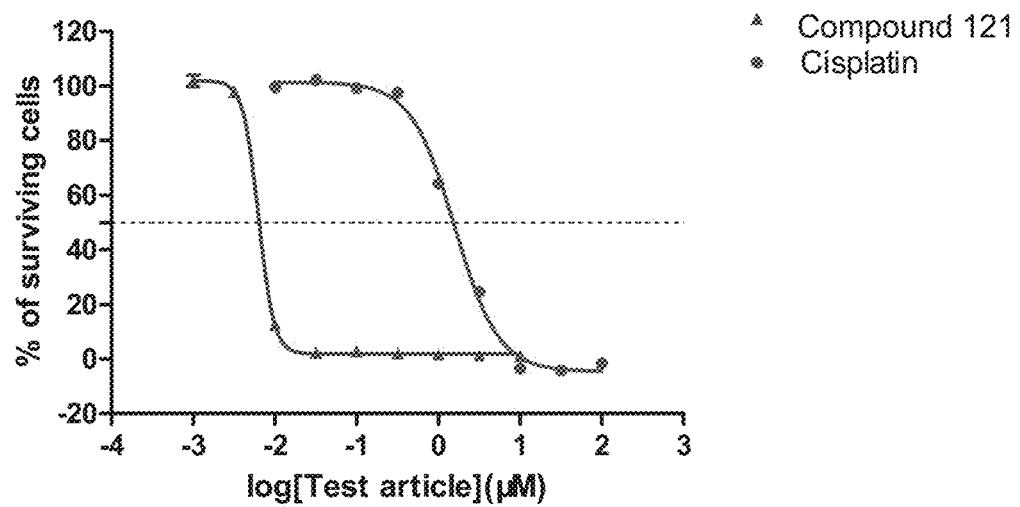
FIG. 21B is a graph indicating the determination of the $GI_{50}$ for Compound 121 and cisplatin in NCI-H1155 cells.
Figure 22A:
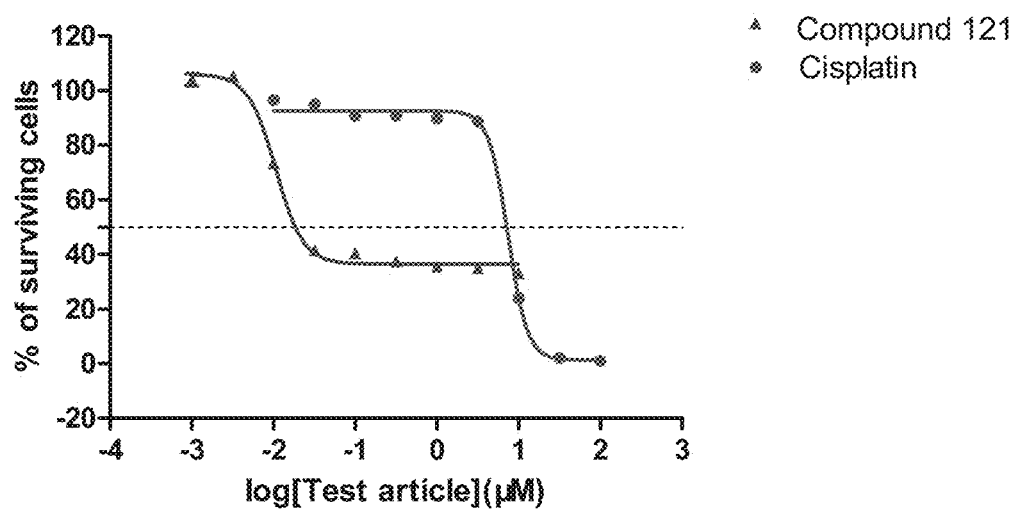
FIG. 22A is a graph indicating the determination of the $IC_{50}$ for Compound 121 and cisplatin in MX-1 cells.
Figure 22B:
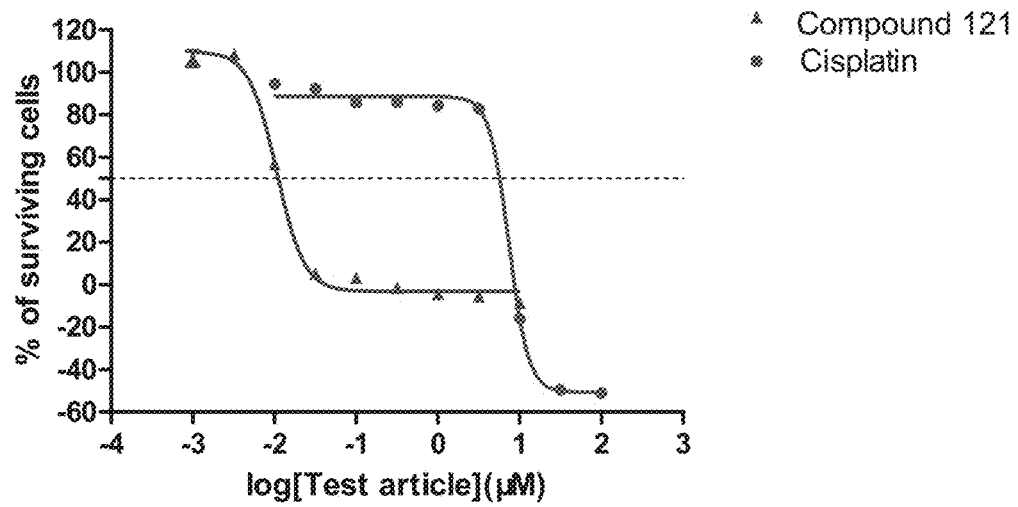
FIG. 22B is a graph indicating the determination of the $GI_{50}$ for Compound 121 and cisplatin in MX-1 cells.
Figure 23A:
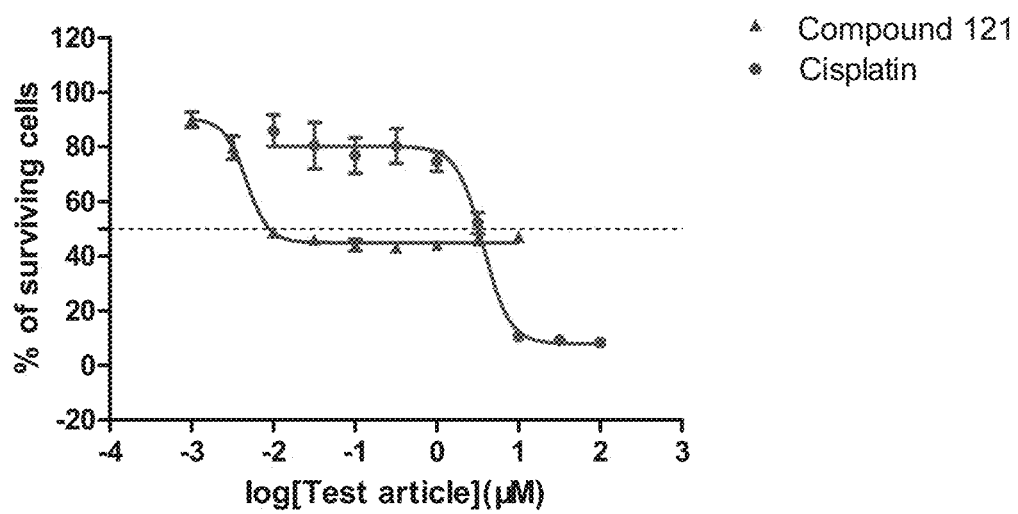
FIG. 23A is a graph indicating the determination of the $IC_{50}$ for Compound 121 and cisplatin in HT-1376 cells.
Figure 23B:
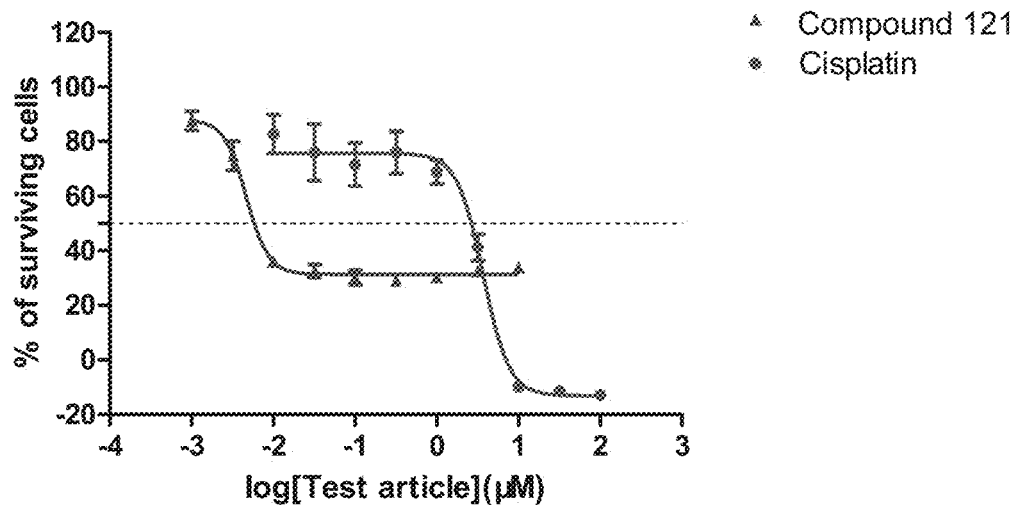
FIG. 23B is a graph indicating the determination of the $GI_{50}$ for Compound 121 and cisplatin in HT-1376 cells.
Figure 24A:
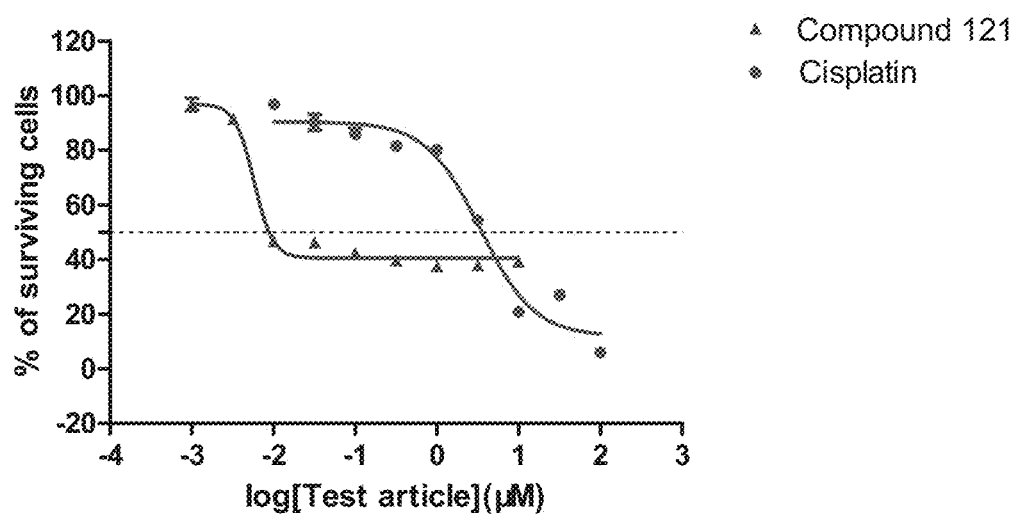
FIG. 24A is a graph indicating the determination of the $IC_{50}$ for Compound 121 and cisplatin in HUH-7 cells. FIG.
Figure 24B:
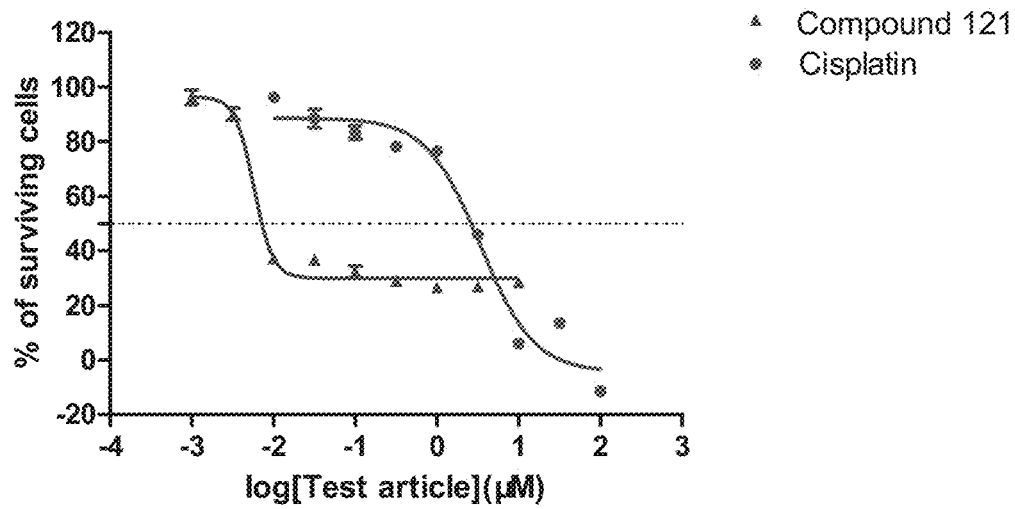
Figure 25A:
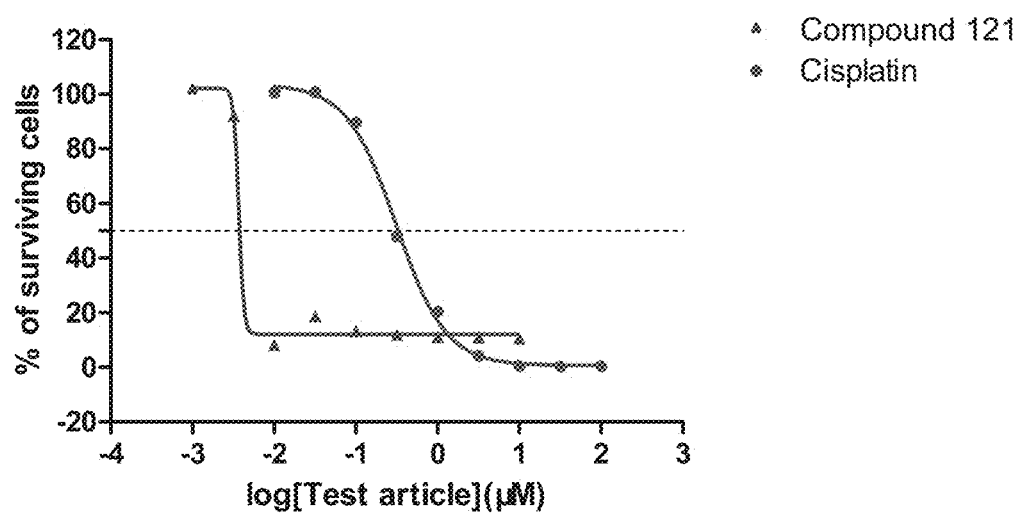
Figure 25B:
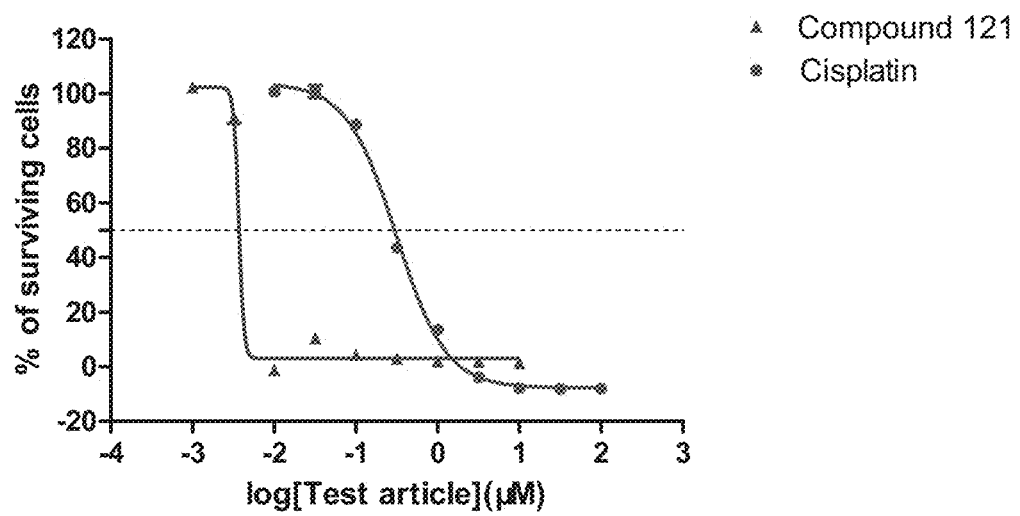

FIG. 25A is a graph indicating the determination of the $IC_{50}$ for Compound 121 and cisplatin in HeLa cells. FIG. 25B is a graph indicating the determination of the $GI_{50}$ for Compound 121 and cisplatin in HeLa cells.

Figure 26A:
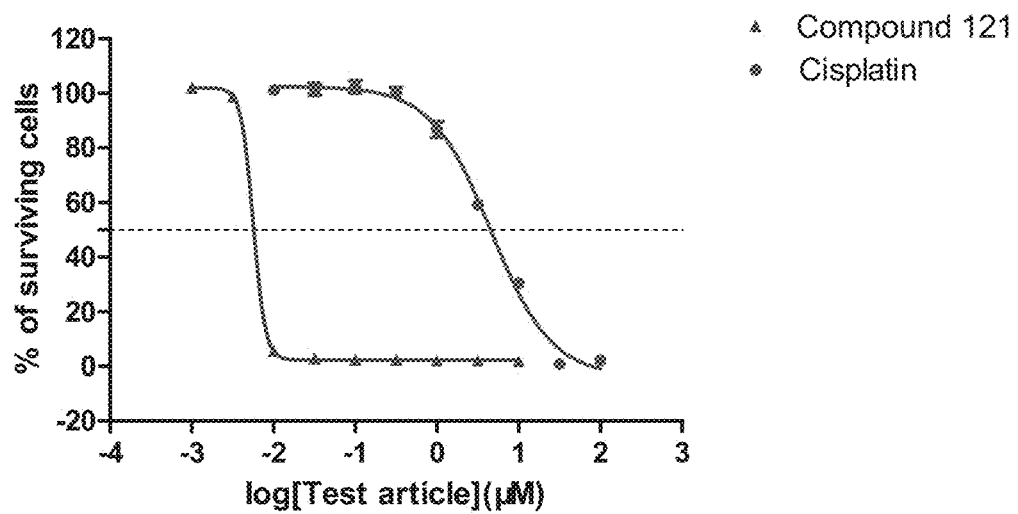
Figure 26B:
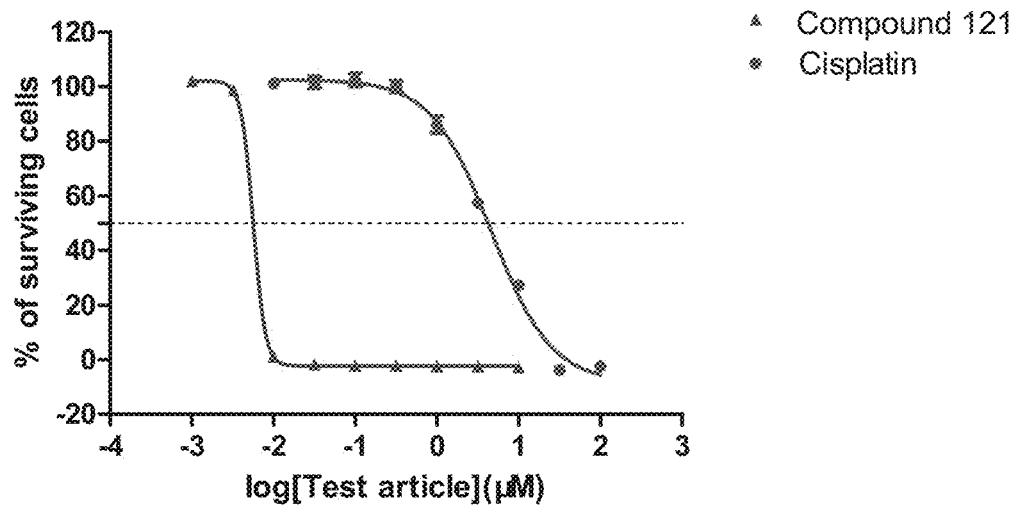

FIG. 26A is a graph indicating the determination of the $IC_{50}$ for Compound 121 and cisplatin in K-562 cells. FIG. 26B is a graph indicating the determination of the $GI_{50}$ for Compound 121 and cisplatin in K-562 cells.

Figure 27A:
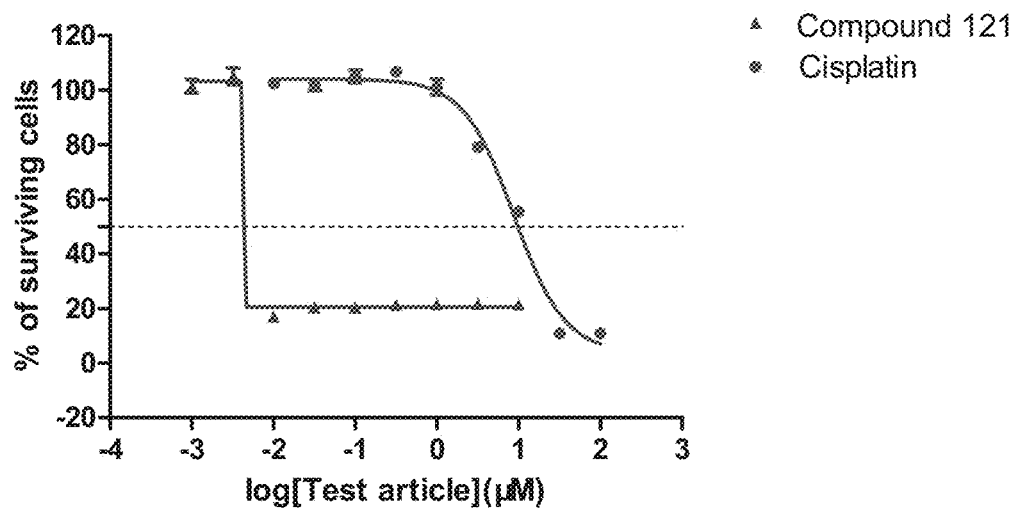
Figure 27B:
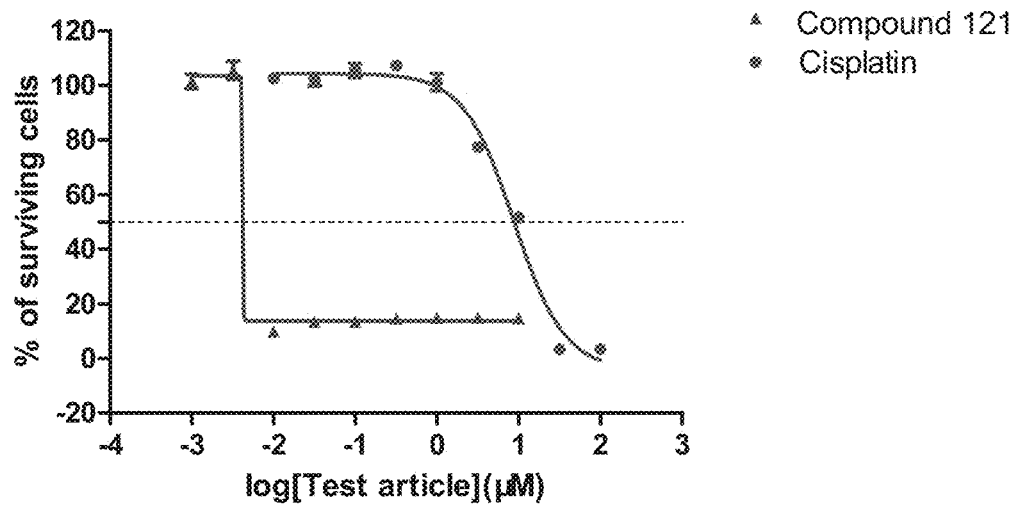

FIG. 27A is a graph indicating the determination of the $IC_{50}$ for Compound 121 and cisplatin in HT-29 cells. FIG. 27B is a graph indicating the determination of the $GI_{50}$ for Compound 121 and cisplatin in HT-29 cells.

Figure 28A:
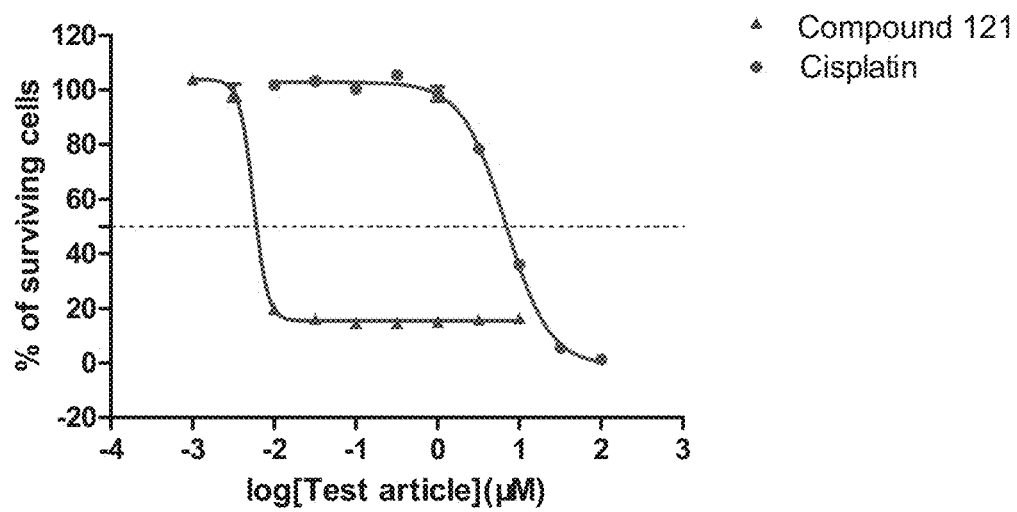
Figure 28B:
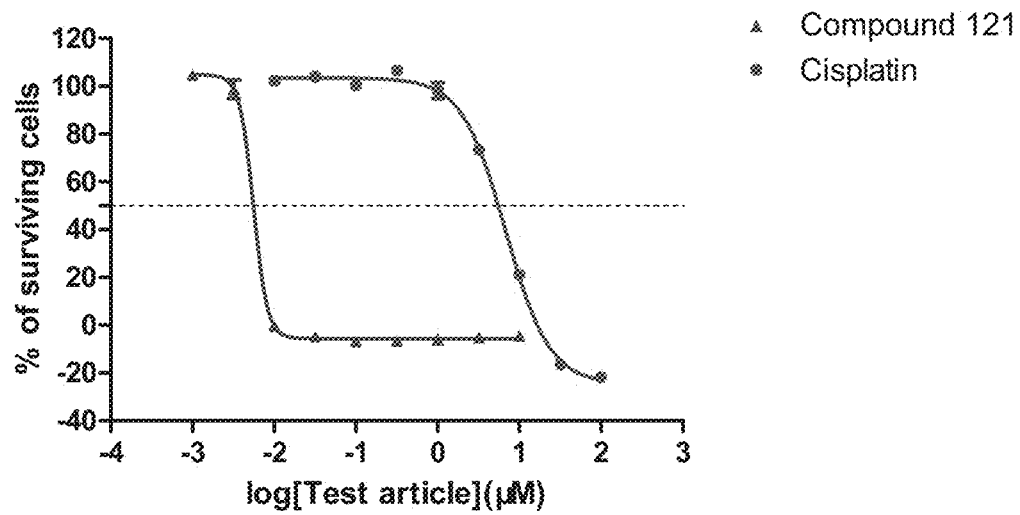

FIG. 28A is a graph indicating the determination of the $IC_{50}$ for Compound 121 and cisplatin in NCI-H1975 cells. FIG. 28B is a graph indicating the determination of the $GI_{50}$ for Compound 121 and cisplatin in NCI-H1975 cells.

Figure 29A:
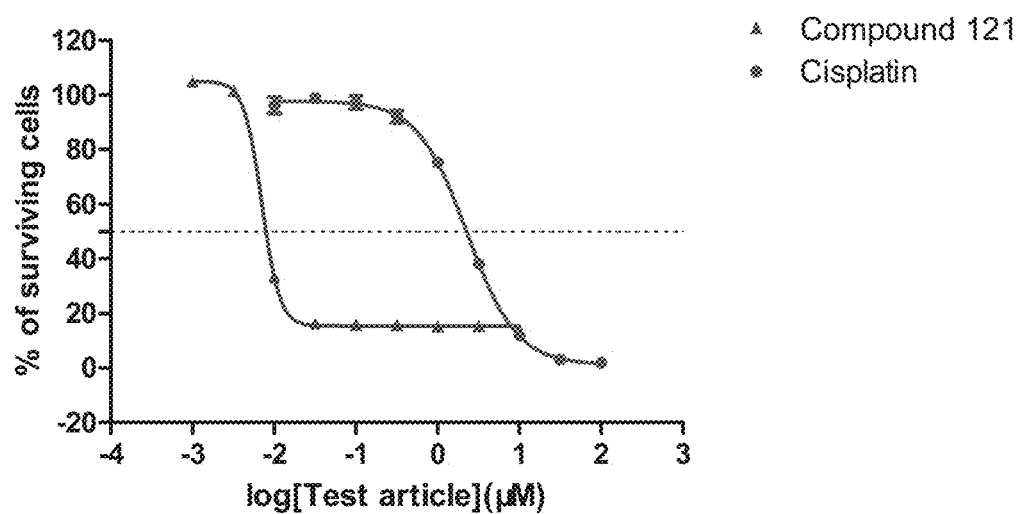
Figure 29B:
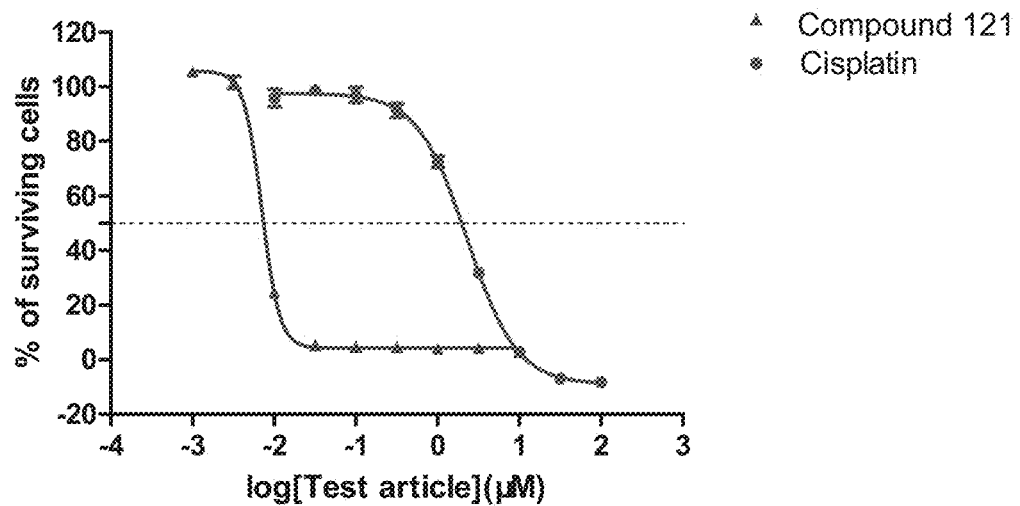

FIG. 29A is a graph indicating the determination of the $IC_{50}$ for Compound 121 and cisplatin in FaDu cells. FIG. 29B is a graph indicating the determination of the $GI_{50}$ for Compound 121 and cisplatin in FaDu cells.

Figure 30A:
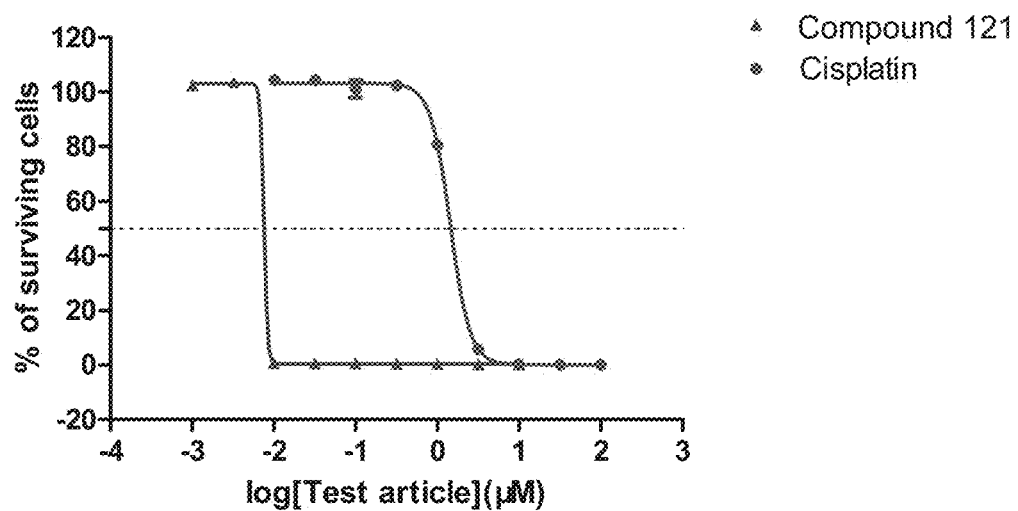
Figure 30B:
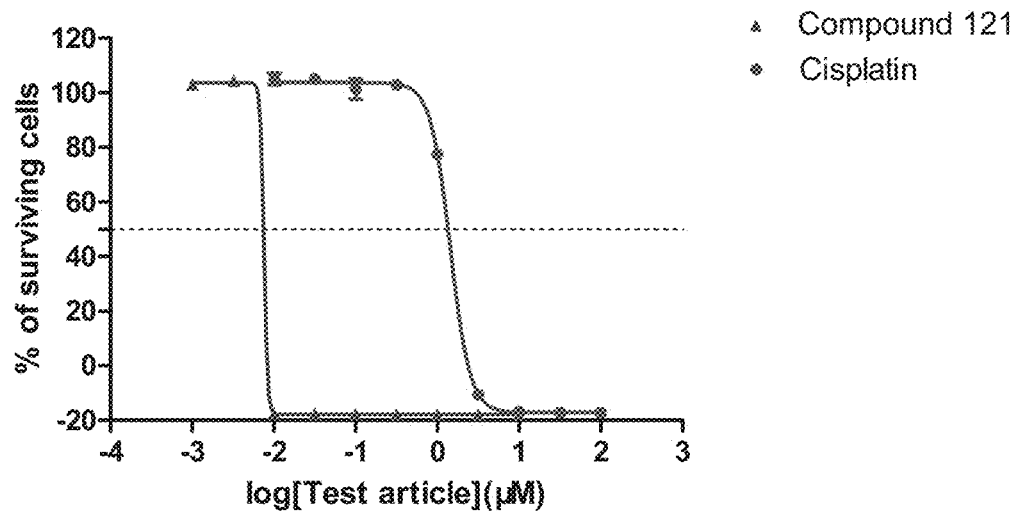

FIG. 30A is a graph indicating the determination of the $IC_{50}$ for Compound 121 and cisplatin in HL-60 cells. FIG. 30B is a graph indicating the determination of the $GI_{50}$ for Compound 121 and cisplatin in HL-60 cells.

Figure 31A:
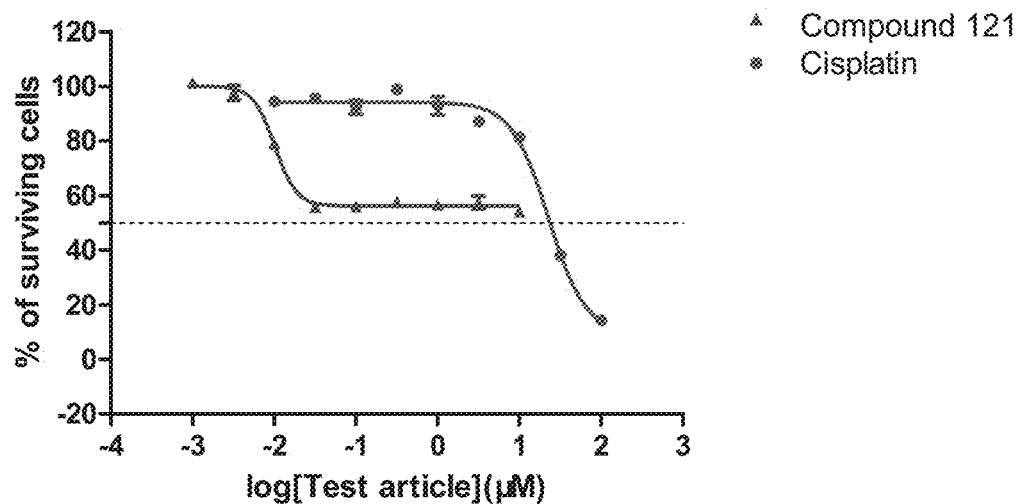
Figure 31B:
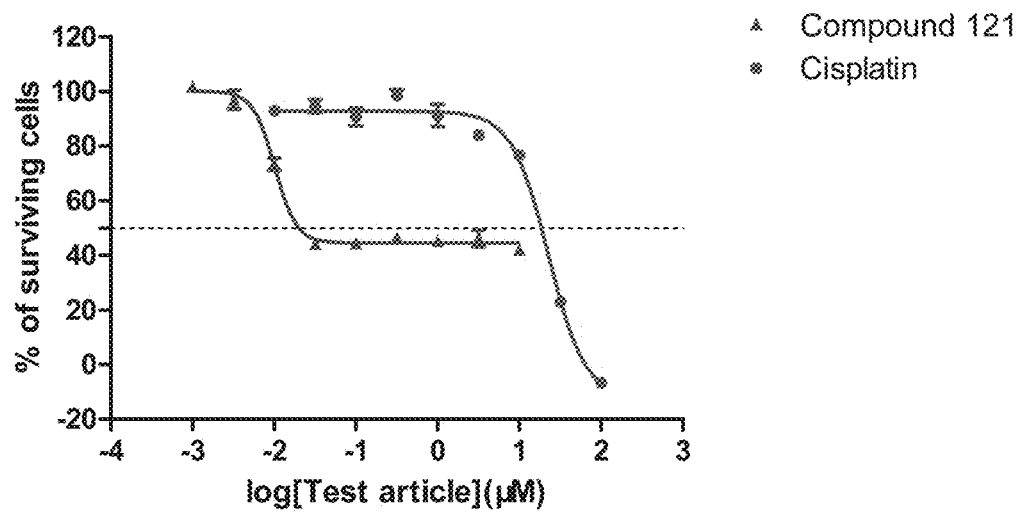

FIG. 31A is a graph indicating the determination of the $IC_{50}$ for Compound 121 and cisplatin in MDA-MB-231 cells. FIG. 31B is a graph indicating the determination of the $GI_{50}$ for Compound 121 and cisplatin in MDA-MB-231 cells.

Figure 32A:
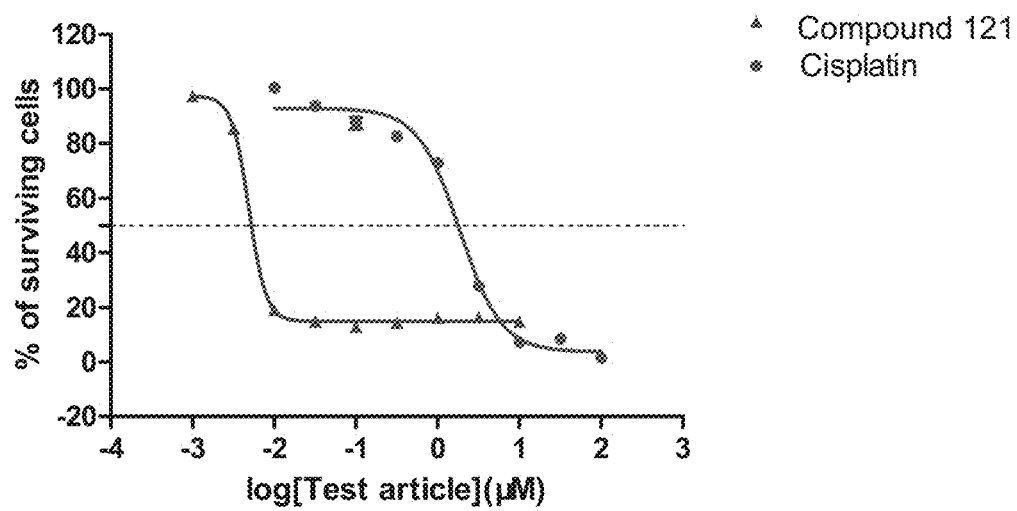
Figure 32B:
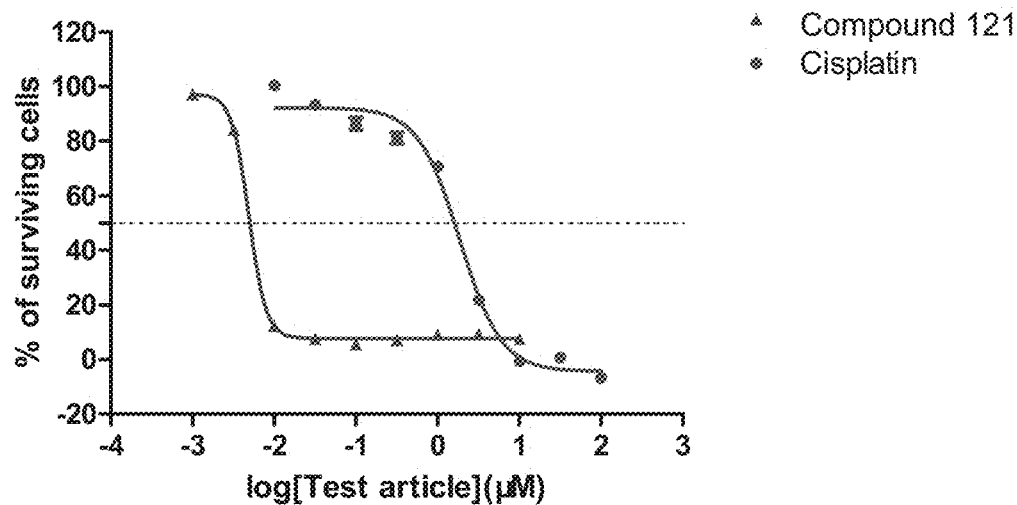

FIG. 32A is a graph indicating the determination of the $IC_{50}$ for Compound 121 and cisplatin in 786-0 cells. FIG. 32B is a graph indicating the determination of the $GI_{50}$ for Compound 121 and cisplatin in 786-0 cells.

Figure 33A:
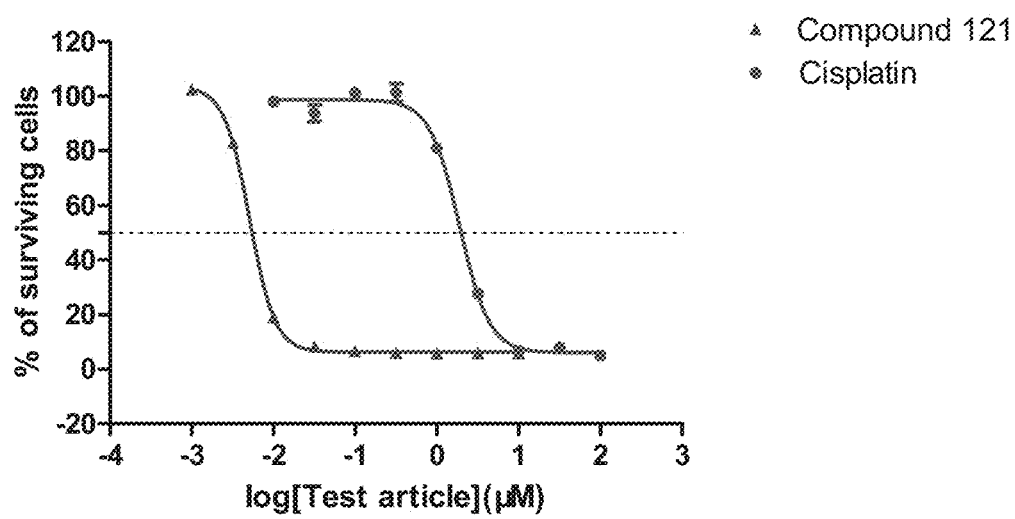
Figure 33B:
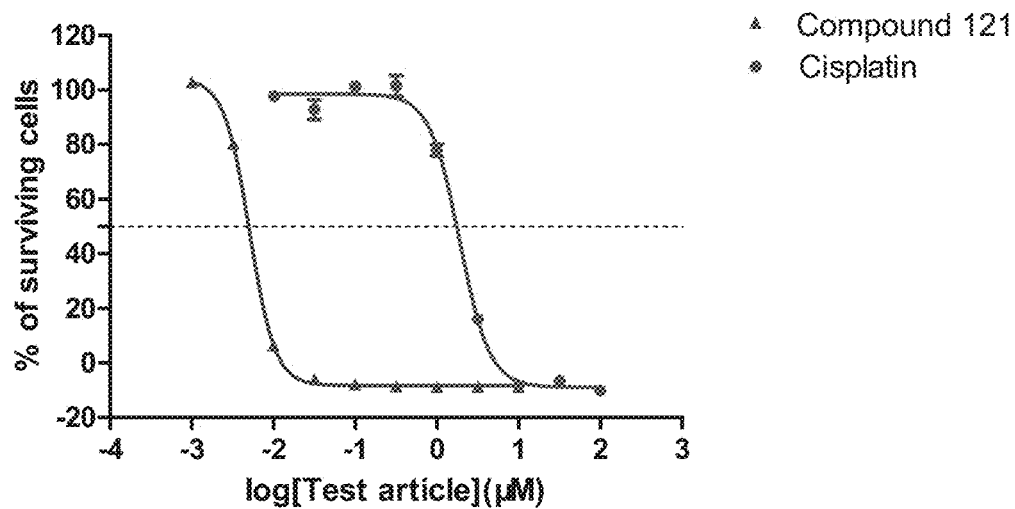

FIG. 33A is a graph indicating the determination of the $IC_{50}$ for Compound 121 and cisplatin in Raji cells. FIG. 33B is a graph indicating the determination of the $GI_{50}$ for Compound 121 and cisplatin in Raji cells.

Figure 34A:
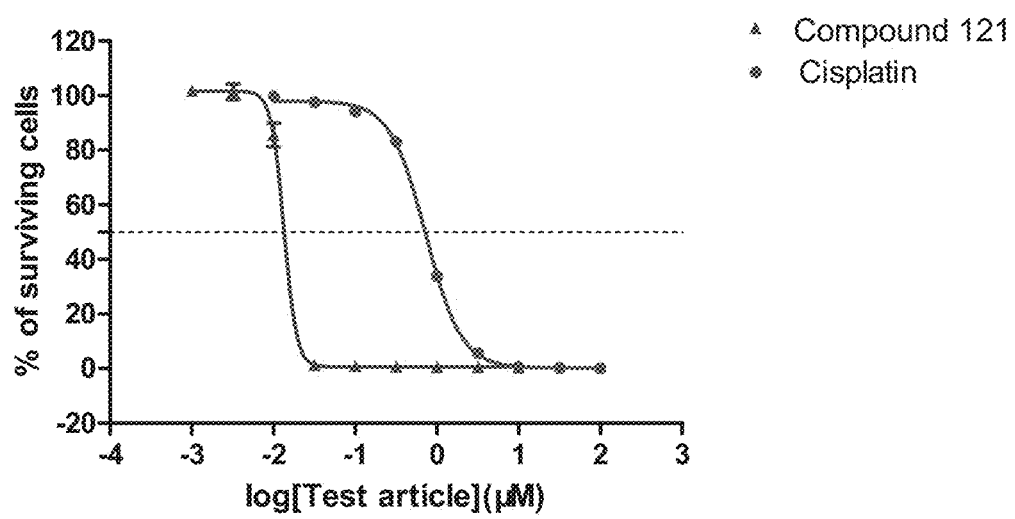
Figure 34B:
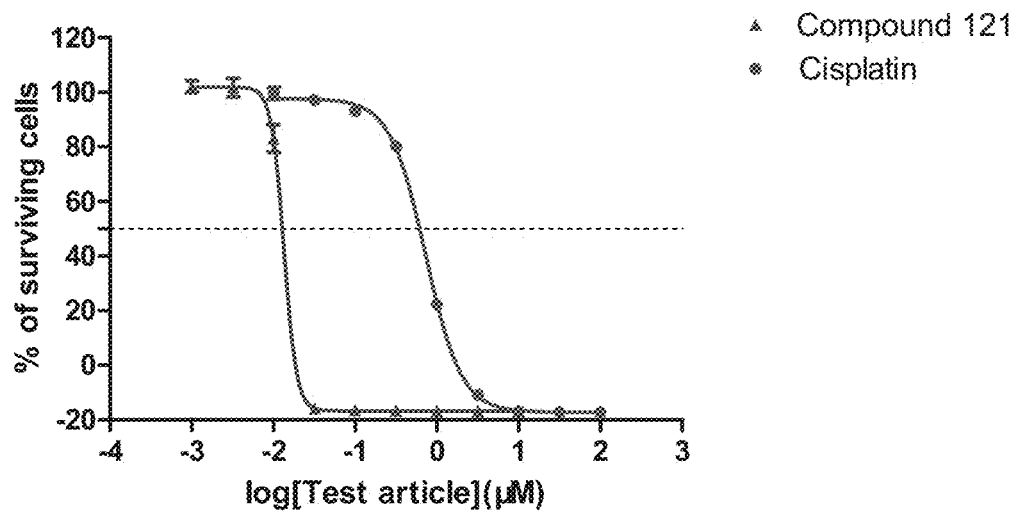

FIG. 34A is a graph indicating the determination of the $IC_{50}$ for Compound 121 and cisplatin in Molt-4 cells. FIG. 34B is a graph indicating the determination of the $GI_{50}$ for Compound 121 and cisplatin in Molt-4 cells.

Figure 35A:
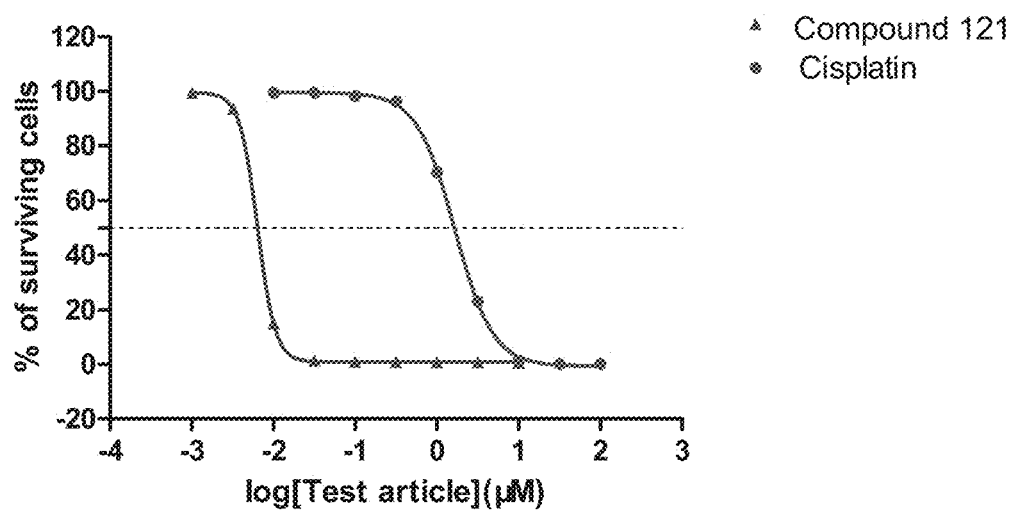
Figure 35B:
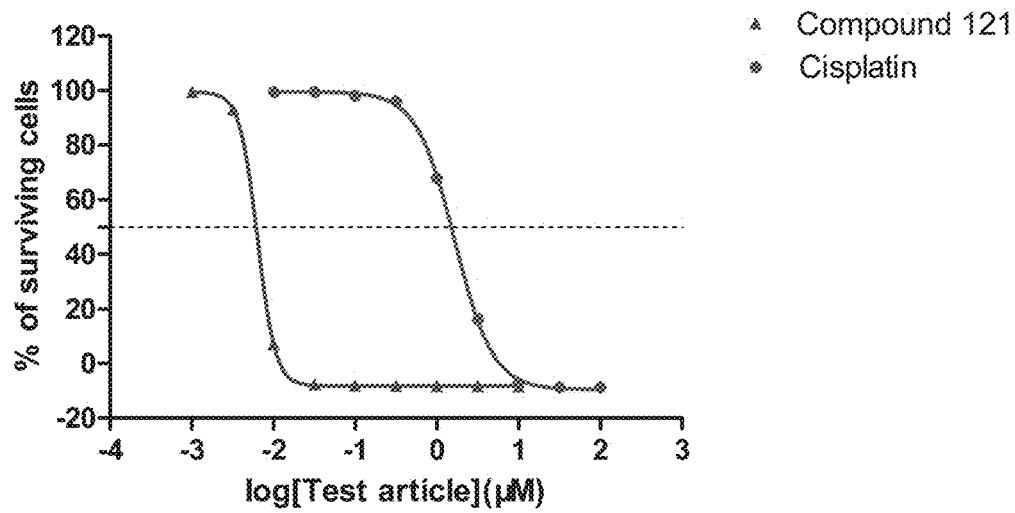

FIG. 35A is a graph indicating the determination of the $IC_{50}$ for Compound 121 and cisplatin in KARPAS-299 cells. FIG. 35B is a graph indicating the determination of the $GI_{50}$ for Compound 121 and cisplatin in KARPAS-299 cells.

Figure 36A:
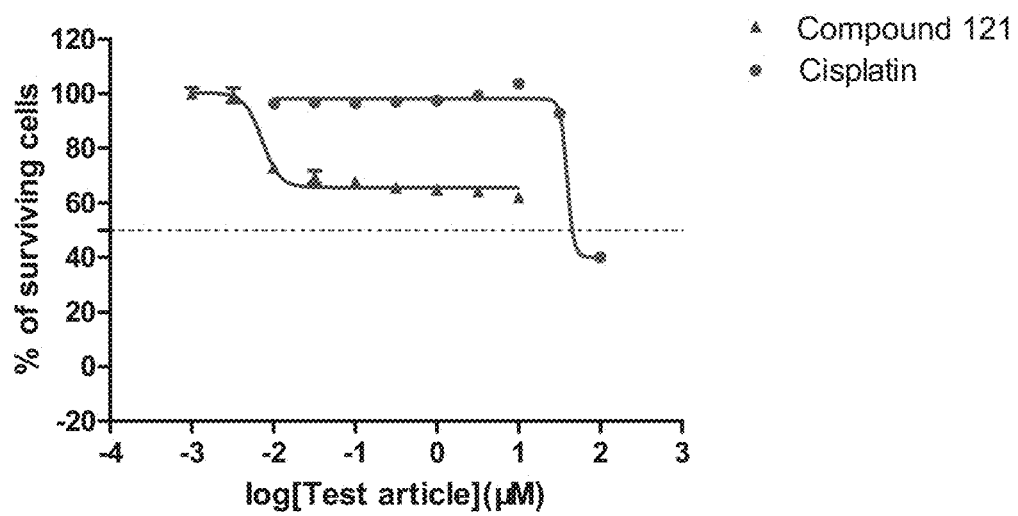
Figure 36B:
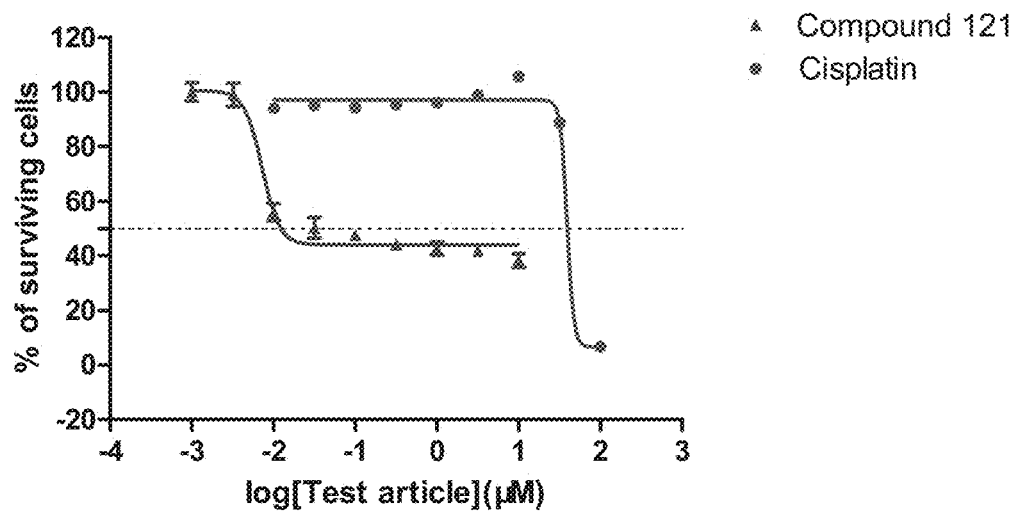

FIG. 36A is a graph indicating the determination of the $IC_{50}$ for Compound 121 and cisplatin in BT474 cells. FIG. 36B is a graph indicating the determination of the $GI_{50}$ for Compound 121 and cisplatin in BT474 cells.

Figure 37A:
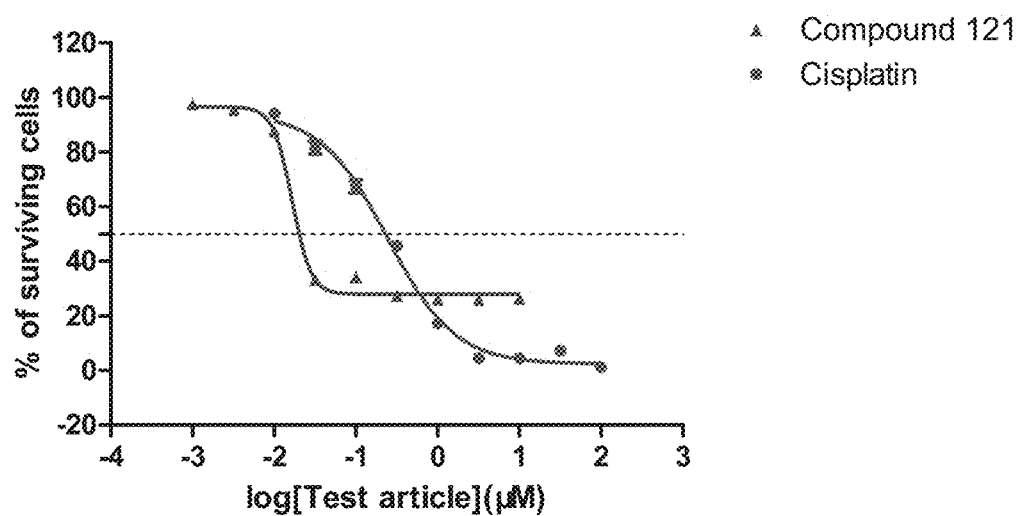
Figure 37B:
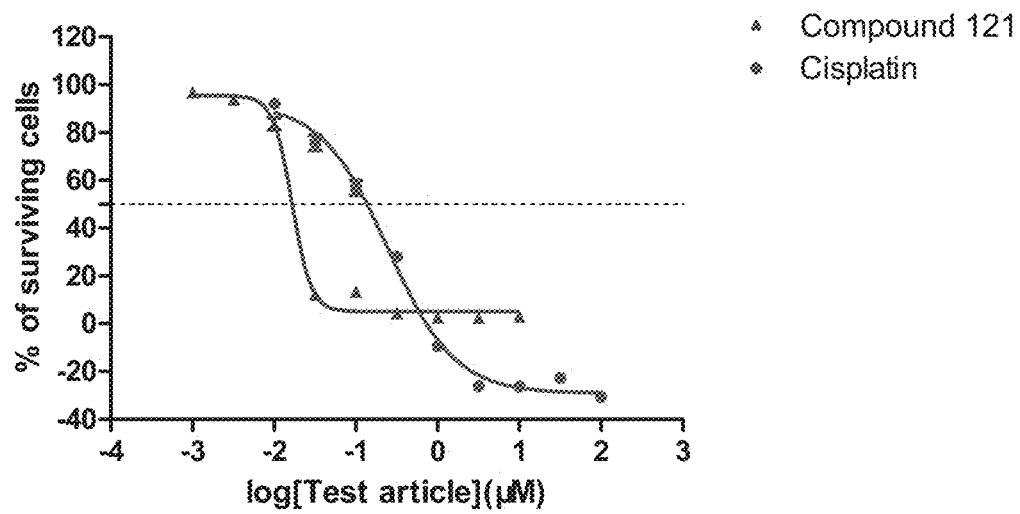

FIG. 37A is a graph indicating the determination of the $IC_{50}$ for Compound 121 and cisplatin in NCI-H209 cells. FIG. 37B is a graph indicating the determination of the $GI_{50}$ for Compound 121 and cisplatin in NCI-H209 cells.

Figure 38A:
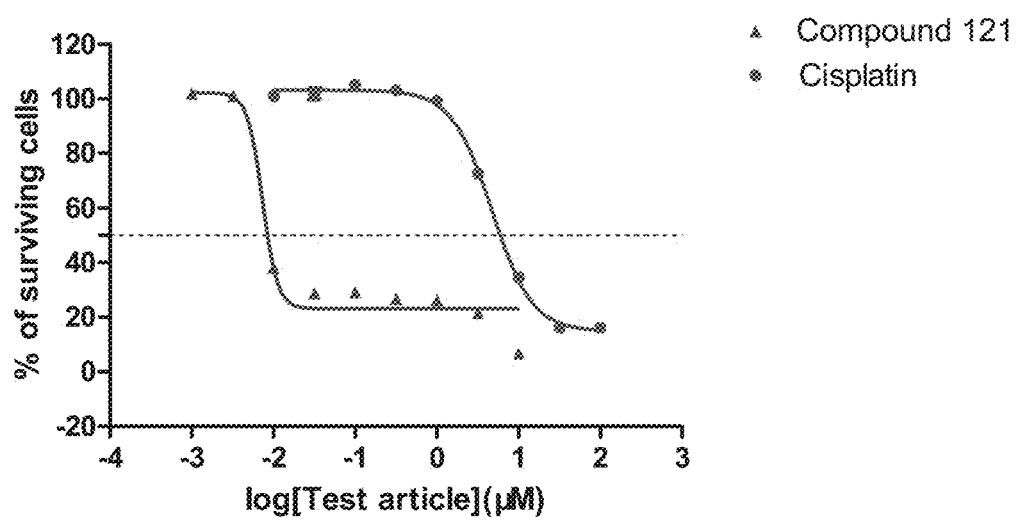
Figure 38B:
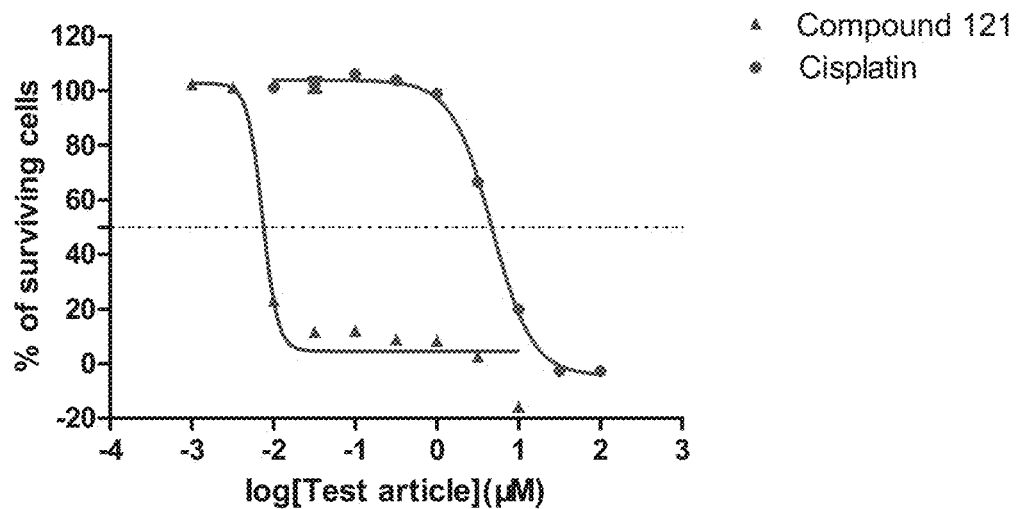

FIG. 38A is a graph indicating the determination of the $IC_{50}$ for Compound 121 and cisplatin in PC-3 cells. FIG. 38B is a graph indicating the determination of the $GI_{50}$ for Compound 121 and cisplatin in PC-3 cells.

Figure 39A:
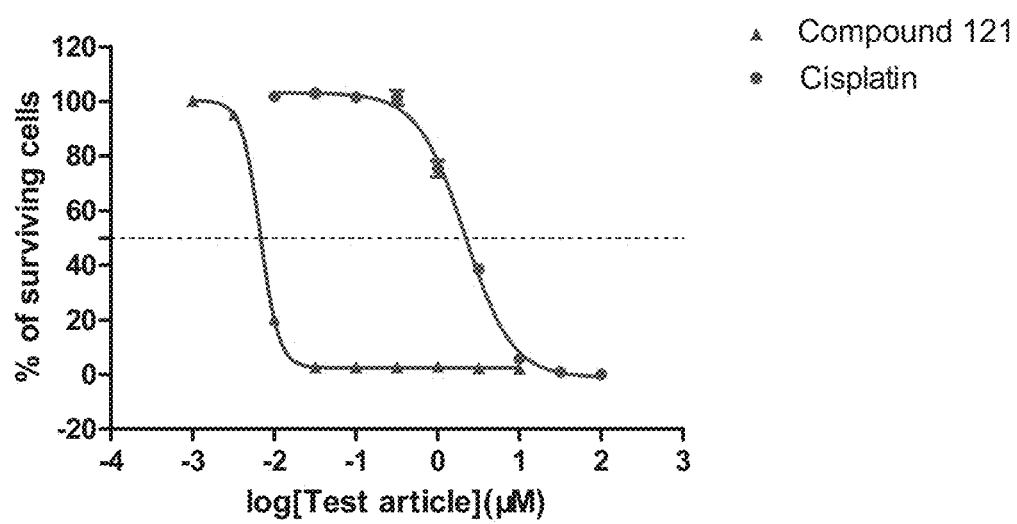
Figure 39B:
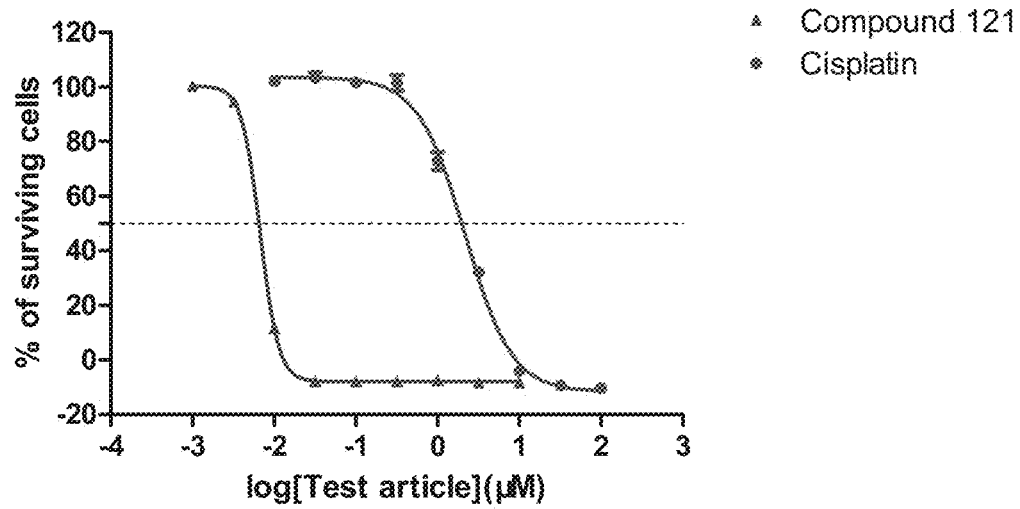

FIG. 39A is a graph indicating the determination of the $IC_{50}$ for Compound 121 and cisplatin in MES-SA/DX5 cells. FIG. 39B is a graph indicating the determination of the $GI_{50}$ for Compound 121 and cisplatin in MES-SA/DX5 cells.

Figure 40A:
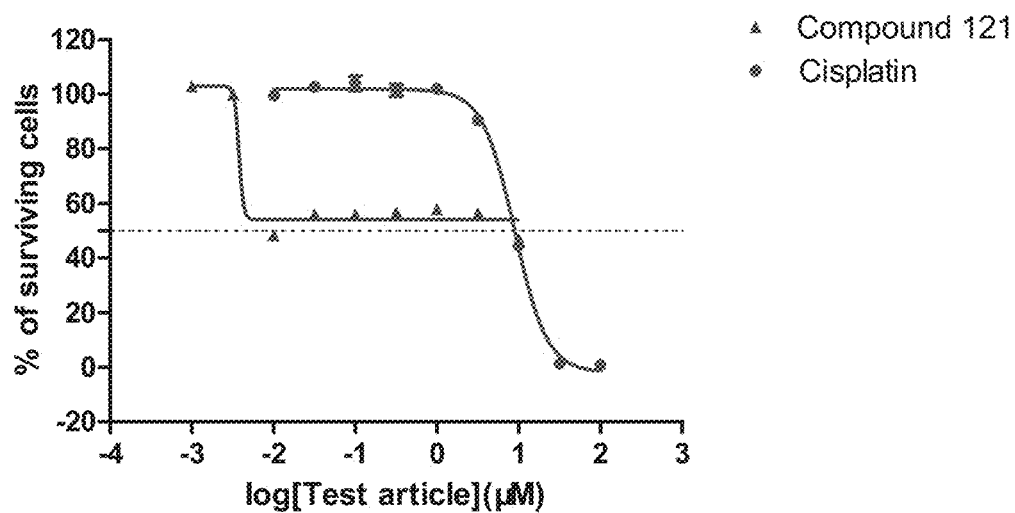

FIG. 40A is a graph indicating the determination of the $IC_{50}$ for Compound 121 and cisplatin in SK-MEL-28 cells.

Figure 40B:
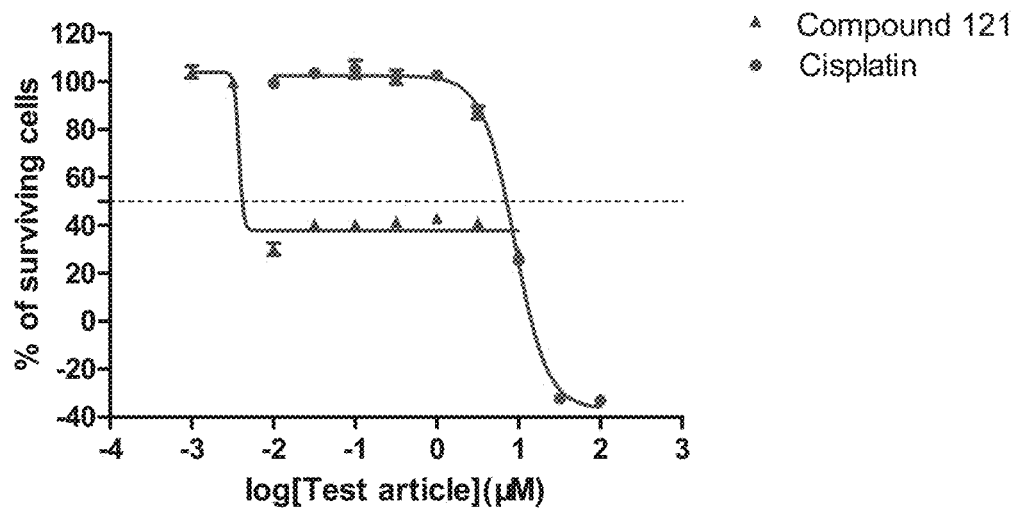

FIG. 40B is a graph indicating the determination of the $GI_{50}$ for Compound 121 and cisplatin in SK-MEL-28 cells.

Figure 41A:
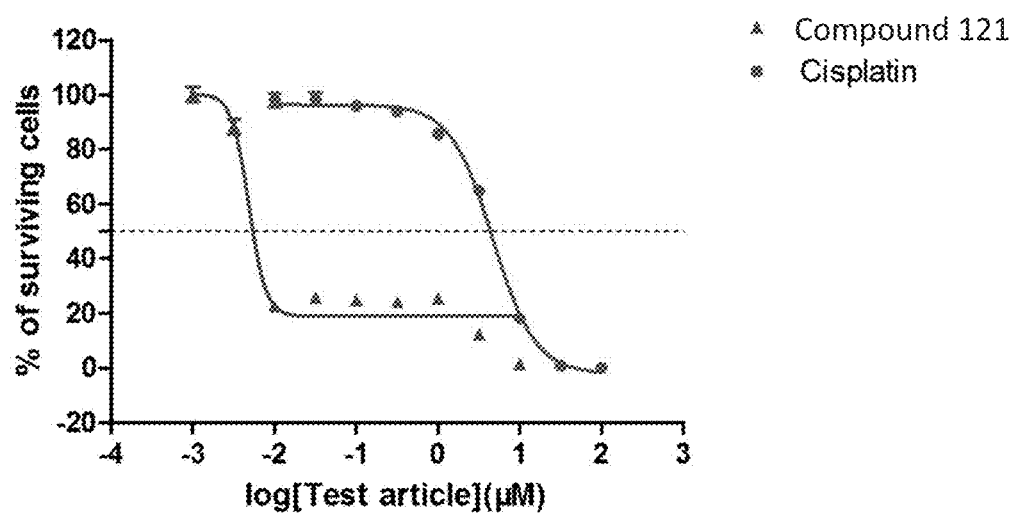
Figure 41B:
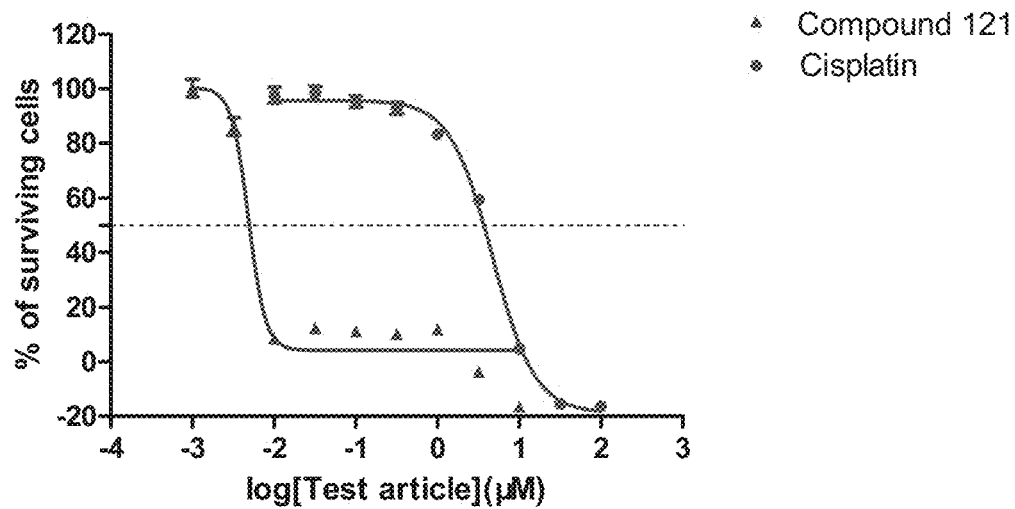

FIG. 41A is a graph indicating the determination of the $IC_{50}$ for Compound 121 and cisplatin in AN3 CA cells. FIG. 41B is a graph indicating the determination of the $GI_{50}$ for Compound 121 and cisplatin AN3 CA cells.

Figure 42A:
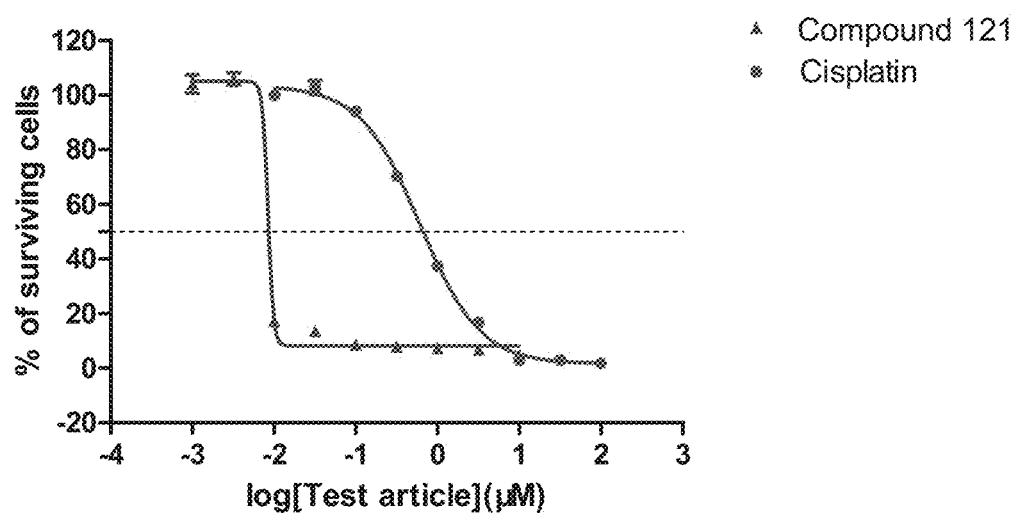
Figure 42B:
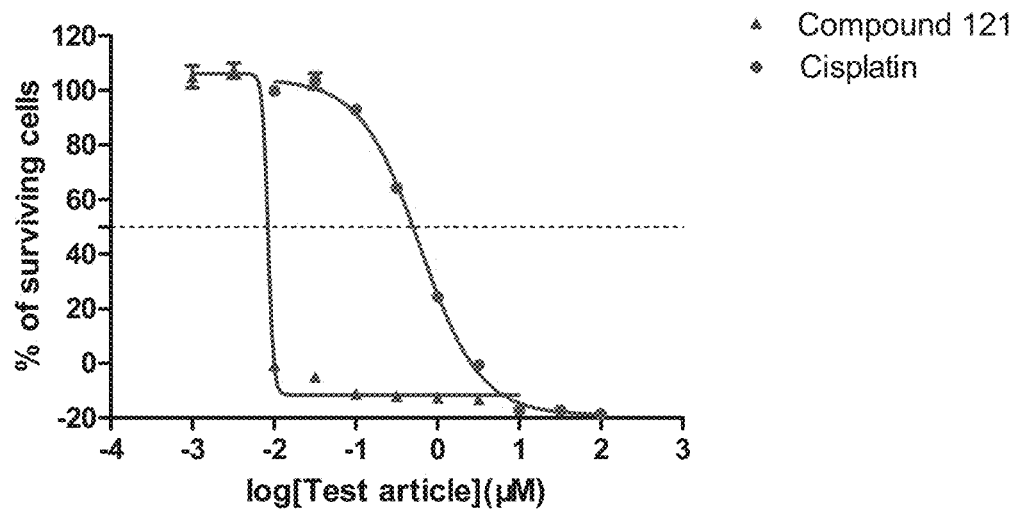

FIG. 42A is a graph indicating the determination of the $IC_{50}$ for Compound 121 and cisplatin in HuT 78 cells. FIG. 42B is a graph indicating the determination of the $GI_{50}$ for Compound 121 and cisplatin in HuT 78 cells.

Figure 43A:
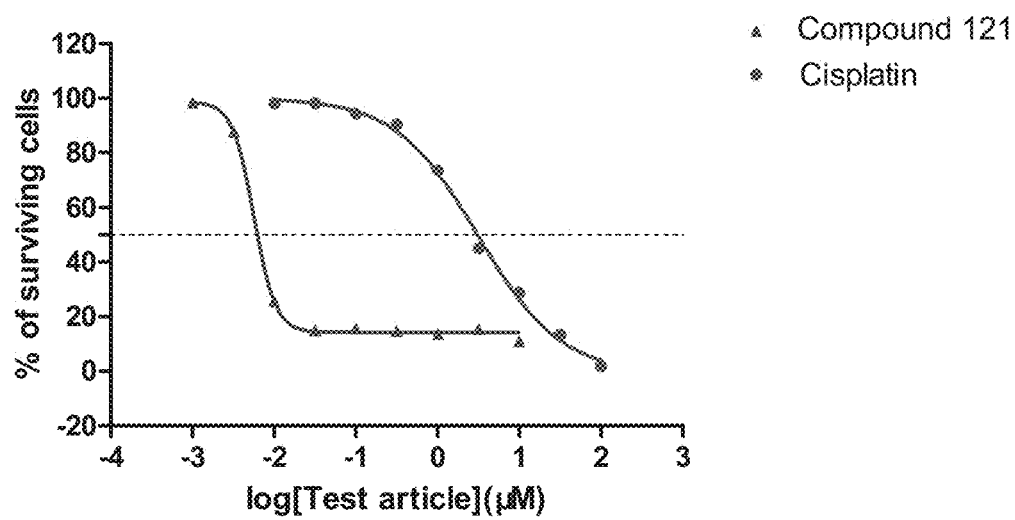
Figure 43B:
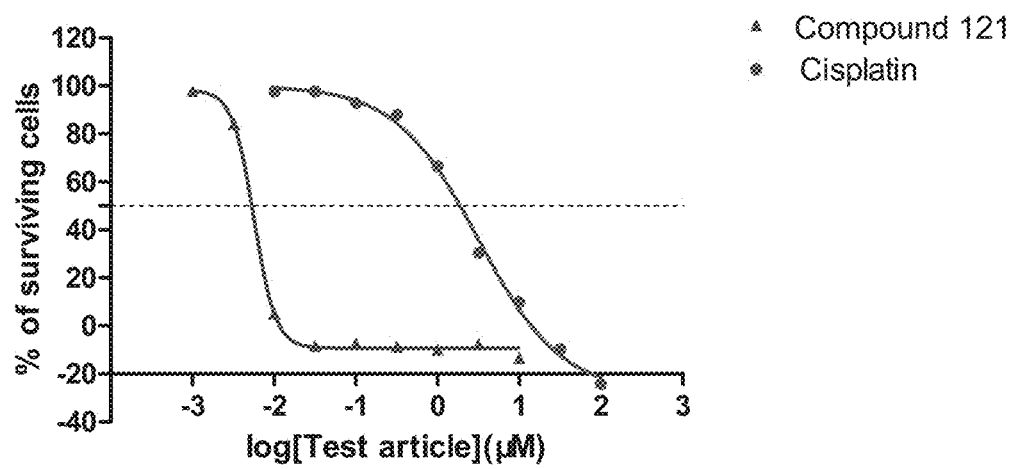

FIG. 43A is a graph indicating the determination of the $IC_{50}$ for Compound 121 and cisplatin in 22Rv1 cells. FIG. 43B is a graph indicating the determination of the $GI_{50}$ for Compound 121 and cisplatin in 22Rv1 cells.

Figure 44A:
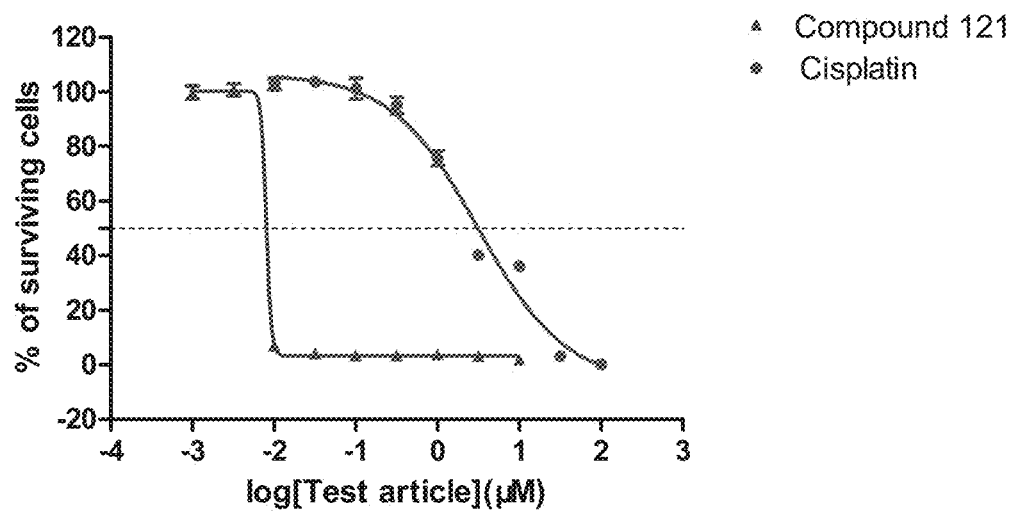
Figure 44B:
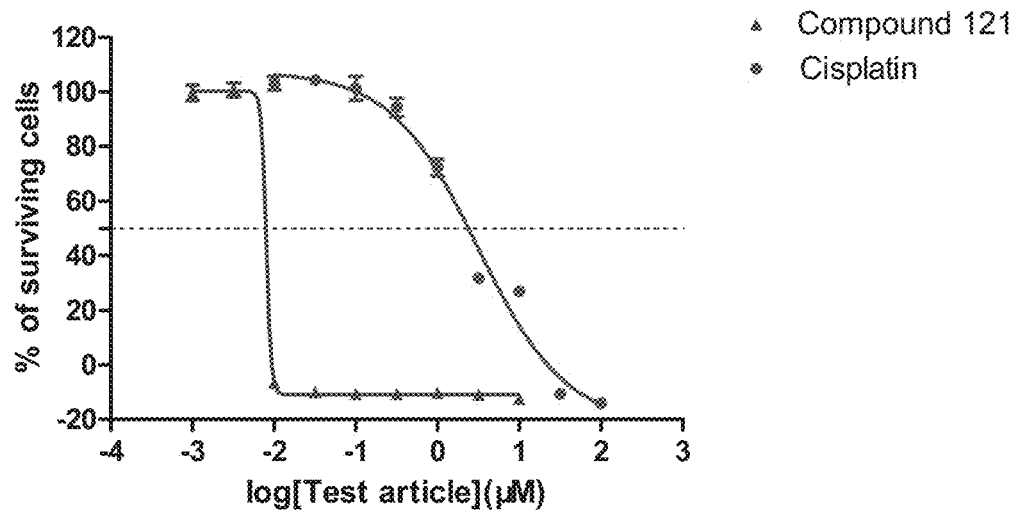

FIG. 44A is a graph indicating the determination of the $IC_{50}$ for Compound 121 and cisplatin in A2058 cells. FIG. 44B is a graph indicating the determination of the $GI_{50}$ for Compound 121 and cisplatin in A2058 cells.

Figure 45A:
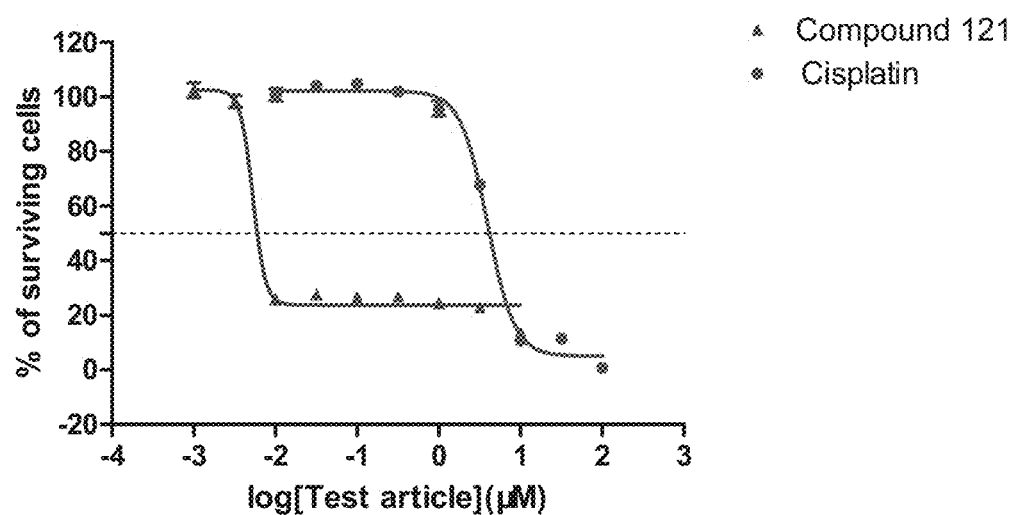
Figure 45B:
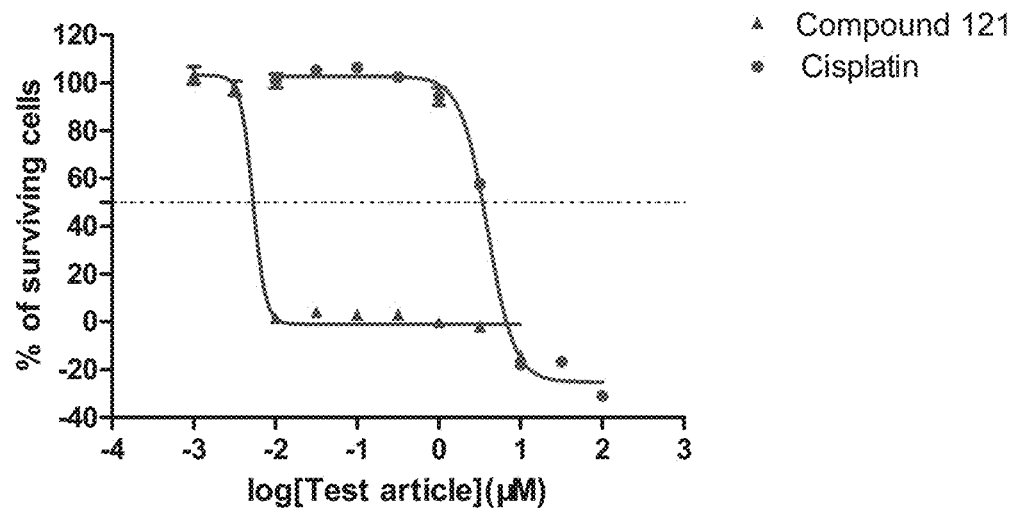

FIG. 45A is a graph indicating the determination of the $IC_{50}$ for Compound 121 and cisplatin in SCC-4 cells. FIG. 45B is a graph indicating the determination of the $GI_{50}$ for Compound 121 and cisplatin in SCC-4 cells.

Figure 46A:
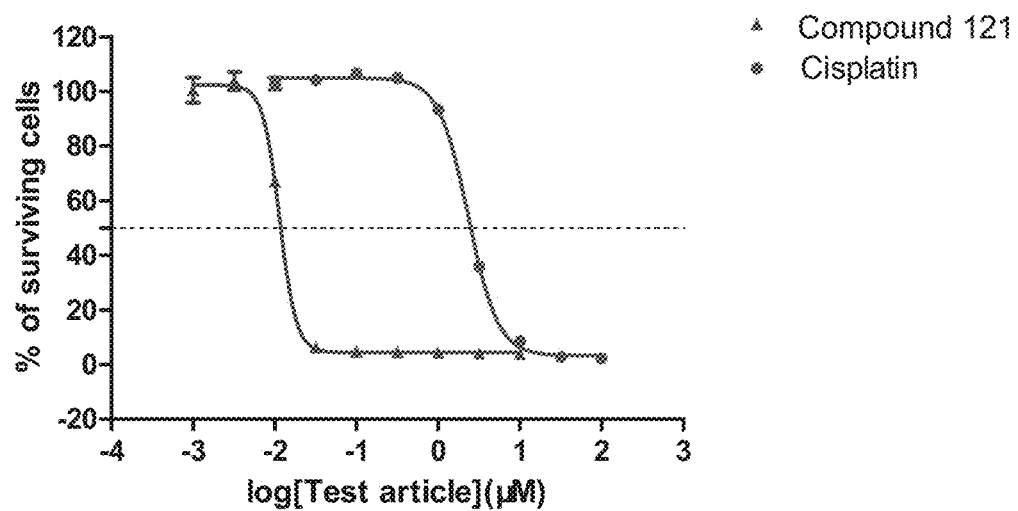
Figure 46B:
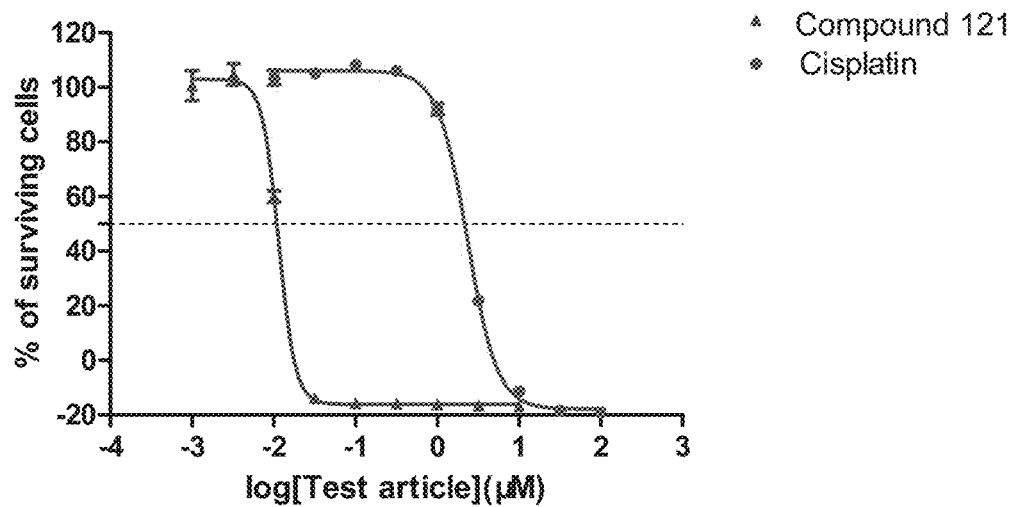

FIG. 46A is a graph indicating the determination of the $IC_{50}$ for Compound 121 and cisplatin in SNU-5 cells. FIG. 46B is a graph indicating the determination of the $GI_{50}$ for Compound 121 and cisplatin in SNU-5 cells.

Figure 47A:
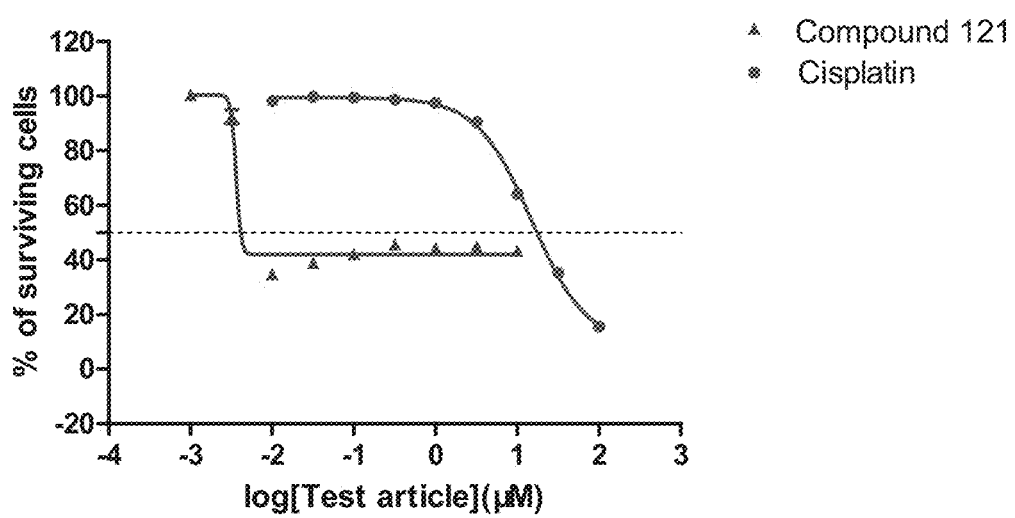
Figure 47B:
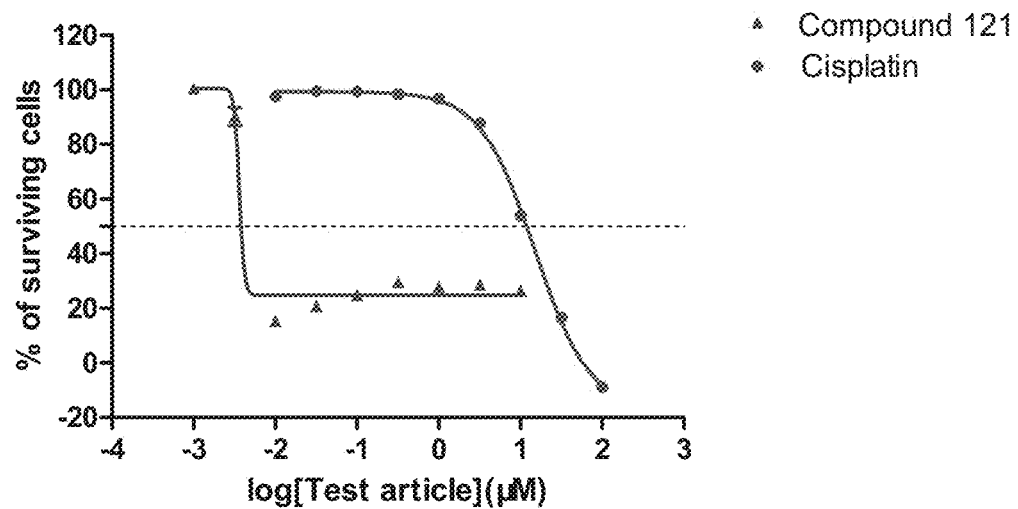

FIG. 47A is a graph indicating the determination of the $IC_{50}$ for Compound 121 and cisplatin in EBC-1 cells. FIG. 47B is a graph indicating the determination of the $GI_{50}$ for Compound 121 and cisplatin in EBC-1 cells.

Figure 48A:
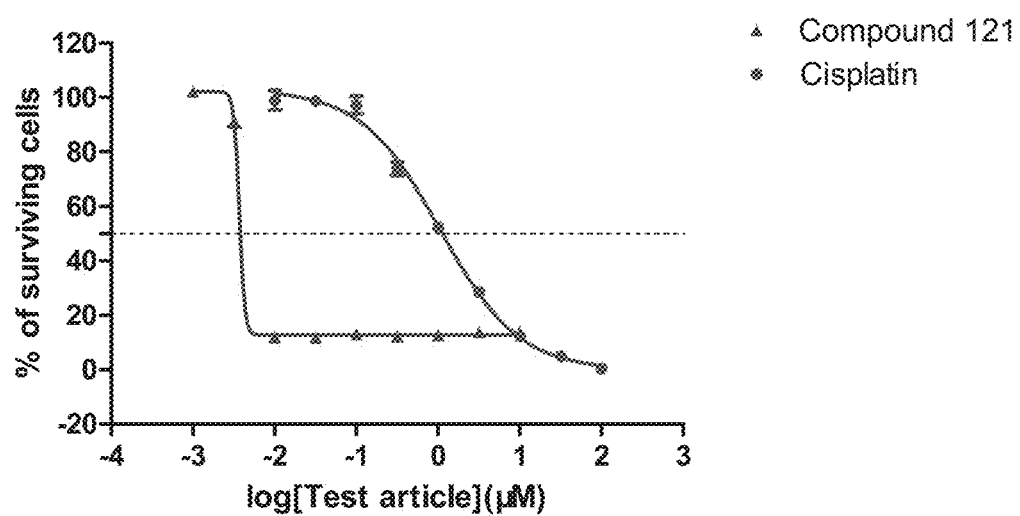
Figure 48B:
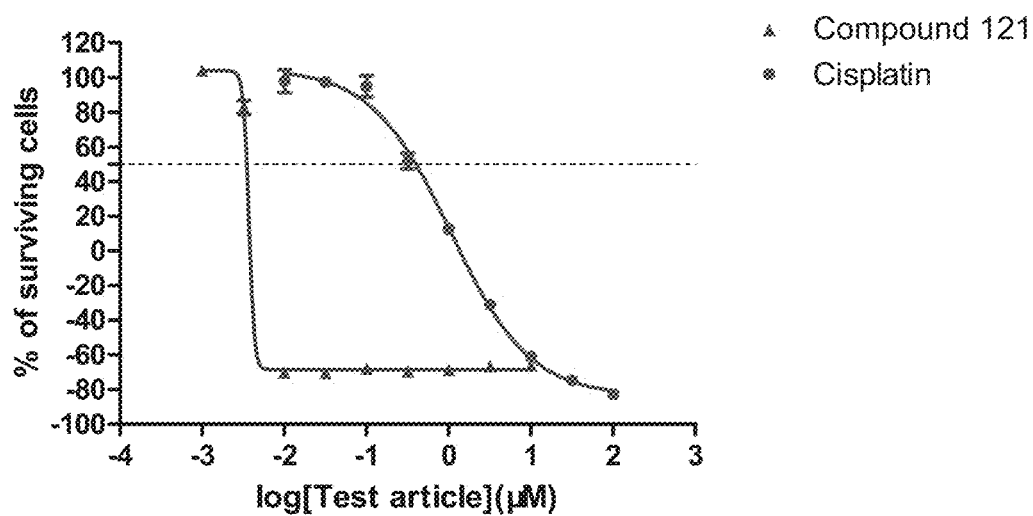

FIG. 48A is a graph indicating the determination of the $IC_{50}$ for Compound 121 and cisplatin in A-673 cells. FIG. 48B is a graph indicating the determination of the $GI_{50}$ for Compound 121 and cisplatin in A-673 cells.

Figure 49A:
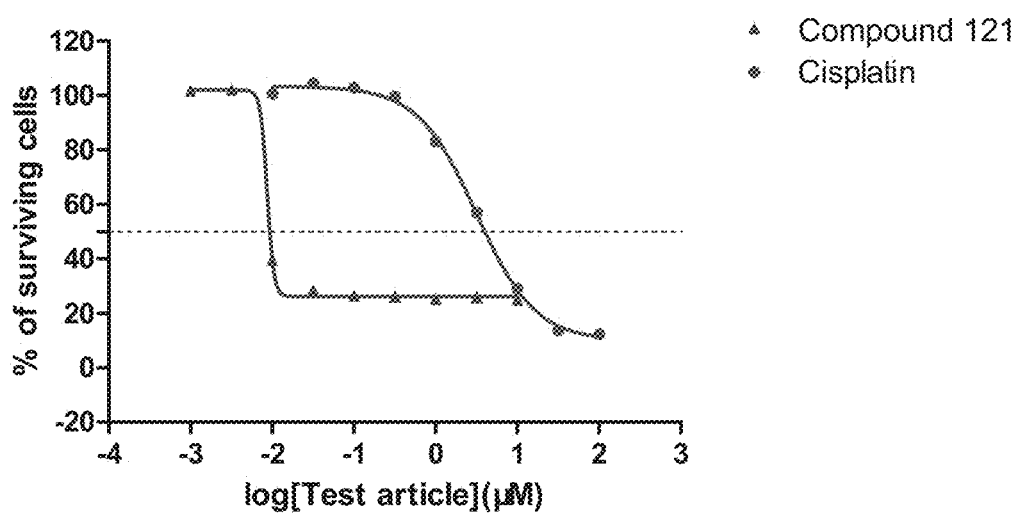
Figure 49B:
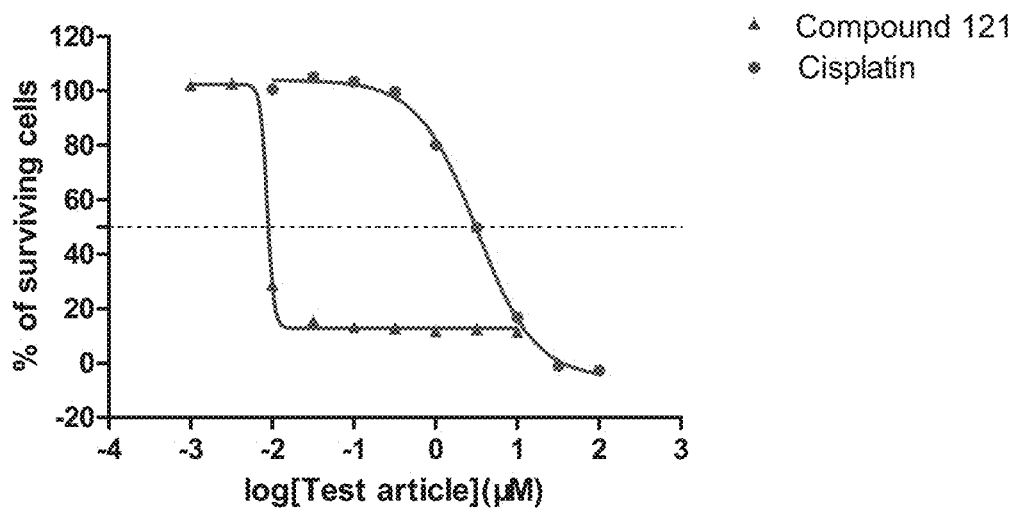

FIG. 49A is a graph indicating the determination of the $IC_{50}$ for Compound 121 and cisplatin in U251 cells. FIG. 49B is a graph indicating the determination of the $GI_{50}$ for Compound 121 and cisplatin in U251 cells.

Figure 50A:
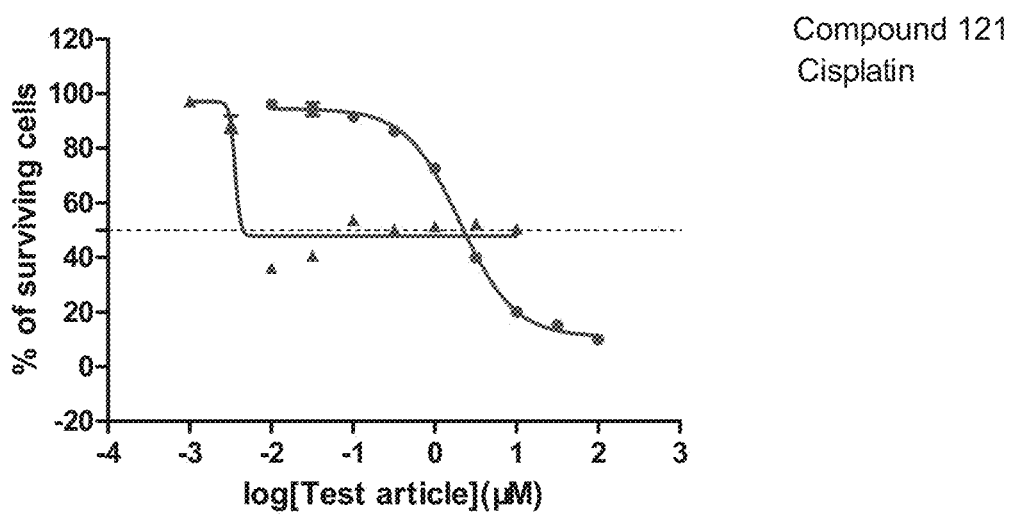
Figure 50B:
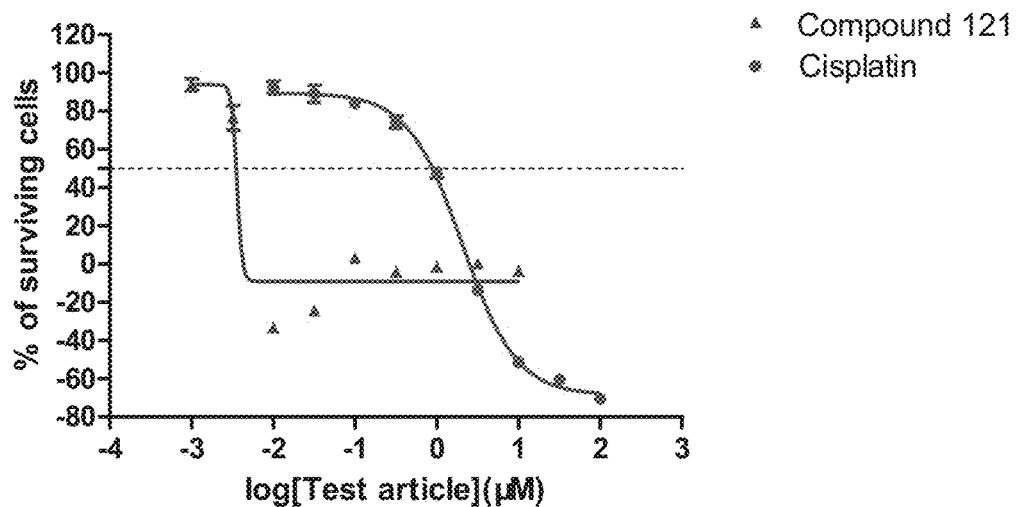

FIG. 50A is a graph indicating the determination of the $IC_{50}$ for Compound 121 and cisplatin in NCI-N87 cells. FIG. 50B is a graph indicating the determination of the $GI_{50}$ for Compound 121 and cisplatin in NCI-N87 cells.

Figure 51:
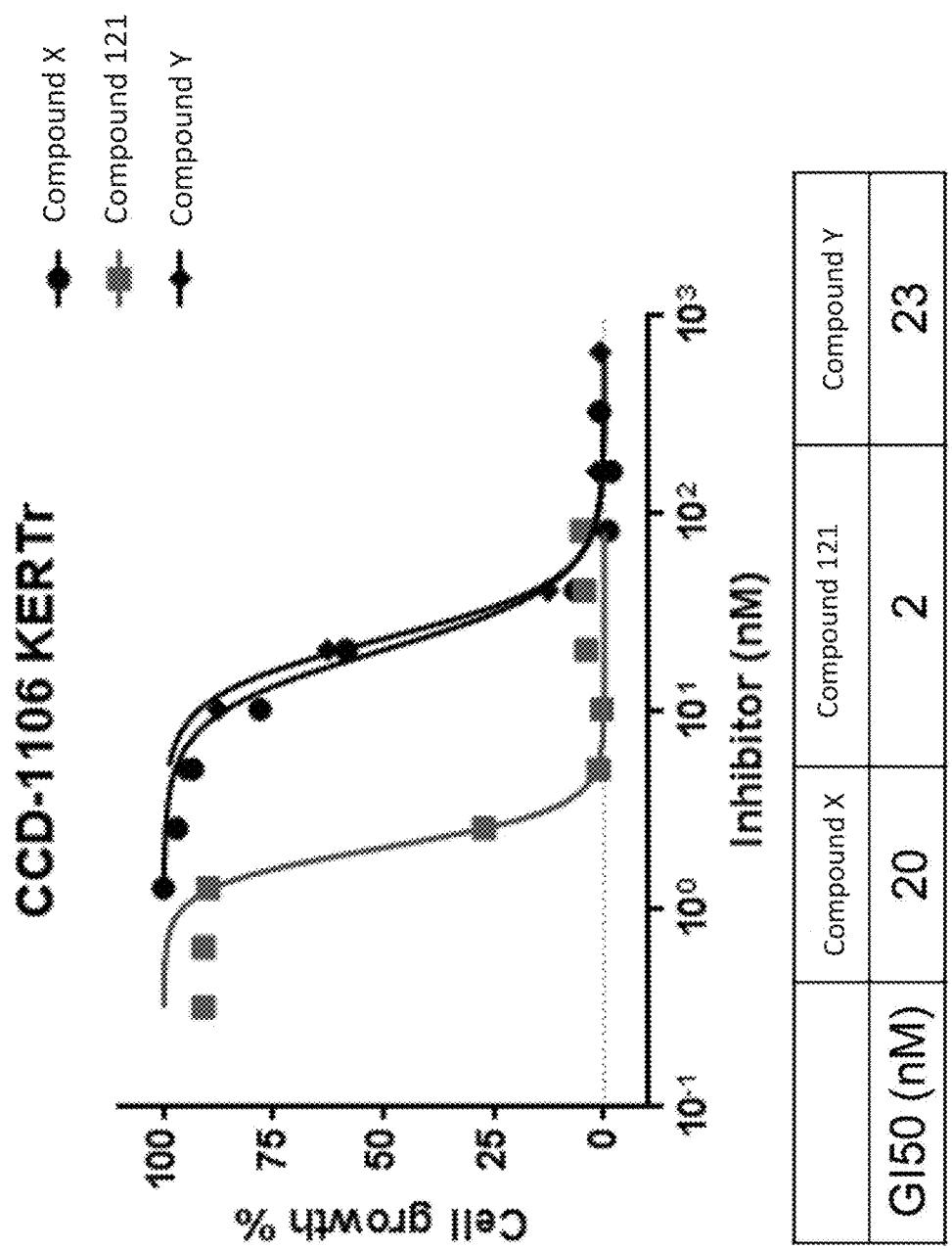

FIG. 51 is a graph indicating the determination of the $GI_{50}$ for Compound 121, Compound X, and Compound Y in CCD-1106 KERTr keratinocyte cells.

FIG. 52 compares several pharmacological and physical properties of Compound 121 and Compound Y.

Figure 53A:
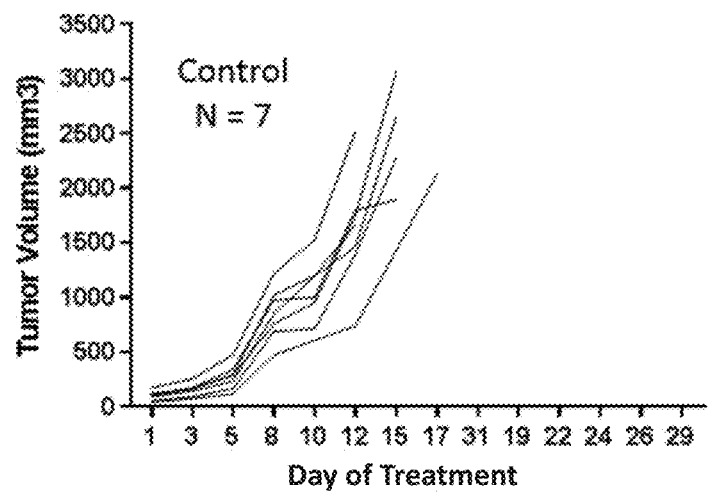
Figure 53B:
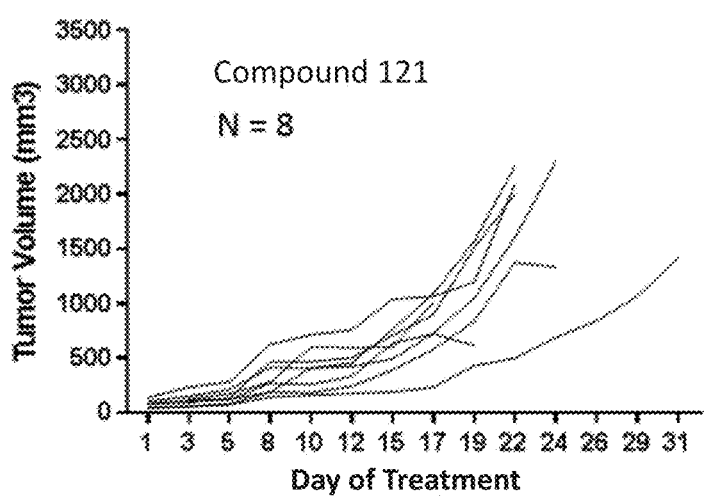
Figure 53C:
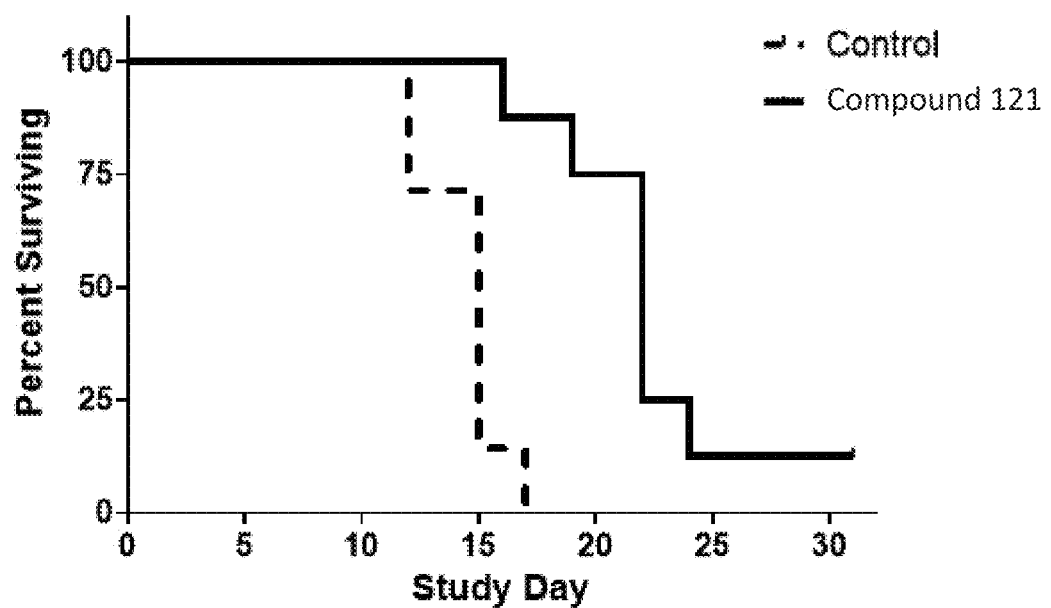

FIG. 53A is a graph indicating the growth of tumors in a U87-luc human glioblastoma subcutaneous xenograft tumor model mice dosed with vehicle. FIG. 53B is a graph indicating the growth of tumors in a U87-luc human glioblastoma subcutaneous xenograft tumor model mice orally dosed with Compound 121. FIG. 53C is a graph indicating the effect of treatment on time to terminal sacrifice of U87-luc human glioblastoma subcutaneous xenograft tumor model mice treated with Compound 121 compared to a control.

Figure 54A:
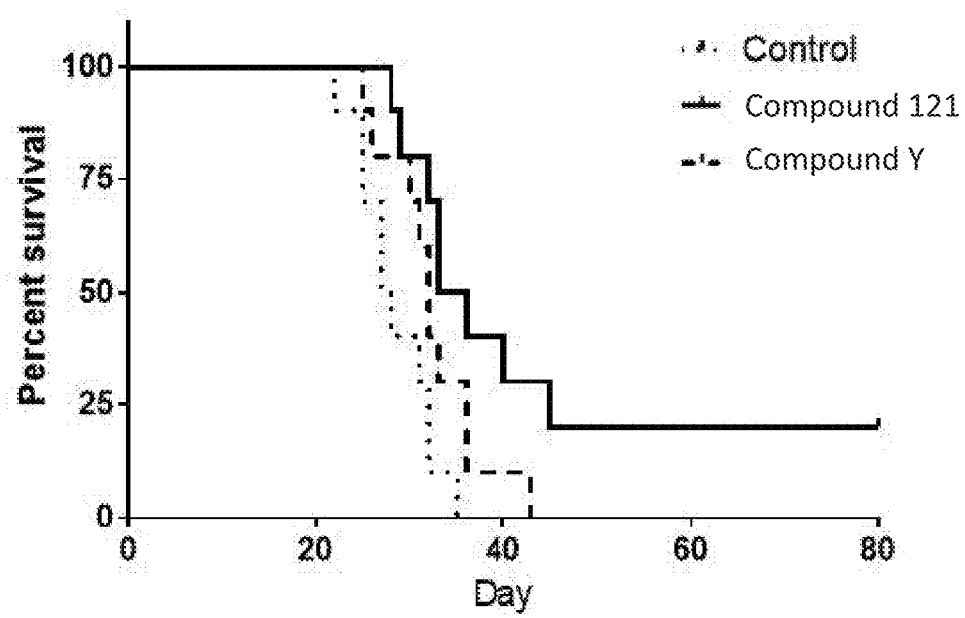
Figure 54B:
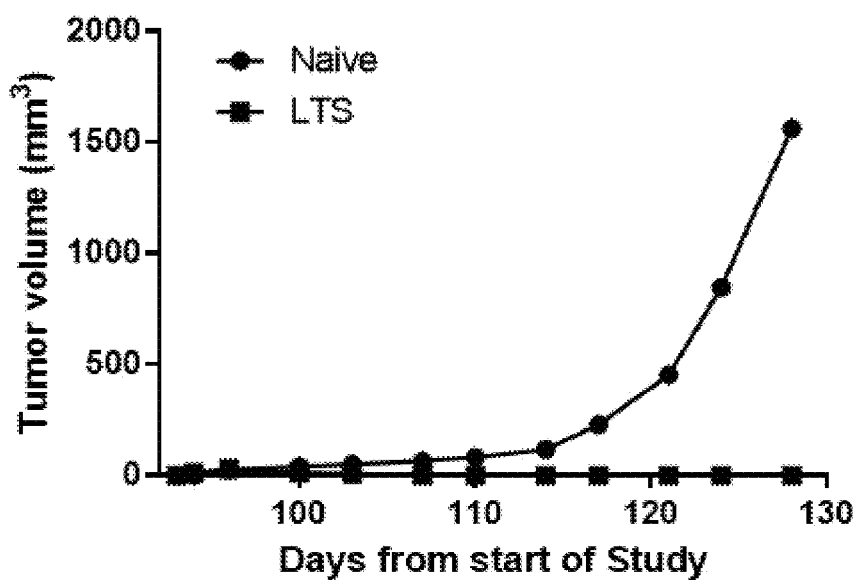

FIG. 54A is a graph indicating that Compound 121 extends survival and supports long term tumor control in the GL261 syngeneic murine model of human glioblastoma compared to Compound Y and a control. FIG. 54B is a graph indicating that Compound 121-treated mice that achieve long term survival (LTS) reject a sub-cutaneous challenge with GL261 cells.

DETAILED DESCRIPTION

The details of one or more embodiments of the application are set forth in the accompanying description below.

Although any methods and materials similar or equivalent to those described herein can be used in the practice or testing of the present application, the preferred methods and materials are now described. Other features, objects, and advantages of the application will be apparent from the description. In the specification, the singular forms also include the plural unless the context clearly dictates otherwise. Unless defined otherwise, all technical and scientific terms used herein have the same meaning as commonly understood by one of ordinary skill in the art to which this application belongs. In the case of conflict, the present specification will control.

The present application relates to a compound of formula (A):

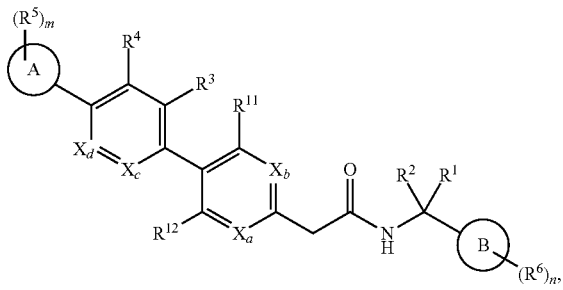

or a pharmaceutically acceptable salt, solvate, or prodrug thereof, wherein:

$X_a$ is $CR^a$ or N;
$X_b$ is $CR^b$ or N;
$X_c$ is $CR^c$ or N;
$X_d$ is $CR^d$ or N;
$R^a$ is H, halogen, $C_1$-$C_6$ alkyl, $C_2$-$C_6$ alkenyl, or $C_2$-$C_6$ alkynyl;
$R^b$ is H, halogen, $C_1$-$C_6$ alkyl, $C_2$-$C_6$ alkenyl, or $C_2$-$C_6$ alkynyl;
$R^c$ is H, halogen, $C_1$-$C_6$ alkyl, $C_2$-$C_6$ alkenyl, or $C_2$-$C_6$ alkynyl;
$R^d$ is H, halogen, $C_1$-$C_6$ alkyl, $C_2$-$C_6$ alkenyl, or $C_2$-$C_6$ alkynyl;
$R^1$ and $R^2$ are each independently H, $C_1$-$C_6$ alkyl, $C_2$-$C_6$ alkenyl, $C_2$-$C_6$ alkynyl, or O—($C_1$-$C_6$ alkyl);

alternatively, $R^1$ and $R^2$, together with the carbon atom to which they are attached, form a 3-8 membered saturated, unsaturated, or partially saturated carbocycle, or a saturated, unsaturated, or partially saturated heterocycle comprising one or two 5-7 membered rings and one or more heteroatoms selected from N, O, and S;

alternatively, one of $R^1$ and $R^2$, together with the carbon atom to which $R^1$ or $R^2$ is attached and Ⓑ, form a 7-12 membered saturated, unsaturated, or partially saturated carbocycle, or a 7-12 membered saturated, unsaturated, or partially saturated heterocycle comprising one or more heteroatoms selected from N, O and S;

$R^3$ and $R^4$ are each independently (a) H, (b) halogen, (c) OH, (d) COOH, (e) $CONH_2$, (f) $NHCOR^{101}$, (g) $NR^{101}COR^{102}$, (h) $S(O)_rR^{101}$, (i) $C_1$-$C_6$ alkyl, (j) $C_2$-$C_6$ alkenyl, (k) $C_2$-$C_6$ alkynyl, (l) O—($C_1$-$C_6$ alkyl), (m) O—($C_2$-$C_6$ alkenyl), (n) O—($C_2$-$C_6$ alkynyl), (o) COO—($C_1$-$C_6$ alkyl), (p) COO—($C_2$-$C_6$ alkenyl), (q) COO—($C_2$-$C_6$ alkynyl), (r) CONH—($C_1$-$C_6$ alkyl), (s) CONH—($C_2$-$C_6$ alkenyl), (t) CONH—($C_2$-$C_6$ alkynyl), (u) CON($C_1$-$C_6$ alkyl)$_2$, (v) CON($C_2$-$C_6$ alkenyl)$_2$, (w) CON($C_2$-$C_6$ alkynyl)$_2$, (x) ($C_1$-$C_6$ alkyl)$_u$-$NH_2$, (y) ($C_2$-$C_6$ alkenyl)$_u$-$NH_2$, (z) ($C_2$-$C_6$ alkynyl)$_u$-$NH_2$, (aa1) ($C_1$-$C_6$ alkyl)$_v$-NH($C_1$-$C_6$ alkyl), (aa2) ($C_1$-$C_6$ alkyl)$_v$-NH($C_2$-$C_6$ alkenyl), (aa3) ($C_1$-$C_6$ alkyl)$_v$-NH($C_2$-$C_6$ alkynyl), (bb1) ($C_2$-$C_6$ alkenyl)$_v$-NH($C_1$-$C_6$ alkyl), (bb2) ($C_2$-$C_6$ alkenyl)$_v$-NH($C_2$-$C_6$ alkenyl), (bb3) ($C_2$-$C_6$ alkenyl)$_v$-NH($C_2$-$C_6$ alkynyl), (cc1) ($C_2$-$C_6$ alkynyl)$_v$-NH($C_1$-$C_6$ alkyl), (cc2) ($C_2$-$C_6$ alkynyl)$_v$-NH($C_2$-$C_6$ alkenyl), (cc3) ($C_2$-$C_6$ alkynyl)$_v$-NH($C_2$-$C_6$ alkynyl), (dd1) ($C_1$-$C_6$ alkyl)$_w$-N($C_1$-$C_6$ alkyl)$_2$, (dd2) ($C_1$-$C_6$ alkyl)$_w$-N($C_2$-$C_6$ alkenyl)$_2$, (dd3) ($C_1$-$C_6$ alkyl)$_w$-N($C_2$-$C_6$ alkynyl)$_2$, (ee1) ($C_2$-$C_6$ alkenyl)$_w$-N($C_1$-$C_6$ alkyl)$_2$, (ee2) ($C_2$-$C_6$ alkenyl)$_w$-N($C_2$-$C_6$ alkenyl)$_2$, (ee3) ($C_2$-$C_6$ alkenyl)$_w$-N($C_2$-$C_6$ alkynyl)$_2$, (ff1) ($C_2$-$C_6$ alkynyl)$_w$-N($C_1$-$C_6$ alkyl)$_2$, (ff2) ($C_2$-$C_6$ alkynyl)$_w$-N($C_2$-$C_6$ alkenyl)$_2$, (ff3) ($C_2$-$C_6$ alkynyl)$_w$-N($C_2$-$C_6$ alkynyl)$_2$, (gg) 3-8 membered saturated, unsaturated, or partially saturated carbocycle, or (hh) 3-8 membered saturated, unsaturated, or partially saturated heterocycle, wherein each of (i)-(hh) is optionally substituted with one or more $R^7$;

Ⓐ represents a saturated, unsaturated, or partially saturated carbocycle comprising one or two 3-8 membered rings, or a saturated, unsaturated, or partially saturated heterocycle comprising one or two 5-8 membered rings and one or more heteroatoms selected from N, O and S, wherein the two 3-8 membered rings or the two 5-8 membered rings can form a fused or bridged ring structure;

Ⓑ represents an aromatic, saturated, unsaturated, or partially saturated carbocycle comprising one or two 3-8 membered rings, or an aromatic, saturated, unsaturated, or partially saturated heterocycle comprising one or two 5-8 membered rings and one or more heteroatoms selected from N, O and S, wherein the two 3-8 membered rings or the two 5-8 membered rings can form a fused or bridged ring structure;

each $R^5$ is independently (a) halogen, (b) OH, (c) $CONH_2$, (d) COOH, (e) CN, (f) $N_3$, (g) $C_1$-$C_6$ alkyl, (h) $C_2$-$C_6$ alkenyl, (i) $C_2$-$C_6$ alkynyl, (j) O—($C_1$-$C_6$ alkyl), (k) O—($C_2$-$C_6$ alkenyl), (l) O—($C_2$-$C_6$ alkynyl), (m) COO—($C_1$-$C_6$ alkyl), (n) COO—($C_2$-$C_6$ alkenyl), (o) COO—($C_2$-$C_6$ alkynyl), (p) CONH—($C_1$-$C_6$ alkyl), (q) CONH—($C_2$-$C_6$ alkenyl), (r) CONH—($C_2$-$C_6$ alkynyl), (s) CON($C_1$-$C_6$ alkyl)$_2$, (t) CON($C_2$-$C_6$ alkenyl)$_2$, (u) CON($C_2$-$C_6$ alkynyl)$_2$, (v1) ($C_1$-$C_6$ alkyl)$_v$-NH($C_1$-$C_6$ alkyl), (v2) ($C_1$-$C_6$ alkyl)$_v$-NH($C_2$-$C_6$ alkenyl), (v3) ($C_1$-$C_6$ alkyl)$_v$-NH($C_2$-$C_6$ alkynyl), (w1) ($C_2$-$C_6$ alkenyl)$_v$-NH($C_1$-$C_6$ alkyl), (w2) ($C_2$-$C_6$ alkenyl)$_v$-NH($C_2$-$C_6$ alkenyl), (w3) ($C_2$-$C_6$ alkenyl)$_v$-NH($C_2$-$C_6$ alkynyl), (x1) ($C_2$-$C_6$ alkynyl)$_v$-NH($C_1$-$C_6$ alkyl), (x2) ($C_2$-$C_6$ alkynyl)$_v$-NH($C_2$-$C_6$ alkenyl), (x3) ($C_2$-$C_6$ alkynyl)$_v$-NH($C_2$-$C_6$ alkynyl), (y1) ($C_1$-$C_6$ alkyl)$_w$-N($C_1$-$C_6$ alkyl)$_2$, (y2) ($C_1$-$C_6$ alkyl)$_w$-N($C_2$-$C_6$ alkenyl)$_2$, (y3) ($C_1$-$C_6$ alkyl)$_w$-N($C_2$-$C_6$ alkynyl)$_2$, (z1) ($C_2$-$C_6$ alkenyl)$_w$-N($C_1$-$C_6$ alkyl)$_2$, (z2) ($C_2$-$C_6$ alkenyl)$_w$-N($C_2$-$C_6$ alkenyl)$_2$, (z3) ($C_2$-$C_6$ alkenyl)$_w$-N($C_2$-$C_6$ alkynyl)$_2$, (aa1) ($C_2$-$C_6$ alkynyl)$_w$-N($C_1$-$C_6$ alkyl)$_2$, (aa2) ($C_2$-$C_6$ alkynyl)$_w$-N($C_2$-$C_6$ alkenyl)$_2$, (aa3) ($C_2$-$C_6$ alkynyl)$_w$-N($C_2$-$C_6$ alkynyl)$_2$, (bb) S—($C_1$-$C_6$ alkyl), (cc) S(O)—($C_1$-$C_6$ alkyl), (dd) S(O)$_2$—($C_1$-$C_6$ alkyl), (ee) S—($C_2$-$C_6$ alkenyl), (ff) S(O)—($C_2$-$C_6$ alkenyl), (gg) S(O)$_2$—($C_2$-$C_6$ alkenyl), (hh) S—($C_2$-$C_6$ alkynyl), (ii) S(O)—($C_2$-$C_6$ alkynyl), (jj) S(O)$_2$—($C_2$-$C_6$ alkynyl), (kk) an aromatic, saturated, unsaturated, or partially saturated carbocycle comprising one or two 3-8 membered rings, or (ll) an aromatic, saturated, unsaturated, or partially saturated heterocycle comprising one or two 5-7 membered rings and one or more heteroatoms selected from N, O and S, wherein each of (g)-(ll) is optionally substituted with one or more $R^8$;

each $R^6$ is independently (a) halogen, (b) OH, (c) $CONH_2$, (d) COOH, (e) CN, (f) $N_3$, (g) $C_1$-$C_6$ alkyl, (h) $C_2$-$C_6$ alkenyl, (i) $C_2$-$C_6$ alkynyl, (j) O—($C_1$-$C_6$ alkyl), (k) O—($C_2$-$C_6$ alkenyl), (l) O—($C_2$-$C_6$ alkynyl), (m) COO—($C_1$-$C_6$ alkyl), (n) COO—($C_2$-$C_6$ alkenyl), (o) COO—($C_2$-$C_6$ alkynyl), (p) CONH—($C_1$-$C_6$ alkyl), (q) CONH—($C_2$-$C_6$ alkenyl), (r) CONH—($C_2$-$C_6$ alkynyl), (s) CON($C_1$-$C_6$ alkyl)$_2$, (t) CON($C_2$-$C_6$ alkenyl)$_2$, (u) CON($C_2$-$C_6$ alkynyl)$_2$, (v1) ($C_1$-$C_6$ alkyl)$_v$-NH($C_1$-$C_6$ alkyl), (v2) ($C_1$-$C_6$ alkyl)$_v$-NH($C_2$-$C_6$ alkenyl), (v3) ($C_1$-$C_6$ alkyl)$_v$-NH($C_2$-$C_6$ alkynyl), (w1) ($C_2$-$C_6$ alkenyl)$_v$-NH($C_1$-$C_6$ alkyl), (w2) ($C_2$-$C_6$ alkenyl)$_v$-NH($C_2$-$C_6$ alkenyl), (w3) ($C_2$-$C_6$ alkenyl)$_v$-NH($C_2$-$C_6$ alkynyl), (x1) ($C_2$-$C_6$ alkynyl)$_v$-NH($C_1$-$C_6$ alkyl), (x2) ($C_2$-$C_6$ alkynyl)$_v$-NH($C_2$-$C_6$ alkenyl), (x3) ($C_2$-$C_6$ alkynyl)$_v$-NH($C_2$-$C_6$ alkynyl), (y1) ($C_1$-$C_6$ alkyl)$_w$-N($C_1$-$C_6$ alkyl)$_2$, (y2) ($C_1$-$C_6$ alkyl)$_w$-N($C_2$-$C_6$ alkenyl)$_2$, (y3) ($C_1$-$C_6$ alkyl)$_w$-N($C_2$-$C_6$ alkynyl)$_2$, (z1) ($C_2$-$C_6$ alkenyl)$_w$-N($C_1$-$C_6$ alkyl)$_2$, (z2) ($C_2$-$C_6$ alkenyl)$_w$-N($C_2$-$C_6$ alkenyl)$_2$, (z3) ($C_2$-$C_6$ alkenyl)$_w$-N($C_2$-$C_6$ alkynyl)$_2$, (aa1) ($C_2$-$C_6$ alkynyl)$_w$-N($C_1$-$C_6$ alkyl)$_2$, (aa2) ($C_2$-$C_6$ alkynyl)$_w$-N($C_2$-$C_6$ alkenyl)$_2$, (aa3) ($C_2$-$C_6$ alkynyl)$_w$-N($C_2$-$C_6$ alkynyl)$_2$, (bb) S—($C_1$-$C_6$ alkyl), (cc) S(O)—($C_1$-$C_6$ alkyl), (dd) S(O)$_2$—($C_1$-$C_6$ alkyl), (ee) S—($C_2$-$C_6$ alkenyl), (ff) S(O)—($C_2$-$C_6$ alkenyl), (gg) S(O)$_2$—($C_2$-$C_6$ alkenyl), (hh) S—($C_2$-$C_6$ alkynyl), (ii) S(O)—($C_2$-$C_6$ alkynyl), (jj) S(O)$_2$—($C_2$-$C_6$ alkynyl), (kk) an aromatic, saturated, unsaturated, or partially saturated carbocycle comprising one or two 3-8 membered rings, or (ll) an aromatic, saturated, unsaturated, or partially saturated heterocycle comprising one or two 5-7 membered rings and one or more heteroatoms selected from N, O and S, wherein each of (g)-(ll) is optionally substituted with one or more $R^9$;

each $R^7$ is independently halogen, OH, O—($C_1$-$C_6$ alkyl), COO—($C_1$-$C_6$ alkyl), CONH—($C_1$-$C_6$ alkyl), CON($C_1$-$C_6$ alkyl)$_2$, COOH, CN, $N_3$, 5-6 membered saturated, unsaturated, or partially saturated carbocycle, or 5-6 membered saturated, unsaturated, or partially saturated heterocycle comprising one or more heteroatoms selected from N, O and S;

each $R^8$ is independently halogen, OH, O—($C_1$-$C_6$ alkyl), $C_1$-$C_6$ haloalkyl, COO—($C_1$-$C_6$ alkyl), CONH—($C_1$-$C_6$ alkyl), CON($C_1$-$C_6$ alkyl)$_2$, COOH, CN, $N_3$, 5-6 membered saturated, unsaturated, or partially saturated carbocycle, or 5-6 membered saturated, unsaturated, or partially saturated heterocycle comprising one or more heteroatoms selected from N, O and S;

each $R^9$ is independently halogen, OH, O—($C_1$-$C_6$ alkyl), COO—($C_1$-$C_6$ alkyl), CONH—($C_1$-$C_6$ alkyl), CON($C_1$-$C_6$ alkyl)$_2$, COOH, CN, $N_3$, 5-6 membered saturated, unsaturated, or partially saturated carbocycle, or 5-6 membered saturated, unsaturated, or partially saturated heterocycle comprising one or more heteroatoms selected from N, O and S;

$R^{101}$ and $R^{102}$ are each independently H, $C_1$-$C_6$ alkyl, $C_2$-$C_6$ alkenyl, or $C_2$-$C_6$ alkynyl;

$R^{11}$ is H, halogen, $C_1$-$C_6$ alkyl, $C_2$-$C_6$ alkenyl, or $C_2$-$C_6$ alkynyl;

$R^{12}$ is H, halogen, $C_1$-$C_6$ alkyl, $C_2$-$C_6$ alkenyl, or $C_2$-$C_6$ alkynyl;

m is 1, 2, 3, 4, 5, or 6;
n is 0, 1, 2, 3, 4, 5, or 6;
t is 0, 1, or 2;
u is 0 or 1;
v is 0 or 1; and
w is 0 or 1, provided that when m is 1,

is not

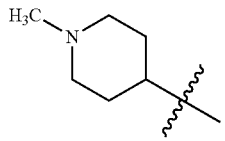 or 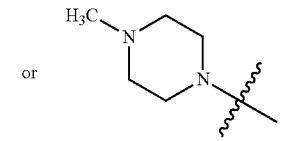.

In one aspect, the present application relates to a compound of formula (A), wherein $X_a$ is $CR^a$; and $X_b$ is $CR^b$. In another aspect, $X_a$ is $CR^a$; and $X_b$ is N. In another aspect, $X_a$ is N; and $X_b$ is $CR^b$. In another aspect, $X_a$ is N; and $X_b$ is N.

In one aspect, the present application relates to a compound of formula (A), wherein $R^a$ is H, halogen, or $C_1$-$C_6$ alkyl.

In one aspect, the present application relates to a compound of formula (A), wherein $R^a$ is H. In another aspect, $R^a$ is halogen (e.g., F, Cl, Br, or I). In a further aspect, $R^a$ is F. In another aspect, $R^a$ is $C_1$-$C_6$ alkyl (e.g., methyl, ethyl, propyl, i-propyl, butyl, i-butyl, t-butyl, pentyl, or hexyl). In a further aspect, $R^a$ is methyl.

In one aspect, the present application relates to a compound of formula (A), wherein $R^a$ is $C_2$-$C_6$ alkenyl.

In one aspect, the present application relates to a compound of formula (A), wherein $R^a$ is $C_2$-$C_6$ alkynyl.

In one aspect, the present application relates to a compound of formula (A), wherein $R^b$ is H, halogen, or $C_1$-$C_6$ alkyl.

In one aspect, the present application relates to a compound of formula (A), wherein $R^b$ is H. In another aspect, $R^b$ is halogen (e.g., F, Cl, Br, or I). In a further aspect, $R^b$ is F. In another aspect, $R^b$ is $C_1$-$C_6$ alkyl (e.g., methyl, ethyl, propyl, i-propyl, butyl, i-butyl, t-butyl, pentyl, or hexyl). In a further aspect, $R^b$ is methyl.

In one aspect, the present application relates to a compound of formula (A), wherein $R^b$ is $C_2$-$C_6$ alkenyl.

In one aspect, the present application relates to a compound of formula (A), wherein $R^b$ is $C_2$-$C_6$ alkynyl.

In one aspect, the present application relates to a compound of formula (A), wherein $R^a$ is H; and $R^b$ is H. In another aspect, one of $R^a$ and $R^b$ is H, and the other is halogen (e.g., F, Cl, Br, or I) or $C_1$-$C_6$ alkyl (e.g., methyl, ethyl, propyl, i-propyl, butyl, i-butyl, t-butyl, pentyl, or hexyl).

In one aspect, the present application relates to a compound of formula (A), wherein $X_a$ is N; $X_b$ is $CR^b$; and $R^b$ is H. In another aspect, $X_b$ is N; $X_a$ is $CR^a$; and $R^a$ is H.

In one aspect, the present application relates to a compound of formula (A), wherein $R^{11}$ is H. In another aspect, $R^{11}$ is halogen (e.g., F, Cl, Br, or I). In a further aspect, $R^{11}$ is F. In another aspect, $R^{11}$ is $C_1$-$C_6$ alkyl (e.g., methyl, ethyl, propyl, i-propyl, butyl, i-butyl, t-butyl, pentyl, or hexyl). In a further aspect, $R^{11}$ is methyl.

In one aspect, the present application relates to a compound of formula (A), wherein $R^{12}$ is H. In another aspect, $R^{12}$ is halogen (e.g., F, Cl, Br, or I). In a further aspect, $R^{12}$ is F. In another aspect, $R^{12}$ is $C_1$-$C_6$ alkyl (e.g., methyl, ethyl, propyl, i-propyl, butyl, i-butyl, t-butyl, pentyl, or hexyl). In a further aspect, $R^{12}$ is methyl.

In one aspect, the present application relates to a compound of formula (A), wherein $X_a$ is N; $X_b$ is $CR^b$; $R^b$ is H; $R^{11}$ is methyl; and $R^{12}$ is H. In another aspect, $X_a$ is N; $X_b$ is $CR^b$; $R^b$ is H; $R^{12}$ is methyl; and $R^{11}$ is H. In another aspect, $X_a$ is N; $X_b$ is $CR^b$; $R^b$ is H; $R^{11}$ is H; and $R^{12}$ is H.

In one aspect, the present application relates to a compound of formula (A), wherein $X_b$ is N; $X_a$ is $CR^a$; $R^a$ is H; $R^{11}$ is methyl; and $R^{12}$ is H. In another aspect, $X_b$ is N; $X_a$ is $CR^a$; $R^a$ is H; $R^{12}$ is methyl; and $R^{11}$ is H. In another aspect, $X_b$ is N; $X_a$ is $CR^a$; $R^a$ is H; $R^{11}$ is H; and $R^{12}$ is H.

In one aspect, the present application relates to a compound of formula (A), wherein $X_c$ is $CR^c$; and $X_d$ is $CR^d$. In another aspect, $X_c$ is $CR^c$; and $X_d$ is N. In another aspect, $X_c$ is N; and $X_d$ is $CR^d$. In another aspect, $X_c$ is N; and $X_d$ is N.

In one aspect, the present application relates to a compound of formula (A), wherein $R^c$ is H, halogen, or $C_1$-$C_6$ alkyl.

In one aspect, the present application relates to a compound of formula (A), wherein $R^c$ is H. In another aspect, $R^c$ is halogen (e.g., F, Cl, Br, or I). In a further aspect, $R^c$ is F. In another aspect, $R^c$ is $C_1$-$C_6$ alkyl (e.g., methyl, ethyl, propyl, i-propyl, butyl, i-butyl, t-butyl, pentyl, or hexyl). In a further aspect, $R^c$ is methyl.

In one aspect, the present application relates to a compound of formula (A), wherein $R^c$ is $C_2$-$C_6$ alkenyl.

In one aspect, the present application relates to a compound of formula (A), wherein $R^c$ is $C_2$-$C_6$ alkynyl.

In one aspect, the present application relates to a compound of formula (A), wherein $R^d$ is H, halogen, or $C_1$-$C_6$ alkyl.

In one aspect, the present application relates to a compound of formula (A), wherein $R^d$ is H. In another aspect, $R^d$ is halogen (e.g., F, Cl, Br, or I). In a further aspect, $R^d$ is F. In another aspect, $R^d$ is $C_1$-$C_6$ alkyl (e.g., methyl, ethyl, propyl, i-propyl, butyl, i-butyl, t-butyl, pentyl, or hexyl). In a further aspect, $R^d$ is methyl.

In one aspect, the present application relates to a compound of formula (A), wherein $R^d$ is $C_2$-$C_6$ alkenyl.

In one aspect, the present application relates to a compound of formula (A), wherein $R^d$ is $C_2$-$C_6$ alkynyl.

In one aspect, the present application relates to a compound of formula (A), wherein $R^c$ is H; and $R^d$ is H. In another aspect, one of $R^c$ and $R^d$ is H, and the other is halogen (e.g., F, Cl, Br, or I) or $C_1$-$C_6$ alkyl (e.g., methyl, ethyl, propyl, i-propyl, butyl, i-butyl, t-butyl, pentyl, or hexyl).

In one aspect, the present application relates to a compound of formula (A), wherein $X_c$ is $CR^c$; $X_d$ is $CR^d$; $R^c$ is H; and $R^d$ is H.

In one aspect, the present application relates to a compound of formula (A), wherein $X_c$ is N; $X_d$ is $CR^d$; and $R^d$ is H. In another aspect, $X_d$ is N; $X_c$ is $CR^c$; and $R^c$ is H.

In one aspect, the present application relates to a compound of formula (A), wherein $R^3$ is (a) H, (b) halogen, (c) OH, (d) COOH, (e) $CONH_2$, (f) $NHCOR^{101}$, (g) $NR^{101}COR^{102}$, (h) $S(O)_rR^{101}$, (i) $C_1$-$C_6$ alkyl, (l) O—($C_1$-$C_6$ alkyl), (o) COO—($C_1$-$C_6$ alkyl), (r) CONH—($C_1$-$C_6$ alkyl), (u) CON($C_1$-$C_6$ alkyl)$_2$, (x) ($C_1$-$C_6$ alkyl)$_u$-$NH_2$, (aa1) ($C_1$-$C_6$ alkyl)$_v$-NH($C_1$-$C_6$ alkyl), (dd1) ($C_1$-$C_6$ alkyl)$_w$-N($C_1$-$C_6$ alkyl)$_2$, (gg) 3-8 membered saturated, unsaturated, or partially saturated carbocycle, or (hh) 3-8 membered saturated, unsaturated, or partially saturated heterocycle, each of which is optionally substituted with one or more $R^7$.

In one aspect, the present application relates to a compound of formula (A), wherein $R^3$ is 5-6 membered saturated, unsaturated, or partially saturated carbocycle, and is optionally substituted with one or more $R^7$.

In one aspect, the present application relates to a compound of formula (A), wherein $R^3$ is H. In another aspect, $R^3$ is halogen (e.g., F, Cl, Br, or I). In a further aspect, $R^3$ is F. In another aspect, $R^3$ is $C_1$-$C_6$ alkyl (e.g., methyl, ethyl, propyl, i-propyl, butyl, i-butyl, t-butyl, pentyl, or hexyl). In a further aspect, $R^3$ is methyl. In another aspect, $R^3$ is OH. In another aspect, $R^3$ is O—$C_1$-$C_6$ alkyl (e.g., methyl, ethyl, propyl, i-propyl, butyl, i-butyl, t-butyl, pentyl, or hexyl). In a further aspect, $R^3$ is O-methyl.

In one aspect, the present application relates to a compound of formula (A), wherein $R^3$ is COOH, $CONH_2$, COO—($C_1$-$C_6$ alkyl), CONH—($C_1$-$C_6$ alkyl), CON($C_1$-$C_6$ alkyl)$_2$, and wherein $C_1$-$C_6$ alkyl is selected from methyl, ethyl, propyl, i-propyl, butyl, i-butyl, t-butyl, pentyl, and hexyl, and is optionally substituted with one or more $R^7$.

In one aspect, the present application relates to a compound of formula (A), wherein $R^3$ is $NHCOR^{101}$, $NR^{101}COR^{102}$, or $S(O)_rR^{101}$, and is optionally substituted with one or more $R^7$.

In one aspect, the present application relates to a compound of formula (A), wherein $R^3$ is ($C_1$-$C_6$ alkyl)$_u$-$NH_2$, ($C_1$-$C_6$ alkyl)$_v$-NH($C_1$-$C_6$ alkyl), or ($C_1$-$C_6$ alkyl)$_w$-N($C_1$-$C_6$ alkyl)$_2$, and is optionally substituted with one or more $R^7$.

In one aspect, the present application relates to a compound of formula (A), wherein $R^3$ is 5-6 membered saturated, unsaturated, or partially saturated carbocycle, and is optionally substituted with one or more $R^7$.

In one aspect, the present application relates to a compound of formula (A), wherein $R^3$ is $C_2$-$C_6$ alkenyl, and is optionally substituted with one or more $R^7$.

In one aspect, the present application relates to a compound of formula (A), wherein $R^3$ is $C_2$-$C_6$ alkynyl, and is optionally substituted with one or more $R^7$.

In one aspect, the present application relates to a compound of formula (A), wherein $R^3$ is O—($C_2$-$C_6$ alkenyl), and is optionally substituted with one or more $R^7$.

In one aspect, the present application relates to a compound of formula (A), wherein $R^3$ is O—($C_2$-$C_6$ alkynyl), and is optionally substituted with one or more $R^7$.

In one aspect, the present application relates to a compound of formula (A), wherein $R^3$ is COO—($C_2$-$C_6$ alkenyl), CONH—($C_2$-$C_6$ alkenyl), or CON($C_2$-$C_6$ alkenyl)$_2$, and is optionally substituted with one or more $R^7$.

In one aspect, the present application relates to a compound of formula (A), wherein $R^3$ is COO—($C_2$-$C_6$ alkynyl), CONH—($C_2$-$C_6$ alkynyl), or CON($C_2$-$C_6$ alkynyl)$_2$, and is optionally substituted with one or more $R^7$.

In one aspect, the present application relates to a compound of formula (A), wherein $R^3$ is ($C_2$-$C_6$ alkenyl)$_u$-$NH_2$, ($C_1$-$C_6$ alkyl)$_v$-NH($C_2$-$C_6$ alkenyl), ($C_2$-$C_6$ alkenyl)$_v$-NH($C_1$-$C_6$ alkyl), ($C_2$-$C_6$ alkenyl)$_v$-NH($C_2$-$C_6$ alkenyl), ($C_2$-$C_6$ alkenyl)$_v$-NH($C_2$-$C_6$ alkynyl), ($C_1$-$C_6$ alkyl)$_w$-N($C_2$-$C_6$ alkenyl)$_2$, ($C_2$-$C_6$ alkenyl)$_w$-N($C_1$-$C_6$ alkyl)$_2$, ($C_2$-$C_6$ alkenyl)$_w$-N($C_2$-$C_6$ alkenyl)$_2$, or ($C_2$-$C_6$ alkenyl)$_w$-N($C_2$-$C_6$ alkynyl)$_2$, and is optionally substituted with one or more $R^7$.

In one aspect, the present application relates to a compound of formula (A), wherein $R^3$ is ($C_2$-$C_6$ alkynyl)$_u$-$NH_2$, ($C_1$-$C_6$ alkyl)$_v$-NH($C_2$-$C_6$ alkynyl), ($C_2$-$C_6$ alkynyl)$_v$-NH($C_1$-$C_6$ alkyl), ($C_2$-$C_6$ alkynyl)$_v$-NH($C_2$-$C_6$ alkenyl), (cc3) ($C_2$-$C_6$ alkynyl)$_v$-NH($C_2$-$C_6$ alkynyl), ($C_1$-$C_6$ alkyl)$_w$-N($C_2$-$C_6$ alkynyl)$_2$, ($C_2$-$C_6$ alkynyl)$_w$-N($C_1$-$C_6$ alkyl)$_2$, ($C_2$-$C_6$ alkynyl)$_w$-N($C_2$-$C_6$ alkenyl)$_2$, or ($C_2$-$C_6$ alkynyl)$_w$-N($C_2$-$C_6$ alkynyl)$_2$, and is optionally substituted with one or more $R^7$.

In one aspect, the present application relates to a compound of formula (A), wherein $R^4$ is (a) H, (b) halogen, (c) OH, (d) COOH, (e) $CONH_2$, (f) $NHCOR^{101}$, (g) $NR^{101}COR^{102}$, (h) $S(O)_rR^{101}$, (i) $C_1$-$C_6$ alkyl, (l) O—($C_1$-$C_6$ alkyl), (o) COO—($C_1$-$C_6$ alkyl), (r) CONH—($C_1$-$C_6$ alkyl), (u) CON($C_1$-$C_6$ alkyl)$_2$, (x) ($C_1$-$C_6$ alkyl)$_u$-NH$_2$, (aa1) ($C_1$-$C_6$ alkyl)$_v$-NH($C_1$-$C_6$ alkyl), (dd1) ($C_1$-$C_6$ alkyl)$_w$-N($C_1$-$C_6$ alkyl)$_2$, (gg) 3-8 membered saturated, unsaturated, or partially saturated carbocycle, or (hh) 3-8 membered saturated, unsaturated, or partially saturated heterocycle, each of which is optionally substituted with one or more $R^7$.

In one aspect, the present application relates to a compound of formula (A), wherein $R^4$ is 5-6 membered saturated, unsaturated, or partially saturated carbocycle, and is optionally substituted with one or more $R^7$.

In one aspect, the present application relates to a compound of formula (A), wherein $R^4$ is H. In another aspect, $R^4$ is halogen (e.g., F, Cl, Br, or I). In a further aspect, $R^4$ is F. In another aspect, $R^4$ is $C_1$-$C_6$ alkyl (e.g., methyl, ethyl, propyl, i-propyl, butyl, i-butyl, t-butyl, pentyl, or hexyl). In a further aspect, $R^4$ is methyl. In another aspect, $R^4$ is OH. In another aspect, $R^4$ is O—$C_1$-$C_6$ alkyl (e.g., methyl, ethyl, propyl, i-propyl, butyl, i-butyl, t-butyl, pentyl, or hexyl). In a further aspect, $R^4$ is O-methyl.

In one aspect, the present application relates to a compound of formula (A), wherein $R^4$ is COOH, CONH$_2$, COO—($C_1$-$C_6$ alkyl), CONH—($C_1$-$C_6$ alkyl), CON($C_1$-$C_6$ alkyl)$_2$, and wherein $C_1$-$C_6$ alkyl is selected from methyl, ethyl, propyl, i-propyl, butyl, i-butyl, t-butyl, pentyl, and hexyl, and is optionally substituted with one or more $R^7$.

In one aspect, the present application relates to a compound of formula (A), wherein $R^4$ is NHCOR$^{101}$, NR$^{101}$COR$^{102}$, or S(O)$_r$R$^{101}$, and is optionally substituted with one or more $R^7$.

In one aspect, the present application relates to a compound of formula (A), wherein $R^4$ is ($C_1$-$C_6$ alkyl)$_u$-NH$_2$, ($C_1$-$C_6$ alkyl)$_v$-NH($C_1$-$C_6$ alkyl), ($C_1$-$C_6$ alkyl)$_w$-N($C_1$-$C_6$ alkyl)$_2$, and is optionally substituted with one or more $R^7$.

In one aspect, the present application relates to a compound of formula (A), wherein $R^4$ is 5-6 membered saturated, unsaturated, or partially saturated carbocycle, and is optionally substituted with one or more $R^7$.

In one aspect, the present application relates to a compound of formula (A), wherein $R^4$ is $C_2$-$C_6$ alkenyl, and is optionally substituted with one or more $R^7$.

In one aspect, the present application relates to a compound of formula (A), wherein $R^4$ is $C_2$-$C_6$ alkynyl, and is optionally substituted with one or more $R^7$.

In one aspect, the present application relates to a compound of formula (A), wherein $R^4$ is O—($C_2$-$C_6$ alkenyl), and is optionally substituted with one or more $R^7$.

In one aspect, the present application relates to a compound of formula (A), wherein $R^4$ is O—($C_2$-$C_6$ alkynyl), and is optionally substituted with one or more $R^7$.

In one aspect, the present application relates to a compound of formula (A), wherein $R^4$ is COO—($C_2$-$C_6$ alkenyl), CONH—($C_2$-$C_6$ alkenyl), or CON($C_2$-$C_6$ alkenyl)$_2$, and is optionally substituted with one or more $R^7$.

In one aspect, the present application relates to a compound of formula (A), wherein $R^4$ is COO—($C_2$-$C_6$ alkynyl), CONH—($C_2$-$C_6$ alkynyl), or CON($C_2$-$C_6$ alkynyl)$_2$, and is optionally substituted with one or more $R^7$.

In one aspect, the present application relates to a compound of formula (A), wherein $R^4$ is ($C_2$-$C_6$ alkenyl)$_u$-NH$_2$, ($C_1$-$C_6$ alkyl)$_v$-NH($C_2$-$C_6$ alkenyl), ($C_2$-$C_6$ alkenyl)$_v$-NH ($C_1$-$C_6$ alkyl), ($C_2$-$C_6$ alkenyl)$_v$-NH($C_2$-$C_6$ alkenyl), ($C_2$-$C_6$ alkenyl)$_v$-NH($C_2$-$C_6$ alkynyl), ($C_1$-$C_6$ alkyl)$_w$-N($C_2$-$C_6$ alkenyl)$_2$, ($C_2$-$C_6$ alkenyl)$_w$-N($C_1$-$C_6$ alkyl)$_2$, ($C_2$-$C_6$ alkenyl)$_w$-N($C_2$-$C_6$ alkenyl)$_2$, or ($C_2$-$C_6$ alkenyl)$_w$-N($C_2$-$C_6$ alkynyl)$_2$, and is optionally substituted with one or more $R^7$.

In one aspect, the present application relates to a compound of formula (A), wherein $R^4$ is ($C_2$-$C_6$ alkynyl)$_u$-NH$_2$, ($C_1$-$C_6$ alkyl)$_v$-NH($C_2$-$C_6$ alkynyl), ($C_2$-$C_6$ alkynyl)$_v$-NH ($C_1$-$C_6$ alkyl), ($C_2$-$C_6$ alkynyl)$_v$-NH($C_2$-$C_6$ alkenyl), (cc3) ($C_2$-$C_6$ alkynyl)$_v$-NH($C_2$-$C_6$ alkynyl), ($C_1$-$C_6$ alkyl)$_w$—N ($C_2$-$C_6$ alkynyl)$_2$, ($C_2$-$C_6$ alkynyl)$_w$-N($C_1$-$C_6$ alkyl)$_2$, ($C_2$-$C_6$ alkynyl)$_w$-N($C_2$-$C_6$ alkenyl)$_2$, or ($C_2$-$C_6$ alkynyl)$_w$-N($C_2$-$C_6$ alkynyl)$_2$, and is optionally substituted with one or more $R^7$.

In one aspect, the present application relates to a compound of formula (A), wherein $R^4$ is H; and $R^3$ is H. In another aspect, $R^4$ is H; and $R^3$ is halogen, OH, COOH, CONH$_2$, NHCOR$^{101}$, NR$^{101}$COR$^{102}$, $C_1$-$C_6$ alkyl, O—($C_1$-$C_6$ alkyl), COO—($C_1$-$C_6$ alkyl), CONH—($C_1$-$C_6$ alkyl), CON($C_1$-$C_6$ alkyl)$_2$, ($C_1$-$C_6$ alkyl)$_u$-NH$_2$, ($C_1$-$C_6$ alkyl)$_v$-NH ($C_1$-$C_6$ alkyl), ($C_1$-$C_6$ alkyl)$_w$-N($C_1$-$C_6$ alkyl)$_2$, or 5-6 membered saturated, unsaturated, or partially saturated carbocycle. In a further aspect, $R^4$ is H; and $R^3$ is halogen (e.g., F, Cl, Br, or I), $C_1$-$C_6$ alkyl (e.g., methyl, ethyl, propyl, propyl, butyl, i-butyl, t-butyl, pentyl, or hexyl), OH, or O—$C_1$-$C_6$ alkyl (e.g., methyl, ethyl, propyl, i-propyl, butyl, i-butyl, t-butyl, pentyl, or hexyl). In a further aspect, $R^4$ is H; and $R^3$ is F, methyl, or O-methyl.

In one aspect, the present application relates to a compound of formula (A), wherein $X_c$ is CR$^c$; $X_d$ is CR$^d$; R$^c$ is H; R$^d$ is H; $R^3$ is H, $C_1$-$C_6$ alkyl (e.g., methyl, ethyl, propyl, i-propyl, butyl, i-butyl, t-butyl, pentyl, or hexyl), or O—$C_1$-$C_6$ alkyl (e.g., methyl, ethyl, propyl, i-propyl, butyl, i-butyl, t-butyl, pentyl, or hexyl); and $R^4$ is H. In a further aspect, wherein $X_c$ is CR$^c$; $X_d$ is CR$^d$; R$^c$ is H; R$^d$ is H; $R^3$ is H, methyl, or O-methyl; and $R^4$ is H.

In one aspect, the present application relates to a compound of formula (A), wherein R$^{101}$ is H. In another aspect, R$^{101}$ is $C_1$-$C_6$ alkyl (e.g., methyl, ethyl, propyl, i-propyl, butyl, i-butyl, t-butyl, pentyl, or hexyl). In a further aspect, R$^{101}$ is methyl.

In one aspect, the present application relates to a compound of formula (A), wherein R$^{102}$ is H. In another aspect, R$^{102}$ is $C_1$-$C_6$ alkyl (e.g., methyl, ethyl, propyl, i-propyl, butyl, i-butyl, t-butyl, pentyl, or hexyl). In a further aspect, R$^{102}$ is methyl.

In one aspect, the present application relates to a compound of formula (A), wherein at least one $R^7$ is halogen (e.g., F, Cl, Br, or I), OH, or O—($C_1$-$C_6$ alkyl) (e.g., methyl, ethyl, propyl, i-propyl, butyl, i-butyl, t-butyl, pentyl, or hexyl). In a further aspect, at least one $R^7$ is F, OH, or O-methyl.

In one aspect, the present application relates to a compound of formula (A), wherein at least one $R^7$ is COO—($C_1$-$C_6$ alkyl), CONH—($C_1$-$C_6$ alkyl), CON($C_1$-$C_6$ alkyl)$_2$, or COOH.

In one aspect, the present application relates to a compound of formula (A), wherein at least one $R^7$ is CN or N$_3$.

In one aspect, the present application relates to a compound of formula (A), wherein at least one $R^7$ is 5-6 membered saturated, unsaturated, or partially saturated carbocycle, or 5-6 membered saturated, unsaturated, or partially saturated heterocycle comprising one or more heteroatoms selected from N, O and S.

In one aspect, the present application relates to a compound of formula (A), wherein $R^1$ is H, $C_1$-$C_6$ alkyl, or O—($C_1$-$C_6$ alkyl). In one aspect, $R^1$ is H. In another aspect, $R^1$ is $C_1$-$C_6$ alkyl (e.g., methyl, ethyl, propyl, i-propyl, butyl, i-butyl, t-butyl, pentyl, or hexyl). In a further aspect, $R^1$ is methyl. In another aspect, $R^1$ is O—$C_1$-$C_6$ alkyl (e.g., methyl, ethyl, propyl, i-propyl, butyl, i-butyl, t-butyl, pentyl, or hexyl). In a further aspect, $R^1$ is O-methyl.

In one aspect, the present application relates to a compound of formula (A), wherein $R^2$ is H, $C_1$-$C_6$ alkyl, or O—($C_1$-$C_6$ alkyl). In one aspect, the present application relates to a compound of formula (A), wherein $R^2$ is H. In another aspect, $R^2$ is $C_1$-$C_6$ alkyl (e.g., methyl, ethyl, propyl, i-propyl, butyl, i-butyl, t-butyl, pentyl, or hexyl). In a further aspect, $R^2$ is methyl. In another aspect, $R^2$ is O—$C_1$-$C_6$ alkyl (e.g., methyl, ethyl, propyl, i-propyl, butyl, i-butyl, t-butyl, pentyl, or hexyl). In a further aspect, $R^2$ is O-methyl.

In one aspect, the present application relates to a compound of formula (A), wherein $R^1$ is H; and $R^2$ is H. In another aspect, one of $R^1$ and $R^2$ is H, and the other is $C_1$-$C_6$ alkyl or O—($C_1$-$C_6$ alkyl).

In one aspect, the present application relates to a compound of formula (A), wherein one of $R^1$ and $R^2$, together with the carbon atom to which $R^1$ or $R^2$ is attached and ⓑ, form a 7-12 membered saturated, unsaturated, or partially saturated carbocycle. In a further aspect, one of $R^1$ and $R^2$, together with the carbon atom to which $R^1$ or $R^2$ is attached and ⓑ, form a dihydroindene. In one aspect, the present application relates to a compound of formula (A), wherein one of $R^1$ and $R^2$, together with the carbon atom to which $R^1$ or $R^2$ is attached and ⓑ, form a 7-12 membered saturated, unsaturated, or partially saturated heterocycle comprising one or more heteroatoms selected from N, O and S.

In one aspect, the present application relates to a compound of formula (A), wherein $R^1$ and $R^2$, together with the carbon atom to which they are attached, form a 3-8 membered saturated, unsaturated, or partially saturated carbocycle.

In one aspect, the present application relates to a compound of formula (A), wherein $R^1$ and $R^2$, together with the carbon atom to which they are attached, form a saturated, unsaturated, or partially saturated heterocycle comprising one or two 5-7 membered rings and one or more heteroatoms selected from N, O, and S In one aspect, the present application relates to a compound of formula (A), wherein ⓐ represents a saturated, unsaturated, or partially saturated carbocycle comprising one or two 3-8 membered rings, wherein the two 3-8 membered rings can form a fused or bridged ring structure.

In one aspect, the present application relates to a compound of formula (A), wherein ⓐ represents a saturated, unsaturated, or partially saturated heterocycle comprising one or two 5-8 membered rings and one or more heteroatoms selected from N, O and S, wherein the two 5-8 membered rings can form a fused or bridged ring structure.

In one aspect, the present application relates to a compound of formula (A), wherein ⓐ represents a 5-6 membered saturated, unsaturated, or partially saturated carbocycle. In another aspect, ⓐ represents a saturated, unsaturated, or partially saturated heterocycle comprising one or more heteroatoms selected from N, O and S. In a further aspect, ⓐ represents a saturated heterocycle comprising one or more heteroatoms selected from N, O and S, and is optionally substituted. In a further aspect, the heterocycle comprises a two-ring bridged ring system. In a further aspect, ⓐ represents an optionally substituted heterocycle selected from:

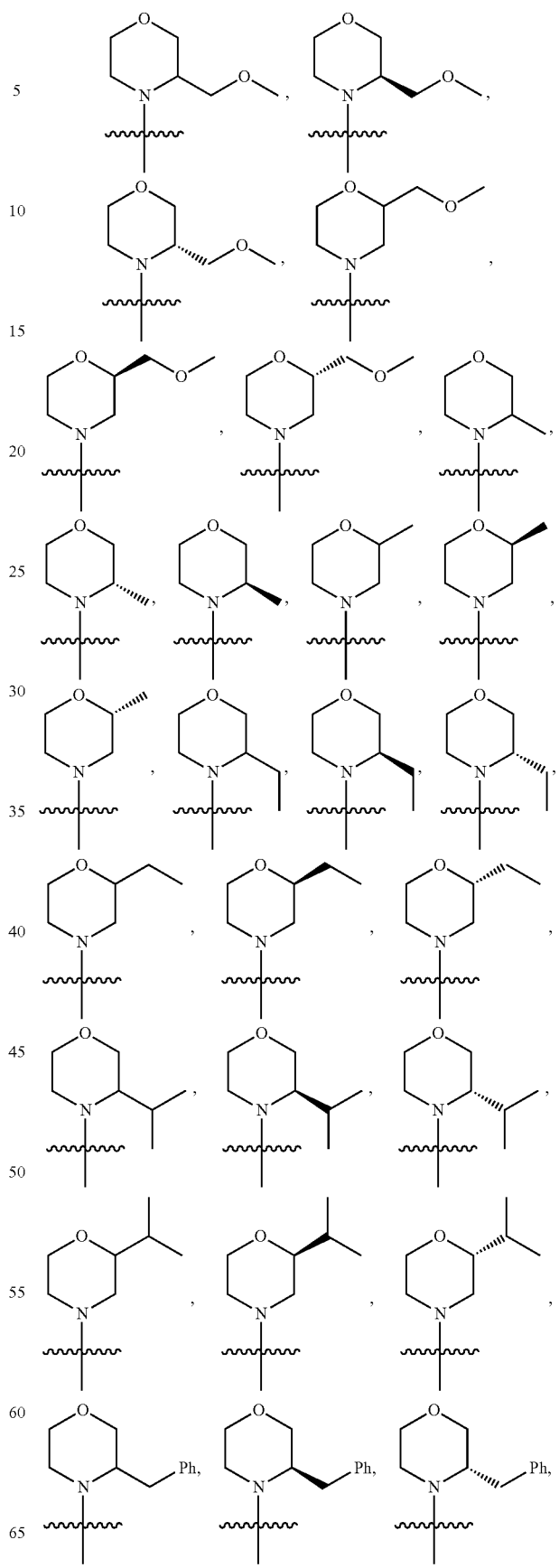

-continued

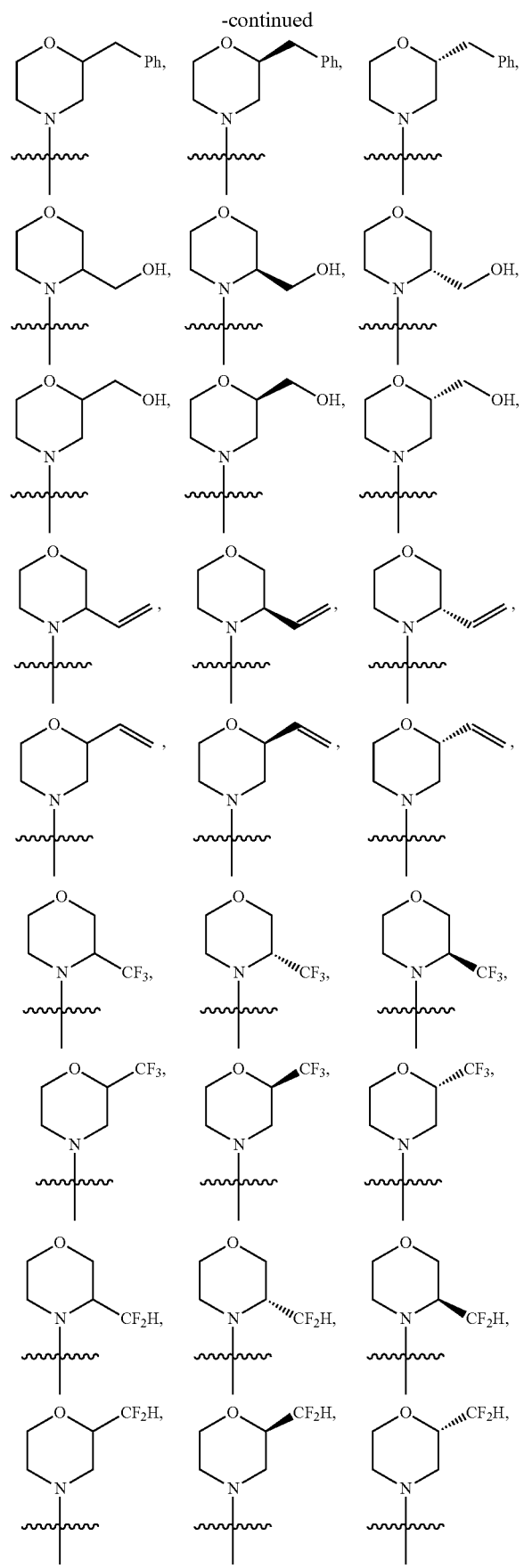

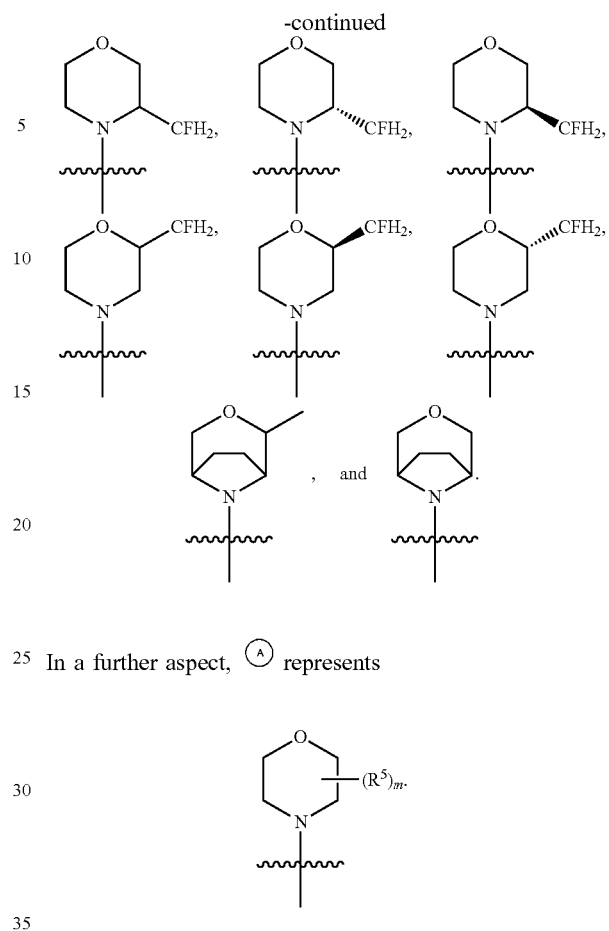

In a further aspect, Ⓐ represents

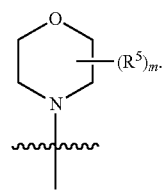

In one aspect, the present application relates to a compound of formula (A), wherein m is 1. In another aspect, m is 2. In another aspect, m is 3. In another aspect, m is 4. In another aspect, m is 5. In another aspect, m is 6.

In one aspect, the present application relates to a compound of formula (A), wherein $R^5$ is (a) halogen, (b) OH, (c) $CONH_2$, (d) COOH, (e) CN, (f) $N_3$, (g) $C_1$-$C_6$ alkyl, (h) $C_2$-$C_6$ alkenyl, (j) O—($C_1$-$C_6$ alkyl), (m) COO—($C_1$-$C_6$ alkyl), (p) CONH—($C_1$-$C_6$ alkyl), or (s) CON($C_1$-$C_6$ alkyl)$_2$, each of which is optionally substituted with one or more $R^8$.

In one aspect, the present application relates to a compound of formula (A), wherein at least one $R^5$ is halogen (e.g., F, Cl, Br, or I). In a further aspect, at least one $R^5$ is F. In another aspect, at least one $R^5$ is $C_1$-$C_6$ alkyl (e.g., methyl, ethyl, propyl, i-propyl, butyl, i-butyl, t-butyl, pentyl, or hexyl). In a further aspect, at least one $R^5$ is methyl. In another aspect, at least one $R^5$ is OH, CN, or $N_3$. In another aspect, at least one $R^5$ is O—$C_1$-$C_6$ alkyl (e.g., methyl, ethyl, propyl, i-propyl, butyl, i-butyl, t-butyl, pentyl, or hexyl). In a further aspect, at least one $R^5$ is O-methyl.

In one aspect, the present application relates to a compound of formula (A), wherein at least one $R^5$ is $C_2$-$C_6$ alkenyl.

In one aspect, the present application relates to a compound of formula (A), wherein at least one $R^5$ is $C_2$-$C_6$ alkynyl.

In one aspect, the present application relates to a compound of formula (A), wherein at least one $R^5$ is COO—($C_1$-$C_6$ alkyl), CONH—($C_1$-$C_6$ alkyl), CON($C_1$-$C_6$ alkyl)$_2$, $CONH_2$, or COOH.

In one aspect, the present application relates to a compound of formula (A), wherein at least one $R^5$ is CN.

In one aspect, the present application relates to a compound of formula (A), wherein at least one $R^5$ is $N_3$.

In one aspect, the present application relates to a compound of formula (A), wherein at least one $R^5$ is O—($C_2$-$C_6$ alkenyl).

In one aspect, the present application relates to a compound of formula (A), wherein at least one $R^5$ is O—($C_2$-$C_6$ alkynyl).

In one aspect, the present application relates to a compound of formula (A), wherein at least one $R^5$ is COO—($C_2$-$C_6$ alkenyl), CONH—($C_2$-$C_6$ alkenyl), or CON($C_2$-$C_6$ alkenyl)$_2$.

In one aspect, the present application relates to a compound of formula (A), wherein at least one $R^5$ is COO—($C_2$-$C_6$ alkynyl), CONH—($C_2$-$C_6$ alkynyl), or CON($C_2$-$C_6$ alkynyl)$_2$.

In one aspect, the present application relates to a compound of formula (A), wherein at least one $R^5$ is ($C_1$-$C_6$ alkyl)$_v$-NH($C_1$-$C_6$ alkyl), or ($C_1$-$C_6$ alkyl)$_w$-N($C_1$-$C_6$ alkyl)$_2$.

In one aspect, the present application relates to a compound of formula (A), wherein at least one $R^5$ is ($C_1$-$C_6$ alkyl)$_v$-NH($C_2$-$C_6$ alkenyl), ($C_2$-$C_6$ alkenyl)$_v$-NH($C_1$-$C_6$ alkyl), ($C_2$-$C_6$ alkenyl)$_v$-NH($C_2$-$C_6$ alkenyl), ($C_2$-$C_6$ alkenyl)$_v$-NH($C_2$-$C_6$ alkynyl), ($C_1$-$C_6$ alkyl)$_w$-N($C_2$-$C_6$ alkenyl)$_2$, ($C_2$-$C_6$ alkenyl)$_w$-N($C_1$-$C_6$ alkyl)$_2$, ($C_2$-$C_6$ alkenyl)$_w$-N($C_2$-$C_6$ alkenyl)$_2$, or ($C_2$-$C_6$ alkenyl)$_w$-N($C_2$-$C_6$ alkynyl)$_2$.

In one aspect, the present application relates to a compound of formula (A), wherein at least one $R^5$ is ($C_1$-$C_6$ alkyl)$_v$-NH($C_2$-$C_6$ alkynyl), ($C_2$-$C_6$ alkynyl)$_v$-NH($C_1$-$C_6$ alkyl), ($C_2$-$C_6$ alkynyl)$_v$-NH($C_2$-$C_6$ alkenyl), (cc3) ($C_2$-$C_6$ alkynyl)$_v$-NH($C_2$-$C_6$ alkynyl), ($C_1$-$C_6$ alkyl)$_w$-N($C_2$-$C_6$ alkynyl)$_2$, ($C_2$-$C_6$ alkynyl)$_w$-N($C_1$-$C_6$ alkyl)$_2$, ($C_2$-$C_6$ alkynyl)$_w$-N($C_2$-$C_6$ alkenyl)$_2$, ($C_2$-$C_6$ alkynyl)$_w$-N($C_2$-$C_6$ alkynyl)$_2$.

In one aspect, the present application relates to a compound of formula (A), wherein at least one $R^5$ is S(O)—($C_2$-$C_6$ alkenyl), S(O)$_2$—($C_2$-$C_6$ alkenyl), S—($C_2$-$C_6$ alkynyl), S(O)—($C_2$-$C_6$ alkynyl), or S(O)$_2$—($C_2$-$C_6$ alkynyl).

In one aspect, the present application relates to a compound of formula (A), wherein at least one $R^5$ is an aromatic, saturated, unsaturated, or partially saturated carbocycle comprising one or two 3-8 membered rings, or an aromatic, saturated, unsaturated, or partially saturated heterocycle comprising one or two 5-7 membered rings and one or more heteroatoms selected from N, O and S.

In one aspect, the present application relates to a compound of formula (A), wherein $R^5$ is in the S-configuration.

In one aspect, the present application relates to a compound of formula (A), wherein at least one $R^8$ is halogen (e.g., F, Cl, Br, or I), OH, O—($C_1$-$C_6$ alkyl) (e.g., methyl, ethyl, propyl, propyl, butyl, i-butyl, t-butyl, pentyl, or hexyl), or $C_1$-$C_6$ haloalkyl (e.g., $CHF_2$, $CH_2F$, $CF_3$, $CH_2CHF_2$, $CH_2CH_2F$, or $CH_2CF_3$). In a further aspect, at least one $R^8$ is F, OH, O-methyl, or $CF_3$.

In one aspect, the present application relates to a compound of formula (A), wherein at least one $R^8$ is COO—($C_1$-$C_6$ alkyl), CONH—($C_1$-$C_6$ alkyl), CON($C_1$-$C_6$ alkyl)$_2$, or COOH.

In one aspect, the present application relates to a compound of formula (A), wherein at least one $R^8$ is CN or $N_3$.

In one aspect, the present application relates to a compound of formula (A), wherein at least one $R^8$ is 5-6 membered saturated, unsaturated, or partially saturated carbocycle, or 5-6 membered saturated, unsaturated, or partially saturated heterocycle comprising one or more heteroatoms selected from N, O and S.

In one aspect, the present application relates to a compound of formula (A), wherein Ⓑ represents a saturated, unsaturated, or partially saturated carbocycle comprising one or two 3-8 membered rings, wherein the two 3-8 membered rings can form a fused or bridged ring structure.

In one aspect, the present application relates to a compound of formula (A), wherein Ⓑ represents a saturated, unsaturated, or partially saturated heterocycle comprising one or two 5-8 membered rings and one or more heteroatoms selected from N, O and S, wherein the two 5-8 membered rings can form a fused or bridged ring structure.

In one aspect, the present application relates to a compound of formula (A), wherein Ⓑ represents a 5-6 membered aromatic, saturated, unsaturated, or partially saturated carbocycle. In a further aspect, Ⓑ represents a 6 membered aromatic carbocycle (e.g., phenyl). In a further aspect, Ⓑ represents phenyl.

In one aspect, the present application relates to a compound of formula (A), wherein Ⓑ represents an aromatic, saturated, unsaturated, or partially saturated heterocycle comprising one or more heteroatoms selected from N, O and S. In a further aspect, Ⓑ represents an aromatic heterocycle comprising one or more heteroatoms selected from N, O and S (e.g., pyridine, pyrazine, or pyrimidine). In a further aspect, Ⓑ represents pyridine.

In one aspect, the present application relates to a compound of formula (A), wherein n is 0. In another aspect, n is 1, 2, 3, 4, 5, or 6. In a further aspect, n is 1.

In one aspect, the present application relates to a compound of formula (A), wherein $R^6$ is (a) halogen, (b) OH, (c) $CONH_2$, (d) COOH, (e) CN, (f) $N_3$, (g) $C_1$-$C_6$ alkyl, (h) $C_2$-$C_6$ alkenyl, (j) O—($C_1$-$C_6$ alkyl), (m) COO—($C_1$-$C_6$ alkyl), (p) CONH—($C_1$-$C_6$ alkyl), or (s) CON($C_1$-$C_6$ alkyl)$_2$, each of which is optionally substituted with one or more $R^9$.

In one aspect, the present application relates to a compound of formula (A), wherein at least one $R^6$ is halogen (e.g., F, Cl, Br, or I). In a further aspect, at least one $R^6$ is F. In a further aspect, $R^6$ is 2-fluoro or 4-fluoro. In a further aspect, $R^6$ is 2-fluoro. In a further aspect, $R^6$ is 4-fluoro. In another aspect, at least one $R^6$ is $C_1$-$C_6$ alkyl (e.g., methyl, ethyl, propyl, i-propyl, butyl, i-butyl, t-butyl, pentyl, or hexyl). In a further aspect, at least one $R^6$ is methyl. In another aspect, at least one $R^6$ is OH. In another aspect, at least one $R^6$ is O—$C_1$-$C_6$ alkyl (e.g., methyl, ethyl, propyl, i-propyl, butyl, i-butyl, t-butyl, pentyl, or hexyl). In a further aspect, at least one $R^6$ is O-methyl.

In one aspect, the present application relates to a compound of formula (A), wherein at least one $R^6$ is $C_2$-$C_6$ alkenyl.

In one aspect, the present application relates to a compound of formula (A), wherein at least one $R^6$ is $C_2$-$C_6$ alkynyl.

In one aspect, the present application relates to a compound of formula (A), wherein at least one $R^6$ is COO—($C_1$-$C_6$ alkyl), CONH—($C_1$-$C_6$ alkyl), CON($C_1$-$C_6$ alkyl)$_2$, $CONH_2$, or COOH.

In one aspect, the present application relates to a compound of formula (A), wherein at least one $R^6$ is CN.

In one aspect, the present application relates to a compound of formula (A), wherein at least one $R^6$ is $N_3$.

In one aspect, the present application relates to a compound of formula (A), wherein at least one $R^6$ is O—($C_2$-$C_6$ alkenyl).

In one aspect, the present application relates to a compound of formula (A), wherein at least one $R^6$ is O—($C_2$-$C_6$ alkynyl).

In one aspect, the present application relates to a compound of formula (A), wherein at least one $R^6$ is COO—($C_2$-$C_6$ alkenyl), CONH—($C_2$-$C_6$ alkenyl), or CON($C_2$-$C_6$ alkenyl)$_2$.

In one aspect, the present application relates to a compound of formula (A), wherein at least one $R^6$ is COO—($C_2$-$C_6$ alkynyl), CONH—($C_2$-$C_6$ alkynyl), or CON($C_2$-$C_6$ alkynyl)$_2$.

In one aspect, the present application relates to a compound of formula (A), wherein at least one $R^6$ is ($C_1$-$C_6$ alkyl)$_v$-NH($C_1$-$C_6$ alkyl), or ($C_1$-$C_6$ alkyl)$_w$-N($C_1$-$C_6$ alkyl)$_2$.

In one aspect, the present application relates to a compound of formula (A), wherein at least one $R^6$ is ($C_1$-$C_6$ alkyl)$_v$-NH($C_2$-$C_6$ alkenyl), ($C_2$-$C_6$ alkenyl)$_v$-NH($C_1$-$C_6$ alkyl), ($C_2$-$C_6$ alkenyl)$_v$-NH($C_2$-$C_6$ alkenyl), ($C_2$-$C_6$ alkenyl)$_v$-NH($C_2$-$C_6$ alkynyl), ($C_1$-$C_6$ alkyl)$_w$-N($C_2$-$C_6$ alkenyl)$_2$, ($C_2$-$C_6$ alkenyl)$_w$-N($C_1$-$C_6$ alkyl)$_2$, ($C_2$-$C_6$ alkenyl)$_w$-N($C_2$-$C_6$ alkenyl)$_2$, or ($C_2$-$C_6$ alkenyl)$_w$-N($C_2$-$C_6$ alkynyl)$_2$.

In one aspect, the present application relates to a compound of formula (A), wherein at least one $R^6$ is ($C_1$-$C_6$ alkyl)$_v$-NH($C_2$-$C_6$ alkynyl), ($C_2$-$C_6$ alkynyl)$_v$-NH($C_1$-$C_6$ alkyl), ($C_2$-$C_6$ alkynyl)$_v$-NH($C_2$-$C_6$ alkenyl), (cc3) ($C_2$-$C_6$ alkynyl)$_v$-NH($C_2$-$C_6$ alkynyl), ($C_1$-$C_6$ alkyl)$_w$-N($C_2$-$C_6$ alkynyl)$_2$, ($C_2$-$C_6$ alkynyl)$_w$-N($C_1$-$C_6$ alkyl)$_2$, ($C_2$-$C_6$ alkynyl)$_w$-N($C_2$-$C_6$ alkenyl)$_2$, ($C_2$-$C_6$ alkynyl)$_w$-N($C_2$-$C_6$ alkynyl)$_2$.

In one aspect, the present application relates to a compound of formula (A), wherein at least one $R^6$ is S(O)—($C_2$-$C_6$ alkenyl), S(O)$_2$—($C_2$-$C_6$ alkenyl), S—($C_2$-$C_6$ alkynyl), S(O)—($C_2$-$C_6$ alkynyl), or S(O)$_2$—($C_2$-$C_6$ alkynyl).

In one aspect, the present application relates to a compound of formula (A), wherein at least one $R^6$ is an aromatic, saturated, unsaturated, or partially saturated carbocycle comprising one or two 3-8 membered rings, or an aromatic, saturated, unsaturated, or partially saturated heterocycle comprising one or two 5-7 membered rings and one or more heteroatoms selected from N, O and S.

In one aspect, the present application relates to a compound of formula (A), wherein at least one $R^6$ is bonded to the 2- or 4-position of Ⓑ. In a further aspect, at least one $R^6$ is 2-F, 2-methyl, 2-OH, 2-O-methyl, 2-CN, or 2-$N_3$. In another aspect, at least one $R^6$ is 4-F, 4-methyl, 4-OH, 4-O-methyl, 4-CN, or 4-$N_3$. In a further aspect, Ⓑ is phenyl or pyridine; and at least one $R^6$ is 2-F, 2-methyl, 2-OH, 2-O-methyl, 2-CN, or 2-$N_3$. In another aspect, Ⓑ is phenyl or pyridine; and at least one $R^6$ is 4-F, 4-methyl, 4-OH, 4-O-methyl, 4-CN, or 4-$N_3$.

In one aspect, the present application relates to a compound of formula (A), wherein at least one $R^9$ is halogen (e.g., F, Cl, Br, or I), OH, or O—($C_1$-$C_6$ alkyl) (e.g., methyl, ethyl, propyl, i-propyl, butyl, i-butyl, t-butyl, pentyl, or hexyl). In a further aspect, at least one $R^9$ is F, OH, or O-methyl.

In one aspect, the present application relates to a compound of formula (A), wherein at least one $R^9$ is COO—($C_1$-$C_6$ alkyl), CONH—($C_1$-$C_6$ alkyl), CON($C_1$-$C_6$ alkyl)$_2$, or COOH.

In one aspect, the present application relates to a compound of formula (A), wherein at least one $R^9$ is CN or $N_3$.

In one aspect, the present application relates to a compound of formula (A), wherein at least one $R^9$ is 5-6 membered saturated, unsaturated, or partially saturated carbocycle, or 5-6 membered saturated, unsaturated, or partially saturated heterocycle comprising one or more heteroatoms selected from N, O and S.

The present application relates to a compound of formula (I):

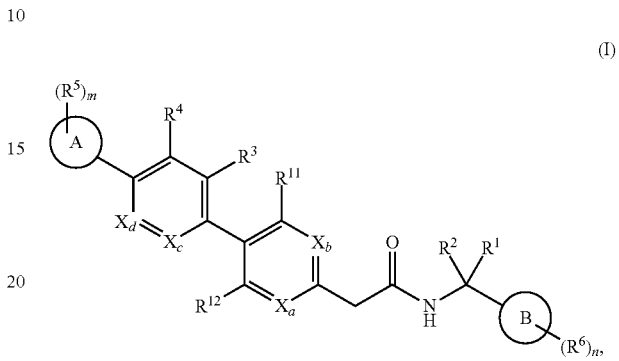

(I)

or a pharmaceutically acceptable salt, solvate, or prodrug thereof, wherein:

$X_a$ is $CR^a$ or N;
$X_b$ is $CR^b$ or N;
$X_c$ is $CR^c$ or N;
$X_d$ is $CR^d$ or N;
$R^a$ is H, halogen, or $C_1$-$C_6$ alkyl;
$R^b$ is H, halogen, or $C_1$-$C_6$ alkyl;
$R^c$ is H, halogen, or $C_1$-$C_6$ alkyl;
$R^d$ is H, halogen, or $C_1$-$C_6$ alkyl;
$R^1$ and $R^2$ are each independently H, $C_1$-$C_6$ alkyl, or O—($C_1$-$C_6$ alkyl);

alternatively, one of $R^1$ and $R^2$, together with the carbon atom to which $R^1$ or $R^2$ is attached and Ⓑ, form a 7-12 membered saturated, unsaturated, or partially saturated carbocycle, or a 7-12 membered saturated, unsaturated, or partially saturated heterocycle containing one or more heteroatoms selected from N, O and S;

$R^3$ and $R^4$ are each independently (a) H, (b) halogen, (c) OH, (d) COOH, (e) CONH$_2$, (f) NHCOR$^{101}$, (g) NR$^{101}$COR$^{102}$, (h) S(O)$_r$R$^{101}$, (i) $C_1$-$C_6$ alkyl, (j) O—($C_1$-$C_6$ alkyl), (k) COO—($C_1$-$C_6$ alkyl), (l) CONH—($C_1$-$C_6$ alkyl), (m) CON($C_1$-$C_6$ alkyl)$_2$, (n) ($C_1$-$C_6$ alkyl)$_u$-NH$_2$, (o) ($C_1$-$C_6$ alkyl)$_v$-NH($C_1$-$C_6$ alkyl), (p) ($C_1$-$C_6$ alkyl)$_w$-N($C_1$-$C_6$ alkyl)$_2$, or (q) 5-6 membered saturated, unsaturated, or partially saturated carbocycle, wherein each of (i)-(q) is optionally substituted with one or more $R^7$;

Ⓐ represents a 5-6 membered saturated, unsaturated, or partially saturated carbocycle, or a 5-6 membered saturated, unsaturated, or partially saturated heterocycle containing one or more heteroatoms selected from N, O and S;

Ⓑ represents a 5-6 membered aromatic, saturated, unsaturated, or partially saturated carbocycle, or a 5-6 membered aromatic, saturated, unsaturated, or partially saturated heterocycle containing one or more heteroatoms selected from N, O and S;

each $R^5$ is independently (a) halogen, (b) OH, (c) $C_1$-$C_6$ alkyl, (d) $C_2$-$C_6$ alkenyl, (e) O—($C_1$-$C_6$ alkyl), (f) COO—($C_1$-$C_6$ alkyl), (g) CONH—($C_1$-$C_6$ alkyl), (h) CON($C_1$-$C_6$ alkyl)$_2$, (i) COOH, (j) CN, or (k) N$_3$, wherein each of (c)-(h) is optionally substituted with one or more R$^8$;

each R$^6$ is independently (a) halogen, (b) OH, (c) C$_1$-C$_6$ alkyl, (d) C$_2$-C$_6$ alkenyl, (e) O—(C$_1$-C$_6$ alkyl), (f) COO—(C$_1$-C$_6$ alkyl), (g) CONH—(C$_1$-C$_6$ alkyl), (h) CON(C$_1$-C$_6$ alkyl)$_2$, (i) COOH, (j) CN, or (k) N$_3$, wherein each of (c)-(h) is optionally substituted with one or more R$^9$;

each R$^7$ is independently halogen, OH, O—(C$_1$-C$_6$ alkyl), COO—(C$_1$-C$_6$ alkyl), CONH—(C$_1$-C$_6$ alkyl), CON(C$_1$-C$_6$ alkyl)$_2$, COOH, CN, N$_3$, 5-6 membered saturated, unsaturated, or partially saturated carbocycle, or 5-6 membered saturated, unsaturated, or partially saturated heterocycle containing one or more heteroatoms selected from N, O and S;

each R$^8$ is independently halogen, OH, O—(C$_1$-C$_6$ alkyl), C$_1$-C$_6$ haloalkyl, COO—(C$_1$-C$_6$ alkyl), CONH—(C$_1$-C$_6$ alkyl), CON(C$_1$-C$_6$ alkyl)$_2$, COOH, CN, N$_3$, 5-6 membered saturated, unsaturated, or partially saturated carbocycle, or 5-6 membered saturated, unsaturated, or partially saturated heterocycle containing one or more heteroatoms selected from N, O and S;

each R$^9$ is independently halogen, OH, O—(C$_1$-C$_6$ alkyl), COO—(C$_1$-C$_6$ alkyl), CONH—(C$_1$-C$_6$ alkyl), CON(C$_1$-C$_6$ alkyl)$_2$, COOH, CN, N$_3$, 5-6 membered saturated, unsaturated, or partially saturated carbocycle, or 5-6 membered saturated, unsaturated, or partially saturated heterocycle containing one or more heteroatoms selected from N, O and S;

R$^{101}$ and R$^{102}$ are each independently H or C$_1$-C$_6$ alkyl;
R$^{11}$ is H, halogen, or C$_1$-C$_6$ alkyl;
R$^{12}$ is H, halogen, or C$_1$-C$_6$ alkyl;
m is 1, 2, 3, 4, 5, or 6;
n is 0, 1, 2, 3, 4, 5, or 6;
t is 0, 1, or 2;
u is 0 or 1;
v is 0 or 1; and
w is 0 or 1,
provided that when m is 1,

is not

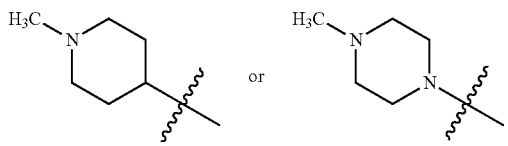

In one aspect, the present application relates to a compound of formula (I), wherein X$_a$ is CR$^a$; and X$_b$ is CR$^b$. In another aspect, X$_a$ is CR$^a$; and X$_b$ is N. In another aspect, X$_a$ is N; and X$_b$ is CR$^b$. In another aspect, X$_a$ is N; and X$_b$ is N.

In one aspect, the present application relates to a compound of formula (I), wherein R$^a$ is H. In another aspect, R$^a$ is halogen (e.g., F, Cl, Br, or I). In a further aspect, R$^a$ is F. In another aspect, R$^a$ is C$_1$-C$_6$ alkyl (e.g., methyl, ethyl, propyl, i-propyl, butyl, i-butyl, t-butyl, pentyl, or hexyl). In a further aspect, R$^a$ is methyl.

In one aspect, the present application relates to a compound of formula (I), wherein R$^b$ is H. In another aspect, R$^b$ is halogen (e.g., F, Cl, Br, or I). In a further aspect, R$^b$ is F. In another aspect, R$^b$ is C$_1$-C$_6$ alkyl (e.g., methyl, ethyl, propyl, i-propyl, butyl, i-butyl, t-butyl, pentyl, or hexyl). In a further aspect, R$^b$ is methyl.

In one aspect, the present application relates to a compound of formula (I), wherein R$^a$ is H; and R$^b$ is H. In another aspect, one of R$^a$ and R$^b$ is H, and the other is halogen (e.g., F, Cl, Br, or I) or C$_1$-C$_6$ alkyl (e.g., methyl, ethyl, propyl, i-propyl, butyl, i-butyl, t-butyl, pentyl, or hexyl).

In one aspect, the present application relates to a compound of formula (I), wherein X$_a$ is N; X$_b$ is CR$^b$; and R$^b$ is H. In another aspect, X$_b$ is N; X$_a$ is CR$^a$; and R$^a$ is H.

In one aspect, the present application relates to a compound of formula (I), wherein R$^{11}$ is H. In another aspect, R$^{11}$ is halogen (e.g., F, Cl, Br, or I). In a further aspect, R$^{11}$ is F. In another aspect, R$^{11}$ is C$_1$-C$_6$ alkyl (e.g., methyl, ethyl, propyl, i-propyl, butyl, i-butyl, t-butyl, pentyl, or hexyl). In a further aspect, R$^{11}$ is methyl.

In one aspect, the present application relates to a compound of formula (I), wherein R$^{12}$ is H. In another aspect, R$^{12}$ is halogen (e.g., F, Cl, Br, or I). In a further aspect, R$^{12}$ is F. In another aspect, R$^{12}$ is C$_1$-C$_6$ alkyl (e.g., methyl, ethyl, propyl, i-propyl, butyl, i-butyl, t-butyl, pentyl, or hexyl). In a further aspect, R$^{12}$ is methyl.

In one aspect, the present application relates to a compound of formula (I), wherein X$_a$ is N; X$_b$ is CR$^b$; R$^b$ is H; R$^{11}$ is methyl; and R$^{12}$ is H. In another aspect, X$_a$ is N; X$_b$ is CR$^b$; R$^b$ is H; R$^{12}$ is methyl; and R$^{11}$ is H. In another aspect, X$_a$ is N; X$_b$ is CR$^b$; R$^b$ is H; R$^{11}$ is H; and R$^{12}$ is H.

In one aspect, the present application relates to a compound of formula (I), wherein X$_b$ is N; X$_a$ is CR$^a$; R$^a$ is H; R$^{11}$ is methyl; and R$^{12}$ is H. In another aspect, X$_b$ is N; X$_a$ is CR$^a$; R$^a$ is H; R$^{12}$ is methyl; and R$^{11}$ is H. In another aspect, X$_b$ is N; X$_a$ is CR$^a$; R$^a$ is H; R$^{11}$ is H; and R$^{12}$ is H.

In one aspect, the present application relates to a compound of formula (I), wherein X$_c$ is CR$^c$; and X$_d$ is CR$^d$. In another aspect, X$_c$ is CR$^c$; and X$_d$ is N. In another aspect, X$_c$ is N; and X$_d$ is CR$^d$. In another aspect, X$_c$ is N; and X$_d$ is N.

In one aspect, the present application relates to a compound of formula (I), wherein R$^c$ is H. In another aspect, R$^c$ is halogen (e.g., F, Cl, Br, or I). In a further aspect, R$^c$ is F. In another aspect, R$^c$ is C$_1$-C$_6$ alkyl (e.g., methyl, ethyl, propyl, i-propyl, butyl, i-butyl, t-butyl, pentyl, or hexyl). In a further aspect, R$^c$ is methyl.

In one aspect, the present application relates to a compound of formula (I), wherein R$^d$ is H. In another aspect, R$^d$ is halogen (e.g., F, Cl, Br, or I). In a further aspect, R$^d$ is F. In another aspect, R$^d$ is C$_1$-C$_6$ alkyl (e.g., methyl, ethyl, propyl, i-propyl, butyl, i-butyl, t-butyl, pentyl, or hexyl). In a further aspect, R$^d$ is methyl.

In one aspect, the present application relates to a compound of formula (I), wherein R$^c$ is H; and R$^d$ is H. In another aspect, one of R$^c$ and R$^d$ is H, and the other is halogen (e.g., F, Cl, Br, or I) or C$_1$-C$_6$ alkyl (e.g., methyl, ethyl, propyl, i-propyl, butyl, i-butyl, t-butyl, pentyl, or hexyl).

In one aspect, the present application relates to a compound of formula (I), wherein X$_c$ is CR$^c$; X$_d$ is CR$^d$; R$^c$ is H; and R$^d$ is H.

In one aspect, the present application relates to a compound of formula (I), wherein X$_c$ is N; X$_d$ is CR$^d$; and R$^d$ is H. In another aspect, X$_d$ is N; X$_c$ is CR$^c$; and R$^c$ is H.

In one aspect, the present application relates to a compound of formula (I), wherein R$^3$ is H. In another aspect, R$^3$ is halogen (e.g., F, Cl, Br, or I). In a further aspect, R$^3$ is F. In another aspect, R$^3$ is C$_1$-C$_6$ alkyl (e.g., methyl, ethyl, propyl, i-propyl, butyl, i-butyl, t-butyl, pentyl, or hexyl). In a further aspect, $R^3$ is methyl. In another aspect, $R^3$ is OH. In another aspect, $R^3$ is O—$C_1$-$C_6$ alkyl (e.g., methyl, ethyl, propyl, i-propyl, butyl, i-butyl, t-butyl, pentyl, or hexyl). In a further aspect, $R^3$ is O-methyl.

In one aspect, the present application relates to a compound of formula (I), wherein $R^3$ is COOH, $CONH_2$, COO—($C_1$-$C_6$ alkyl), CONH—($C_1$-$C_6$ alkyl), CON($C_1$-$C_6$ alkyl)$_2$, and wherein $C_1$-$C_6$ alkyl is selected from methyl, ethyl, propyl, i-propyl, butyl, i-butyl, t-butyl, pentyl, and hexyl, and is optionally substituted with one or more $R^7$.

In one aspect, the present application relates to a compound of formula (I), wherein $R^3$ is $NHCOR^{101}$, $NR^{101}COR^{102}$, or $S(O)_tR^{101}$, and is optionally substituted with one or more $R^7$. In one aspect, the present application relates to a compound of formula (I), wherein $R^3$ is ($C_1$-$C_6$ alkyl)$_u$-$NH_2$, ($C_1$-$C_6$ alkyl)$_v$-NH($C_1$-$C_6$ alkyl), ($C_1$-$C_6$ alkyl)$_w$-N($C_1$-$C_6$ alkyl)$_2$, and is optionally substituted with one or more $R^7$.

In one aspect, the present application relates to a compound of formula (I), wherein $R^3$ is 5-6 membered saturated, unsaturated, or partially saturated carbocycle, and is optionally substituted with one or more $R^7$.

In one aspect, the present application relates to a compound of formula (I), wherein $R^4$ is H. In another aspect, $R^4$ is halogen (e.g., F, Cl, Br, or I). In a further aspect, $R^4$ is F. In another aspect, $R^4$ is $C_1$-$C_6$ alkyl (e.g., methyl, ethyl, propyl, i-propyl, butyl, i-butyl, t-butyl, pentyl, or hexyl). In a further aspect, $R^4$ is methyl. In another aspect, $R^4$ is OH. In another aspect, $R^4$ is O—$C_1$-$C_6$ alkyl (e.g., methyl, ethyl, propyl, i-propyl, butyl, i-butyl, t-butyl, pentyl, or hexyl). In a further aspect, $R^4$ is O-methyl.

In one aspect, the present application relates to a compound of formula (I), wherein $R^4$ is COOH, $CONH_2$, COO—($C_1$-$C_6$ alkyl), CONH—($C_1$-$C_6$ alkyl), CON($C_1$-$C_6$ alkyl)$_2$, and wherein $C_1$-$C_6$ alkyl is selected from methyl, ethyl, propyl, i-propyl, butyl, i-butyl, t-butyl, pentyl, and hexyl, and is optionally substituted with one or more $R^7$.

In one aspect, the present application relates to a compound of formula (I), wherein $R^4$ is $NHCOR^{101}$, $NR^{101}COR^{102}$, or $S(O)_tR^{101}$, and is optionally substituted with one or more $R^7$.

In one aspect, the present application relates to a compound of formula (I), wherein $R^4$ is ($C_1$-$C_6$ alkyl)$_u$-$NH_2$, ($C_1$-$C_6$ alkyl)$_v$-NH($C_1$-$C_6$ alkyl), ($C_1$-$C_6$ alkyl)$_w$-N($C_1$-$C_6$ alkyl)$_2$, and is optionally substituted with one or more $R^7$.

In one aspect, the present application relates to a compound of formula (I), wherein $R^4$ is 5-6 membered saturated, unsaturated, or partially saturated carbocycle, and is optionally substituted with one or more $R^7$.

In one aspect, the present application relates to a compound of formula (I), wherein $R^4$ is H; and $R^3$ is H. In another aspect, $R^4$ is H; and $R^3$ is halogen, OH, COOH, $CONH_2$, $NHCOR^{101}$, $NR^{101}COR^{102}$, $S(O)_tR^{101}$, $C_1$-$C_6$ alkyl, O—($C_1$-$C_6$ alkyl), COO—($C_1$-$C_6$ alkyl), CONH—($C_1$-$C_6$ alkyl), CON($C_1$-$C_6$ alkyl)$_2$, ($C_1$-$C_6$ alkyl)$_u$-$NH_2$, ($C_1$-$C_6$ alkyl)$_v$-NH($C_1$-$C_6$ alkyl), ($C_1$-$C_6$ alkyl)$_w$-N($C_1$-$C_6$ alkyl)$_2$, or 5-6 membered saturated, unsaturated, or partially saturated carbocycle. In a further aspect, $R^4$ is H; and $R^3$ is halogen (e.g., F, Cl, Br, or I), $C_1$-$C_6$ alkyl (e.g., methyl, ethyl, propyl, i-propyl, butyl, i-butyl, t-butyl, pentyl, or hexyl), OH, or O—$C_1$-$C_6$ alkyl (e.g., methyl, ethyl, propyl, i-propyl, butyl, i-butyl, t-butyl, pentyl, or hexyl). In a further aspect, $R^4$ is H; and $R^3$ is F, methyl, or O-methyl.

In one aspect, the present application relates to a compound of formula (I), wherein $X_c$ is $CR^c$; $X_d$ is $CR^d$; $R^c$ is H; $R^d$ is H; $R^3$ is H, $C_1$-$C_6$ alkyl (e.g., methyl, ethyl, propyl, i-propyl, butyl, i-butyl, t-butyl, pentyl, or hexyl), or O—$C_1$-$C_6$ alkyl (e.g., methyl, ethyl, propyl, i-propyl, butyl, i-butyl, t-butyl, pentyl, or hexyl); and $R^4$ is H. In a further aspect, wherein $X_c$ is $CR^c$; $X_d$ is $CR^d$; $R^c$ is H; $R^d$ is H; $R^3$ is H, methyl, or O-methyl; and $R^4$ is H.

In one aspect, the present application relates to a compound of formula (I), wherein $R^{101}$ is H. In another aspect, $R^{101}$ is $C_1$-$C_6$ alkyl (e.g., methyl, ethyl, propyl, i-propyl, butyl, i-butyl, t-butyl, pentyl, or hexyl). In a further aspect, $R^{101}$ is methyl.

In one aspect, the present application relates to a compound of formula (I), wherein $R^{102}$ is H. In another aspect, $R^{102}$ is $C_1$-$C_6$ alkyl (e.g., methyl, ethyl, propyl, i-propyl, butyl, i-butyl, t-butyl, pentyl, or hexyl). In a further aspect, $R^{102}$ is methyl.

In one aspect, the present application relates to a compound of formula (I), wherein at least one $R^7$ is halogen (e.g., F, Cl, Br, or I), OH, or O—($C_1$-$C_6$ alkyl) (e.g., methyl, ethyl, propyl, i-propyl, butyl, i-butyl, t-butyl, pentyl, or hexyl). In a further aspect, at least one $R^7$ is F, OH, or O-methyl.

In one aspect, the present application relates to a compound of formula (I), wherein at least one $R^7$ is COO—($C_1$-$C_6$ alkyl), CONH—($C_1$-$C_6$ alkyl), CON($C_1$-$C_6$ alkyl)$_2$, or COOH.

In one aspect, the present application relates to a compound of formula (I), wherein at least one $R^7$ is CN or $N_3$.

In one aspect, the present application relates to a compound of formula (I), wherein at least one $R^7$ is 5-6 membered saturated, unsaturated, or partially saturated carbocycle, or 5-6 membered saturated, unsaturated, or partially saturated heterocycle containing one or more heteroatoms selected from N, O and S.

In one aspect, the present application relates to a compound of formula (I), wherein $R^1$ is H. In another aspect, $R^1$ is $C_1$-$C_6$ alkyl (e.g., methyl, ethyl, propyl, i-propyl, butyl, i-butyl, t-butyl, pentyl, or hexyl). In a further aspect, $R^1$ is methyl. In another aspect, $R^1$ is O—$C_1$-$C_6$ alkyl (e.g., methyl, ethyl, propyl, i-propyl, butyl, i-butyl, t-butyl, pentyl, or hexyl). In a further aspect, $R^1$ is O-methyl.

In one aspect, the present application relates to a compound of formula (I), wherein $R^2$ is H. In another aspect, $R^2$ is $C_1$-$C_6$ alkyl (e.g., methyl, ethyl, propyl, i-propyl, butyl, i-butyl, t-butyl, pentyl, or hexyl). In a further aspect, $R^2$ is methyl. In another aspect, $R^2$ is O—$C_1$-$C_6$ alkyl (e.g., methyl, ethyl, propyl, i-propyl, butyl, i-butyl, t-butyl, pentyl, or hexyl). In a further aspect, $R^2$ is O-methyl.

In one aspect, the present application relates to a compound of formula (I), wherein $R^1$ is H; and $R^2$ is H. In another aspect, one of $R^1$ and $R^2$ is H, and the other is $C_1$-$C_6$ alkyl or O—($C_1$-$C_6$ alkyl).

In one aspect, the present application relates to a compound of formula (I), wherein one of $R^1$ and $R^2$, together with the carbon atom to which $R^1$ or $R^2$ is attached and ⓑ, form a 7-12 membered saturated, unsaturated, or partially saturated carbocycle. In a further aspect, one of $R^1$ and $R^2$, together with the carbon atom to which $R^1$ or $R^2$ is attached and ⓑ, form a dihydroindene, i.e., indane or benzocyclopentane. In one aspect, the present application relates to a compound of formula (I), wherein one of $R^1$ and $R^2$, together with the carbon atom to which $R^1$ or $R^2$ is attached and ⓑ, form a 7-12 membered saturated, unsaturated, or partially saturated heterocycle containing one or more heteroatoms selected from N, O and S.

In one aspect, the present application relates to a compound of formula (I), wherein Ⓐ represents a 5-6 membered saturated, unsaturated, or partially saturated carbocycle. In another aspect, Ⓐ represents a saturated, unsaturated, or partially saturated heterocycle containing one or more heteroatoms selected from N, O and S. In a further aspect, Ⓐ represents a saturated heterocycle containing one or more heteroatoms selected from N, O and S, and is optionally substituted. In a further aspect, the heterocycle comprises a two-ring bridged ring system. In a further aspect, Ⓐ represents an optionally substituted heterocycle selected from:

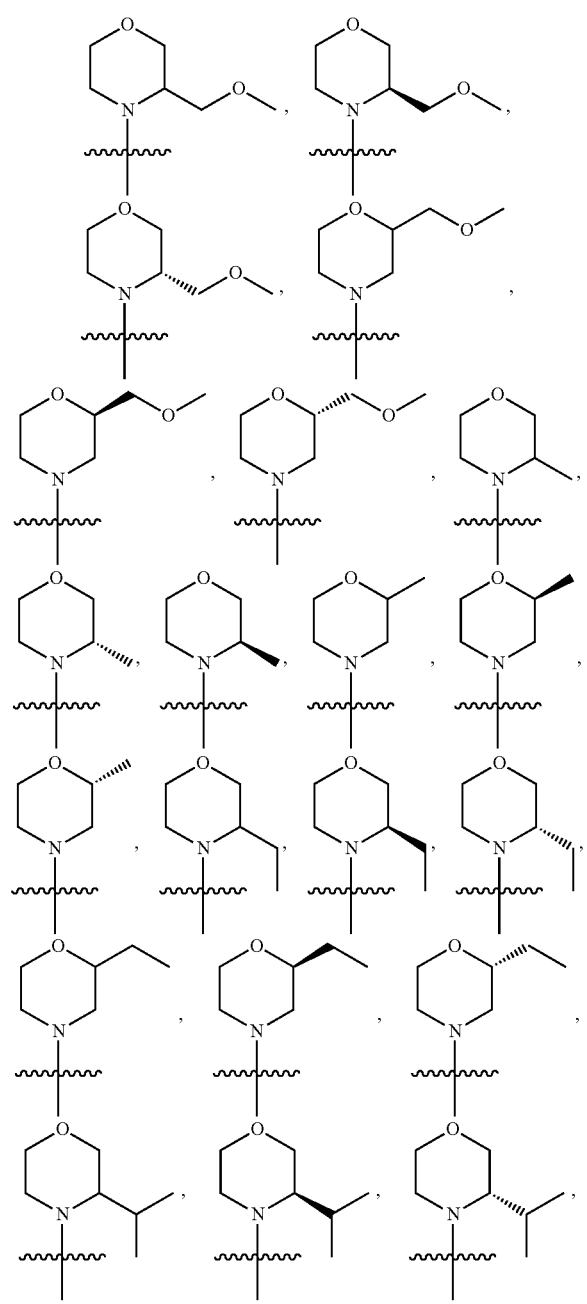

-continued

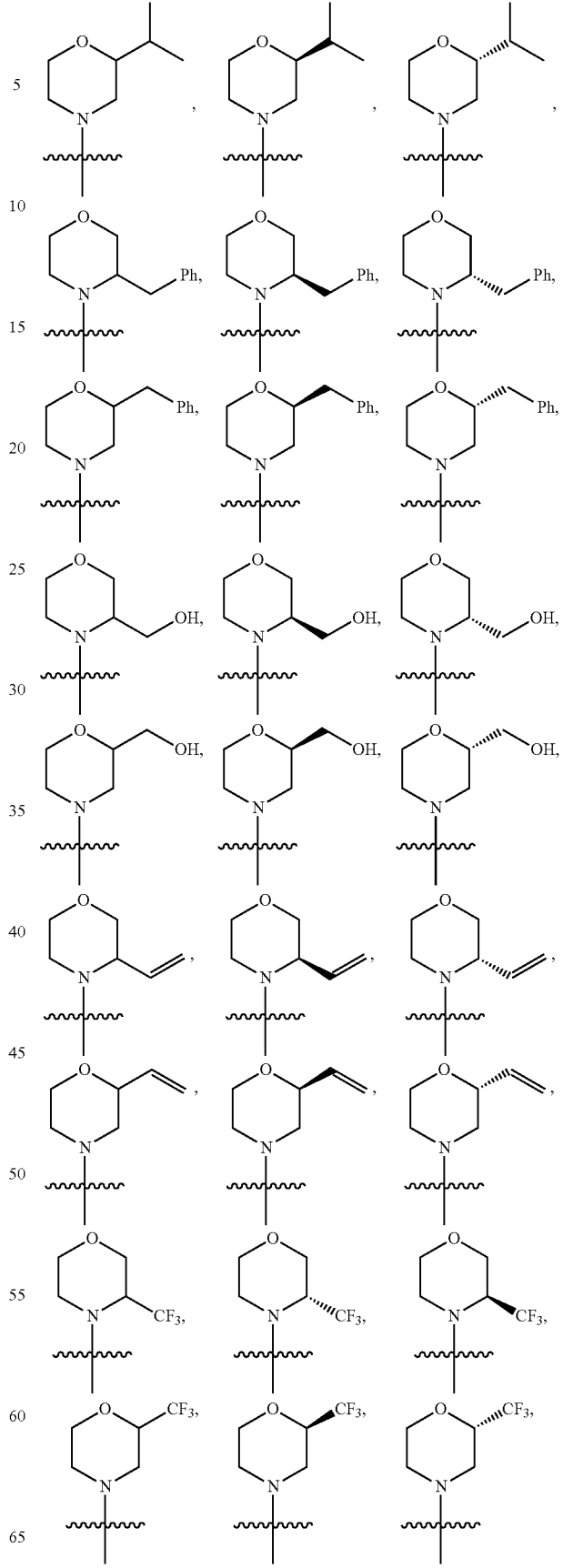

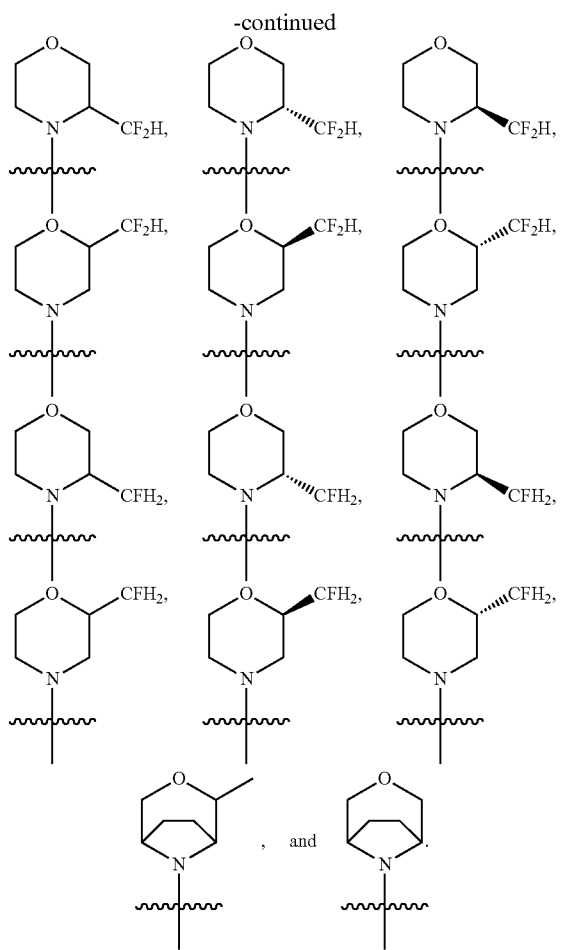

In a further aspect, 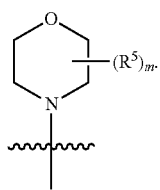 represents

In one aspect, the present application relates to a compound of formula (I), wherein m is 1. In another aspect, m is 2. In another aspect, m is 3. In another aspect, m is 4. In another aspect, m is 5. In another aspect, m is 6.

In one aspect, the present application relates to a compound of formula (I), wherein at least one $R^5$ is halogen (e.g., F, Cl, Br, or I). In a further aspect, at least one $R^5$ is F. In another aspect, at least one $R^5$ is $C_1$-$C_6$ alkyl (e.g., methyl, ethyl, propyl, i-propyl, butyl, i-butyl, t-butyl, pentyl, or hexyl). In a further aspect, at least one $R^5$ is methyl. In another aspect, at least one $R^5$ is OH, CN, or $N_3$. In another aspect, at least one $R^5$ is O—$C_1$-$C_6$ alkyl (e.g., methyl, ethyl, propyl, i-propyl, butyl, i-butyl, t-butyl, pentyl, or hexyl). In a further aspect, at least one $R^5$ is O-methyl.

In one aspect, the present application relates to a compound of formula (I), wherein at least one $R^5$ is $C_2$-$C_6$ alkenyl.

In one aspect, the present application relates to a compound of formula (I), wherein $R^5$ is in the S-configuration.

In one aspect, the present application relates to a compound of formula (I), wherein at least one $R^5$ is COO—($C_1$-$C_6$ alkyl), CONH—($C_1$-$C_6$ alkyl), CON($C_1$-$C_6$ alkyl)$_2$, or COOH.

In one aspect, the present application relates to a compound of formula (I), wherein at least one $R^8$ is halogen (e.g., F, Cl, Br, or I), OH, O—($C_1$-$C_6$ alkyl) (e.g., methyl, ethyl, propyl, i-propyl, butyl, i-butyl, t-butyl, pentyl, or hexyl), or $C_1$-$C_6$ haloalkyl (e.g., $CHF_2$, $CH_2F$, $CF_3$, $CH_2CHF_2$, $CH_2CH_2F$, or $CH_2CF_3$). In a further aspect, at least one $R^8$ is F, OH, O-methyl, or $CF_3$.

In one aspect, the present application relates to a compound of formula (I), wherein at least one $R^8$ is COO—($C_1$-$C_6$ alkyl), CONH—($C_1$-$C_6$ alkyl), CON($C_1$-$C_6$ alkyl)$_2$, or COOH. In one aspect, the present application relates to a compound of formula (I), wherein at least one $R^8$ is CN or $N_3$.

In one aspect, the present application relates to a compound of formula (I), wherein at least one $R^8$ is 5-6 membered saturated, unsaturated, or partially saturated carbocycle, or 5-6 membered saturated, unsaturated, or partially saturated heterocycle containing one or more heteroatoms selected from N, O and S.

In one aspect, the present application relates to a compound of formula (I), wherein Ⓑ represents a 5-6 membered aromatic, saturated, unsaturated, or partially saturated carbocycle. In a further aspect, Ⓑ represents a 6 membered aromatic carbocycle (e.g., phenyl). In a further aspect, Ⓑ represents phenyl.

In one aspect, the present application relates to a compound of formula (I), wherein Ⓑ represents an aromatic, saturated, unsaturated, or partially saturated heterocycle containing one or more heteroatoms selected from N, O and S. In a further aspect, Ⓑ represents an aromatic heterocycle containing one or more heteroatoms selected from N, O and S (e.g., pyridine, pyrazine, or pyrimidine). In a further aspect, Ⓑ represents pyridine.

In one aspect, the present application relates to a compound of formula (I), wherein n is 0. In another aspect, n is 1, 2, 3, 4, 5, or 6. In a further aspect, n is 1.

In one aspect, the present application relates to a compound of formula (I), wherein at least one $R^6$ is halogen (e.g., F, Cl, Br, or I). In a further aspect, at least one $R^6$ is F. In a further aspect, $R^6$ is 2-fluoro or 4-fluoro. In a further aspect, $R^6$ is 2-fluoro. In a further aspect, $R^6$ is 4-fluoro. In another aspect, at least one $R^6$ is $C_1$-$C_6$ alkyl (e.g., methyl, ethyl, propyl, i-propyl, butyl, i-butyl, t-butyl, pentyl, or hexyl). In a further aspect, at least one $R^6$ is methyl. In another aspect, at least one $R^6$ is OH. In another aspect, at least one $R^6$ is O—$C_1$-$C_6$ alkyl (e.g., methyl, ethyl, propyl, i-propyl, butyl, i-butyl, t-butyl, pentyl, or hexyl). In a further aspect, at least one $R^6$ is O-methyl.

In one aspect, the present application relates to a compound of formula (I), wherein at least one $R^6$ is $C_2$-$C_6$ alkenyl.

In one aspect, the present application relates to a compound of formula (I), wherein at least one $R^6$ is COO—($C_1$-$C_6$ alkyl), CONH—($C_1$-$C_6$ alkyl), CON($C_1$-$C_6$ alkyl)$_2$, or COOH.

In one aspect, the present application relates to a compound of formula (I), wherein at least one $R^6$ is CN.

In one aspect, the present application relates to a compound of formula (I), wherein at least one $R^6$ is $N_3$.

In one aspect, the present application relates to a compound of formula (I), wherein at least one $R^6$ is bonded to the 2- or 4-position of Ⓑ. In a further aspect, at least one $R^6$ is 2-F, 2-methyl, 2-OH, 2-O-methyl, 2-CN, or 2-$N_3$. In another aspect, at least one $R^6$ is 4-F, 4-methyl, 4-OH, 4-O-methyl, 4-CN, or 4-$N_3$. In a further aspect, Ⓑ is phenyl or pyridine; and at least one $R^6$ is 2-F, 2-methyl, 2-OH, 2-O-methyl, 2-CN, or 2-$N_3$. In another aspect, Ⓑ is phenyl or pyridine; and at least one $R^6$ is 4-F, 4-methyl, 4-OH, 4-O-methyl, 4-CN, or 4-$N_3$.

In one aspect, the present application relates to a compound of formula (I), wherein at least one $R^9$ is halogen (e.g., F, Cl, Br, or I), OH, or O—($C_1$-$C_6$ alkyl) (e.g., methyl, ethyl, propyl, i-propyl, butyl, i-butyl, t-butyl, pentyl, or hexyl). In a further aspect, at least one $R^9$ is F, OH, or O-methyl.

In one aspect, the present application relates to a compound of formula (I), wherein at least one $R^9$ is COO—($C_1$-$C_6$ alkyl), CONH—($C_1$-$C_6$ alkyl), CON($C_1$-$C_6$ alkyl)$_2$, or COOH.

In one aspect, the present application relates to a compound of formula (I), wherein at least one $R^9$ is CN or $N_3$.

In one aspect, the present application relates to a compound of formula (I), wherein at least one $R^9$ is 5-6 membered saturated, unsaturated, or partially saturated carbocycle, or 5-6 membered saturated, unsaturated, or partially saturated heterocycle containing one or more heteroatoms selected from N, O and S.

In one aspect, the present application relates to a compound of formula (I), wherein at least one of $R^3$, $R^4$, $R^{11}$, or $R^{12}$ is methyl. In a further aspect, one of $R^3$, $R^{11}$, or $R^{12}$ is methyl.

In one aspect, the present application relates to a compound of formula (I), wherein at $R^3$ is methyl and $R^4$, $R^{11}$, and $R^{12}$ are H.

In one aspect, the present application relates to a compound of formula (I), wherein at $R^4$ is methyl and $R^3$, $R^{11}$, and $R^{12}$ are H.

In one aspect, the present application relates to a compound of formula (I), wherein at $R^{11}$ is methyl and $R^3$, $R^4$, and $R^{12}$ are H.

In one aspect, the present application relates to a compound of formula (I), wherein at is methyl and $R^3$, $R^4$, and $R^{11}$ are H.

In one aspect, the present application relates to a compound of formula (I), wherein at least one of $R^3$, $R^4$, $R^{11}$, or $R^{12}$ is O-methyl. In a further aspect, one of $R^3$, or $R^{12}$ is O-methyl.

In one aspect, the present application relates to a compound of formula (I), wherein at $R^3$ is O-methyl and $R^4$, $R^{11}$, and $R^{12}$ are H.

In one aspect, the present application relates to a compound of formula (I), wherein at $R^4$ is O-methyl and $R^3$, $R^{11}$, and $R^{12}$ are H.

In one aspect, the present application relates to a compound of formula (I), wherein at $R^{11}$ is O-methyl and $R^3$, $R^4$, and $R^{12}$ are H.

In one aspect, the present application relates to a compound of formula (I), wherein at is O-methyl and $R^3$, $R^4$, and $R^{11}$ are H.

In one aspect, the present application relates to a compound of formula (II):

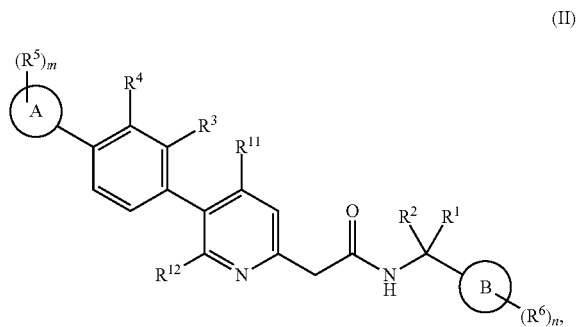

(II)

or a pharmaceutically acceptable salt, solvate, or prodrug thereof, wherein each of the variables is as defined in formula (I). In a further aspect, Ⓐ, Ⓑ, $R^1$, $R^2$, $R^3$, $R^4$, $R^5$, $R^6$, $R^{11}$, $R^{12}$, m, and n are selected from the moieties described herein.

In one aspect, the present application relates to a compound of formula (III):

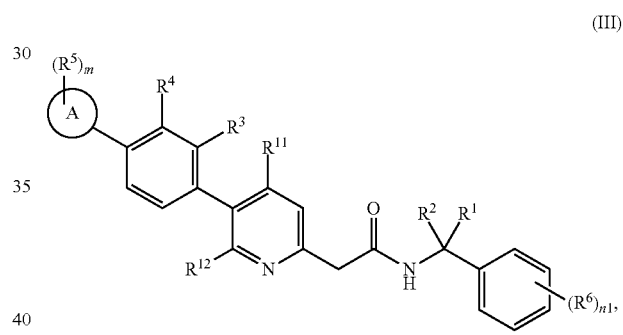

(III)

or a pharmaceutically acceptable salt, solvate, or prodrug thereof, wherein each of Ⓐ, $R^1$, $R^2$, $R^3$, $R^4$, $R^5$, $R^6$, $R^{11}$, $R^{12}$, and m is as defined in formula (I), and n1 is 0, 1, 2, 3, 4, or 5. In a further aspect, Ⓐ $R^1$, $R^2$, $R^3$, $R^4$, $R^5$, $R^6$, $R^{11}$, $R^{12}$, and m are selected from the moieties described herein. In a further aspect, n1 is 0. In another aspect, n1 is 1.

In one aspect, the present application relates to a compound of a formula selected from:

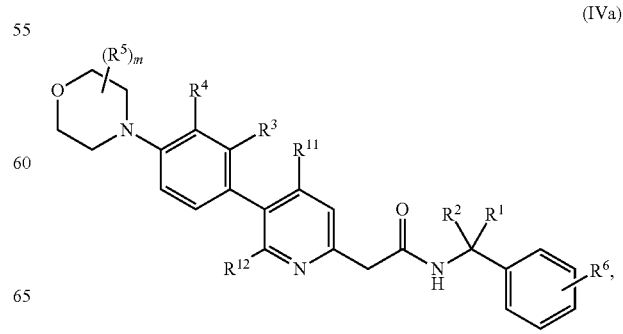

(IVa)

(IVb)

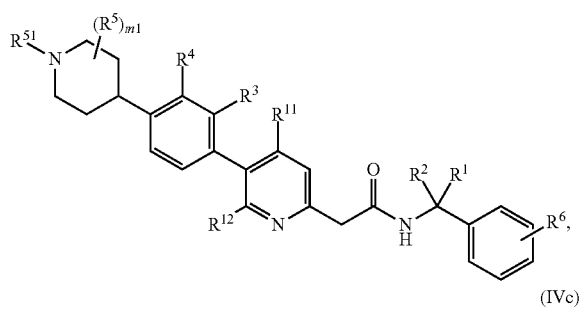

(IVc)

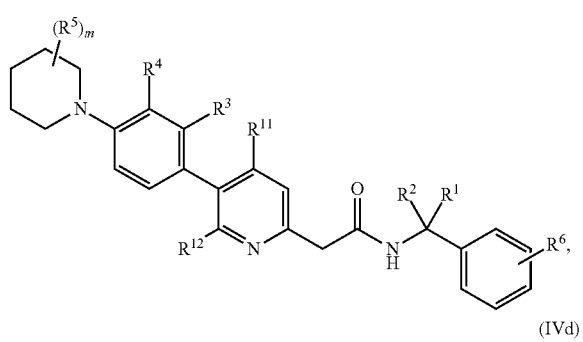

(IVd)

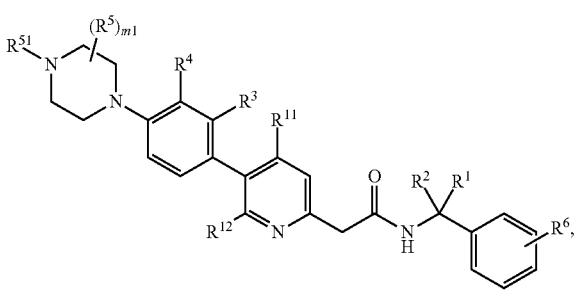

or a pharmaceutically acceptable salt, solvate, or prodrug thereof, wherein each of $R^1$, $R^2$, $R^3$, $R^4$, $R^5$, $R^6$, $R^{11}$, $R^{12}$, and m is as defined in formula (I); $R^{51}$ is $C_1$-$C_6$ alkyl, $C_2$-$C_6$ alkenyl, O—($C_1$-$C_6$ alkyl), COO—($C_1$-$C_6$ alkyl), CONH—($C_1$-$C_6$ alkyl), CON($C_1$-$C_6$ alkyl)$_2$, or CN, each of which is optionally substituted with one or more $R^8$; and m1 is 0, 1, 2, 3, or 4. In a further aspect, $R^1$, $R^2$, $R^3$, $R^4$, $R^5$, $R^6$, $R^{11}$, $R^{12}$ and m are selected from the moieties described herein. In a further aspect, m1 is 0. In another aspect, m1 is 1. In a further aspect, each of the substituents defined for $R^{51}$ can be selected from the moieties described herein for the corresponding substituent defined for $R^5$.

In one aspect, the present application relates to a compound of a formula selected from:

(Va)

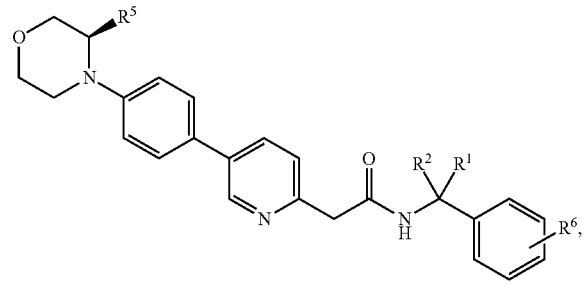

(Vb)

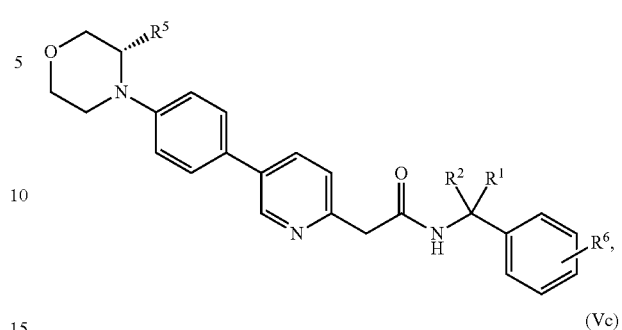

(Vc)

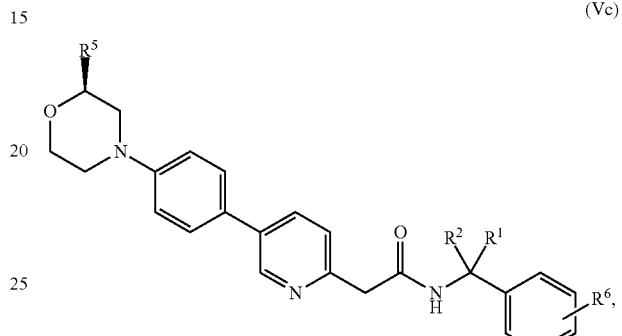

(Vd)

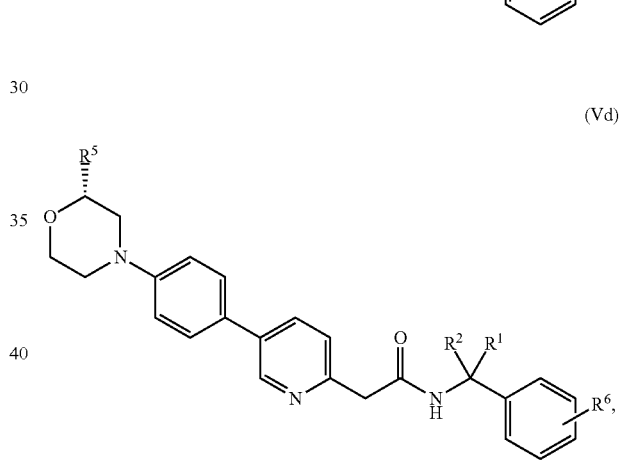

or a pharmaceutically acceptable salt, solvate, or prodrug thereof, wherein each of the variables is as defined in formula (I). In a further aspect, $R^1$, $R^2$, $R^5$, and $R^6$ are selected from the moieties described herein.

In one aspect, the present application relates to a compound of a formula selected from:

(VIa)

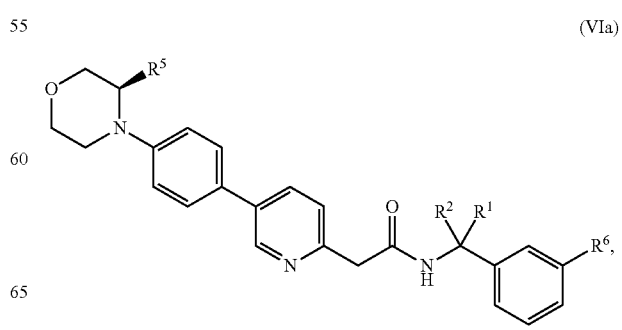

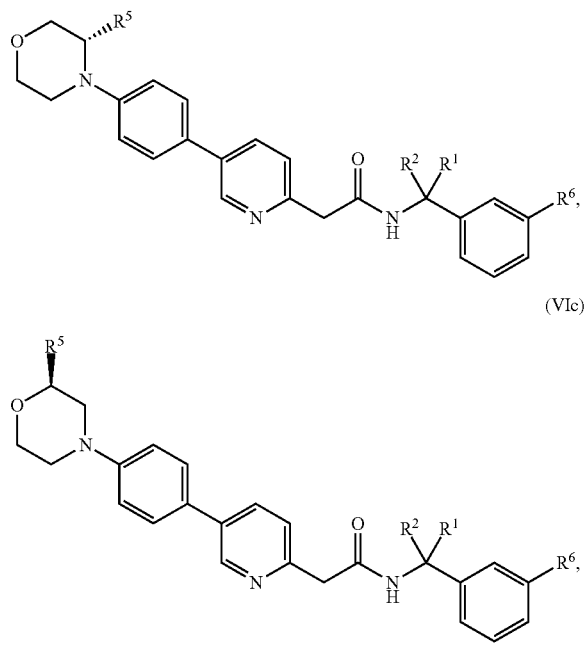

or a pharmaceutically acceptable salt, solvate, or prodrug thereof, wherein each of the variables is as defined in formula (I). In a further aspect, $R^1$, $R^2$, $R^5$, and $R^6$ are selected from the moieties described herein.

In one aspect, the present application relates to a compound of formula (VIIa), (VIIb), (VIIc), (VIId), or (VIIe):

or a pharmaceutically acceptable salt, solvate, or prodrug thereof, wherein each of $R^1$, $R^2$, $R^3$, $R^5$, and $R^6$ is as defined in formula (I); n2 is 0, 1, 2, or 3; n3 is 0, 1, or 2; $A^1$, $A^2$, and $A^3$ are each independently $CR^{61}$ or N, wherein only one of $A^1$, $A^2$, and $A^3$ is N; and each $R^{61}$ is independently H or $R^6$. In a further aspect, $R^1$, $R^2$, $R^3$, $R^5$, and $R^6$ are selected from the moieties described herein.

In one aspect, $R^3$ is H, methyl, or O-methyl. In a further aspect, $R^3$ is methyl or O-methyl. In a further aspect, $R^3$ is methyl.

In one aspect, $R^5$ is methyl.
In one aspect, $R^5$ is in the S-configuration.
In one aspect, n2 is 0. In another aspect, n2 is 1.
In one aspect, n3 is 0. In another aspect, n3 is 1.
In one aspect, $R^6$ is halogen, $C_1$-$C_6$ alkyl, O—$C_1$-$C_6$ alkyl, or CN. In one aspect, $R^6$ is F, methyl, O-methyl, or CN. In a further aspect, $R^6$ is F, O-methyl, or CN. In a further aspect, $R^6$ is at the 2- or 4-position. In a further aspect, at least one $R^6$ is F. In a further aspect, $R^6$ is 2-fluoro or 4-fluoro. In a further aspect, $R^6$ is 2-fluoro. In a further aspect, $R^6$ is 4-fluoro.

In one aspect, $A^1$ is N. In another aspect, $A^2$ is N. In another aspect, $A^3$ is N.

In one aspect, $R^{61}$ is H. In another aspect, $R^{61}$ is $R^6$.

In one aspect, the present application relates to a compound of any of the formulae herein, wherein at least one $R^5$ is, or as where applicable, $R^5$ is, $C_1$-$C_6$ alkyl and $R^3$ is $C_1$-$C_6$ alkyl. In one aspect, the present application relates to a compound of any of the formulae herein, wherein at least one $R^5$ is, or as where applicable, $R^5$ is, $C_1$-$C_3$ alkyl and $R^3$ is $C_1$-$C_3$ alkyl. In one aspect, the present application relates to a compound of any of the formulae herein, wherein at least one $R^5$ is, or as where applicable, $R^5$ is, methyl and $R^3$ is $C_1$-$C_6$ alkyl. In one aspect, the present application relates to a compound of any of the formulae herein, wherein at least one $R^5$ is, or as where applicable, $R^5$ is, methyl and $R^3$ is $C_1$-$C_3$ alkyl. In one aspect, the present application relates to a compound of any of the formulae herein, wherein at least one $R^5$ is, or as where applicable, $R^5$ is, $C_1$-$C_6$ alkyl and $R^3$ is methyl. In one aspect, the present application relates to a compound of any of the formulae herein, wherein at least one $R^5$ is, or as where applicable, $R^5$ is, $C_1$-$C_3$ alkyl and $R^3$ is methyl. In one aspect, the present application relates to a compound of any of the formulae herein, wherein at least one $R^5$ is, or as where applicable, $R^5$ is, methyl and $R^3$ is methyl.

In one aspect, the present application relates to a compound of any of the formulae herein, wherein at least one $R^5$ is, or as where applicable, $R^5$ is, $C_1$-$C_6$ alkyl and at least one $R^6$ is, or as where applicable, $R^6$ is, halogen. In one aspect, the present application relates to a compound of any of the formulae herein, wherein at least one $R^5$ is, or as where applicable, $R^5$ is, $C_1$-$C_3$ alkyl and at least one $R^6$ is, or as where applicable, $R^6$ is, halogen. In one aspect, the present application relates to a compound of any of the formulae herein, wherein at least one $R^5$ is, or as where applicable, $R^5$ is, methyl and at least one $R^6$ is, or as where applicable, $R^6$ is, halogen. In one aspect, the present application relates to a compound of any of the formulae herein, wherein at least one $R^5$ is, or as where applicable, $R^5$ is, $C_1$-$C_6$ alkyl and at least one $R^6$ is, or as where applicable, $R^6$ is, F. In one aspect, the present application relates to a compound of any of the formulae herein, wherein at least one $R^5$ is, or as where applicable, $R^5$ is, $C_1$-$C_3$ alkyl and at least one $R^6$ is, or as where applicable, $R^6$ is, F. In one aspect, the present application relates to a compound of any of the formulae herein, wherein at least one $R^5$ is, or as where applicable, $R^5$ is, methyl and at least one $R^6$ is, or as where applicable, $R^6$ is, F.

In one aspect, the present application relates to a compound of any of the formulae herein, wherein $R^3$ is $C_1$-$C_6$ alkyl and at least one $R^6$ is, or as where applicable, $R^6$ is, halogen. In one aspect, the present application relates to a compound of any of the formulae herein, wherein $R^3$ is $C_1$-$C_3$ alkyl and at least one $R^6$ is, or as where applicable, $R^6$ is, halogen. In one aspect, the present application relates to a compound of any of the formulae herein, wherein $R^3$ is methyl and at least one $R^6$ is, or as where applicable, $R^6$ is, halogen. In one aspect, the present application relates to a compound of any of the formulae herein, wherein $R^3$ is $C_1$-$C_6$ alkyl and at least one $R^6$ is, or as where applicable, $R^6$ is, F. In one aspect, the present application relates to a compound of any of the formulae herein, wherein $R^3$ is $C_1$-$C_3$ alkyl and at least one $R^6$ is, or as where applicable, $R^6$ is, F. In one aspect, the present application relates to a compound of any of the formulae herein, wherein $R^3$ is methyl and at least one $R^6$ is, or as where applicable, $R^6$ is, F. In one aspect, the present application relates to a compound of any of the formulae herein, wherein at least one $R^5$ is, or as where applicable, $R^5$ is, $C_1$-$C_6$ alkyl, $R^3$ is $C_1$-$C_6$ alkyl, and at least one $R^6$ is, or as where applicable, $R^6$ is, halogen. In one aspect, the present application relates to a compound of any of the formulae herein, wherein at least one $R^5$ is, or as where applicable, $R^5$ is, $C_1$-$C_3$ alkyl, $R^3$ is $C_1$-$C_3$ alkyl, and at least one $R^6$ is, or as where applicable, $R^6$ is, halogen. In one aspect, the present application relates to a compound of any of the formulae herein, wherein at least one $R^5$ is, or as where applicable, $R^5$ is, methyl, $R^3$ is $C_1$-$C_6$ alkyl, and at least one $R^6$ is, or as where applicable, $R^6$ is, halogen. In one aspect, the present application relates to a compound of any of the formulae herein, wherein at least one $R^5$ is, or as where applicable, $R^5$ is, methyl, $R^3$ is $C_1$-$C_3$ alkyl, and at least one $R^6$ is, or as where applicable, $R^6$ is, halogen. In one aspect, the present application relates to a compound of any of the formulae herein, wherein at least one $R^5$ is, or as where applicable, $R^5$ is, $C_1$-$C_6$ alkyl, $R^3$ is methyl, and at least one $R^6$ is, or as where applicable, $R^6$ is, halogen. In one aspect, the present application relates to a compound of any of the formulae herein, wherein at least one $R^5$ is, or as where applicable, $R^5$ is, $C_1$-$C_3$ alkyl, $R^3$ is methyl, and at least one $R^6$ is, or as where applicable, $R^6$ is, halogen. In one aspect, the present application relates to a compound of any of the formulae herein, wherein at least one $R^5$ is, or as where applicable, $R^5$ is, methyl, $R^3$ is methyl, and at least one $R^6$ is, or as where applicable, $R^6$ is, halogen.

In one aspect, the present application relates to a compound of any of the formulae herein, wherein at least one $R^5$ is, or as where applicable, $R^5$ is, $C_1$-$C_6$ alkyl, $R^3$ is $C_1$-$C_6$ alkyl, and at least one $R^6$ is, or as where applicable, $R^6$ is, F. In one aspect, the present application relates to a compound of any of the formulae herein, wherein at least one $R^5$ is, or as where applicable, $R^5$ is, $C_1$-$C_3$ alkyl, $R^3$ is $C_1$-$C_3$ alkyl, and at least one $R^6$ is, or as where applicable, $R^6$ is, F. In one aspect, the present application relates to a compound of any of the formulae herein, wherein at least one $R^5$ is, or as where applicable, $R^5$ is, methyl, $R^3$ is $C_1$-$C_6$ alkyl, and at least one $R^6$ is, or as where applicable, $R^6$ is, F. In one aspect, the present application relates to a compound of any of the formulae herein, wherein at least one $R^5$ is, or as where applicable, $R^5$ is, methyl, $R^3$ is $C_1$-$C_3$ alkyl, and at least one $R^6$ is, or as where applicable, $R^6$ is, F. In one aspect, the present application relates to a compound of any of the formulae herein, wherein at least one $R^5$ is, or as where applicable, $R^5$ is, $C_1$-$C_6$ alkyl, $R^3$ is methyl, and at least one $R^6$ is, or as where applicable, $R^6$ is, F. In one aspect, the present application relates to a compound of any of the formulae herein, wherein at least one $R^5$ is, or as where applicable, $R^5$ is, $C_1$-$C_3$ alkyl, $R^3$ is methyl, and at least one $R^6$ is, or as where applicable, $R^6$ is, F. In one aspect, the present application relates to a compound of any of the formulae herein, wherein at least one $R^5$ is, or as where applicable, $R^5$ is, methyl, $R^3$ is methyl, and at least one $R^6$ is, or as where applicable, $R^6$ is, F.

Representative compounds of the application are listed in Table 1.

TABLE 1

| Compound No. | Structure | Melting Point (° C.) |
|---|---|---|
| 100 | 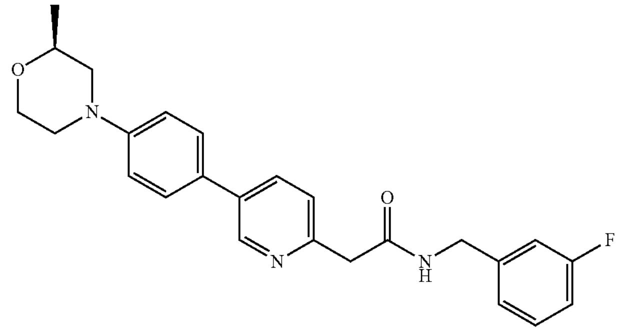 [SMILES: C[C@H]1CN(c2ccc(-c3ccc(CC(=O)NCc4cccc(F)c4)nc3)cc2)CCO1] | 154-155 |
| 101 | 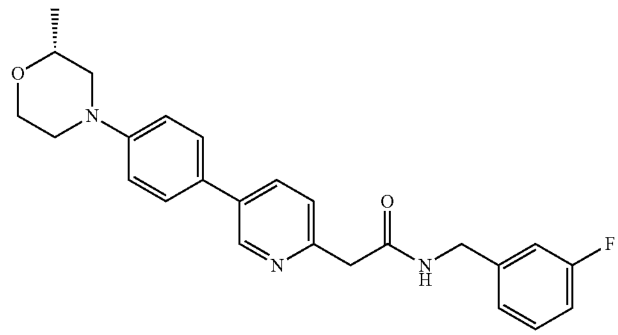 [SMILES: C[C@@H]1CN(c2ccc(-c3ccc(CC(=O)NCc4cccc(F)c4)nc3)cc2)CCO1] | 164-166 |
| 102 | 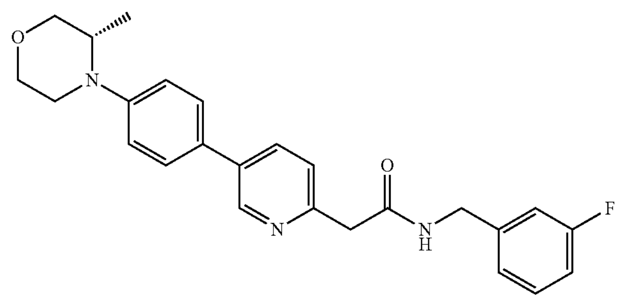 [SMILES: C[C@H]1COCCN1c1ccc(-c2ccc(CC(=O)NCc3cccc(F)c3)nc2)cc1] | 165-167 |
| 103 | 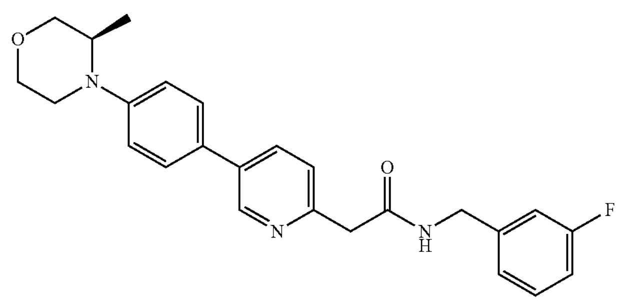 [SMILES: C[C@@H]1COCCN1c1ccc(-c2ccc(CC(=O)NCc3cccc(F)c3)nc2)cc1] | 148-151 |
| 104 | 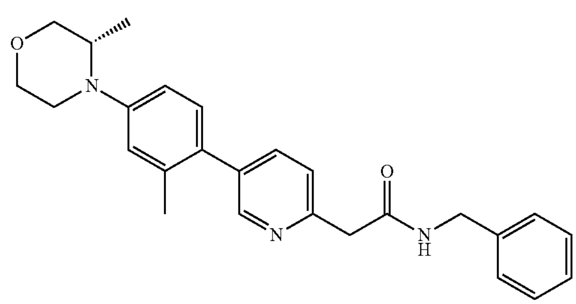 [SMILES: Cc1cc(N2CCOC[C@@H]2C)ccc1-c1ccc(CC(=O)NCc2ccccc2)nc1] | 106-108 |

TABLE 1-continued

| Compound No. | Structure | Melting Point (° C.) |
|---|---|---|
| 105 | 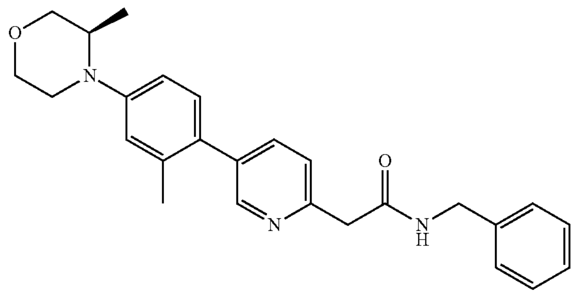 [SMILES: Cc1cc(N2CCOC[C@H]2C)ccc1-c1ccc(CC(=O)NCc2ccccc2)nc1] | 98-100 |
| 106 | 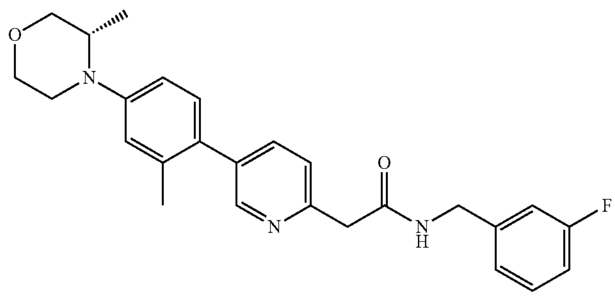 [SMILES: Cc1cc(N2CCOC[C@@H]2C)ccc1-c1ccc(CC(=O)NCc2cccc(F)c2)nc1] | |
| 107 | 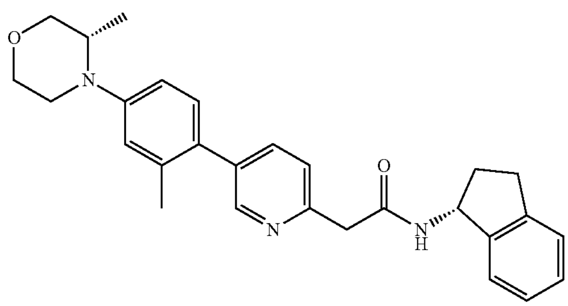 [SMILES: Cc1cc(N2CCOC[C@@H]2C)ccc1-c1ccc(CC(=O)N[C@@H]2CCc3ccccc32)nc1] | |
| 108 | 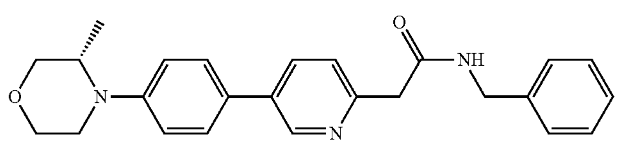 | |
| 109 | 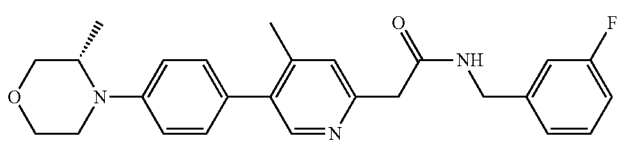 [SMILES: Cc1cc(CC(=O)NCc2cccc(F)c2)ncc1-c1ccc(N2CCOC[C@@H]2C)cc1] | |
| 110 | 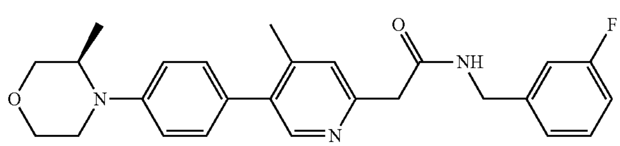 [SMILES: Cc1cc(CC(=O)NCc2cccc(F)c2)ncc1-c1ccc(N2CCOC[C@H]2C)cc1] | |
| 111 | 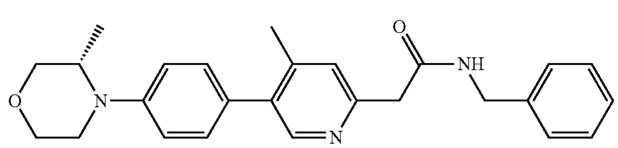 | |

TABLE 1-continued

| Compound No. | Structure | Melting Point (° C.) |
|---|---|---|
| 112 | 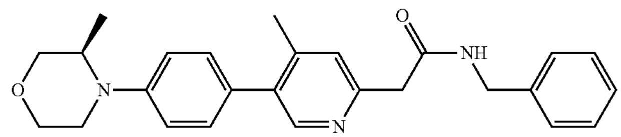 | |
| 113 | 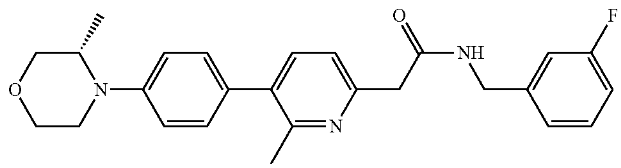 [SMILES: Cc1nc(CC(=O)NCc2cccc(F)c2)ccc1-c1ccc(N2CCOC[C@@H]2C)cc1] | |
| 114 | 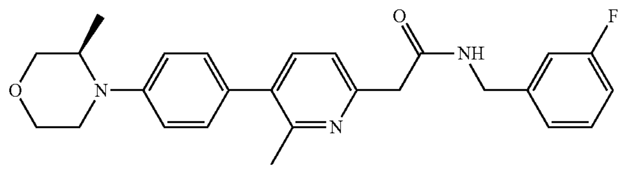 [SMILES: Cc1nc(CC(=O)NCc2cccc(F)c2)ccc1-c1ccc(N2CCOC[C@H]2C)cc1] | |
| 115 | 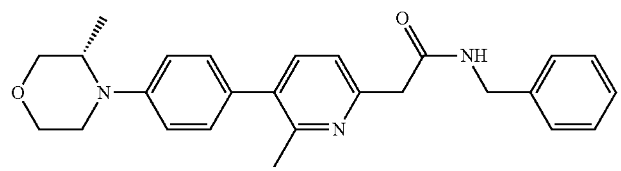 | |
| 116 | 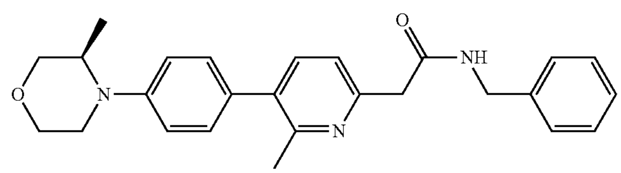 [SMILES: Cc1nc(CC(=O)NCc2ccccc2)ccc1-c1ccc(N2CCOC[C@H]2C)cc1] | |
| 117 | 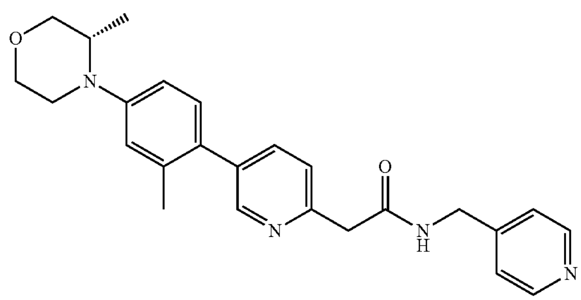 [SMILES: Cc1cc(N2CCOC[C@@H]2C)ccc1-c1ccc(CC(=O)NCc2ccncc2)nc1] | |
| 118 | 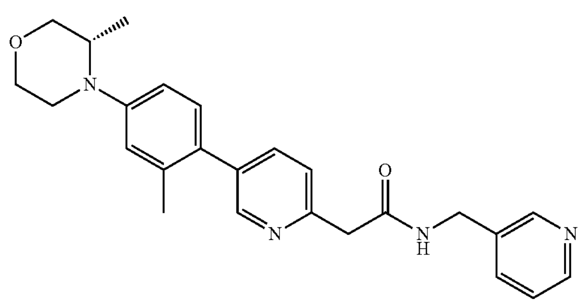 [SMILES: Cc1cc(N2CCOC[C@@H]2C)ccc1-c1ccc(CC(=O)NCc2cccnc2)nc1] | |

TABLE 1-continued

| Compound No. | Structure | Melting Point (° C.) |
|---|---|---|
| 119 | 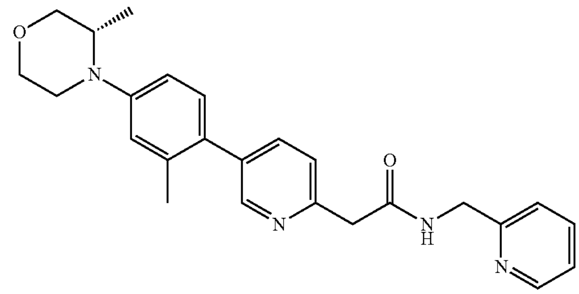 [SMILES: Cc1cc(N2CCOC[C@@H]2C)ccc1-c1ccc(CC(=O)NCc2ccccn2)nc1] | |
| 120 | 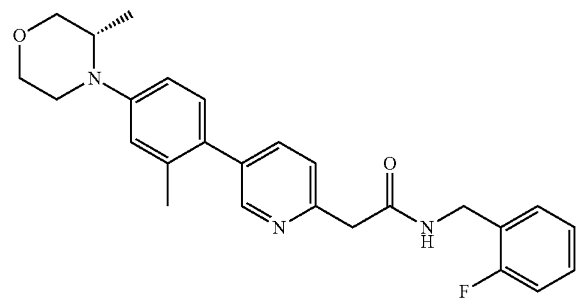 [SMILES: Cc1cc(N2CCOC[C@@H]2C)ccc1-c1ccc(CC(=O)NCc2ccccc2F)nc1] | |
| 121 | 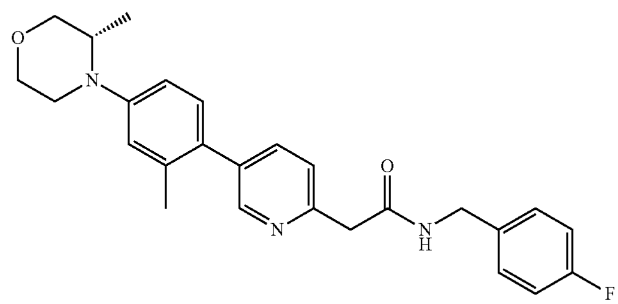 [SMILES: Cc1cc(N2CCOC[C@@H]2C)ccc1-c1ccc(CC(=O)NCc2ccc(F)cc2)nc1] | |
| 122 | 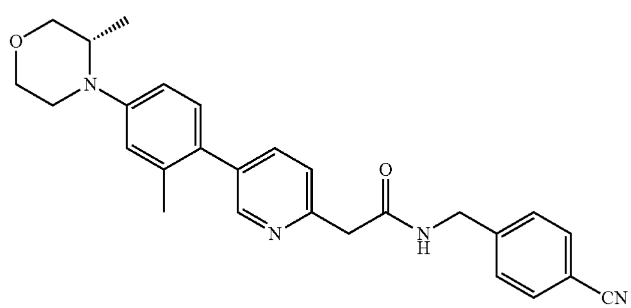 [SMILES: Cc1cc(N2CCOC[C@@H]2C)ccc1-c1ccc(CC(=O)NCc2ccc(C#N)cc2)nc1] | |
| 123 | 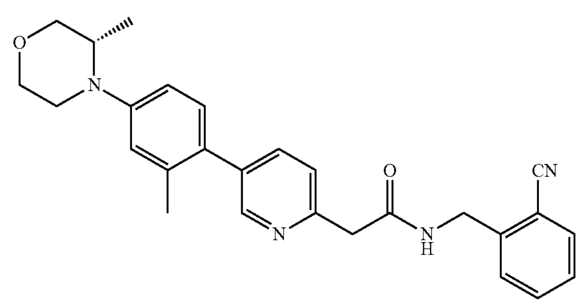 [SMILES: Cc1cc(N2CCOC[C@@H]2C)ccc1-c1ccc(CC(=O)NCc2ccccc2C#N)nc1] | |

TABLE 1-continued

| Compound No. | Structure | Melting Point (° C.) |
|---|---|---|
| 124 | 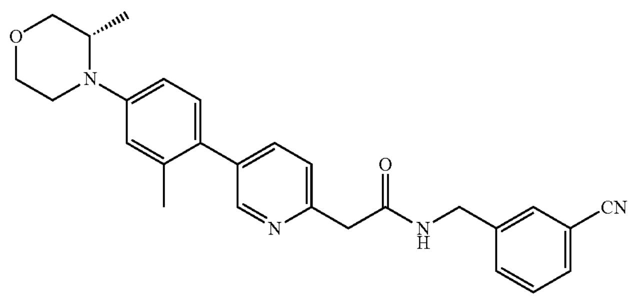 [SMILES: Cc1cc(N2CCOC[C@@H]2C)ccc1-c1ccc(CC(=O)NCc2cccc(C#N)c2)nc1] | |
| 125 | 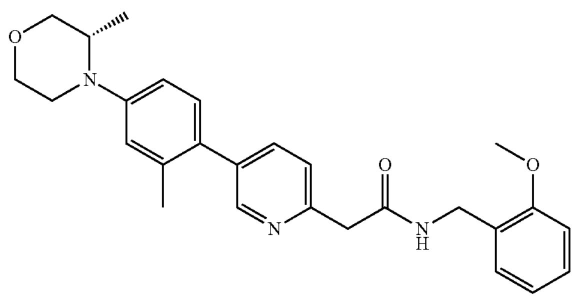 [SMILES: COc1ccccc1CNC(=O)Cc1ccc(-c2ccc(N3CCOC[C@@H]3C)cc2C)cn1] | |
| 126 | 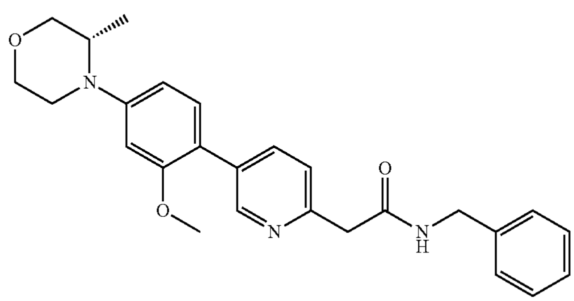 [SMILES: COc1cc(N2CCOC[C@@H]2C)ccc1-c1ccc(CC(=O)NCc2ccccc2)nc1] | |
| 127 | 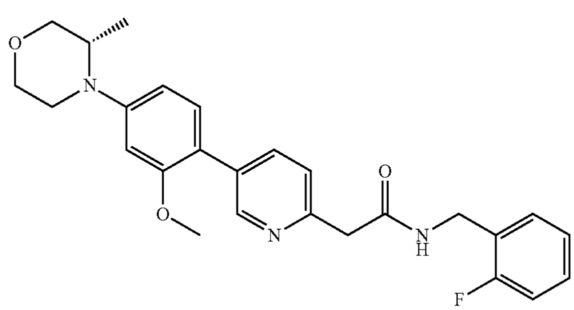 [SMILES: COc1cc(N2CCOC[C@@H]2C)ccc1-c1ccc(CC(=O)NCc2ccccc2F)nc1] | |
| 128 | 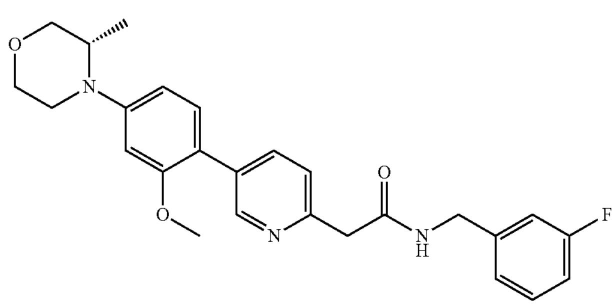 [SMILES: COc1cc(N2CCOC[C@@H]2C)ccc1-c1ccc(CC(=O)NCc2cccc(F)c2)nc1] | |

TABLE 1-continued

| Compound No. | Structure | Melting Point (° C.) |
|---|---|---|
| 129 | 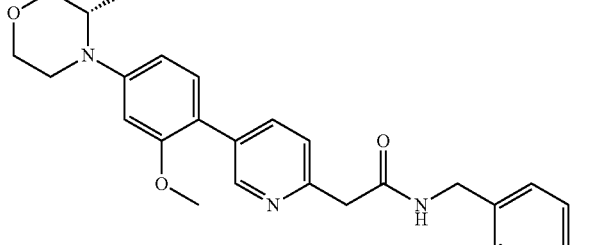 | |
| 130 | 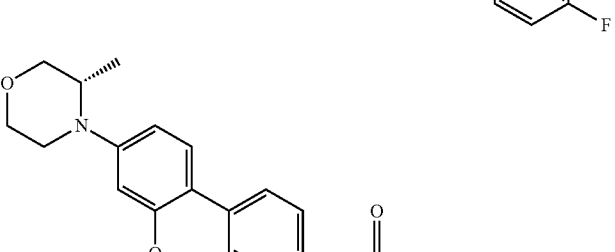 | |

In one aspect, a compound of the application displays high brain permeability. Brain permeability can be measured by various methods known in the art. For example, brain permeability can be measured by calculating the ratio between the concentration of a compound of the application in the brain and the concentration of the compound in the plasma (i.e., B:P ratio). In one aspect, a compound of the application has a B:P ratio of at least 1.0, 1.1, 1.2, 1.3, 1.4, 1.5, 1.6, 1.7, 1.8, 1.9, or 2.0 at 1 hour after administration of the compound to a subject. In one aspect, a compound of the application has a B:P ratio of at least 1.5, 1.6, 1.7, 1.8, 1.9, or 2.0 at 1 hour after administration of the compound to a subject. In one aspect, a compound of the application has a B:P ratio of at least 1.4, 1.5, 1.6, 1.7, 1.8, 1.9, 2.0, 2.1, 2.2, or 2.3 at 2 hours after administration of the compound to a subject. In one aspect, a compound of the application has a B:P ratio of at least 1.9, 2.0, 2.1, 2.2, or 2.3 at 2 hours after administration of the compound to a subject. In one aspect, a compound of the application has a B:P ratio of at least 1.7, 1.8, 1.9, 2.0, 2.1, 2.2, 2.3, 2.4, or 2.5 at 4 hours after administration of the compound to a subject. In one aspect, a compound of the application has a B:P ratio of at least 2.2, 2.3, 2.4, or 2.5 at 4 hours after administration of the compound to a subject. In one aspect, the compound that displays high brain permeability is a compound of formula (VIIa), (VIIb), (VIIc), (VIId), or (VIIe) wherein $R^6$ is F. In a further aspect, the compound that displays high brain permeability is a compound of formula (VIIa), (VIIb), (VIIc), (VIId), or (VIIe), wherein $R^6$ is 2-fluoro or 4-fluoro.

In a further aspect, the compound that displays high brain permeability is a compound of formula (VIIa), (VIIb), (VIIc), (VIId), or (VIIe), wherein $R^6$ is 2-fluoro. In a further aspect, the compound that displays high brain permeability is a compound of formula (VIIa), (VIIb), (VIIc), (VIId), or (VIIe), wherein $R^6$ is 4-fluoro.

In one aspect, a compound of the application displays a low melting point (M.P.). In one aspect, a low M.P. is below 150° C., 145° C., 140° C., 135° C., 130° C., 125° C., 120° C., 115° C., 110° C., 105° C., 100° C., 95° C., 90° C., or 85° C. In a further aspect, a low M.P. is below 115° C., 110° C., 105° C., 100° C., 95° C., 90° C., or 85° C. In one aspect, the compound that has a low M.P. is any compound of the application, wherein $R^3$ is not H. In a further aspect, $R^3$ is $C_1$-$C_6$ alkyl. In a further aspect, $R^3$ is methyl.

In one aspect, a compound of the application displays improved aqueous solubility compared to

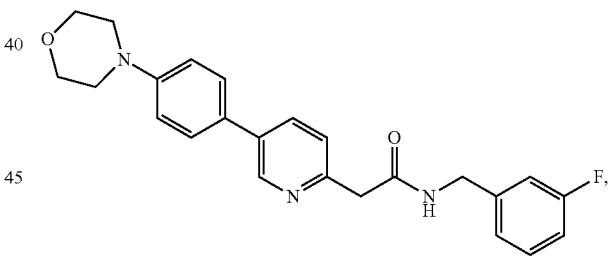

i.e., Compound Y, a compound known to be useful in treating diseases and disorders that are modulated by tyrosine kinase inhibition, at a pH of 4.4. In one aspect, a compound of the application is about 10 to about 100 times more soluble in water at a pH of 4.4 compared to Compound Y. In a further aspect, the compound is about 15 to about 75 times more soluble in water at a pH of 4.4 compared to Compound Y. In a further aspect, the compound is about 20 to about 50 times more soluble in water at a pH of 4.4 compared to Compound Y. In a further aspect, the compound is about 20 times more soluble in water at a pH of 4.4 compared to Compound Y. In a further aspect, the compound is about 30 times more soluble in water at a pH of 4.4 compared to Compound Y. In a further aspect, the compound is about 40 times more soluble in water at a pH of 4.4 compared to Compound Y. In a further aspect, the compound is about 50 times more soluble in water at a pH of 4.4 compared to Compound Y.

In one aspect, a compound of the application has a solubility of about 30 µM to about 100 µM in water at a pH of 4.4. In a further aspect, the compound has a solubility of about 40 µM to about 90 µM in water at a pH of 4.4. In a further aspect, the compound has a solubility of about 40 µM to about 80 µM in water at a pH of 4.4. In a further aspect, the compound has a solubility of about 40 µM to about 70 µM in water at a pH of 4.4. In a further aspect, the compound has a solubility of about 40 µM in water at a pH of 4.4. In a further aspect, the compound has a solubility of about 50 µM in water at a pH of 4.4. In a further aspect, the compound has a solubility of about 60 µM in water at a pH of 4.4. In a further aspect, the compound has a solubility of about 70 µM in water at a pH of 4.4. In a further aspect, the compound has a solubility of about 80 µM in water at a pH of 4.4. In a further aspect, the compound has a solubility of about 90 µM in water at a pH of 4.4.

In one aspect, a compound of the application displays improved aqueous solubility compared to Compound Y at a pH of 7.4. In one aspect, a compound of the application is about 5 to about 60 times more soluble in water at a pH of 7.4 compared to Compound Y. In a further aspect, the compound is about 10 to about 50 times more soluble in water at a pH of 7.4 compared to Compound Y. In a further aspect, the compound is about 15 to about 40 times more soluble in water at a pH of 7.4 compared to Compound Y. In a further aspect, the compound is about 10 to about 20 times more soluble in water at a pH of 7.4 compared to Compound Y. In a further aspect, the compound is about 20 to about 30 times more soluble in water at a pH of 7.4 compared to Compound Y. In a further aspect, the compound is about 30 to about 40 times more soluble in water at a pH of 7.4 compared to Compound Y. In a further aspect, the compound is about 40 to about 50 times more soluble in water at a pH of 7.4 compared to Compound Y.

In one aspect, a compound of the application has a solubility of about 10 µM to about 40 µM in water at a pH of 7.4. In a further aspect, the compound has a solubility of about 15 µM to about 30 µM in water at a pH of 7.4. In a further aspect, the compound has a solubility of about 15 µM in water at a pH of 7.4. In a further aspect, the compound has a solubility of about 20 µM in water at a pH of 7.4. In a further aspect, the compound has a solubility of about 25 µM. In a further aspect, the compound has a solubility of about 30 µM in water at a pH of 7.4.

In one aspect, the application relates to a pharmaceutical composition comprising a compound of the application, or a pharmaceutically acceptable salt, solvate, or prodrug thereof, and a pharmaceutically acceptable carrier.

In one aspect, the application relates to a method of preventing or treating a disease or disorder comprising administering to a subject in need thereof an effective amount of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application.

In one aspect, the application relates to a method of preventing or treating a disease or disorder comprising administering to a subject in need thereof an effective amount of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, wherein $R^5$ is in the S-configuration. In one aspect, $R^5$ is in the S-configuration and is selected from the group consisting of halogen, OH, $CONH_2$, COOH, CN, $N_3$, $C_1$-$C_6$ alkyl, $C_2$-$C_6$ alkenyl, and $C_2$-$C_6$ alkynyl. In one aspect, $R^5$ is in the S-configuration and is selected from the group consisting of halogen, OH, and $C_1$-$C_6$ alkyl. In one aspect, $R^5$ is in the S-configuration and is halogen. In one aspect, $R^5$ is in the S-configuration and is OH. In one aspect, $R^5$ is in the S-configuration and is $C_1$-$C_6$ alkyl. In one aspect, $R^5$ is in the S-configuration and is methyl.

In one aspect, the application relates to the use of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, for preventing or treating a disease or disorder in a subject in need thereof.

In one aspect, the application relates to the use of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, for preventing or treating a disease or disorder in a subject in need thereof, wherein $R^5$ is in the S-configuration. In one aspect, $R^5$ is in the S-configuration and is selected from the group consisting of halogen, OH, $CONH_2$, COOH, CN, $N_3$, $C_1$-$C_6$ alkyl, $C_2$-$C_6$ alkenyl, and $C_2$-$C_6$ alkynyl. In one aspect, $R^5$ is in the S-configuration and is selected from the group consisting of halogen, OH, and $C_1$-$C_6$ alkyl. In one aspect, $R^5$ is in the S-configuration and is halogen. In one aspect, $R^5$ is in the S-configuration and is OH. In one aspect, $R^5$ is in the S-configuration and is $C_1$-$C_6$ alkyl. In one aspect, $R^5$ is in the S-configuration and is methyl.

In one aspect, the application relates to the use of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, in the manufacture of a medicament for preventing or treating a disease or disorder in a subject in need thereof.

In one aspect, the application relates to the use of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, in the manufacture of a medicament for preventing or treating a disease or disorder in a subject in need thereof, wherein $R^5$ is in the S-configuration. In one aspect, $R^5$ is in the S-configuration and is selected from the group consisting of halogen, OH, $CONH_2$, COOH, CN, $N_3$, $C_1$-$C_6$ alkyl, $C_2$-$C_6$ alkenyl, and $C_2$-$C_6$ alkynyl. In one aspect, $R^5$ is in the S-configuration and is selected from the group consisting of halogen, OH, and $C_1$-$C_6$ alkyl. In one aspect, $R^5$ is in the S-configuration and is halogen. In one aspect, $R^5$ is in the S-configuration and is OH. In one aspect, $R^5$ is in the S-configuration and is $C_1$-$C_6$ alkyl. In one aspect, $R^5$ is in the S-configuration and is methyl.

In one aspect, the application relates to a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application for use in preventing or treating a disease or disorder in a subject in need thereof.

In one aspect, the application relates to a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, for use in preventing or treating a disease or disorder in a subject in need thereof, wherein $R^5$ is in the S-configuration. In one aspect, $R^5$ is in the S-configuration and is selected from the group consisting of halogen, OH, $CONH_2$, COOH, CN, $N_3$, $C_1$-$C_6$ alkyl, $C_2$-$C_6$ alkenyl, and $C_2$-$C_6$ alkynyl. In one aspect, $R^5$ is in the S-configuration and is selected from the group consisting of halogen, OH, and $C_1$-$C_6$ alkyl. In one aspect, $R^5$ is in the S-configuration and is halogen. In one aspect, $R^5$ is in the S-configuration and is OH. In one aspect, $R^5$ is in the S-configuration and is $C_1$-$C_6$ alkyl. In one aspect, $R^5$ is in the S-configuration and is methyl.

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer.

In one aspect, the disorder is proliferative disorder. In another aspect, the proliferative disorder is selected from a group consisting of a proliferative disorder of the skin, such as psoriasis and actinic keratosis. In another aspect, the proliferative disorder is selected from a group consisting of brain cancer, liver cancer, pancreatic cancer, gastric cancer, breast cancer, ovarian cancer, nerve cancer, bone cancer, cervical cancer, colorectal cancer, esophageal cancer, kidney cancer, lung cancer, muscle cancer, pharyngeal cancer, placental cancer, prostate cancer, skin cancer, soft tissue cancer, stomach cancer, thyroid cancer, tongue cancer, uterine cancer, bladder cancer, blood cancer, hematologic tumor, childhood leukemia, lymphoma, multiple myeloma, Hodgkin's disease, lymphoma of lymphocytic origin, lymphoma of cutaneous origin, acute leukemia, chronic leukemia, acute lymphoblastic leukemia, plasma cell neoplasm, lymphoid neoplasm, cancer associated with AIDS, acute myelocytic leukemia, chronic myelocytic leukemia, malignant melanoma, non-melanoma skin cancer, epidermic cyst, dermoid cyst, lipoma, adenoma, capillary or cutaneous hemangioma, lymphangioma, nevi lesion, teratoma, nephroma, myofibromatosis, osteoplastic tumor, dysplastic mass, and dysplasia.

In one aspect, the disorder is cancer. In another aspect, the cancer is selected from a group consisting of bladder cancer, blood cancer, bone cancer, brain cancer, nerve cancer, breast cancer, cervical cancer, colorectal cancer, esophageal cancer, kidney cancer, lung cancer, muscle cancer, ovarian cancer, pancreatic cancer, pharyngeal cancer, placental cancer, prostate cancer, skin cancer, soft tissue cancer, stomach cancer, gastric cancer, thyroid cancer, tongue cancer, and uterine cancer. In another aspect, the cancer is brain cancer. In a further aspect, the brain cancer is glioblastoma.

In one aspect, the application relates to a method of preventing or treating a brain cancer comprising administering to a subject in need thereof an effective amount of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application. In one aspect, $R^5$ is in the S-configuration. In one aspect, $R^5$ is in the S-configuration and is selected from the group consisting of halogen, OH, $CONH_2$, COOH, CN, $N_3$, $C_1$-$C_6$ alkyl, $C_2$-$C_6$ alkenyl, and $C_2$-$C_6$ alkynyl. In one aspect, $R^5$ is in the S-configuration and is selected from the group consisting of halogen, OH, and $C_1$-$C_6$ alkyl. In one aspect, $R^5$ is in the S-configuration and is halogen. In one aspect, $R^5$ is in the S-configuration and is OH. In one aspect, $R^5$ is in the S-configuration and is $C_1$-$C_6$ alkyl. In one aspect, $R^5$ is in the S-configuration and is methyl.

In one aspect, the application relates to the use of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, for preventing or treating a brain cancer. In one aspect, $R^5$ is in the S-configuration. In one aspect, $R^5$ is in the S-configuration and is selected from the group consisting of halogen, OH, $CONH_2$, COOH, CN, $N_3$, $C_1$-$C_6$ alkyl, $C_2$-$C_6$ alkenyl, and $C_2$-$C_6$ alkynyl. In one aspect, $R^5$ is in the S-configuration and is selected from the group consisting of halogen, OH, and $C_1$-$C_6$ alkyl. In one aspect, $R^5$ is in the S-configuration and is halogen. In one aspect, $R^5$ is in the S-configuration and is OH. In one aspect, $R^5$ is in the S-configuration and is $C_1$-$C_6$ alkyl. In one aspect, $R^5$ is in the S-configuration and is methyl.

In one aspect, the application relates to the use of a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, in the manufacture of a medicament for preventing or treating a brain cancer. In one aspect, $R^5$ is in the S-configuration. In one aspect, $R^5$ is in the S-configuration and is selected from the group consisting of halogen, OH, $CONH_2$, COOH, CN, $N_3$, $C_1$-$C_6$ alkyl, $C_2$-$C_6$ alkenyl, and $C_2$-$C_6$ alkynyl. In one aspect, $R^5$ is in the S-configuration and is selected from the group consisting of halogen, OH, and $C_1$-$C_6$ alkyl. In one aspect, $R^5$ is in the S-configuration and is halogen. In one aspect, $R^5$ is in the S-configuration and is OH. In one aspect, $R^5$ is in the S-configuration and is $C_1$-$C_6$ alkyl. In one aspect, $R^5$ is in the S-configuration and is methyl.

In one aspect, the application relates to a compound of the application, e.g., a compound according to formula A, I, II, III, IVa, IVb, IVc, IVd, Va, Vb, Vc, Vd, VIa, VIb, VIc, VId, VIIa, VIIb, VIIc, VIId, or VIIe or a pharmaceutically acceptable salt, solvate, or prodrug thereof, or a pharmaceutical composition of the application, for use in preventing or treating a brain cancer. In one aspect, $R^5$ is in the S-configuration. In one aspect, $R^5$ is in the S-configuration and is selected from the group consisting of halogen, OH, $CONH_2$, COOH, CN, $N_3$, $C_1$-$C_6$ alkyl, $C_2$-$C_6$ alkenyl, and $C_2$-$C_6$ alkynyl. In one aspect, $R^5$ is in the S-configuration and is selected from the group consisting of halogen, OH, and $C_1$-$C_6$ alkyl. In one aspect, $R^5$ is in the S-configuration and is halogen. In one aspect, $R^5$ is in the S-configuration and is OH. In one aspect, $R^5$ is in the S-configuration and is $C_1$-$C_6$ alkyl. In one aspect, $R^5$ is in the S-configuration and is methyl. In one aspect, the proliferative disorder is brain cancer. In another aspect, the brain cancer is a primary tumor. In another aspect, the primary brain tumor is selected from glioblastoma, astrocytoma, meningioma, pituitary adenoma, vestibular schwannoma, ependymoma, oligodendroglioma, choroid plexus papillomas, and medullablastoma.

In one aspect, the disorder is angiogenic disorder. In another aspect, the angiogenic disorder is selected from cancer, wet macular degeneration, and dry macular degeneration.

In one aspect, the disorder is abnormal vascularization.

In one aspect, the disorder is ocular myopathy.

In one aspect, the compound of the application or composition is administered orally, parenterally, subcutaneously, intravenously, intramuscularly, intraperitoneally, by intranasal instillation, by intracavitary or intravesical instillation, topically, intraarterially, intralesionally, by metering pump, or by application to mucous membranes. In another aspect, the compound of the application or composition is administered orally, parenterally, or intravenously. In one aspect, the compound of the application or composition is administered orally.

Definitions

For convenience, certain terms used in the specification, examples and appended claims are collected here.

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylates particular protein/peptide substrates, they all bind the same second substrate ATP in a highly conserved pocket. About 50% of the known oncogene products are protein tyrosine kinases (PTKs), and their kinase activity has been shown to lead to cell transformation.

The PTKs can be classified into two categories, the membrane receptor PTKs (e.g., growth factor receptor PTKs) and the non-receptor PTKs (e.g., the Src family of proto-oncogene products and focal adhesion kinase (FAK)). The hyperactivation of Src has been reported in a number of human cancers, including those of the colon, breast, lung, bladder, and skin, as well as in gastric cancer, hairy cell leukemia, and neuroblastoma.

The phrase "inhibits one or more components of a protein kinase signaling cascade" means that one or more components of the kinase signaling cascade are effected such that the function of the cell changes. Components of a protein kinase signaling cascade include any proteins involved directly or indirectly in the kinase signaling pathway including second messengers and upstream and downstream targets.

"Treating", includes any effect, e.g., lessening, reducing, modulating, or eliminating, that results in the improvement of the condition, disease, disorder, etc. "Treating" or "treatment" of a disease state includes: (1) inhibiting the disease state, i.e., arresting the development of the disease state or its clinical symptoms; or (2) relieving the disease state, i.e., causing temporary or permanent regression of the disease state or its clinical symptoms.

"Preventing", refers to causing the clinical symptoms of the disease state not to develop in a subject that may be exposed to or predisposed to the disease state, but does not yet experience or display symptoms of the disease state.

As used herein, the term "proliferative disorder" refers to conditions in which the unregulated and/or abnormal growth of cells can lead to the development of an unwanted condition or disease, which can be cancerous or non-cancerous, for example a psoriatic condition.

As used herein, the terms "psoriatic condition" or "psoriasis" refers to disorders involving keratinocyte hyperproliferation, inflammatory cell infiltration, and cytokine alteration. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells.

The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer.

As used herein, the term "cancer" includes solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS. Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body. Cancers include metastatic cancer, for example, cancer that has spread from the place where it first started to another place in the body.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

The term "brain cancer" encompasses a variety of cancers. There can be actual brain tumors which arise from the brain itself, known as primary brain cancers of which there are several. The term "brain cancer" refers to malignant tumors i.e., tumors that grow and spread aggressively, overpowering healthy cells by taking up their space, blood, and nutrients. Tumors that do not spread aggressively are called benign tumors. Benign tumors are generally less serious than a malignant tumor, but a benign tumor can still cause problems in the brain. There can also be brain metastases, which represent the spread of other cancers, such as lung or breast to the brain.

Brain tumors are classified by both the cell of the brain that makes them up and how the tumor looks under the microscope. Primary brain tumors arise from any of the cells in the brain, or from specific structures in the brain. Glia cells support the neurons of the brain and tumors which arise from these cells are known as glial tumors. The membrane that surrounds the brain can also develop tumors and these are known as meningiomas. There are other types of tumors, which involve other structures of the brain including ependymoma. The most common primary brain tumors are gliomas, meningiomas, pituitary adenomas, vestibular schwannomas, and primitive neuroectodermal tumors (medullablastomas).

Glioblastoma is a malignant rapidly growing astrocytoma of the central nervous system and usually of a cerebral hemisphere. Synonyms for glioblastoma include glioblastoma multiforme (GBM), giant cell glioblastoma, and multiforme spongioblastoma multiforme. Glioblastoma is the most common malignant primary brain tumor and has proven very difficult to treat. These tumors are often aggressive and infiltrate surrounding brain tissue. Glioblastomas arise from glial cells, which are cells that form the tissue that surrounds and protects other nerve cells found within the brain and spinal cord. Glioblastomas are mainly composed of star-shaped glial cells known as astrocytes.

The term "glioma" includes any type of brain tumor such as astrocytomas, oligodendrogliomas, ependymomas, and choroid plexus papillomas. Astrocytomas come in four grades based on how fast the cells are reproducing and the likelihood that they will infiltrate nearby tissue. Grades I or II astrocytomas are nonmalignant and may be referred to as low-grade. Grades III and IV astrocytomas are malignant and may be referred to as high-grade astrocytomas. Grade II astrocytomas are known as anaplastic astrocytomas. Grade IV astrocytomas are known as glioblastoma multiforme.

Medulloblastoma is a highly malignant primary brain tumor that originates in the cerebellum or posterior fossa. Originally considered to be a glioma, medulloblastoma is now known to be of the family of cranial primitive neuroectodermal tumors (PNET).

Tumors that originate in the cerebellum are referred to as infratentorial because they occur below the tentorium, a thick membrane that separates the cerebral hemispheres of the brain from the cerebellum. Another term for medulloblastoma is infratentorial PNET.

Medulloblastoma is the most common PNET originating in the brain. All PNET tumors of the brain are invasive and rapidly growing tumors that, unlike most brain tumors, spread through the cerebrospinal fluid (CSF) and frequently metastasize to different locations in the brain and spine. The peak of occurrence of medullablastoma is seven years of age. Seventy percent of medulloblastomas occur in individuals younger than 16. Desmoplastic medulloblastoma is encountered especially in adulthood. This type of tumor rarely occurs beyond the fifth decade of life.

Neuroblastoma is a cancer that forms in nerve tissue. The cells of neuroblastoma usually resemble very primitive developing nerve cells found in an embryo or fetus. The term neuro indicates "nerves," while blastoma refers to a cancer that affects immature or developing cells.

Neurons (nerve cells) are the main component of the brain and spinal cord and of the nerves that connect them to the rest of the body. Neuroblastoma usually begins in the adrenal glands, but it may also begin in the spinal cord. Neuroblastoma is the most common extracranial solid cancer in childhood. In 2007, neuroblastoma was the most common cancer in infancy, with an annual incidence of about 650 new cases per year in the US. Close to 50 percent of neuroblastoma cases occur in children younger than two years old. It is a neuroendocrine tumor, arising from any neural crest element of the sympathetic nervous system or SNS. A branch of the autonomic nervous system, the SNS is a nerve network that carries messages from the brain throughout the body and is responsible for the fight-or-flight response and production of adrenaline or epinephrine.

Neuroepithelioma is malignant tumors of the neuroepithelium. Neuroepithelioma is found most commonly in children and young adults. It arises most often in the chest wall, pelvis, or extremity, either in bone or soft tissue. Procedures used in the diagnosis may include blood and urine tests, X rays of the affected bone and the whole body and lungs, bone marrow aspirations, CT scans, and fluoroscopy. Treatments include surgery, radiation therapy and chemotherapy. Ewing's tumors are an example of a type of peripheral neuroepithelioma.

In addition to psoriatic conditions, the types of proliferative diseases which may be treated using the compositions of the present application are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. The proliferative diseases can include dysplasias and disorders of the like.

The term "angiogenic disorder" refers to conditions in which the unregulated and/or abnormal growth of blood vessels can lead to development of unwanted condition or disease, which can be cancerous or non-cancerous, for example, wet and dry macular degeneration.

An "effective amount" of a compound of the disclosed application is the quantity which, when administered to a subject having a disease or disorder, results in regression of the disease or disorder in the subject. Thus, an effective amount of a compound of the disclosed application is the quantity which, when administered to a subject having a cell proliferation disorder, results in regression of cell growth in the subject. The amount of the disclosed compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

As used herein, the term "effective amount" refers to an amount of a compound, or a combination of compounds, of the present application effective when administered alone or in combination as an anti-proliferative agent. For example, an effective amount refers to an amount of the compound present in a formulation or on a medical device given to a recipient patient or subject sufficient to elicit biological activity, for example, anti-proliferative activity, such as e.g., anti-cancer activity or anti-neoplastic activity. The combination of compounds optionally is a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, or increased anti-proliferative effect, or some other beneficial effect of the combination compared with the individual components.

The term "compounds of the application" or "a compound of the application" refers to a compound according to formula A, I, II, III, IVa, IVb, IVc, IVd, Va, Vb, Vc, Vd, VIa, VIb, VIc, VId, VIIa, VIIb, VIIc, VIId, or VIIe or any specific compound described herein (e.g., a compound in Table 1).

Compound X is of the following structure:

Compound Y is of the following structure:

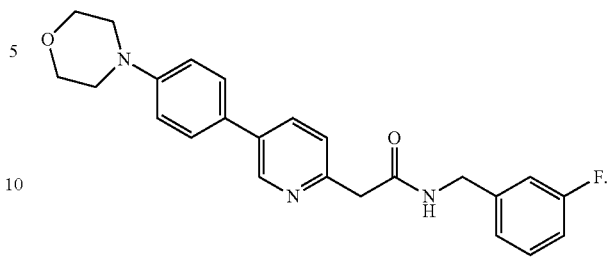

With respect to the chemical compounds useful in the present application, the following terms can be applicable:

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present application containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present application. Cis and trans geometric isomers of the compounds of the present application are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present application.

When any variable (e.g., $R_5$) occurs more than one time in any constituent or formula for a compound, its definition at each occurrence is independent of its definition at every other occurrence. Thus, for example, if a group is shown to be substituted with 0-2 $R_5$ moieties, then the group may optionally be substituted with up to two $R_5$ moieties and $R_5$ at each occurrence is selected independently from the definition of $R_5$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present application that contain nitrogens can be converted to N-oxides by treatment with an oxidizing agent (e.g., 3-chloroperoxybenzoic acid (m-CPBA) and/or hydrogen peroxides) to afford other compounds of the present application. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present application can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, $C_{1-6}$ alkenyl, $C_{1-6}$ alkynyl, $C_3$-14 carbocycle, or 3-14-membered heterocycle) derivatives.

When an atom or chemical moiety is followed by a subscripted numeric range (e.g., $C_{1-6}$), the application is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), and in another embodiment, a straight chain or branched chain alkyl has four or fewer carbon atoms.

"Substituted alkyl" refers to alkyl moieties having substituents replacing one or more hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Cycloalkyl" refers to cyclic moieties having 3 to 14 carbon atoms in their ring structure. In another embodiment, cycloalkyls have 3 to 8 carbon atoms in their ring structure. In another embodiment, cycloalkyls have 5 or 6 carbons in the ring structure. Cycloalkyls can be further substituted, e.g., with the substituents described above.

"Alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, alkyl or alkenyl substituted cycloalkenyl groups, and cycloalkyl or cycloalkenyl substituted alkenyl groups. The term "alkenyl" further includes alkenyl groups, which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

"Substituted alkenyl" refers to alkenyl moieties having substituents replacing one or more hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Cycloalkenyl," e.g., cyclopropenyl, cyclopentenyl, cyclohexenyl, cycloheptenyl, cyclooctenyl, refers to cyclic moieties having 3 to 14 carbon atoms in their ring structure and at least one double bond. In another embodiment cycloalkenyls may have from 3 to 8 carbon atoms in their ring structure. In another embodiment cycloalkenyl groups may have 5 or 6 carbons in the ring structure. Cycloalkenyls can be further substituted, e.g., with the substituents described above.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_4$-$C_6$ for branched chain). The term "$C_2$-$C_6$" includes alkynyl groups containing two to six carbon atoms. The term "$C_3$-$C_6$" includes alkynyl groups containing three to six carbon atoms.

"Substituted alkynyl" refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Cycloalkynyl," e.g., cyclooctynyl, refers to cyclic moieties having 8 to 14 carbon atoms in their ring structure and at least one triple bond. In one embodiment the cycloalkynyl moiety may have 8 or 9 carbons in the ring structure. Cycloalkynyls can be further substituted, e.g., with the substituents described above.

Unless the number of carbons is otherwise specified, "lower alkyl" includes an alkyl group, as defined above, but having from one to ten, or in another embodiment from one to six, carbon atoms in its backbone structure. "Lower alkenyl" and "lower alkynyl" have chain lengths of, for example, 2-6 carbon atoms.

An "alkylaryl" or an "aralkyl" moiety is an alkyl substituted with an aryl (e.g., phenylmethyl (benzyl)).

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "halo" or "halogen" refers to fluoro, chloro, bromo, and iodo. The term "perhalogenated" generally refers to a moiety wherein all hydrogens are replaced by halogen atoms.

The term "haloalkyl" refers to both branched and straight-chain saturated aliphatic hydrocarbon groups having the specified number of carbon atoms, substituted with 1 or more halogen (for example —$C_vF_w$ wherein v=1 to 3 and w=1 to (2v+1)). Examples of haloalkyl include, but are not limited to, trifluoromethyl, trichloromethyl, pentafluoroethyl, and pentachloroethyl.

The term "non-hydrogen substituent" refers to substituents other than hydrogen. Nonlimiting examples include alkyl groups, alkoxy groups, halogen groups, hydroxyl groups, aryl groups, etc.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_3$-14 carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctynyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N—O and $S(O)_p$, where p=1 or 2). When a nitrogen atom is included in the ring it is either N or NH, depending on whether or not the nitrogen atom is attached to a double bond in the ring (i.e., a hydrogen is present if needed to maintain the tri-valency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. In one embodiment, when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

The term "hydroxy" or "hydroxyl" includes groups with an —OH or —O⁻.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

In the present specification, the structural formula of the compound represents a certain isomer for convenience in some cases, but the present application includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present application is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present application.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J., Chem. Educ. 1964, 41, 116).

"Enantiomerically pure" or "enantiopure" refers to a sample of a chiral substance all of whose molecules (within the limits of detection) have the same chirality sense. In one aspect, a compound of the application is in an enantiopure form, such as in about 85%, 86%, 87%, 88%, 89%, 90%, 91%, 92%, 93%, 94%, 95%, 97%, 97%, 98%, 99%, or greater than 99% enantiomeric excess. In another aspect, the enantiomeric excess is about 90%, 95%, 97%, 99%, or greater than 99%. In another aspect, the enantiomeric excess is about 95%, 97%, 99%, or greater than 99%. In another aspect, the enantiomeric excess is about 99% or greater than 99%. In another aspect, In another aspect, the enantiomeric excess is about greater than 99%.

"Enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

Additionally, the compounds of the present application, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomers" refers to compounds whose structures differ markedly in arrangement of atoms, but which exist in easy and rapid equilibrium. It is to be understood that the compounds of the application may be depicted as different tautomers. It should also be understood that when compounds have tautomeric forms, all tautomeric forms are intended to be within the scope of the application, and the naming of the compounds does not exclude any tautomer form.

Some compounds of the present application can exist in tautomeric forms which are also intended to be encompassed within the scope of the present application.

The compounds, salts and prodrugs of the present application can exist in several tautomeric forms, including the enol and imine form, and the keto and enamine form and geometric isomers and mixtures thereof. All such tautomeric forms are included within the scope of the present application. Tautomers exist as mixtures of a tautomeric set in solution. In solid form, usually one tautomer predominates. Even though one tautomer may be described, the present application includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

Common tautomeric pairs are: ketone-enol, enamine-imine, lactam-lactim, amide-imidic acid tautomerism in heterocyclic rings (e.g., in the nucleobases guanine, thymine, and cytosine), amine-enamine and enamine-enamine.

It will be noted that the structure of some of the compounds of the application include asymmetric carbon atoms. It is to be understood accordingly that the isomers arising from such asymmetry (e.g., all enantiomers and diastereomers) are included within the scope of the application, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate. The compounds of this application may exist in stereoisomeric form, therefore can be produced as individual stereoisomers or as mixtures.

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salt, hydrate, solvate, or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this application include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds of the application are capable of further forming salts. All of these forms are also contemplated within the scope of the claimed application.

"Pharmaceutically acceptable salt" of a compound means a salt that is pharmaceutically acceptable and that possesses the desired pharmacological activity of the parent compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates), as defined herein, of the same salt.

The pharmaceutically acceptable salts of the present application can be synthesized from a parent compound that contains a basic or acidic moiety by conventional chemical methods.

Generally, such salts can be prepared by reacting the free acid or base forms of these compounds with a stoichiometric amount of the appropriate base or acid in water or in an organic solvent, or in a mixture of the two; non-aqueous media like ether, ethyl acetate, ethanol, isopropanol, or acetonitrile can be used. Lists of suitable salts are found in Remington's Pharmaceutical Sciences, 18th ed. (Mack Publishing Company, 1990). For example, salts can include, but are not limited to, the hydrochloride and acetate salts of the aliphatic amine-containing, hydroxyl amine-containing, and imine-containing compounds of the present application.

The compounds of the present application can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present application can also be prepared as prodrugs, for example pharmaceutically acceptable prodrugs. The terms "pro-drug" and "prodrug" are used interchangeably herein and refer to any compound which releases an active parent drug in vivo.

Since prodrugs are known to enhance numerous desirable qualities of pharmaceuticals (e.g., solubility, bioavailability, manufacturing, etc.) the compounds of the present application can be delivered in prodrug form. Thus, the present application is intended to cover prodrugs of the presently claimed compounds, methods of delivering the same and compositions containing the same. "Prodrugs" are intended to include any covalently bonded carriers that release an active parent drug of the present application in vivo when such prodrug is administered to a subject.

Prodrugs the present application are prepared by modifying functional groups present in the compound in such a way that the modifications are cleaved, either in routine manipulation or in vivo, to the parent compound. Prodrugs include compounds of the present application wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of formula I, and the like, See Bundegaard, H. "Design of Prodrugs" p 1-92, Elesevier, New York-Oxford (1985).

In the specification, the singular forms also include the plural, unless the context clearly dictates otherwise. Unless defined otherwise, all technical and scientific terms used herein have the same meaning as commonly understood by one of ordinary skill in the art to which this application belongs. In the case of conflict, the present specification will control.

All percentages and ratios used herein, unless otherwise indicated, are by weight.

"Combination therapy" (or "co-therapy") includes the administration of a compound of the application and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present application.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the application remains operable. Moreover, two or more steps or actions may be conducted simultaneously.

The compounds, or pharmaceutically acceptable salts thereof, is administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the application can be found in Remington: the Science and Practice of Pharmacy, $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

In one embodiment, the compound is prepared for oral administration, wherein the disclosed compounds or salts thereof are combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose, saccharin, xylitol, and the like. When a dosage unit form is a capsule, it often contains, in addition to materials of the above type, a liquid carrier such as a fatty oil.

In some embodiments, various other materials are present as coatings or to modify the physical form of the dosage unit. For instance, in some embodiments, tablets are coated with shellac, sugar or both. In some embodiments, a syrup or elixir contains, in addition to the active ingredient, sucrose as a sweetening agent, methyl and propylparabens as preservatives, a dye and a flavoring such as cherry or orange flavor, and the like.

For some embodiments relating to parental administration, the disclosed compounds, or salts, solvates, tautomers or polymorphs thereof, can be combined with sterile aqueous or organic media to form injectable solutions or suspensions. In one embodiment, injectable compositions are aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, the compositions contain about 1 to 50%, of the active ingredient. For example, injectable solutions are produced using solvents such as sesame or peanut oil or aqueous propylene glycol, as well as aqueous solutions of water-soluble pharmaceutically-acceptable salts of the compounds. In some embodiments, dispersions are prepared in glycerol, liquid polyethylene glycols and mixtures thereof in oils. Under ordinary conditions of storage and use, these preparations contain a preservative to prevent the growth of microorganisms. The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

For rectal administration, suitable pharmaceutical compositions are, for example, topical preparations, suppositories or enemas. Suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, in another embodiment, compositions contain about 1 to 50%, of the active ingredient.

In some embodiments, the compounds are formulated to deliver the active agent by pulmonary administration, e.g., administration of an aerosol formulation containing the active agent from, for example, a manual pump spray, nebulizer or pressurized metered-dose inhaler.

In some embodiments, suitable formulations of this type also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a headspace representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. In some embodiments where the liquid carrier is used, the formulation is administered as a nasal spray or drops and includes oil or aqueous solutions of the active ingredients.

Also contemplated are formulations that are rapidly dispersing dosage forms, also known as "flash dose" forms. In particular, some embodiments of the present application are formulated as compositions that release their active ingredients within a short period of time, e.g., typically less than about five minutes, in another embodiment, less than about ninety seconds, in another embodiment, less than about thirty seconds and in another embodiment, in less than about ten or fifteen seconds. Such formulations are suitable for administration to a subject via a variety of routes, for example by insertion into a body cavity or application to a moist body surface or open wound.

Typically, a "flash dosage" is a solid dosage form that is administered orally, which rapidly disperses in the mouth, and hence does not require great effort in swallowing and allows the compound to be rapidly ingested or absorbed through the oral mucosal membranes. In some embodiments, suitable rapidly dispersing dosage forms are also used in other applications, including the treatment of wounds and other bodily insults and diseased states in which release of the medicament by externally supplied moisture is not possible.

"Flash dose" forms are known in the art; see for example, effervescent dosage forms and quick release coatings of insoluble microparticles in U.S. Pat. Nos. 5,578,322 and 5,607,697; freeze dried foams and liquids in U.S. Pat. Nos. 4,642,903 and 5,631,023; melt spinning of dosage forms in U.S. Pat. Nos. 4,855,326, 5,380,473 and 5,518,730; solid, free-form fabrication in U.S. Pat. No. 6,471,992; saccharide-based carrier matrix and a liquid binder in U.S. Pat. Nos. 5,587,172, 5,616,344, 6,277,406, and 5,622,719; and other forms known to the art.

The compounds of the application are also formulated as "pulsed release" formulations, in which the compound is released from the pharmaceutical compositions in a series of releases (i.e., pulses). The compounds are also formulated as "sustained release" formulations in which the compound is continuously released from the pharmaceutical composition over a prolonged period.

Also contemplated are formulations, e.g., liquid formulations, including cyclic or acyclic encapsulating or solvating agents, e.g., cyclodextrins, polyethers, or polysaccharides (e.g., methylcellulose), or in another embodiment, polyanionic β-cyclodextrin derivatives with a sodium sulfonate salt group separate from the lipophilic cavity by an alkyl ether spacer group or polysaccharides. In one embodiment, the agent is methylcellulose. In another embodiment, the agent is a polyanionic β-cyclodextrin derivative with a sodium sulfonate salt separated from the lipophilic cavity by a butyl ether spacer group, e.g., CAPTISOL® (CyDex, Overland, Kans.). One skilled in the art can evaluate suitable agent/disclosed compound formulation ratios by preparing a solution of the agent in water, e.g., a 40% by weight solution; preparing serial dilutions, e.g., to make solutions of 20%, 10, 5%, 2.5%, 0% (control), and the like; adding an excess (compared to the amount that can be solubilized by the agent) of the disclosed compound; mixing under appropriate conditions, e.g., heating, agitation, sonication, and the like; centrifuging or filtering the resulting mixtures to obtain clear solutions; and analyzing the solutions for concentration of the disclosed compound.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The application having now been described by way of written description, those of skill in the art will recognize that the application can be practiced in a variety of embodiments and that the foregoing description and examples below are for purposes of illustration and not limitation of the claims that follow.

Synthesis of the Compounds of the Application

Compounds of the application can be synthesized according to the following scheme.

Scheme 1

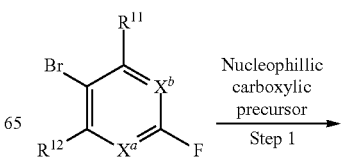

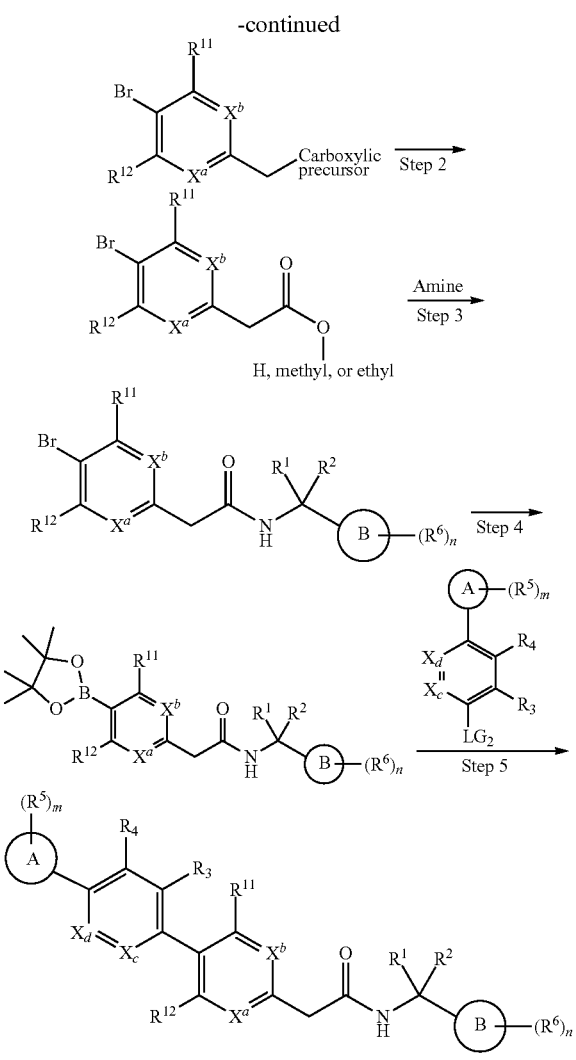

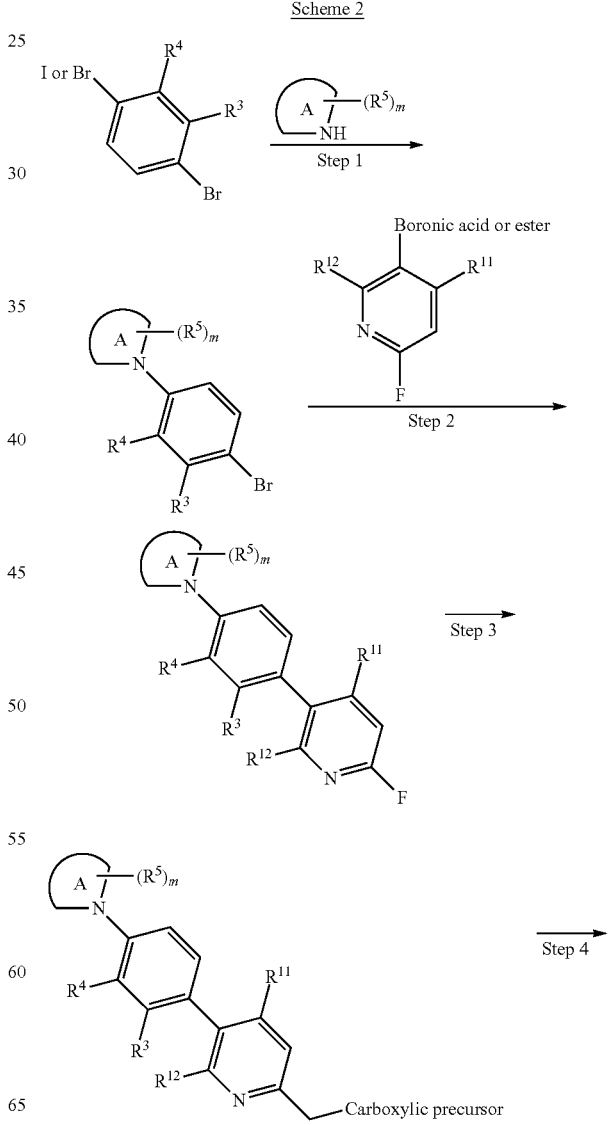

Scheme 1 shows the synthesis of some of the claimed compounds following a general route that utilizes well-established chemistry. Step 1 shows an aromatic substitution reaction involving displacement of a leaving group by a nucleophillic carboxylic precursor that can provide the desired arrangement of the carboxylic precursor. In this example the leaving group is fluoride but could be another leaving group such as a halogen or an alkoxide. The nucleophillic carboxylic precursor could be acetonitrile, an acetic acid analog, or malonate with inherent nucleophillicity induced by deprotonation with a base such as lithium hexamethyldisilazide, potassium hexamethyldisilazide, alkyl lithium, lithium diisopropylamide, or a similar base.

Step 2 shows the conversion of the carboxylic precursor to the desired carboxylic acid or ester. The carboxylic precursor can be a cyano group which is converted to the desired carboxylic acid or ester by acid or base catalyzed hydrolysis. The carboxylic precursor can also be a malonate that can be converted to the desired carboxylic acid or ester by acid or base catalyzed hydrolysis and subsequent decarboxylation.

Step 3 shows the conversion of the carboxylic acid or ester to the desired amide. The carboxylic acid can be converted to the amide by established amide coupling techniques facilitated by many established reagents such as PyBOP or carbodiimide-based reagents. Alternatively, the amide can be synthesized by heating the amine and ester in a high boiling solvent such as anisole. This same amide coupling reaction can be conducted with the amine and ester at lower temperature by first activating the amine by reaction with trimethyl aluminum followed by addition of the ester.

Step 4 shows the conversion of the aryl bromide to the boronic ester. This conversion is typically palladium-catalyzed in the presence of a boronate, such as bis(pinocolato) diboron. As an alternative, lithium-halogen exchange followed by a quench with a boronic acid or ester can be used to accomplish this conversion.

The formation of the boronate facilitates the bi-aryl coupling by Suzuki conversion with the aryl-LG2 shown in Step 5. As an alternative, LG2 can be converted to the boronate and reacted with the aryl bromide produced by Step 3. The well-established Suzuki reaction, Step 5, is typically conducted with a palladium catalyst in the presence of a weak base such as sodium carbonate, potassium carbonate, or sodium bicarbonate with heating to 80-110° C.

-continued

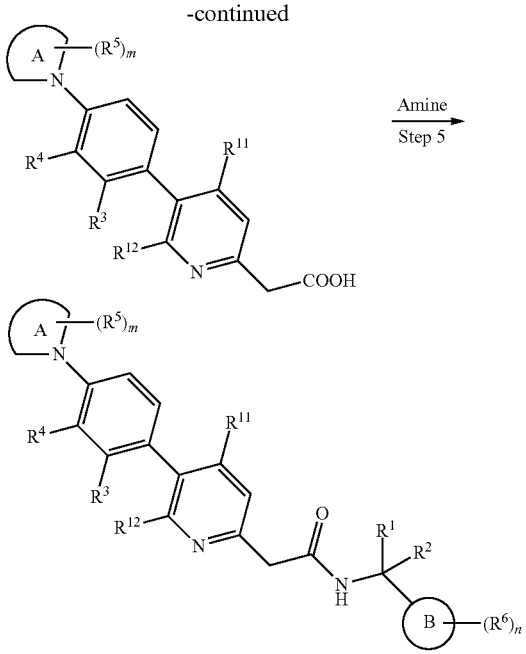

Scheme 2 shows the synthesis of some of the compounds of the present application that belong to formula A, I, II, III, IVa, IVc, IVd, Va, Vb, Vc, Vd, VIa, VIb, VIc, VId, VIIa, VIIb VIIc, VIId, or VIIe following an alternative general route that utilizes well-established chemistry. Step 1 shows either an aromatic substitution reaction involving displacement of an iodo or bromo group by a substituted cyclic amine or a Buchwald-Hartwig amination. The aromatic substitution can be induced by deprotonation of the cyclic amine with a base such as lithium hexamethyldisilazide, potassium hexamethyldisilazide, alkyl lithium, lithium diisopropylamide, or a similar base. Buchwald-Hartwig amination reactions can be achieved using palladium catalyst, such as palladium acetate, in the presence of phosphine ligand, such as tri(o-tolyl phosphine) or racemic BINAP (2,2'-bis(diphenylphosphino)-1,1'-binaphthyl), and a base, such as sodium or potassium tert-butoxide.

Step 2 involves bi-aryl coupling by Suzuki conversion of the aryl bromide obtained from step 1 with aryl boronic acid or ester. The Suzuki reaction is typically conducted with a palladium catalyst in the presence of a weak base such as sodium carbonate, potassium carbonate, or sodium bicarbonate with heating at 80-110° C.

Step 3 shows an aromatic substitution reaction involving displacement of a leaving group by a nucleophillic carboxylic precursor that can provide the desired arrangement of the carboxylic precursor. In this example the leaving group is fluoride but could be another leaving group such as a halogen or an alkoxide, depending on the boronic acid or ester used in step 2. The nucleophillic carboxylic precursor could be acetonitrile, acetic acid analog, or malonate with inherent nucleophillicity induced by deprotonation with a base such as lithium hexamethyldisilazide, potassium hexamethyldisilazide, alkyl lithium, lithium diisopropylamide, or a similar base.

Step 4 shows the conversion of the carboxylic precursor to the desired carboxylic acid. The carboxylic precursor can be a cyano group which is converted to the desired carboxylic acid by acid or base catalyzed hydrolysis. The carboxylic precursor can also be a malonate that can be converted to the desired carboxylic acid by acid or base catalyzed hydrolysis and subsequent decarboxylation.

Step 5 shows the conversion of the carboxylic acid or ester to the desired amide, which is the final product. The carboxylic acid can be converted to the amide by reacting with an amine and PyBOP (benzotriazol-1-yl-oxytripyrrolidinophosphonium hexafluorophosphate) or a carbodiimide-based reagent.

General Assays

The activity of the compounds of the application can be tested in assays known in the art. For example, the drug concentration required to block net cell growth by 50% relative to a control sample can be measured as the $GI_{50}$.

For example, in an MTT assay, the U87 and GL261 cells is seeded in 96-well plate (e.g., $6 \times 10^3$ cells in 100 µl of DMEM+10% FBS media per well) and incubated overnight at about 30-40° C. with about 2-10% $CO_2$. All test compounds is diluted (10 point 2-fold serial dilution) in a separate 96-well plate to yield 10× of final the concentrations (e.g., 0.5-256 nM). A volume of about 11 µl of 10× dilutions is added to appropriate wells (n=3). To value (reflecting the starting number of cells upon drug treatment) can be determined by following steps as described below. After 3 days incubation at about 30-40° C. with about 2-10% $CO_2$, about 10 µl of MTT solution (e.g., 5 mg/ml in PBS) is added to each well and plates are incubated at about 30-40° C. for about 2-6 h to allow MTT to form formazan crystals by reacting with metabolically active cells. About 100 µl of 20% SDS is added to each well and plates are incubated overnight at about 30-40° C. with 5% $CO_2$. Afterward, $OD_{570}$ is measured using microplate reader. The cell growth percentage of control is calculated according to percentage of control=$(T-T_0)/(C-T_0) \times 100\%$ or OD value of the test well exposure to test drug–OD value at time zero/(OD of the control well without drug treatment–OD value at time zero)×100%. Growth inhibition curves and $GI_{50}$ are determined using GraphPad Prism 5 software.

EXAMPLES

Example 1: Syntheses

Preparation of Compound 100

(Compound 100)

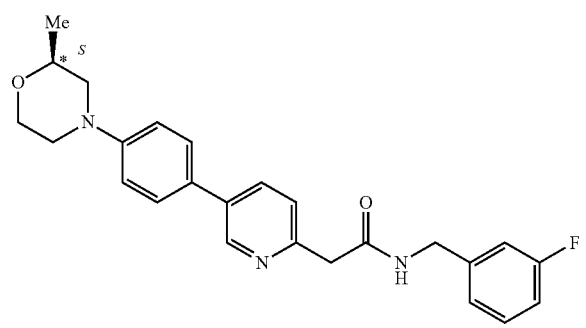

Synthesis of (Compound 1)

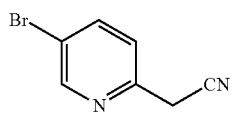

Under a rapid stream of nitrogen, a suspension of potassium bis(trimethylsilyl)amide (41.58 g, 0.208 mol) in 100 ml of anhydrous THF was prepared in a 500 ml round-bottomed flask equipped with a stir bar. The suspension was cooled using an ice/methanol bath and a solution of anhydrous MeCN (7.00 g, 0.170 mol) in anhydrous THF (11 ml) was slowly added to the suspension (over a period of 3-5 min). This was followed by the rapid addition of a solution of 2-fluoro-5-bromopyridine (4.93 g, 0.0280 mol) in anhydrous THF (40 ml). The reaction mixture was stirred under nitrogen for 2-3 hours, and checked by LCMS for the complete consumption of the starting material. Upon reaction completion EtOAc (500 ml) was added. The solution was washed twice with saturated brine (250 ml), and dried with anhydrous $Na_2SO_4$. Anhydrous $Na_2SO_4$ was filtered off, and the organic solution was concentrated in vacuo to give a residual red oily substance. This oily material was dissolved in EtOAc (25 ml), adsorbed on silica gel, and purified with flash chromatography using heptanes: EtOAc as a mobile phase to give Compound 1 as red oil (4.03 g, yield: 73%). Purity by HPLC (UV 254 nm) found to be >90%; LCMS: (198/200[M+H]$^+$). $^1$H NMR (400 MHz, CDCl$_3$): 3.91 (s, 2H), 7.35 (d, 1H), 7.88 (dd, 1H), 8.64 (fine d, 1H).

Synthesis of

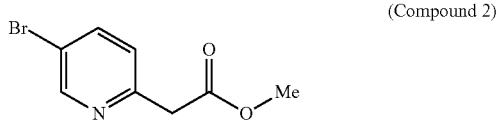 [SMILES: COC(=O)Cc1ccc(Br)cn1]
(Compound 2)

A single-necked round-bottomed flask was charged with Compound 1 (4.55 g, 23.1 mmol) and MeOH (40 g) followed by the dropwise addition of 96% $H_2SO_4$ (28 g). The resulting homogeneous solution stirred at reflux (115° C. oil bath) until the reaction was complete by TLC. After brief cooling, MgSO$_4$ (9 g) was added and the mixture swirled and allowed to stand an additional 45 min. The reaction mixture was then added slowly to a rapidly stirred and cooled (ice-water bath) mixture of DCM (250 mL) and a solution of $K_2CO_3$ (50 g) in $H_2O$ (70 mL). The resulting emulsion was allowed to stand overnight. The clear portions of organic solution were siphoned off and the remainder portions were treated iteratively with water and DCM, the clear organics being combined with the original portion that was siphoned off. The combined organics were dried (Na$_2$SO$_4$), filtered, concentrated, and purified by silica gel chromatography. The desired product, Compound 2, was obtained as a colorless solid (3.82 g, 72% yield) and characterized by LCMS (230.7[M+H]$^+$).

Synthesis of

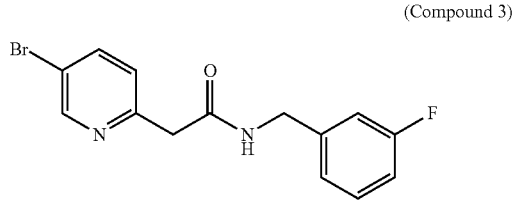 [SMILES: O=C(Cc1ccc(Br)cn1)NCc1cccc(F)c1]
(Compound 3)

A single-necked round-bottomed flask was charged with Compound 2 (1.80 g, 7.82 mmol), 3-fluorobenzylamine (2.94 g, 23.5 mmol), and anhydrous anisole (15 g). The reaction was stirred at 150° C. until reaction was complete LCMS (~23 h) and then allowed to cool to near RT. Crystals of the desired product, Compound 3, formed during the cooling process and were collected by filtration and washed with toluene. Compound 3 was obtained as colorless crystalline solid (1.59 g, 63% yield) and characterized by $^1$H NMR (400 MHz, DMSO-d$_6$): 3.69 (s, 2H), 4.30 (d, 2H), 7.0-7.15 (m, 3H), 7.3-7.4 (m, 2H), 7.99 (dd, 1H), 8.61 (fine d, 1H), 8.66 (br t, 1H).

Synthesis of

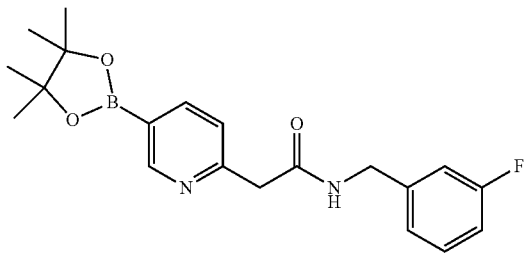
(Compound 4)

In a single-neck round bottom flask Compound 3 (292 mg, 0.904 mmol), bis(pinacolato)diboron (729 mg, 2.87 mmol), [1,1'-Bis(diphenylphosphino)ferrocene]dichloropalladium(II), complex with dichloromethane (39 mg, 0.0479 mmol), and potassium acetate (234 mg, 2.39 mmol) were combined neat. The flask was equipped with a condenser, sealed, and purged with nitrogen. Anhydrous 1,4-dioxane was added and the reaction was refluxed for 24 hr. The reaction was cooled and solvent removed in vacuo. The residue was taken up in DCM and washed twice with 0.5N NaOH and twice with brine. The organic layer was dried with sodium sulfate and concentrated. This provided crude Compound 4 (378 mg) as a dark brown tar which was characterized by LCMS (371[M+H]$^+$).

Synthesis of

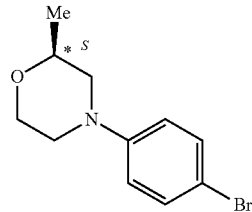
(Compound 5)

In a microwave vial 2-S-methylmorpholine (120 mg, 1.19 mmol), 4-iodo-bromobenzene (336 mg, 1.19 mmol), bis(dibenzylideneacetone)palladium (54 mg, 0.059 mmol), 2-dicyclohexylphosphino-2'-(N,N-dimethylamino)biphenyl (48 mg, 0.119 mmol), and sodium tert-butoxide (340 mg, 3.56 mmol) were combined neat. The vial was sealed and purged with nitrogen. Anhydrous toluene (2 mL), degassed with nitrogen purge, was added to the vial. The reaction was heated at 100° C. for 30 minutes in a microwave reactor. LCMS indicated complete consumption of the 4-iodo-bromobenzene. The reaction solvent was removed in vacuo and the residue was purified by preparative HPLC. The desired product, Compound 5, was obtained (69 mg, 23% yield, colorless oil) and characterized by LCMS (256/258[M+H]$^+$) and $^1$H NMR (400 MHz, DMSO): 1.11 (s, 3H), 2.27 (dd, 10.4, 11.2 hz, 1H), 2.59 (td 3.6, 11.2 Hz, 1H), 3.30 (d, 17.2 Hz, 1H), 3.50-3.65 (m, 3H), 3.85-3.90 (m, 1H), 6.87 (d, 8.8 Hz, 2H), 7.32 (d, 8.8 Hz, 2H).

Synthesis of (Compound 100)

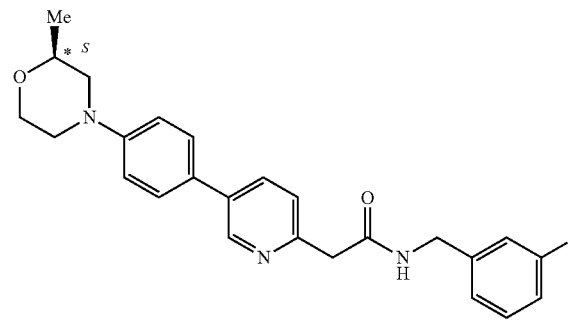

Compound 4 (230 mg, 0.625 mmol), Compound 5 (64 mg, 0.25 mmol), and tetrakis(triphenylphosphine)-palladium(O) (14 mg, 0.0125 mmol) were combined neat in a reaction vial that was capped and purged with nitrogen. 1,2-Dimethoxyethane (1.5 mL, purged with nitrogen) and 2M sodium carbonate (0.5 mL, purged with nitrogen) were added to the reaction. The reaction was stirred and heated at 80° C. for 3 hours. LCMS indicated complete consumption of Compound 5. The reaction solvent was removed in vacuo and the residue was purified by preparative HPLC. The desired product, Compound 6, was obtained (43 mg, yellow solid) and characterized by LCMS (420 [M+H]$^+$). A small aliquot (10 mg) of the product was taken up in DCM, washed with saturated sodium bicarbonate, and dried with sodium sulfate. The DCM was removed in vacuo to provide the desired product, Compound 100, as the free base (7 mg, colorless solid) and characterized by LCMS (420[M+H]$^+$) and melting point (154-155° C.).

Preparation of Compound 101

(Compound 101)

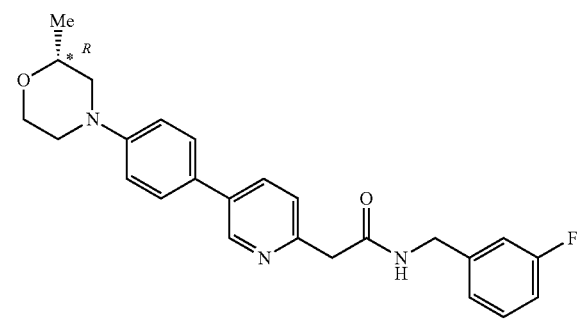

Synthesis of (Compound 7)

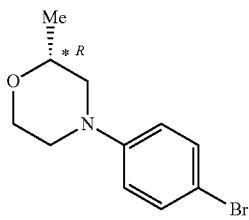

In a microwave vial 2-R-methylmorpholine hydrochloride (250 mg, 1.82 mmol), 4-iodo-bromobenzene (514 mg, 1.82 mmol, bis(dibenzylideneacetone)palladium (83 mg, 0.09 mmol), 2-dicyclohexylphosphino-2'-(N,N-dimethylamino)biphenyl (72 mg, 0.0182 mmol), and sodium tert-butoxide (700 mg, 7.28 mmol) were combined neat. The vial was sealed and purged with nitrogen. Anhydrous toluene (4 mL, degassed with nitrogen purge) was added to the vial. The reaction was heated at 100° C. for 30 minutes in a microwave reactor. LCMS indicated complete consumption of the 4-iodo-bromobenzene. The reaction solvent was removed in vacuo and the residue was purified by preparative HPLC. The desired product, Compound 7, was obtained (244 mg, 52% yield) as a colorless oil and characterized by LCMS (256/258[M+H]$^+$).

Synthesis of (Compound 101)

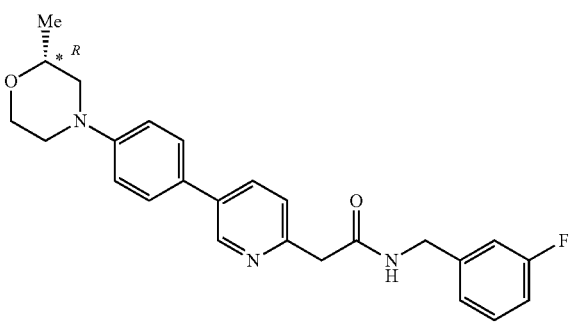

Compound 4 (60 mg, 0.162 mmol), Compound 7 (23 mg, 0.090 mmol), and tetrakis(triphenylphosphine)-palladium (O) (5 mg, 0.005 mmol) were combined neat in a reaction vial that was capped and purged with nitrogen. 1,2-Dimethoxyethane (1.5 mL, purged with nitrogen) and 2M sodium carbonate (0.5 mL, purged with nitrogen) were added to the reaction. The reaction was stirred and heated at 95° C. for 3 hours. LCMS indicated complete consumption of Compound 7. The reaction solvent was removed in vacuo, the residue was taken up in EtOAc, and washed with saturated sodium bicarbonate. The EtOAc was removed in vacuo and the residue was purified by preparative HPLC. The product was taken up in DCM, washed with saturated sodium bicarbonate, and dried with sodium sulfate. The DCM was removed in vacuo to provide the desired product, Compound 101 (5 mg, 14% yield, colorless solid) and characterized by LCMS (420[M+H]$^+$) and melting point (164-166° C.).

Preparation of Compound 102

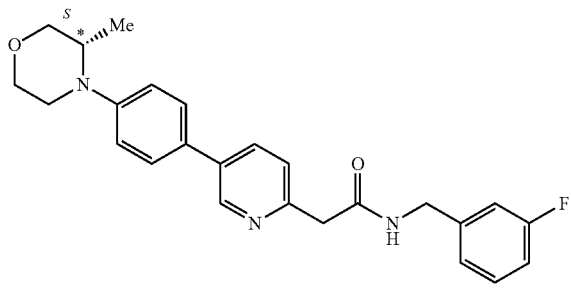
(Compound 102)

Synthesis of

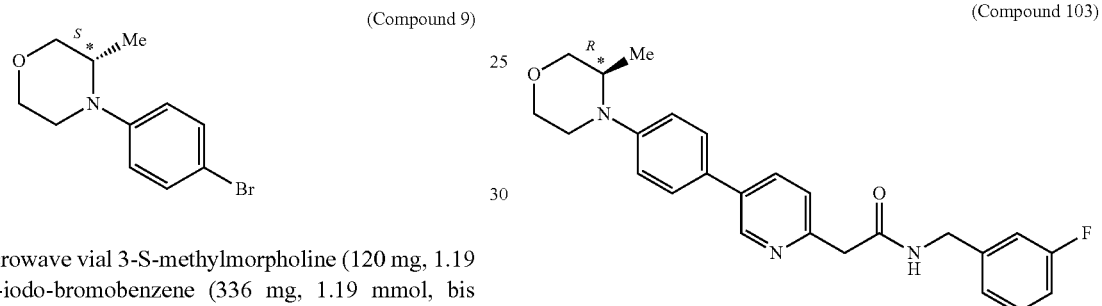

Compound 4 (107 mg, 0.288 mmol), Compound 9 (64 mg, 0.25 mmol), and tetrakis(triphenylphosphine)-palladium(O) (15 mg, 0.0125 mmol) were combined neat in a reaction vial that was capped and purged with nitrogen. 1,2-Dimethoxyethane (1.5 mL, purged with nitrogen) and 2M sodium carbonate (0.5 mL, purged with nitrogen) were added to the reaction. The reaction was stirred and heated at 95° C. for 3 hours. LCMS indicated complete consumption of Compound 9. The reaction solvent was removed in vacuo, the residue was taken up in EtOAc, and washed with saturated sodium bicarbonate. The EtOAc was removed in vacuo and the residue was purified by preparative HPLC. The product was taken up in DCM, washed with saturated sodium bicarbonate, and dried with sodium sulfate. The DCM was removed in vacuo to provide the desired product, Compound 102 was obtained (16 mg, 15% yield, colorless solid) and characterized by LCMS (420[M+H]$^+$) and melting point (165-167° C.).

Preparation of Compound 103

In a microwave vial 3-S-methylmorpholine (120 mg, 1.19 mmol), 4-iodo-bromobenzene (336 mg, 1.19 mmol, bis(dibenzylideneacetone)palladium (54 mg, 0.059 mmol), 2-dicyclohexylphosphino-2'-(N,N-dimethylamino)biphenyl (48 mg, 0.119 mmol), and sodium tert-butoxide (340 mg, 3.56 mmol) were combined neat. The vial was sealed and purged with nitrogen. Anhydrous toluene (2 mL), degassed with nitrogen purge, was added to the vial. The reaction was heated at 100° C. for 30 minutes in a microwave reactor. LCMS indicated complete consumption of the 4-iodo-bromobenzene. The reaction solvent was removed in vacuo and the residue was purified by preparative HPLC. The desired product, Compound 9, was obtained (64 mg, colorless oil) and characterized by LCMS (256/258[M+H]$^+$).

Synthesis of

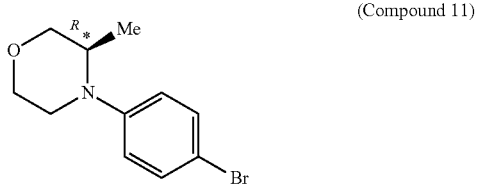
(Compound 103)

Synthesis of

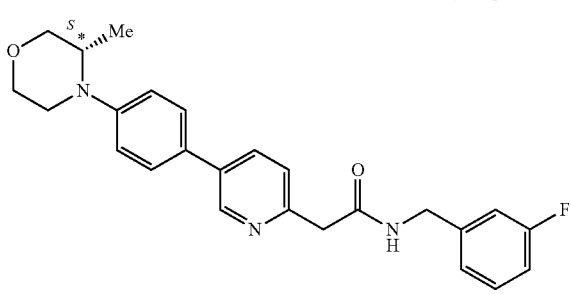
(Compound 11)

In a microwave vial 3-R-methylmorpholine (250 mg, 2.50 mmol), 4-iodo-bromobenzene (699 mg, 2.50 mmol, bis(dibenzylideneacetone)palladium (113 mg, 0.125 mmol), 2-dicyclohexylphosphino-2'-(N,N-dimethylamino)biphenyl (97 mg, 0.250 mmol), and sodium tert-butoxide (715 mg, 7.50 mmol) were combined neat. The vial was sealed and purged with nitrogen. Anhydrous toluene (5 mL, degassed with nitrogen purge) was added to the vial. The reaction was heated at 90° C. for 18 hr. LCMS indicated complete consumption of the 4-iodo-bromobenzene. The reaction solvent was removed in vacuo and the residue was taken up in DCM. The solution was filtered through a plug of silica gel, concentrated, and purified by preparative HPLC. The desired product, Compound 11, was obtained (144 mg, 23% yield, colorless oil) and characterized by LCMS (256/258 [M+H]$^+$).

Synthesis of

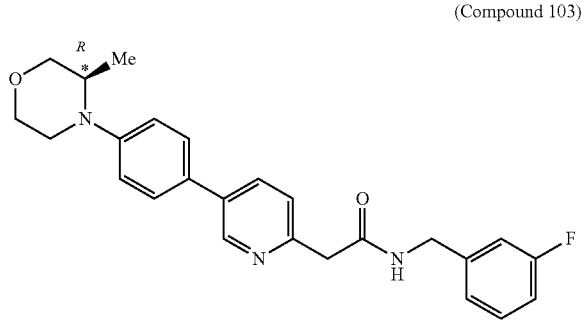
(Compound 103)

Compound 4 (152 mg, 0.426 mmol), Compound 11 (72 mg, 0.284 mmol), and tetrakis(triphenylphosphine)-palladium(O) (16 mg, 0.0142 mmol) were combined neat in a reaction vial that was capped and purged with nitrogen. 1,2-Dimethoxyethane (1.5 mL, purged with nitrogen) and 2M sodium carbonate (0.5 mL, purged with nitrogen) were added to the reaction. The reaction was stirred and heated at 95° C. for 3 hours. LCMS indicated complete consumption of Compound 11. The reaction solvent was removed in vacuo, the residue was taken up in EtOAc, and washed with saturated sodium bicarbonate. The EtOAc was removed in vacuo and the residue was purified by preparative HPLC. The product was taken up in DCM, washed with saturated sodium bicarbonate, and dried with sodium sulfate. The DCM was removed in vacuo to provide the desired product, Compound 103 was obtained (27 mg, 23% yield, colorless solid) and characterized by LCMS (420[M+H]$^+$) and melting point (148-151° C.).

Preparation of Compound 104

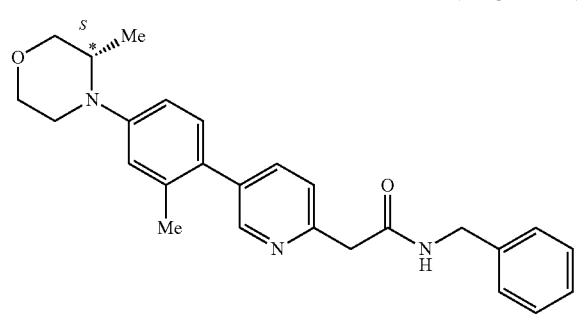
(Compound 104)

Synthesis of

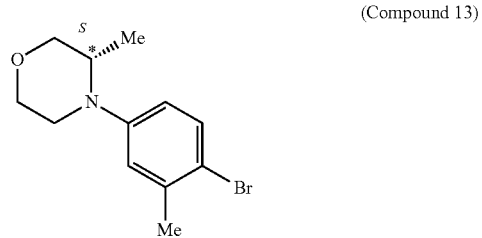
(Compound 13)

In a dry 500 ml round-bottomed flask (equipped with a water-cooled condenser, a gas outlet, and a stir bar) palladium acetate (0.449 g, 2.00 mmol), tri(o-tolyl)phosphine (1.22 g, 4.00 mmol), and potassium tert-butoxide (11.2 g, 100 mmol) were combined. The apparatus was sealed, purged with nitrogen, and 60 mL anhydrous toluene was added. To the resulting suspension 3-S-methylmorpholine (4.04 g, 40.0 mmol), and 2,5-dibromotoluene (12.5 g, 50.0 mmol) dissolved in 30 ml anhydrous toluene were added. The mixture was then stirred and refluxed at an oil-bath temperature of 90-100° C. for 3 days (The system was purged with nitrogen every 6-12 hours). The reaction mixture was cooled to room temperature, filtered, diluted with 250 ml EtOAc, and concentrated in vacuo providing an oily residue. This residue was then dissolved in 30 ml EtOAc, adsorbed on silica gel, and purified by flash chromatography (gradient method starting with 100% heptanes up to 40:60% EtOAc:heptanes) to provide Compound 13 as a yellowish oil (1.4 g, 13% yield). LCMS (270/272: [M+H]$^+$), $^1$H NMR (400 MHz, MeOD): 1.02 (d, J=6.5 Hz, 3H), 2.32 (s, 3H), 3.06 (m, 2H), 3.60-3.80 (m, 4H) 3.90 (m, 1H) 6.65 (dd, J=7.0, 2.5 Hz, 1H) 6.84 (d, J=2.5 Hz, 1H) 7.35 (d, J=7 Hz, 1H); COSY and NOESY studies confirmed that the desired regioisomer was obtained.

Synthesis of

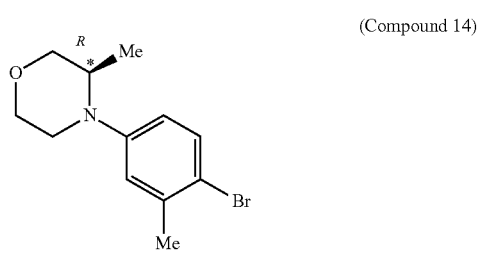
(Compound 14)

In a dry 500 ml round-bottomed flask (equipped with a water-cooled condenser, a gas outlet, and a stir bar) palladium acetate (0.337 g, 1.5 mmol), tri(o-tolyl)phosphine (0.912 g, 2.98 mmol), and potassium tert-butoxide (8.41 g, 75 mmol) were combined. The apparatus was sealed, purged with nitrogen, and 45 mL anhydrous toluene was added. To the resulting suspension 3-R-methylmorpholine (3.03 g, 30 mmol), and 2,5-dibromotoluene (9.38 g, 37.5 mmol) dissolved in 23 ml anhydrous toluene were added. The mixture was then stirred and refluxed at an oil-bath temperature of 90-100° C. for 3 days (The system was purged with nitrogen every 6-12 hours). The reaction mixture was cooled to room temperature, filtered, diluted with 250 ml EtOAc, and concentrated in vacuo providing an oily residue. This residue was then dissolved in 30 ml EtOAc, adsorbed on silica gel, and purified by flash chromatography (gradient method starting with 100% heptanes up to 40:60% EtOAc:heptanes) to provide Compound 14 as a yellowish oil (890 mg; 11% yield). LCMS (270/272: [M+H]$^+$), $^1$H NMR (400 MHz, MeOD): 1.02 (d, J=6.5 Hz, 3H), 2.32 (s, 3H), 3.06 (m, 2H), 3.60-3.80 (m, 4H) 3.90 (m, 1H) 6.65 (dd, J=7.0, 2.5 Hz, 1H) 6.84 (d, J=2.5 Hz, 1H) 7.35 (d, J=7 Hz, 1H).

Synthesis of

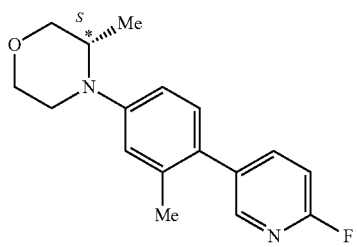

(Compound 15)

In a 50 ml round-bottomed flask equipped with a stir bar, and connected to a water-cooled condenser, Compound 13 (1.35 g, 5.00 mmol), 2-fluoropyridine-5-boronic acid (1.06 g, 7.50 mmol), and tetrakis (triphenylphosphine)-palladium (O) (312 mg, 0.270 mmol) were dissolved in 15 ml 1,4-dioxane and 5 ml of 4M aqueous sodium carbonate solution. The reaction mixture was then stirred, and refluxed at an oil-bath temperature of 90° C. for 24 hours. LCMS indicated a complete reaction. The reaction was cooled to room temperature, and diluted with 100 ml EtOAc. The reaction mixture was then washed with 100 ml water and twice with 50 mL brine. The organic layer was dried with anhydrous sodium sulfate, filtered, and concentrated in vacuo to give an oily residue which was purified by flash chromatography. Compound 15 was obtained as a yellow crystalline solid (1.1 g, 77% yield). LCMS (287 [M+H]$^+$). $^1$H NMR (400 MHz, DMSO): 0.99 (d, J=8.0 Hz, 3H), 2.18 (s, 3H), 2.95 (m, 1H), 3.10 (m, 1H) 3.55 (m, 1H) 3.68 (m, 2H) 3.90 (m, 2H) 6.78 (m, 2H) 7.08 (d, J=7 Hz, 1H) 7.20 (dd, J=7.0, 2.5 Hz, 1H) 7.92 (m, 1H) 8.16 (d, J=2.5 Hz, 1H).

Synthesis of

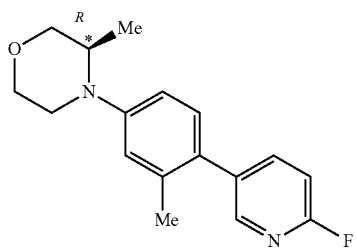

(Compound 16)

In a 50 ml round-bottomed flask equipped with a stir bar, and connected to a water-cooled condenser, Compound 14 (810 mg, 3.00 mmol), 2-fluoropyridine-5-boronic acid (636 mg, 4.50 mmol), and tetrakis (triphenylphosphine)-palladium(O) (187 mg, 0.162 mmol) were dissolved in 9 ml 1,4-dioxane and 3 ml of 4M aqueous sodium carbonate. The reaction mixture was then stirred, and refluxed at an oil-bath temperature of 90° C. for 24 hours. LCMS indicated a complete reaction. The reaction was cooled to room temperature and diluted with 60 ml EtOAc. The reaction mixture was then washed with 60 ml water, and twice with 30 mL brine. The organic layer was dried with anhydrous sodium sulfate, filtered, and concentrated in vacuo to give an oily residue which was purified by flash chromatography to provide Compound 16 (629 mg, 73% yield). LCMS (287 [M+H]$^+$). $^1$H NMR (400 MHz, DMSO): 0.99 (d, J=8.0 Hz, 3H), 2.18 (s, 3H), 2.95 (m, 1H), 3.10 (m, 1H) 3.55 (m, 1H) 3.68 (m, 2H) 3.90 (m, 2H) 6.78 (m, 2H) 7.08 (d, J=7 Hz, 1H) 7.20 (dd, J=7.0, 2.5 Hz, 1H) 7.92 (m, 1H) 8.16 (d, J=2.5 Hz, 1H).

Synthesis of

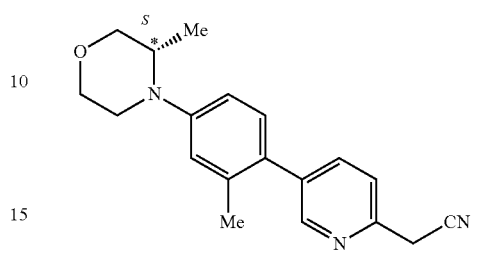

(Compound 17)

Under a rapid stream of nitrogen, a suspension of potassium bis(trimethylsilyl)amide (5.41 g, 27.1 mmol) in 13 ml anhydrous THF was prepared in a 50 ml round-bottomed flask equipped with a stir bar. The suspension was cooled using an ice/methanol bath and a solution of anhydrous MeCN (910 mg) in anhydrous THF (1.5 ml) was slowly added (over a period of 3-5 min) to the suspension. This was followed by the rapid addition of a solution of Compound 15 (1.04 g, 3.64 mmol) in anhydrous THF (5.5 ml). The reaction mixture was stirred under nitrogen for 2-3 hours, and monitored by LCMS for the complete consumption of the starting material. Upon reaction completion EtOAc (60 ml) was added and washed twice with saturated brine (30 ml). The organic layer was dried with anhydrous Na$_2$SO$_4$, filtered, and concentrated in vacuo to provide a red oil. This oil was dissolved in EtOAc (10 ml), adsorbed on silica gel, and purified with flash chromatography using heptanes: EtOAc as a mobile phase to provide Compound 17 as red oil (793 mg, 71% yield). LCMS: (308 [M+H]$^+$). $^1$H NMR (400 MHz, DMSO): 0.99 (d, J=8.0 Hz, 3H), 2.19 (s, 3H), 2.98 (m, 1H), 3.21 (m, 1H) 3.51 (m, 1H) 3.66 (m, 2H) 3.88 (m, 2H) 4.20 (s, 2H) 6.80 (m, 2H) 7.10 (d, J=7 Hz, 1H) 7.40 (d, J=7 Hz, 1H) 7.79 (dd, J=7.0, 2.5 Hz, 1H) 8.48 (d, J=2.5 Hz, 1H).

Synthesis of

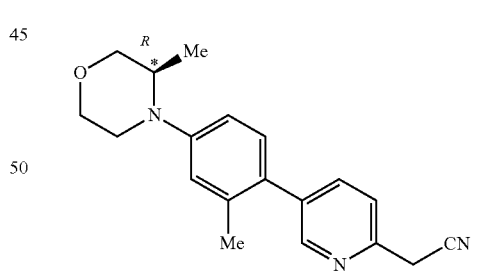

(Compound 18)

Under a rapid stream of nitrogen, a suspension of potassium bis(trimethylsilyl)amide (3.25 g, 16.2 mmol) in 8 ml anhydrous THF was prepared in a 50 ml round-bottomed flask equipped with a stir bar. The suspension was cooled using an ice/methanol bath and a solution of anhydrous MeCN (550 mg) in anhydrous THF (1.5 ml) was slowly added (over a period of 3-5 min) to the suspension. This was followed by the rapid addition of a solution of Compound 16 (623 mg, 2.18 mmol) in anhydrous THF (3.5 ml). The reaction mixture was stirred under nitrogen for 4 hours and monitored by LCMS for the complete consumption of the starting material. Upon reaction completion EtOAc (60 ml)

was added and the mixture was washed twice with saturated brine (30 ml). The organic layer was dried with anhydrous Na$_2$SO$_4$, filtered, and concentrated in vacuo to provide a red oil. This oil was dissolved in EtOAc (10 ml), adsorbed on silica gel, and purified with flash chromatography using heptanes: EtOAc as a mobile phase to provide Compound 18 as red oil (436 mg, 65% yield). LCMS: (308[M+H]$^+$). $^1$H NMR (400 MHz, DMSO): 0.99 (d, J=8.0 Hz, 3H), 2.19 (s, 3H), 2.98 (m, 1H), 3.21 (m, 1H) 3.51 (m, 1H) 3.66 (m, 2H) 3.88 (m, 2H) 4.20 (s, 2H) 6.80 (m, 2H) 7.10 (d, J=7 Hz, 1H) 7.40 (d, J=7 Hz, 1H) 7.79 (dd, J=7.0, 2.5 Hz, 1H) 8.48 (d, J=2.5 Hz, 1H).

Synthesis of (Compound 19)

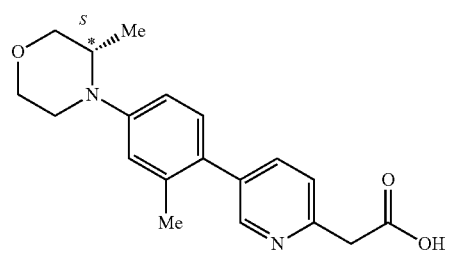

Compound 17 (750 mg, 2.44 mmol) was slowly added to an ice-cooled 10 ml 37% hydrochloric acid in a 50 ml round-bottomed flask equipped with a stir bar. Each addition was accompanied by shaking the flask in order to dissolve the solid. The round-bottomed flask was equipped with a water-cooled condenser. The reaction mixture was stirred and heated to 65-70° C. for 3 hours. The reaction was monitored by LCMS. Upon reaction completion the mixture was cooled to room temperature, and the solution was concentrated in vacuo to provide crude Compound 19 as a yellow solid. LCMS: (327[M+H]$^+$, 325[M–H]$^-$).

Synthesis of (Compound 20)

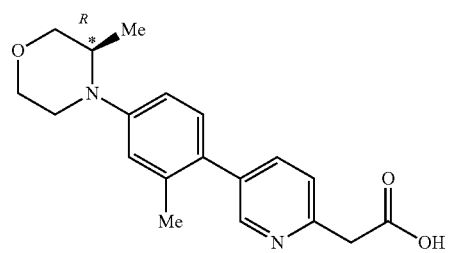

Compound 17 (430 mg, 1.3 mmol) was slowly added to an ice-cooled 10 ml 37% hydrochloric acid in a 50 ml round-bottomed flask equipped with a stir bar. Each addition was accompanied by shaking the flask in order to dissolve the solid. The round-bottomed flask was then connected to a water-cooled condenser. The reaction mixture was stirred, and heated to 65-70° C. for 3 hours. The reaction was monitored by LCMS. Upon reaction completion the mixture was cooled to room temperature, and the solution was concentrated in vacuo to provide crude Compound 20 as a yellow solid. LCMS: (327[M+H]$^+$, 325[M–H]$^-$).

Synthesis of (Compound 104)

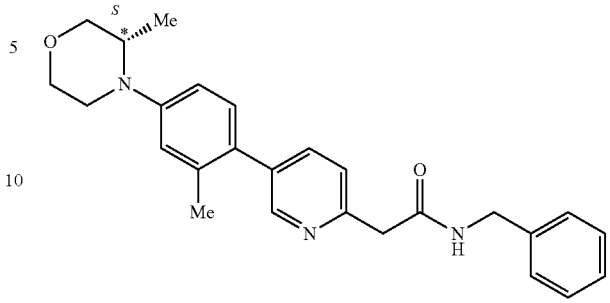

In a 40 ml vial equipped with a stir bar Compound 19 (350 mg, 1.00 mmol) and HATU (1-[Bis(dimethylamino)methylene]-1H-1,2,3-triazolo[4,5-b]pyridinium 3-oxid hexafluorophosphate) (380 mg, 1.00 mmol) were dissolved in 3 ml of a mixture of DMF:water (2:1). A solution of benzylamine (107 mg, 1.00 mmol) and diisopropylethylamine (0.66 ml, 5.0 mmol) in 5 ml DMF was then added to Compound 19 solution at 0-5° C. The mixture was then stirred at room temperature overnight, and the reaction was checked for completion using LCMS. Upon reaction completion, the mixture was diluted with EtOAc (60 ml), washed with water (60 ml), and saturated brine solution (60 ml) twice. The organic layer was dried using anhydrous sodium sulfate, and the EtOAc was concentrated in vacuo after filtering the sodium sulfate off. The resulting residue was dissolved in 20 ml EtOAc, adsorbed to silica gel, and purified by flash chromatography. Compound 104 was obtained as a yellow solid (155 mg, 47% yield). The product was characterized by LCMS (416[M+H]$^+$; purity was estimated to be >95%), and $^1$H NMR (400 MHz, DMSO): 0.99 (d, J=8.0 Hz, 3H), 2.20 (s, 3H), 2.98 (m, 1H), 3.20 (m, 1H) 3.50 (m, 1H) 3.60-3.70 (m, 4H) 3.90 (m, 2H) 4.28 (d, 2H) 6.80 (m, 2H) 7.08 (d, J=7 Hz, 1H) 7.20-7.40 (m, 6H) 7.65 (dd, J=7.0, 2.5 Hz, 1H) 8.40 (d, J=2.5 Hz, 1H) 8.60 (t, 1H). Meting point was found to be 106-108° C.

Preparation of Compound 105

(Compound 105)

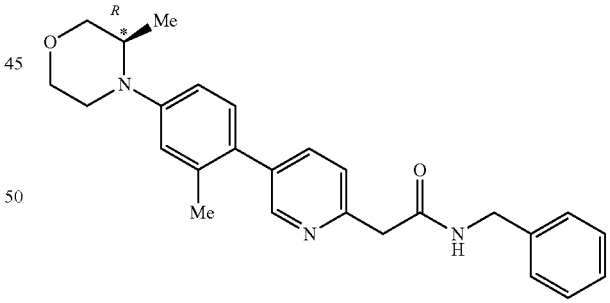

In a 40 ml vial equipped with a stir bar Compound 20 (350 mg, 1.00 mmol), and HATU (380 mg, 1.00 mmol) were dissolved in 3 ml of a mixture of DMF:water (2:1). A solution of benzylamine (107 mg, 1.00 mmol) and diisopropylethylamine (0.66 ml, 5.00 mmol) in 5 ml DMF was then added to Compound 20 solution at 0-5° C. The mixture was then stirred at room temperature overnight, and the reaction was checked for completion using LCMS. Upon reaction completion, the mixture was diluted with EtOAc (60 ml), washed with water (60 ml), and saturated brine solution (60 ml) twice. The organic layer was dried using anhydrous sodium sulfate, and the EtOAc was concentrated in vacuo after filtering the sodium sulfate off. The resulting residue was dissolved in 20 ml EtOAc, adsorbed to silica gel, and purified by flash chromatography. Compound 105 was obtained as a yellow solid (225 mg, 68% yield). The product was characterized by LCMS (416[M+H]$^+$; purity was estimated to be >95%), and $^1$H NMR (400 MHz, DMSO): 0.99 (d, J=8.0 Hz, 3H), 2.20 (s, 3H), 2.98 (m, 1H), 3.20 (m, 1H) 3.50 (m, 1H) 3.60-3.70 (m, 4H) 3.90 (m, 2H) 4.28 (d, 2H) 6.80 (m, 2H) 7.08 (d, J=7 Hz, 1H) 7.20-7.40 (m, 6H) 7.65 (dd, J=7.0, 2.5 Hz, 1H) 8.40 (d, J=2.5 Hz, 1H) 8.60 (t, 1H). Meting point was found to be 98-100° C.

Preparation of Compound 106

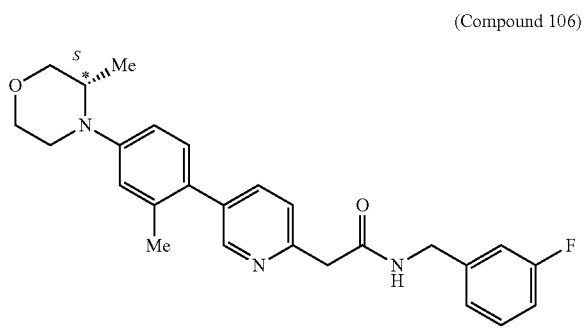

(Compound 106)

In a 40 ml vial equipped with a stir bar Compound 19 (350 mg, 1.00 mmol) and HATU (380 mg, 1.00 mmol) were dissolved in 3 ml of a mixture of DMF:water (2:1). A solution of 3-fluorobenzylamine (125 mg, 1.00 mmol) and diisopropyl ethylamine (0.66 ml, 5.00 mmol) in 5 ml DMF was then added to Compound 19 solution at 0-5° C. The mixture was then stirred at room temperature overnight, and the reaction was checked for completion using LCMS. Upon reaction completion, the mixture was diluted with EtOAc (60 ml), washed with water (60 ml), and saturated brine solution (60 ml) twice. The organic layer was dried using anhydrous sodium sulfate, and the EtOAc was concentrated in vacuo after filtering the sodium sulfate off. Oily residue was obtained which was dissolved in 20 ml EtOAc, applied to silica gel and purified by flash chromatography. Compound 106 was obtained as a yellow solid (165 mg, 48% yield). The product was characterized by LCMS (434[M+H]$^+$; purity was estimated to be >95%), and $^1$H NMR (400 MHz, DMSO): 0.99 (d, J=8.0 Hz, 3H), 2.20 (s, 3H), 2.98 (m, 1H), 3.20 (m, 1H) 3.54 (m, 1H) 3.60-3.75 (m, 4H) 3.87 (m, 2H) 4.30 (d, 2H) 6.80 (m, 2H) 7.08 (d, J=7 Hz, 1H) 7.00-7.10 (m, 4H) 7.30-7.40 (m, 2H) 7.65 (dd, J=7.0, 2.5 Hz, 1H) 8.40 (d, J=2.5 Hz, 1H) 8.65 (t, 1H).

Preparation of Compound 107

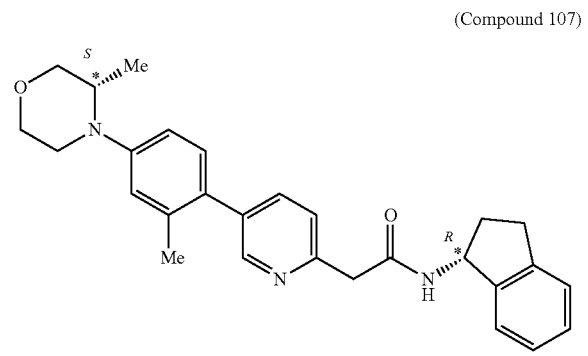

(Compound 107)

In a 40 ml vial equipped with a stir bar, Compound 19 (328 mg, 1.00 mmol of this compound) and HATU (380 mg, 1.00 mmol) were dissolved in 3 ml of a mixture of DMF: water (2:1). A solution of R-(−)-1-aminoindane (133 mg, 1.00 mmol) and diisopropylethylamine (0.66 ml, 5.00 mmol) in 5 ml DMF was then added to Compound 19 solution at 0-5° C. The mixture was then stirred at room temperature overnight, and the reaction was checked for completion using LCMS. Upon reaction completion, the mixture was diluted with EtOAc (60 ml), washed with water (60 ml), and the saturated brine solution (60 ml) twice. The organic layer was dried using anhydrous sodium sulfate, and the EtOAc was concentrated in vacuo after filtering the sodium sulfate off. The residue was dissolved in 20 ml EtOAc, adsorbed on to silica gel, and purified by flash chromatography. Compound 107 was obtained as a dark yellow solid (208 mg, 63% yield). Compound 107 was characterized by LCMS (434[M+H]$^+$; and purity was estimated to be 90%).

Preparation of Compound 117

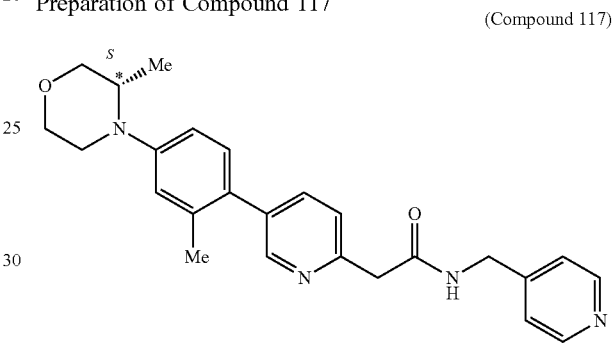

(Compound 117)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 4-aminomethyl pyridine (27 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 45 mg of the product (yield: 54%). Compound 117 was characterized by LCMS (417 [M+H]$^+$; and purity was estimated to be 90%).

Preparation of Compound 118

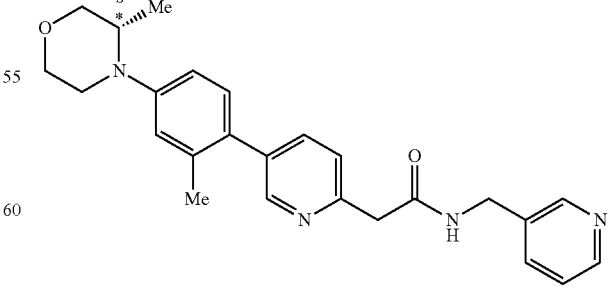

(Compound 118)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 3-aminomethyl pyridine (27 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 42 mg of the product (yield: 50%); Compound 118 was characterized by LCMS (417 [M+H]$^+$; and purity was estimated to be 90%).

Preparation of Compound 119

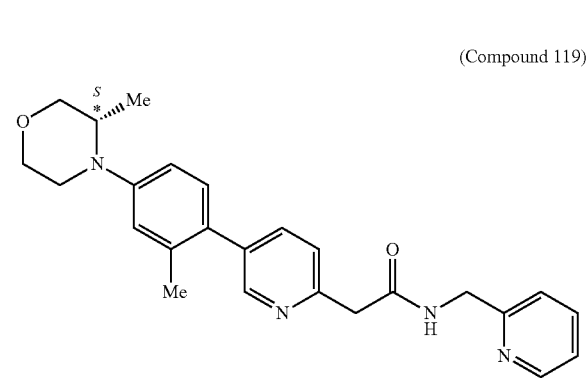

(Compound 119)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 2-aminomethyl pyridine (27 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 49 mg of the product (yield: 59%); Compound 119 was characterized by LCMS (417 [M+H]$^+$; and purity was estimated to be 90%).

Preparation of Compound 120

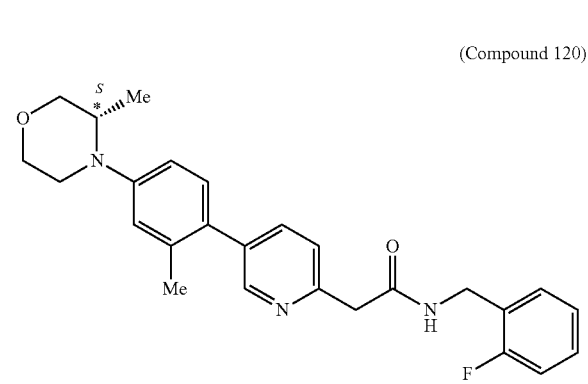

(Compound 120)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 2-fluorobenzylamine (31 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 40 mg of the product (yield: 46%); Compound 120 was characterized by LCMS (434 [M+H]$^+$; and purity was estimated to be 95%).

Preparation of Compound 121

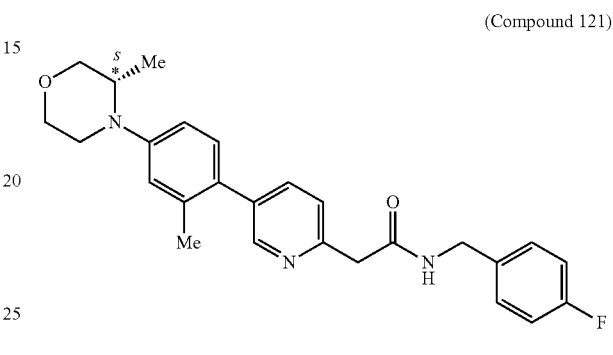

(Compound 121)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 4-fluorobenzylamine (31 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 51 mg of the product (yield: 59%); Compound 121 was characterized by LCMS (434 [M+H]$^+$; and purity was estimated to be 95%).

Preparation of Compound 122

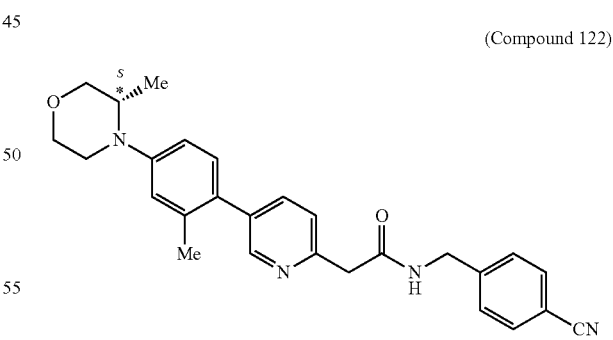

(Compound 122)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 4-cyanobenzylamine (33 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 53 mg of the product (yield: 60%); Compound 122 was characterized by LCMS (441 [M+H]$^+$; and purity was estimated to be 90%).

Preparation of Compound 123

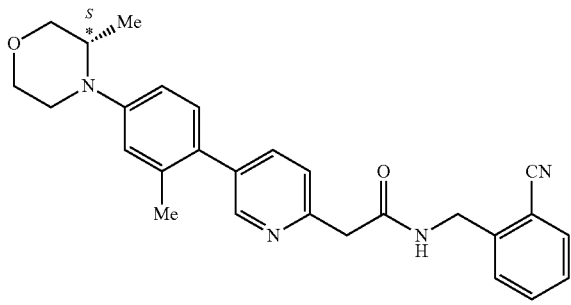

(Compound 123)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 2-cyanobenzylamine (33 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 45 mg of the product (yield: 51%); Compound 123 was characterized by LCMS (441 [M+H]$^+$; and purity was estimated to be 90%).

Preparation of Compound 124

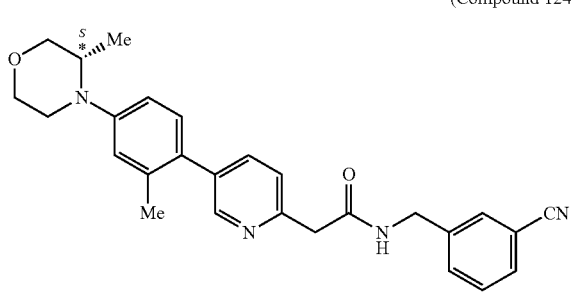

(Compound 124)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 3-cyanobenzylamine (33 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 49 mg of the product (yield: 56%); Compound 124 was characterized by LCMS (441 [M+H]$^+$; and purity was estimated to be 90%).

Preparation of Compound 125

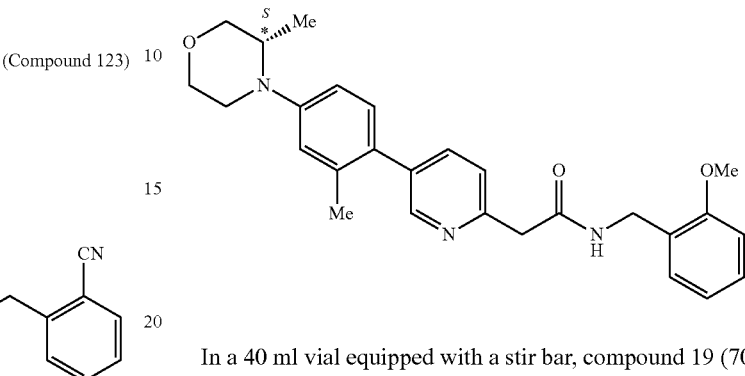

(Compound 125)

In a 40 ml vial equipped with a stir bar, compound 19 (70 mg, 0.20 mmol) and HATU (95 mg, 0.25 mmol) were dissolved in 3 ml of a mixture of DMF:water (2:1). A solution of 2-methoxybenzylamine (34 mg, 0.25 mmol) and diisopropylethylamine (0.17 ml, 1.00 mmol) was then added to compound 19 solution at 0-5° C. The mixture was then stirred at room temperature overnight. Upon the completion of the reaction, the mixture was diluted with EtOAc (50 ml), and then washed with water and brine (50 ml of each). The organic layer was then dried over anhydrous sodium sulfate, and the EtOAc was evaporated under vacuum. The residue was then purified by flash chromatography to give 51 mg of the product (yield: 57%); Compound 125 was characterized by LCMS (446 [M+H]$^+$; and purity was estimated to be 95%).

Example 2: Cell Growth Inhibition

The drug concentration required to block net cell growth by 50% relative to a control sample is measured as the $GI_{50}$. The $GI_{50}$s for several of the compounds of the application were assayed as described.

MTT assay: U87 and GL261 cells were seeded in 96-well plate ($6 \times 10^3$ cells in 100 µl of DMEM+10% FBS media per well) and incubated overnight at 37° C. with 5% $CO_2$. All test compounds were diluted (10 point 2-fold serial dilution) in a separate 96-well plate to yield 10× of final concentrations (0.5-256 nM). A volume of 11 µl of 10× dilutions was added to appropriate wells (n=3). To value (reflecting the starting number of cells upon drug treatment) was determined by following steps as described below. After 3 days incubation at 37° C. with 5% $CO_2$, 10 µl of MTT solution (5 mg/ml in PBS) was added to each well and plates were incubated at 37° C. for 3 h to allow MTT to form formazan crystals by reacting with metabolically active cells. 100 µl of 20% SDS was added to each well and plates were incubated overnight at 37° C. with 5% $CO_2$. Afterward, $OD_{570}$ was measured using microplate reader. The cell growth percentage of control was calculated according to percentage of control=$(T-T_0)/(C-T_0) \times 100\%$ or OD value of the test well exposure to test drug–OD value at time zero/(OD of the control well without drug treatment–OD value at time zero)×100%. Growth inhibition curves and $GI_{50}$ were determined using GraphPad Prism 5 software.

The $GI_{50}$ of representative compounds of the application against various cell lines is shown in Table 2.

TABLE 2

| Cmpd No. | GL261 GI$_{50}$ (nM) | U87 GI$_{50}$ (nM) | Jurkat | HT-29 |
|---|---|---|---|---|
| 100 | 129, 127 | 203, 151 | | |
| 101 | 76 | 96 | | |
| 102 | 24, 42 | 25, 37 | | |
| 103 | 113 | 146 | | |
| 104 | 3.0, 2.8, 3.8, 3.4, 3.9, 6.8, 6.2, 5.3, 5.7, 12.6, 10, 10, 7.4, 5.3 | 4.0, 3.5, 3.7, 4.8, 4.0, 7.2, 6.9, 6.4, 6.1, 16.3, 15.6, 13.1, 14.6, 15.2 | 2.5, 2.3 | 2.5, 3.1 |
| 105 | 5.7, 6.9 | 10.8, 12.2 | | |
| 106 | 27.3, 30.9, 36.2, 59.1, 43.2 | 27.5, 19.5, 75.6, 52.2, 40.4 | | |
| 107 | 19.4, 28.3 | 22.1, 23.4 | | |
| 108 | 6.8 | 6.6 | | 3 |
| 109 | >1024 | >1024 | | |
| 110 | >1024 | >1024 | | |
| 111 | 195, 170 | 239, 224 | | |
| 112 | 210, 240 | 352, 401 | | |
| 113 | 180, 120, 99 | 212, 182, 103 | | 46 |
| 114 | 340, 500 | 382, >1024 | | |
| 115 | 80, 29, 20, 17.3 | 30, 30, 15, 15.6 | | |
| 116 | 110, 90, 74 | 120, 115, 98 | | |
| 117 | 488, 387 | >729 | | |
| 118 | 262 | 621 | | |
| 119 | 164, 216, 139 | 129, 233, 224 | | |
| 120 | 17, 13.6, 18.9, 15.8, 13.4, 10.7 | 20.2, 22.3, 18.4, 17.7, 18.6, 18.6 | | |
| 121 | 4.6, 6.5, 7.9, 3.2, 1.6, 5.0 | 7.9, 7.1, 5.2, 5.2, 3.3, 8.0 | | |
| 122 | 13.8, 18.9 | 24.7, 17.3 | | |
| 123 | 456 | 473 | | |
| 124 | 1027 | 860 | | |
| 125 | 140, 158 | 195, 230 | | |
| 126 | 47.9, 38.6 | 41.9, 46.0 | | |
| 127 | 207 | 269 | | |
| 128 | 303 | 377 | | |
| 129 | 51.7, 30.3 | 36, 38.1 | | |
| 130 | 111, 107 | 104, 135 | | |

Example 3: Pharmacokinetic of the Compounds of the Application

The pharmacokinetic properties of representative compounds of the application are listed in Table 3. The compounds of application displayed improved potency with similar pharmacokinetics, allowing for decreased dosing.

TABLE 3

| Cmpd No. | IV Administration (5 mg/kg) | | | | | PO Administration (20 mg/kg) | | |
|---|---|---|---|---|---|---|---|---|
| | $C_0$ (ng/ml) | $t_{0.5}$ (h) | CL (L/h/kg) | $V_{ss}$ (L/kg) | [1]AUC$_{IV}$ | [1]AUC$_{PO}$ | $C_{max}$ | [2]F (%) |
| Cmpd Y | 4620 | 0.364 | 1.81 | 0.962 | 553 | 217 | 2593 | 39.3 |
| 120 | 1590 | 0.663 | 5.32 | 3.63 | 188 | 76.8 | 798 | 40.9 |
| 121 | 2848 | 0.959 | 1.74 | 2.24 | 575 | 199 | 2170 | 34.8 |

[1]Dose-normalized AUC values (hr · kg · ng/mL/mg);

[2]F (%) = 100 × AUC$_{PO}$/AUC$_{IV}$

Example 4: Brain Permeability of the Compounds of the Application

The brain permeability of representative compounds of the application is listed in Table 4. The compounds of application showed improved bioavailability to the brain.

TABLE 4

| time point (h) | Brain:Plasma (B:P) Average (ng/ml) | | |
|---|---|---|---|
| | Compound Y | Compound 120 | Compound 121 |
| 0.25 | 1.56 | 1.24 | 1.08 |
| 0.5 | 1.46 | 1.39 | 1.37 |
| 1 | 1.33 | 1.72 | 1.53 |
| 2 | 0.712 | 1.38 | 1.93 |
| 4 | 0.834 | 1.04 | 2.29 |
| 6 | 0.633 | 0.820 | 1.66 |
| 8 | 0.685 | 1.12 | 1.24 |

Example 5: Effect on Compound 121 on 50 Cancer Cell Lines

The cell viability of 50 cancer cell lines was studied after treatment with Compound 121. Inhibition concentration values at 50% ($IC_{50}$) were determined using CellTiter-Glo luminescent cell viability assay after incubation with different compound concentrations. $GI_{50}$ values were determined according to the examples described above. Each cell line was treated with Compound 121, a standard chemotherapy drug as a reference control, and culture medium as a vehicle control.

All cells were cultured in media supplemented with 10-15% FBS at 37° C. in the presence of 5% $CO_2$ and at 95% humidity. The culture medium was purchased from GIBCO or Sigma, USA. Cisplatin was chosen as the reference control and purchased from Hospira Australia Pty Ltd. The cell lines studied are presented in Table 5.

TABLE 5

| No. | Cell Line Name | Tissue Origin |
|---|---|---|
| 1 | HT-1376 | Bladder |
| 2 | HL-60 | Blood |
| 3 | HuT 78 | |
| 4 | K-562 | |
| 5 | KARPAS-299 | |
| 6 | Molt-4 | |
| 7 | Raji | |
| 8 | RPMI 8226 | |
| 9 | 143B | Bone |
| 10 | A-172 | Brain and Nerves |
| 11 | SK-N-FI | |
| 12 | TJ905 | |
| 13 | U251 | |
| 14 | BT474 | Breast |
| 15 | MDA-MB-231 | |
| 16 | MDA-MB-453 | |
| 17 | MDA-MB-468 | |
| 18 | MX-1 | |
| 19 | HeLa | Cervix |
| 20 | HCT-116 | Colorectum |
| 21 | HCT-15 | |
| 22 | HT-29 | |
| 23 | KYSE-150 | Esophagus |
| 24 | 786-O | Kidney |
| 25 | HuCCT1 | Liver |
| 26 | HUH-7 | |
| 27 | JHH-5 | |
| 28 | EBC-1 | Lung |
| 29 | NCI-H1155 | |
| 30 | NCI-H1975 | |
| 31 | NCI-H209 | |
| 32 | NCI-H226 | |
| 33 | A-673 | Muscle |
| 34 | OVCAR-3 | Ovary |
| 35 | SK-OV-3 | |
| 36 | AsPC-1 | Pancreas |
| 37 | KP4 | |
| 38 | FaDu | Pharynx |
| 39 | JEG-3 | Placenta |
| 40 | 22Rv1 | Prostate |
| 41 | PC-3 | |
| 42 | A2058 | Skin |
| 43 | SK-MEL-28 | |
| 44 | HT-1080 | Soft tissue |
| 45 | NCI-N87 | Stomach/Gastric |
| 46 | SNU-5 | |
| 47 | SW579 | Thyroid |
| 48 | SCC-4 | Tongue |
| 49 | AN3 CA | Uterus |
| 50 | MES-SA/DX5 | |

Cells were harvested during a logarithmic growth period and cell number count was determined using Count-star. Cell concentrations were adjusted to $4.44 \times 10^4$ cells/mL with respective culture medium. 90 µL of cell suspensions were added to two 96-well plates (plates A and B) with a final cell density of $4 \times 10^3$ cells/well.

10 µL of culture medium was added to each well of plate A for T0 reading. The plate was allowed to equilibrate at room temperature for approximately 30 min. 50 µL of CellTiter-Glo was added to each well and the contents were mixed for 5 min on an orbital shaker to induce cell lysis. The plate was allowed to incubate at room temperature for 20 min to stabilize luminescent signal.

10 µM Compound 121 in media was serially diluted 3.16-fold to achieve 9 dose levels. Similarly, 100 µM reference control in media was serially diluted 3.16-fold to prepare reference control solutions. 10 µL drug solution and 10 µL of reference control was dispensed into each well in plate B.

Test plate B was incubated for 72 h in a humidified incubator at 37° C. in the presence of 5% $CO_2$ and then subjected to CTG assay. The plate was allowed to equilibrate at room temperature for about 30 min. 50 µL of CellTiter-Glo was added to each well and the contents were mixed for 5 min on an orbital shaker to induce cell lysis. The plate was allowed to incubate at room temperature for 20 min to stabilize luminescent signal.

$IC_{50}$ and $GI_{50}$ values for each of the 50 cell lines are presented in Table 6 and were calculated based on the dose-response curves depicted in FIGS. 1-50. The dose-response curves were fitted using nonlinear regression model with a sigmoidal dose response. The formula for calculating survival rate was calculated by the formula:

Survival rate (%)=(LumTest article−LumMedium control)/(LumNone treated−LumMedium control)×100.

TABLE 6

| Cell No. | Cell lines | Absolute IC50(μM) Compound 121 | Absolute IC50(μM) Cisplatin | Absolute GI50(μM) Compound 121 | Absolute GI50(μM) Cisplatin | % inhibition at top conc. Compound 121 | % inhibition at top conc. Cisplatin |
|---|---|---|---|---|---|---|---|
| 1 | TJ905 | 0.004 | 9.85 | 0.004 | 6.56 | 69.96% | 80.57% |
| 2 | JEG-3 | 0.009 | 9.40 | 0.008 | 5.50 | 86.49% | 99.90% |
| 3 | SW579 | 0.007 | 2.24 | 0.006 | 1.83 | 88.21% | 99.88% |
| 4 | KYSE-150 | 0.006 | 8.14 | 0.005 | 6.26 | 80.04% | 91.28% |
| 5 | 143B | 0.008 | 1.08 | 0.008 | 1.02 | 97.85% | 99.94% |
| 6 | HT-1080 | 0.005 | 2.22 | 0.005 | 1.98 | 97.15% | 99.59% |
| 7 | KP4 | 0.008 | 8.80 | 0.007 | 6.87 | 90.78% | 98.30% |
| 8 | HCT-15 | 0.006 | 4.76 | 0.005 | 4.27 | 96.76% | 98.22% |
| 9 | SK-N-FI | 0.004 | 9.26 | 0.003 | 5.80 | 91.37% | 99.77% |
| 10 | HuCCT1 | 0.004 | 8.44 | 0.004 | 6.59 | 53.99% | 90.42% |
| 11 | AsPC-1 | >10 | 3.31 | 0.012 | 2.73 | 51.16% | 72.39% |
| 12 | OVCAR-3 | 0.006 | 4.29 | 0.005 | 3.81 | 64.84% | 91.14% |
| 13 | MDA-MB-453 | 0.004 | 9.51 | 0.004 | 7.05 | 67.55% | 96.82% |
| 14 | RPMI 8226 | 0.006 | 3.62 | 0.005 | 2.38 | 94.85% | 99.76% |
| 15 | NCI-H226 | 0.013 | 7.36 | 0.010 | 5.72 | 61.68% | 94.81% |
| 16 | HCT-116 | 0.009 | 4.35 | 0.009 | 4.14 | 94.36% | 95.29% |
| 17 | JHH-5 | 0.007 | 2.27 | 0.007 | 1.97 | 80.50% | 87.18% |
| 18 | A-172 | 0.007 | 20.33 | 0.006 | 15.86 | 92.77% | 93.09% |
| 19 | SK-OV-3 | 0.004 | 6.69 | 0.004 | 5.08 | 66.23% | 81.79% |
| 20 | MDA-MB-468 | 0.009 | 0.93 | 0.007 | 0.65 | 80.02% | 99.91% |
| 21 | NCI-H1155 | 0.007 | 1.75 | 0.006 | 1.52 | 87.27% | 90.61% |
| 22 | MX-1 | 0.018 | 7.12 | 0.011 | 5.69 | 66.85% | 98.97% |
| 23 | HT-1376 | 0.009 | 3.26 | 0.006 | 2.64 | 52.98% | 91.76% |
| 24 | HUH-7 | 0.009 | 3.54 | 0.007 | 2.61 | 60.77% | 93.92% |
| 25 | HeLa | 0.004 | 0.33 | 0.004 | 0.30 | 89.52% | 99.60% |
| 26 | K-562 | 0.006 | 4.51 | 0.006 | 4.21 | 98.12% | 97.94% |
| 27 | HT-29 | 0.004 | 9.80 | 0.004 | 8.78 | 78.51% | 89.05% |
| 28 | NCI-H1975 | 0.006 | 6.93 | 0.006 | 5.52 | 83.68% | 98.75% |
| 29 | FaDu | 0.008 | 2.25 | 0.007 | 1.96 | 85.88% | 98.16% |
| 30 | HL-60 | 0.008 | 1.46 | 0.007 | 1.34 | 99.81% | 99.99% |
| 31 | MDA-MB-231 | >10 | 23.66 | 0.020 | 18.55 | 45.84% | 85.68% |
| 32 | 786-O | 0.005 | 1.77 | 0.005 | 1.60 | 85.35% | 98.46% |
| 33 | Raji | 0.005 | 1.97 | 0.005 | 1.74 | 94.22% | 94.98% |
| 34 | Molt-4 | 0.014 | 0.71 | 0.013 | 0.61 | 99.59% | 99.96% |
| 35 | KARPAS-299 | 0.006 | 1.63 | 0.006 | 1.49 | 99.37% | 99.99% |
| 36 | BT474 | >10 | 45.14 | 0.012 | 39.33 | 37.93% | 59.96% |
| 37 | NCI-H209 | 0.020 | 0.23 | 0.017 | 0.14 | 73.69% | 98.81% |
| 38 | PC-3 | 0.008 | 5.94 | 0.008 | 4.68 | 93.31% | 83.88% |
| 39 | MES-SA/DX5 | 0.007 | 2.21 | 0.007 | 1.96 | 97.85% | 99.94% |
| 40 | SK-MEL-28 | >10 | 8.90 | 0.004 | 7.09 | 52.92% | 99.29% |
| 41 | AN3 CA | 0.005 | 4.38 | 0.005 | 3.68 | 98.57% | 99.95% |
| 42 | HuT 78 | 0.009 | 0.66 | 0.008 | 0.50 | 95.15% | 98.27% |
| 43 | 22Rv1 | 0.006 | 3.07 | 0.005 | 1.88 | 89.05% | 98.28% |
| 44 | A2058 | 0.008 | 3.11 | 0.008 | 2.38 | 98.14% | 99.85% |
| 45 | SCC-4 | 0.006 | 4.15 | 0.005 | 3.43 | 86.11% | 99.29% |
| 46 | SNU-5 | 0.012 | 2.50 | 0.011 | 2.15 | 96.19% | 97.80% |
| 47 | EBC-1 | 0.004 | 17.34 | 0.004 | 11.82 | 56.75% | 84.49% |
| 48 | A-673 | 0.004 | 1.12 | 0.003 | 0.40 | 86.11% | 99.59% |
| 49 | U251 | 0.009 | 3.98 | 0.009 | 3.07 | 75.02% | 87.70% |
| 50 | NCI-N87 | 0.004 | 2.26 | 0.004 | 0.88 | 49.56% | 90.08% |

Example 6: Compound 121 Delays Growth of Human U87 Glioblastoma Cells in Xenograft Model The anti-tumor activity of Compound 121, as a single agent, was studied in a U87-luc human glioblastoma subcutaneous xenograft tumor model. Significant endpoints were used to assess the treatment effects on subcutaneous tumor growth, as determined by tumor growth inhibition.

Human glioblastoma U87 cells (1×10$^6$ cells) were implanted into the right flank of athymic nude mice via subcutaneous injection. Dosing was initiated when the average tumor size reached 90-100 mm$^3$, which was designated as Day 1.

Compound 121 was dosed at 5 mg/kg once per day through Days 1-7 and dosed 2.5 mg/kg once per day through Days 15-21. A control group of mice (N=7) was administered a vehicle per the same schedule. Tumor volume was determined every 2 to 3 days via bidimensional caliper measurements. Body weight and general observations were recorded.

The mice were euthanized once the tumor reached 2000 mm$^3$ in volume.

Tumor growth inhibition (TGI) was calculated with the following formula:

TGI=(1−(mean volume of treated tumors)/(mean volume of control tumors))×100.

Compound 121 repressed tumor growth based according to evaluation of tumor volumes in individual mice over time (FIG. 53A and FIG. 53B). Therefore, the time to terminal sacrifice (based on tumor volume) was significantly extended compared to the control group (P<0.05; FIG. 53C). On Day 12, the mean tumor volume in the Compound 121-treated group was significantly reduced compared to the control group (P<0.05). Mean tumor volume and % TGI at Day 12 is provided in Table 7.

TABLE 7

Mean Tumor Volume and Tumor Growth Inhibition in a U87-luc Human Glioblastoma Subcutaneous Xenograft Tumor Model Orally Dosed with Compound 121 Compared to a Control.

| Group | Mean Tumor Volume (mm3) ± SEM | % TGI |
|---|---|---|
| Control | 1615.1 ± 201.3 | — |
| Compound 121 | 442.9 ± 67.2 | 76.8 |

Example 7: Compound 121 Extends Survival and Supports Long-Term Tumor Control in the GL261 Murine Model of Glioblastoma The anti-tumor activity of Compound 121, as a single agent, was studied in the GL261 murine model of human glioblastoma. Murine GL261 glioblastoma cells were injected intra-cranially into syngeneic, immune-competent hosts ($C_{57}BL/6$). In order for oral therapeutics to be effective, it is required that the therapeutic be able to cross the blood-brain barrier in order to achieve sufficient levels in the brain to exert an anti-tumor effect. Survival was the major endpoint for the study. The mice either succumbed to the tumor or were euthanized based on severity of tumor-dependent morbidity. Mice that achieved long-term survival (>80 days) were re-challenged with a sub-cutaneous injection of GL261 cells to assess the development of a durable immune response to GL261. Mice that underwent the re-challenge phase were not treated with Compound 121.

GL261 cells ($1 \times 10^5$ cells) were implanted into the brain of a $C_{57}BL/6$ host using stereotactice injection. Compound 121 was dosed orally once per day at 1 mg/kg (N=10) for 45 days beginning 3 days post-tumor cell implantation. Compound Y was dosed orally once per day at 5 mg/kg (N=10) for 45 days beginning 3 days post-tumor implantation. A vehicle was administered to a control group of mice (N=10) per the same schedule.

Mice were monitored for signs of tumor dependent morbidity, including head tilt, hunching, ataxia, and limb weakness. Mice were euthanized when cumulative signs of high tumor burden were evident.

Re-challenge phase: Mice surviving past 80 days were injected with GL261 cell subcutaneously on Day 93. A control group (naïve $C_{57}BL/6$ mice, N=5) were also injected with GL261 cells subcutaneously. Tumor volumes were calculated from bidimensional caliper measurements every 3 to 4 days. Further, all mice were administered oral doses of a *Bifidobacterium* mixture on three separate occasions. The objective of the administration of *Bifidobacterium* was to transiently modify the intestinal microbiome as a means to influence the immune response to GL261. Based on the observed survival rates in the control group, the bacterial gavages had minimal, if any, impact on intra-cranial growth of GL261.

Compound 121 significantly extended survival when compared to vehicle control (P<0.5). Survival was supported beyond 80 days in 2 of the 10 mice treated, as shown in FIG. 54A. The two mice with a long term survival (LTS) past 60 days were re-challenged with a sub-cutaneous injection of GL261 cells in the flank. Three naïve $C_{57}BL/6$ mice were also injected subcutaneously with GL261 cells as a control. Tumors failed to grow in both LTS mice, whereas tumor growth was readily evident in each of the three control mice, as shown in FIG. 54B. These observations were consistent with the generation of a durable immune response to GL261 in animals that achieved LTS with Compound 121 oral therapy.

Compound Y, a closely related analog to Compound 121, had only a marginal, insignificant effect on survival when dosed at 5 mg/kg; however, Compound Y demonstrated activity when dosed once daily at >20 mg/kg.

Other Embodiments

While the application has been described in conjunction with the detailed description thereof, the foregoing description is intended to illustrate and not limit the scope of the application, which is defined by the scope of the appended claims. Other aspects, advantages, and modifications are within the scope of the following claims. It will be understood by those skilled in the art that various changes in form and details may be made therein without departing from the scope of the application encompassed by the appended claims.

The invention claimed is:

1. A compound of formula (A):

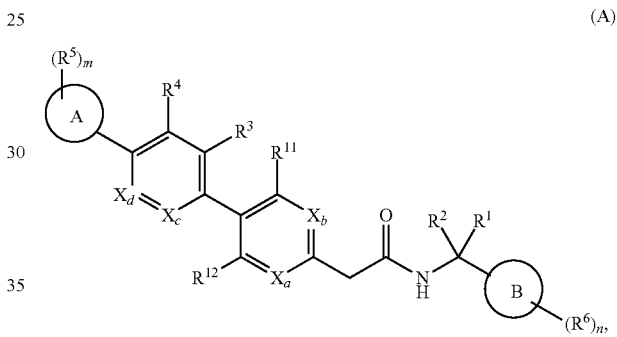

(A)

or a pharmaceutically acceptable salt or solvate thereof, wherein:
$X_a$ is $CR^a$ or N;
$X_b$ is $CR^b$ or N;
$X_c$ is $CR^c$ or N;
$X_d$ is $CR^d$ or N;
$R^a$ is H, halogen, $C_1$-$C_6$ alkyl, $C_2$-$C_6$ alkenyl, or $C_2$-$C_6$ alkynyl;
$R^b$ is H, halogen, $C_1$-$C_6$ alkyl, $C_2$-$C_6$ alkenyl, or $C_2$-$C_6$ alkynyl;
$R^c$ is H, halogen, $C_1$-$C_6$ alkyl, $C_2$-$C_6$ alkenyl, or $C_2$-$C_6$ alkynyl;
$R^d$ is H, halogen, $C_1$-$C_6$ alkyl, $C_2$-$C_6$ alkenyl, or $C_2$-$C_6$ alkynyl;
$R^1$ and $R^2$ are each independently H, $C_1$-$C_6$ alkyl, $C_2$-$C_6$ alkenyl, $C_2$-$C_6$ alkynyl, or O—($C_1$-$C_6$ alkyl);
$R^3$ is H or O—($C_1$-$C_6$ alkyl);
$R^4$ is (a) H, (b) halogen, (c) OH, (d) COOH, (e) $CONH_2$, (f) $NHCOR^{101}$, (g) $NR^{101}COR^{102}$, (h) $S(O)_tR^{101}$, (i) $C_1$-$C_6$ alkyl, (j) $C_2$-$C_6$ alkenyl, (k) $C_2$-$C_6$ alkynyl, (l) O—($C_1$-$C_6$ alkyl), (m) O—($C_2$-$C_6$ alkenyl), (n) O—($C_2$-$C_6$ alkynyl), (o) COO—($C_1$-$C_6$ alkyl), (p) COO—($C_2$-$C_6$ alkenyl), (q) COO—($C_2$-$C_6$ alkynyl), (r) CONH—($C_1$-$C_6$ alkyl), (s) CONH—($C_2$-$C_6$ alkenyl), (t) CONH—($C_2$-$C_6$ alkynyl), (u) CON($C_1$-$C_6$ alkyl)$_2$, (v) CON($C_2$-$C_6$ alkenyl)$_2$, (w) CON($C_2$-$C_6$ alkynyl)$_2$, (x) ($C_1$-$C_6$ alkyl)$_u$-$NH_2$, (y) ($C_2$-$C_6$ alkenyl)$_u$-$NH_2$, (z) ($C_2$-$C_6$ alkynyl)$_u$-$NH_2$, (aa1) ($C_1$-$C_6$ alkyl)$_v$-NH($C_1$-$C_6$ alkyl), (aa2) ($C_1$-$C_6$ alkyl)$_v$-NH(C$_2$-C$_6$ alkenyl), (aa3) (C$_1$-C$_6$ alkyl)$_v$-NH(C$_2$-C$_6$ alkynyl), (bb1) (C$_2$-C$_6$ alkenyl)$_v$—NH(C$_1$-C$_6$ alkyl), (bb2) (C$_2$-C$_6$ alkenyl)$_v$—NH(C$_2$-C$_6$ alkenyl), (bb3) (C$_2$-C$_6$ alkenyl)$_v$—NH(C$_2$-C$_6$ alkynyl), (cc1) (C$_2$-C$_6$ alkynyl)$_v$-NH(C$_1$-C$_6$ alkyl), (cc2) (C$_2$-C$_6$ alkynyl)$_v$-NH(C$_2$-C$_6$ alkenyl), (cc3) (C$_2$-C$_6$ alkynyl)$_v$-NH(C$_2$-C$_6$ alkynyl), (dd1) (C$_1$-C$_6$ alkyl)$_w$-N(C$_1$-C$_6$ alkyl)$_2$, (dd2) (C$_1$-C$_6$ alkyl)$_w$-N(C$_2$-C$_6$ alkenyl)$_2$, (dd3) (C$_1$-C$_6$ alkyl)$_w$-N(C$_2$-C$_6$ alkynyl)$_2$, (ee1) (C$_2$-C$_6$ alkenyl)$_w$-N(C$_1$-C$_6$ alkyl)$_2$, (ee2) (C$_2$-C$_6$ alkenyl)$_w$-N(C$_2$-C$_6$ alkenyl)$_2$, (ee3) (C$_2$-C$_6$ alkenyl)$_w$-N(C$_2$-C$_6$ alkynyl)$_2$, (ff1) (C$_2$-C$_6$ alkynyl)$_w$-N(C$_1$-C$_6$ alkyl)$_2$, (ff2) (C$_2$-C$_6$ alkynyl)$_w$-N(C$_2$-C$_6$ alkenyl)$_2$, (ff3) (C$_2$-C$_6$ alkynyl)$_w$-N(C$_2$-C$_6$ alkynyl)$_2$, (gg) 3-8 membered saturated, unsaturated, or partially saturated carbocycle, or (hh) 3-8 membered saturated, unsaturated, or partially saturated heterocycle, wherein each of (i)-(hh) is optionally substituted with one or more R$^7$;

(A) is morpholinyl;

(B) represents an aromatic, saturated, unsaturated, or partially saturated carbocycle comprising one or two 3-8 membered rings, or an aromatic, saturated, unsaturated, or partially saturated heterocycle comprising one or two 5-8 membered rings and one or more heteroatoms selected from N, O and S, wherein the two 3-8 membered rings or the two 5-8 membered rings can form a fused or bridged ring structure;

each R$^5$ is independently C$_1$-C$_6$ alkyl;

each R$^6$ is independently (a) halogen, (b) OH, (e) CN, (g) C$_1$-C$_6$ alkyl, or (j) O—(C$_1$-C$_6$ alkyl, wherein each of (g) or (j) is optionally substituted with one or more R$^9$;

each R$^7$ is independently halogen, OH, O—(C$_1$-C$_6$ alkyl), COO—(C$_1$-C$_6$ alkyl), CONH—(C$_1$-C$_6$ alkyl), CON(C$_1$-C$_6$ alkyl)$_2$, COOH, CN, N$_3$, 5-6 membered saturated, unsaturated, or partially saturated carbocycle, or 5-6 membered saturated, unsaturated, or partially saturated heterocycle comprising one or more heteroatoms selected from N, O and S;

each R$^9$ is independently halogen, OH, O—(C$_1$-C$_6$ alkyl), COO—(C$_1$-C$_6$ alkyl), CONH—(C$_1$-C$_6$ alkyl), CON(C$_1$-C$_6$ alkyl)$_2$, COOH, CN, N$_3$, 5-6 membered saturated, unsaturated, or partially saturated carbocycle, or 5-6 membered saturated, unsaturated, or partially saturated heterocycle comprising one or more heteroatoms selected from N, O and S;

R$^{101}$ and R$^{102}$ are each independently H, C$_1$-C$_6$ alkyl, C$_2$-C$_6$ alkenyl, or C$_2$-C$_6$ alkynyl;

R$^{11}$ is H, halogen, C$_1$-C$_6$ alkyl, C$_2$-C$_6$ alkenyl, or C$_2$-C$_6$ alkynyl;

R$^{12}$ is H, halogen, C$_1$-C$_6$ alkyl, C$_2$-C$_6$ alkenyl, or C$_2$-C$_6$ alkynyl;

m is 1, 2, 3, 4, 5, or 6;
n is 0, 1, 2, 3, 4, 5, or 6;
t is 0, 1, or 2;
u is 0 or 1;
v is 0 or 1; and
w is 0 or 1.

2. The compound of claim 1, wherein X$_a$ is N; and X$_b$ is CR$^b$.

3. The compound of claim 1, wherein X$_c$ is CR$^c$; and X$_d$ is CR$^d$.

4. The compound of claim 1, wherein R$^3$ is O—(C$_1$-C$_6$ alkyl).

5. The compound of claim 1, wherein R$^5$ is methyl.

6. The compound of claim 1, wherein R$^5$ is in the S-configuration.

7. The compound of claim 1, wherein R$^6$ is halogen, C$_1$-C$_6$ alkyl, or O—C$_1$-C$_6$ alkyl.

8. The compound of claim 1, wherein R$^6$ is at the 2- or 4-position.

9. The compound of claim 1, wherein the compound is of formula (I):

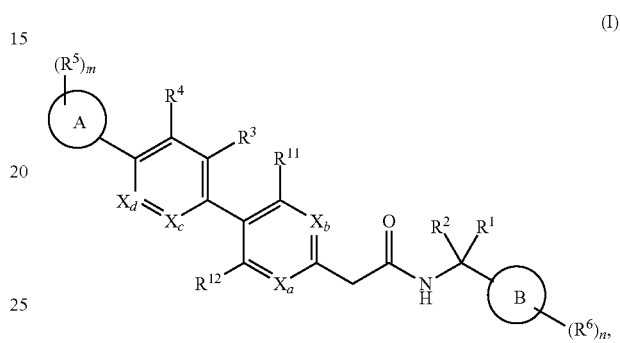

(I)

or a pharmaceutically acceptable salt or solvate thereof, wherein:

X$_a$ is CR$^a$ or N;
X$_b$ is CR$^b$ or N;
X$_c$ is CR$^c$ or N;
X$_d$ is CR$^d$ or N;
R$^a$ is H, halogen, or C$_1$-C$_6$ alkyl;
R$^b$ is H, halogen, or C$_1$-C$_6$ alkyl;
R$^c$ is H, halogen, or C$_1$-C$_6$ alkyl;
R$^d$ is H, halogen, or C$_1$-C$_6$ alkyl;
R$^1$ and R$^2$ are each independently H, C$_1$-C$_6$ alkyl, or O—(C$_1$-C$_6$ alkyl);
R$^3$ is H or O—(C$_1$-C$_6$ alkyl);
R$^4$ is (a) H, (b) halogen, (c) OH, (d) COOH, (e) CONH$_2$, (f) NHCOR$^{101}$, (g) NR$^{101}$COR$^{102}$, (h) S(O)$_t$R$^{101}$, (i) C$_1$-C$_6$ alkyl, (j) O—(C$_1$-C$_6$ alkyl), (k) COO—(C$_1$-C$_6$ alkyl), (l) CONH—(C$_1$-C$_6$ alkyl), (m) CON(C$_1$-C$_6$ alkyl)$_2$, (n) (C$_1$-C$_6$ alkyl)$_u$-NH$_2$, (o) (C$_1$-C$_6$ alkyl)$_v$-NH(C$_1$-C$_6$ alkyl), (p) (C$_1$-C$_6$ alkyl)$_w$-N(C$_1$-C$_6$ alkyl)$_2$, or (q) 5-6 membered saturated, unsaturated, or partially saturated carbocycle, wherein each of (i)-(q) is optionally substituted with one or more R$^7$;

(A) is morpholinyl;
(B) represents a 5-6 membered aromatic, saturated, unsaturated, or partially saturated carbocycle, or a 5-6 membered aromatic, saturated, unsaturated, or partially saturated heterocycle containing one or more heteroatoms selected from N, O and S;

each R$^5$ is independently C$_1$-C$_6$ alkyl;

each R$^6$ is independently (a) halogen, (b) OH, (c) C$_1$-C$_6$ alkyl, (e) O—(C$_1$-C$_6$ alkyl), or (j) CN, wherein each of (c) or (e) is optionally substituted with one or more R$^9$;

each R$^7$ is independently halogen, OH, O—(C$_1$-C$_6$ alkyl), COO—(C$_1$-C$_6$ alkyl), CONH—(C$_1$-C$_6$ alkyl), CON(C$_1$-C$_6$ alkyl)$_2$, COOH, CN, N$_3$, 5-6 membered saturated, unsaturated, or partially saturated carbocycle, or 5-6 membered saturated, unsaturated, or partially saturated heterocycle containing one or more heteroatoms selected from N, O and S;

each $R^9$ is independently halogen, OH, O—($C_1$-$C_6$ alkyl), COO—($C_1$-$C_6$ alkyl), CONH—($C_1$-$C_6$ alkyl), CON($C_1$-$C_6$ alkyl)$_2$, COOH, CN, $N_3$, 5-6 membered saturated, unsaturated, or partially saturated carbocycle, or 5-6 membered saturated, unsaturated, or partially saturated heterocycle containing one or more heteroatoms selected from N, O and S;

$R^{101}$ and $R^{102}$ are each independently H or $C_1$-$C_6$ alkyl;

$R^{11}$ is H, halogen, or $C_1$-$C_6$ alkyl;

$R^{12}$ is H, halogen, or $C_1$-$C_6$ alkyl;

m is 1, 2, 3, 4, 5, or 6;

n is 0, 1, 2, 3, 4, 5, or 6;

t is 0, 1, or 2;

u is 0 or 1;

v is 0 or 1; and w is 0 or 1.

10. The compound of claim 1, wherein the compound is of formula (II) or (III):

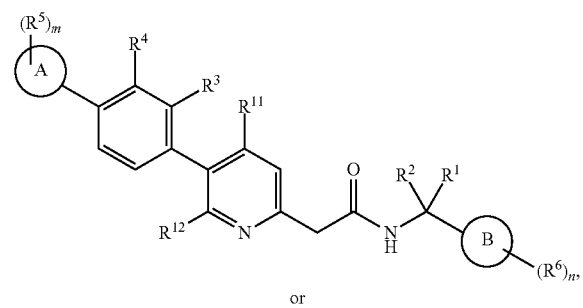
(II)

or

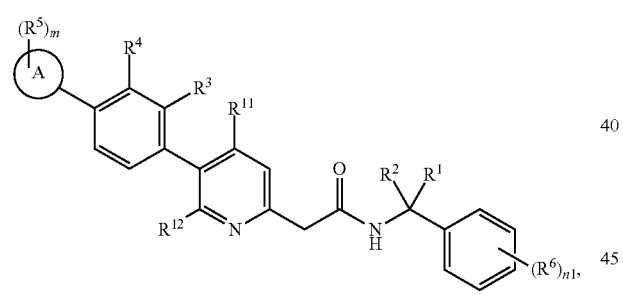
(III)

or a pharmaceutically acceptable salt or solvate thereof, wherein n1 is 0, 1, 2, 3, 4, or 5.

11. The compound of claim 1, wherein the compound is of the following formula:

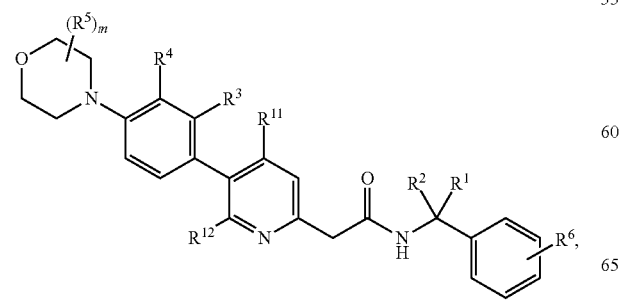
(IVa)

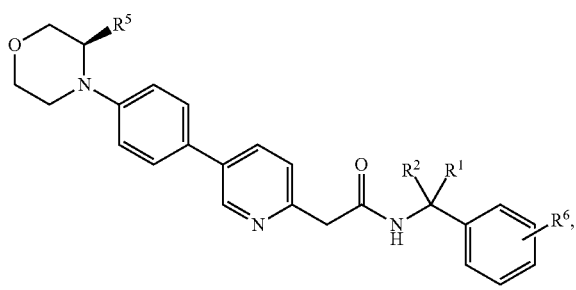
(Va)

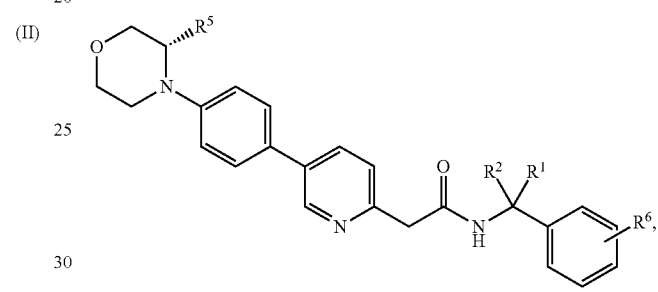
(Vb)

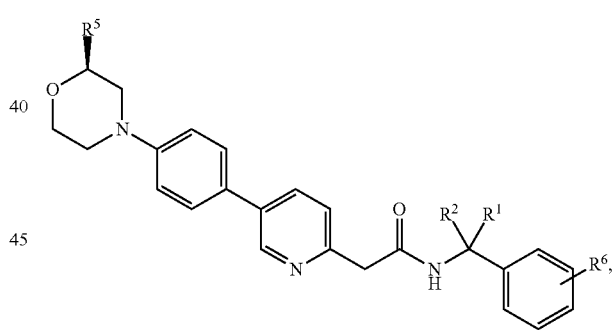
(Vc)

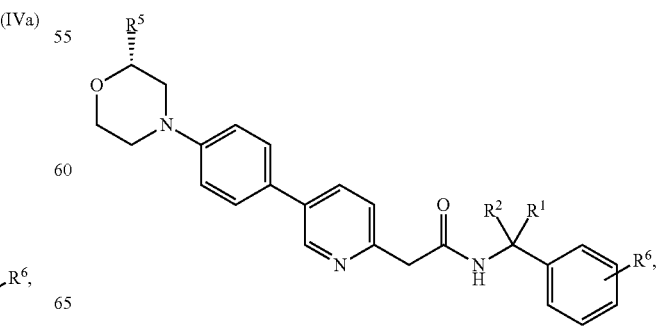
(Vd)

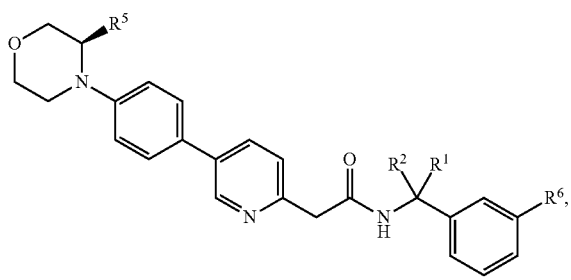
(VIa)
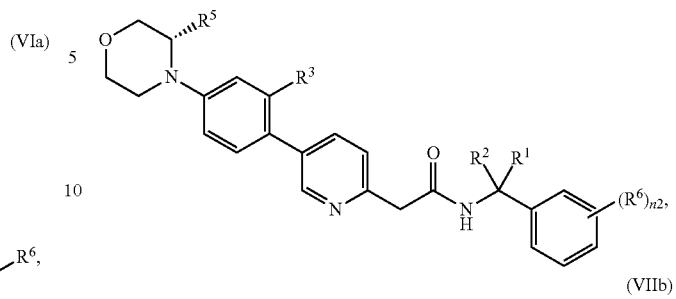
(VIIa)
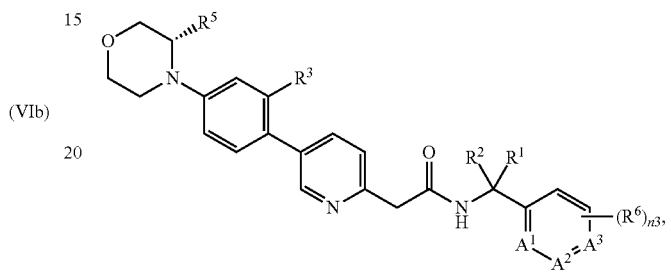
(VIIb)
(VIb)
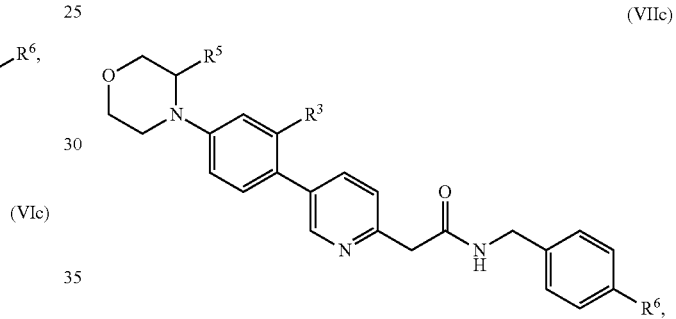
(VIIc)
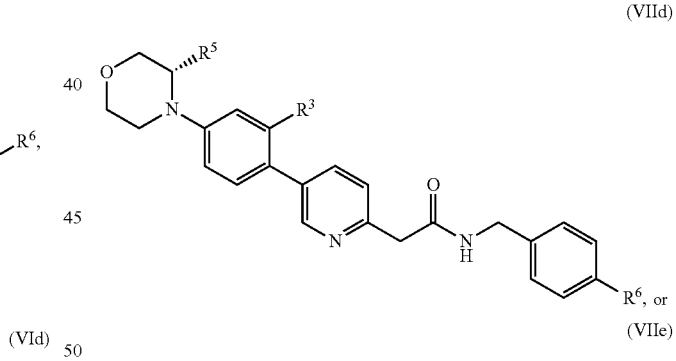
(VIId)
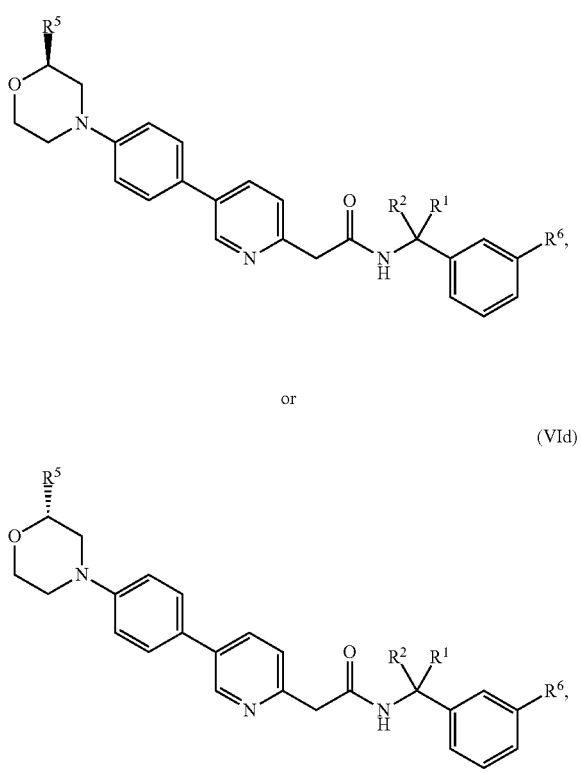
(VIIe)
or a pharmaceutically acceptable salt or solvate thereof.
12. The compound of claim 1, wherein the compound is of the following formula:
or a pharmaceutically acceptable salt or solvate thereof, wherein:
n2 is 0, 1, 2, or 3;
n3 is 0, 1, or 2; and $A^1$, $A^2$, and $A^3$ are each independently $CR^{61}$ or N, and wherein only one of $A^1$, $A^2$, and $A^3$ is N; and $R^{61}$ is H or $R^6$.

13. The compound of claim 12, wherein $R^5$ is methyl.

14. The compound of claim 12, wherein $R^6$ is halogen, $C_1$-$C_6$ alkyl, O—$C_1$-$C_6$ alkyl, or CN.

15. The compound of claim 12, wherein $R^6$ is halogen.

16. The compound of claim 12, wherein $R^3$ is O—($C_1$-$C_6$ alkyl).

17. A pharmaceutical composition comprising the compound of claim 1, or a pharmaceutically acceptable salt or solvate thereof, and a pharmaceutically acceptable carrier.

18. The compound of claim 1, selected from the group consisting of

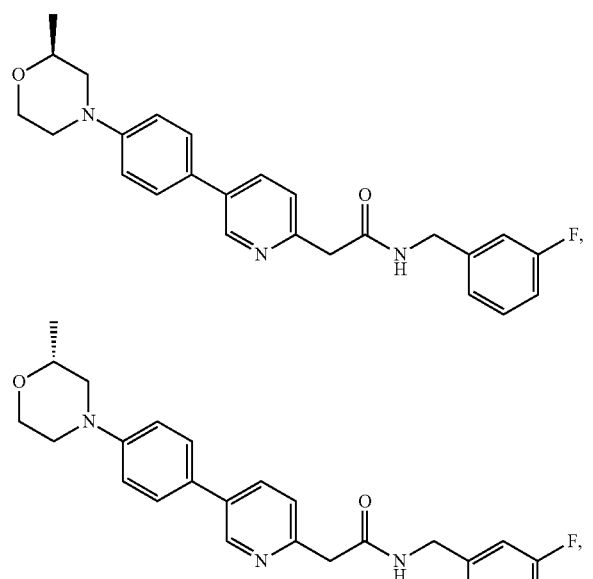

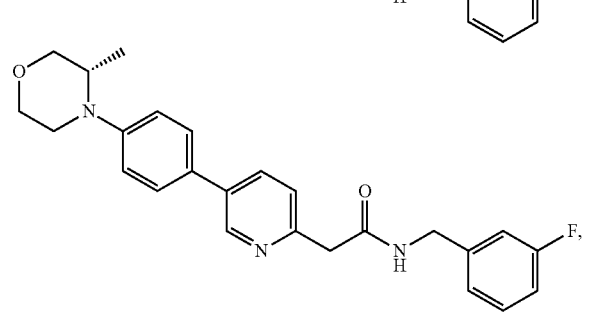

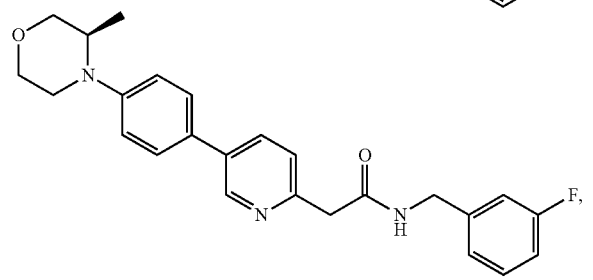

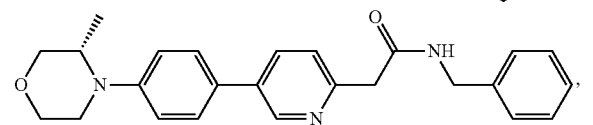

-continued

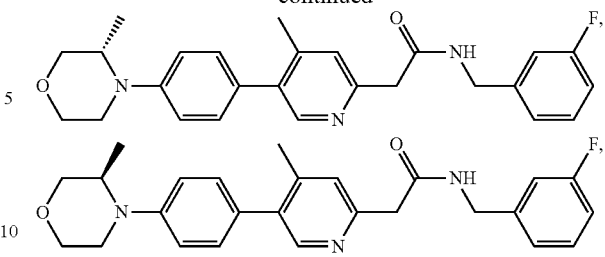

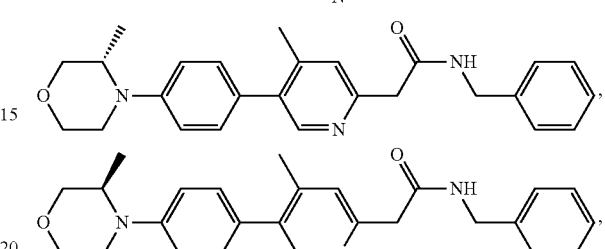

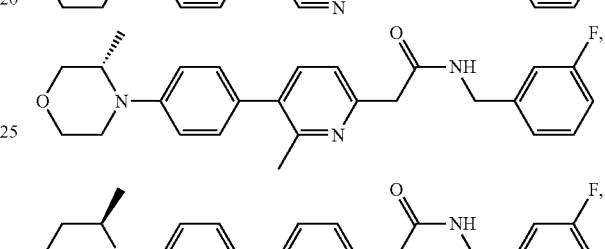

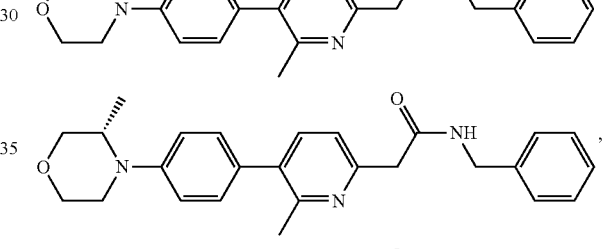

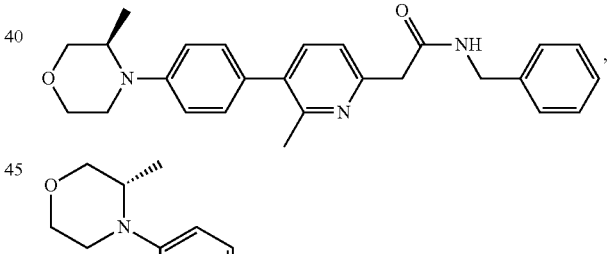

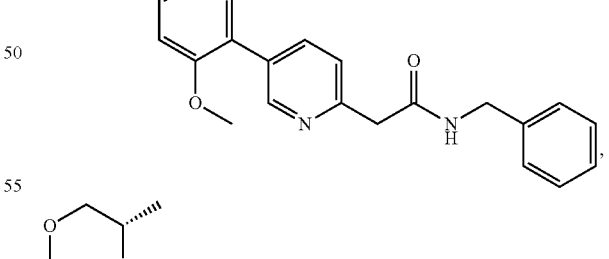

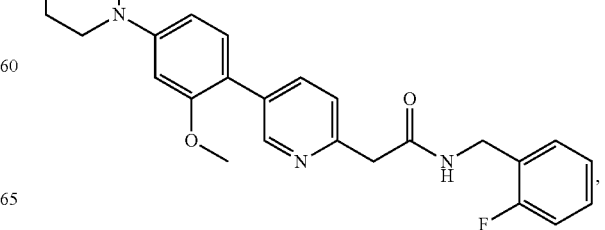

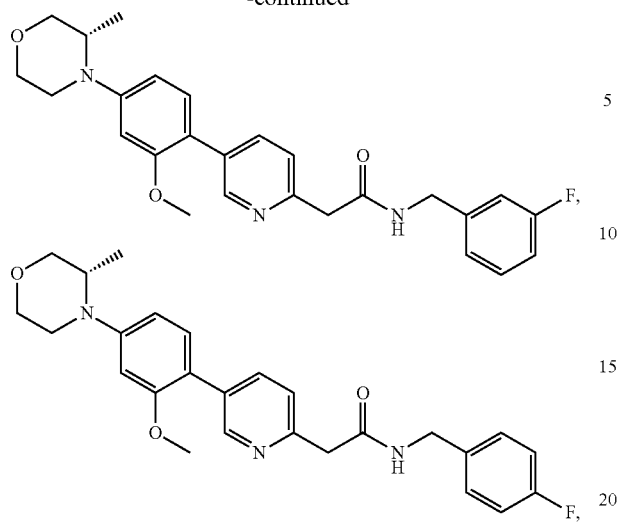
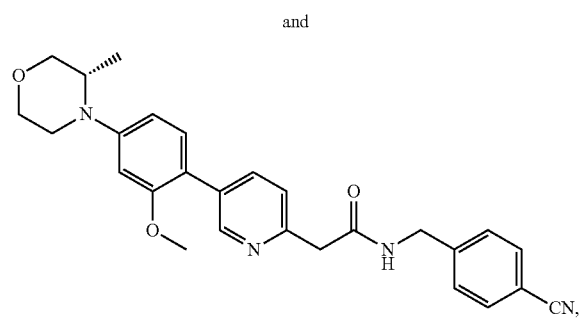
or a pharmaceutically acceptable salt or solvate thereof.
* * * * *

UNITED STATES PATENT AND TRADEMARK OFFICE
CERTIFICATE OF CORRECTION

PATENT NO.         : 10,973,828 B2                                    Page 1 of 1
APPLICATION NO.    : 16/232229
DATED              : April 13, 2021
INVENTOR(S)        : Michael P. Smolinski et al.

It is certified that error appears in the above-identified patent and that said Letters Patent is hereby corrected as shown below:

On the Title Page

Item (72) Inventors, replace:
"Nader N. Nasief Abdel-Sayed"
With:
--Nader N. Nasief Abdel Sayed--.

In the Claims

At Column 108, Claim number 1, Line number 44, replace:
"$X_a$ is $CR^d$ or N;"
With:
--$X_d$ is $CR^d$ or N;--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*